(12) United States Patent
Kumar et al.

(10) Patent No.: US 9,884,900 B2
(45) Date of Patent: Feb. 6, 2018

(54) METHODS FOR TREATING JANUS KINASE-ASSOCIATED DISORDERS BY ADMINISTERING SOLUBLE TRANSFORMING GROWTH FACTOR BETA TYPE II RECEPTOR

(71) Applicant: Acceleron Pharma Inc., Cambridge, MA (US)

(72) Inventors: Ravindra Kumar, Acton, MA (US); Naga Venkata Sai Rajasekhar Suragani, Norwood, MA (US)

(73) Assignee: ACCELERON PHARMA INC., Cambridge, MA (US)

( * ) Notice: Subject to any disclaimer, the term of this patent is extended or adjusted under 35 U.S.C. 154(b) by 0 days.

(21) Appl. No.: 15/228,956

(22) Filed: Aug. 4, 2016

(65) Prior Publication Data

US 2017/0037100 A1    Feb. 9, 2017

Related U.S. Application Data

(60) Provisional application No. 62/201,058, filed on Aug. 4, 2015, provisional application No. 62/263,603, filed on Dec. 4, 2015.

(51) Int. Cl.
| | | |
|---|---|---|
| *C07K 14/495* | (2006.01) | |
| *A61K 31/519* | (2006.01) | |
| *A61K 45/06* | (2006.01) | |

(52) U.S. Cl.
CPC .......... *C07K 14/495* (2013.01); *A61K 31/519* (2013.01); *A61K 45/06* (2013.01); *C07K 2319/30* (2013.01)

(58) Field of Classification Search
CPC . C07K 14/495; C07K 2319/30; A61K 31/519
See application file for complete search history.

(56) References Cited

U.S. PATENT DOCUMENTS

| | | | |
|---|---|---|---|
| 5,543,143 | A | 8/1996 | Reed |
| 5,571,714 | A | 11/1996 | Dasch et al. |
| 5,662,904 | A | 9/1997 | Ferguson et al. |
| 5,693,607 | A | 12/1997 | Segarini et al. |
| 5,772,998 | A | 6/1998 | Dasch et al. |
| 5,783,185 | A | 7/1998 | Dasch et al. |
| 5,844,099 | A | 12/1998 | Stahl et al. |
| 6,001,969 | A | 12/1999 | Lin et al. |
| 6,008,011 | A | 12/1999 | Lin et al. |
| 6,046,157 | A | 4/2000 | Lin et al. |
| 6,090,383 | A | 7/2000 | Dasch et al. |
| 6,294,350 | B1 | 9/2001 | Peterson |
| 6,419,928 | B1 | 7/2002 | Dasch et al. |
| 6,630,326 | B2 | 10/2003 | Markowitz et al. |
| 6,998,125 | B2 | 2/2006 | Hanna et al. |
| 7,026,283 | B2 | 4/2006 | Fleming et al. |
| 7,786,261 | B2 | 8/2010 | De Crescenzo et al. |
| 7,795,389 | B2 | 9/2010 | Sun et al. |
| 7,867,496 | B2 | 1/2011 | Khanna et al. |
| 8,067,389 | B2 | 11/2011 | Kumar et al. |
| 8,283,449 | B2 | 10/2012 | Galipeau et al. |
| 8,318,135 | B2 | 11/2012 | O'Connor-Mccourt et al. |
| 8,591,901 | B2 | 11/2013 | Ledbetter et al. |
| 8,658,135 | B2 | 2/2014 | O'Connor-Mccourt et al. |
| 2002/0004037 | A1 | 1/2002 | Koteliansky et al. |
| 2004/0192583 | A1 | 9/2004 | Medicherla et al. |
| 2004/0234967 | A1 | 11/2004 | Moskowitz |
| 2005/0148555 | A1 | 7/2005 | Gupta et al. |
| 2005/0203022 | A1 | 9/2005 | Gotwals et al. |
| 2006/0286105 | A1 | 12/2006 | Ledbetter et al. |
| 2008/0261879 | A1 | 10/2008 | Melton et al. |
| 2009/0004182 | A1 | 1/2009 | Baiocchi et al. |
| 2009/0036382 | A1 | 2/2009 | Bressan et al. |
| 2009/0042780 | A1 | 2/2009 | Knopf et al. |
| 2010/0003256 | A1 | 1/2010 | Lu et al. |
| 2010/0008911 | A1 | 1/2010 | Streisand et al. |

(Continued)

FOREIGN PATENT DOCUMENTS

| | | |
|---|---|---|
| CN | 101852804 A | 10/2010 |
| EP | 0 975 771 A1 | 2/2000 |

(Continued)

OTHER PUBLICATIONS

Dong M and Blobe GC. Blood. 107(12): 4589-4596. Jun. 15, 2006. Available online at—doi: 10.1182/blood-2005-10-4169.*
Sonbol MB, et al. Ther Adv Hematol. 4(1):15-35. Feb 2013. Available online at—doi: 10.1177/2040620712461047.*
O'Shea JJ, et al. Ann. Rheum. Dis. 72(0 2):ii12-ii15. Apr. 2013. Available online at—doi:10.1136/annrheumdis-2012-202576.*
Abelsson et al., "Patients with polycythemia vera have worst impairment of quality of life among patients with newly diagnosed myeloproliferative neoplasms," Leuk Lymphoma, vol. 54(10):2226-2230 (2013).
Agarwal et al., "Bone marrow fibrosis in primary myelofibrosis: pathogenic mechanisms and the role of TGF-beta," Stem Cell Investigation. vol. 3(5): 1-10. (General Review) (2016).
Akhurst et al., "Targeting the TGF beta signalling pathway in disease," Nature Review Drug Discovery. vol. 11(10): 790-810 (2012).

(Continued)

*Primary Examiner* — Robert Landsman
(74) *Attorney, Agent, or Firm* — White & Case LLP

(57) ABSTRACT

In part, the present disclosure relates methods for treating, preventing, or reducing the severity of a myeloproliferative disorder (e.g., polycythemia vera, essential thrombocythemia, and myelofibrosis) or one or more complications of a myeloproliferative disorder. The present disclosure further relates methods for treating, preventing, or reducing the severity of a Janus kinase-associated disorder or one or more complications of a Janus kinase-associated disorder. In certain aspects the disclosure provides TβRII antagonists for treating, preventing, or reducing the severity of a myeloproliferative disorder (e.g., polycythemia vera, essential thrombocythemia, and myelofibrosis) or a Janus kinase-associated disorder or one or more complications of a myeloproliferative disorder or a Janus kinase-associated disorder.

34 Claims, 8 Drawing Sheets
(2 of 8 Drawing Sheet(s) Filed in Color)

(56) References Cited

U.S. PATENT DOCUMENTS

| | | |
|---|---|---|
| 2010/0204104 A1 | 8/2010 | Qiu et al. |
| 2011/0008364 A1 | 1/2011 | Ledbetter et al. |
| 2011/0104121 A1 | 5/2011 | Wira et al. |
| 2011/0177070 A1 | 7/2011 | Lofquist et al. |
| 2011/0236309 A1 | 9/2011 | O'Connor-Mccourt et al. |
| 2011/0245107 A1 | 10/2011 | Kuchroo et al. |
| 2012/0010178 A1 | 1/2012 | Rubin et al. |
| 2012/0114640 A1 | 5/2012 | Kulkarni et al. |
| 2013/0011397 A1 | 1/2013 | Pasricha |
| 2013/0039911 A1 | 2/2013 | Bedi et al. |
| 2013/0045272 A1 | 2/2013 | Niitsu et al. |
| 2015/0056199 A1 | 2/2015 | Kumar et al. |
| 2015/0080320 A1 | 3/2015 | Desai |
| 2015/0225483 A1 | 8/2015 | Lo |
| 2016/0017026 A1 | 1/2016 | Wei et al. |
| 2016/0298093 A1 | 10/2016 | Kumar et al. |

FOREIGN PATENT DOCUMENTS

| | | |
|---|---|---|
| WO | WO-91/19513 A1 | 12/1991 |
| WO | WO-98/48024 A1 | 10/1998 |
| WO | WO-99/65948 A1 | 12/1999 |
| WO | WO-01/66140 A1 | 9/2001 |
| WO | WO-03/011908 A2 | 2/2003 |
| WO | WO-03/061587 A2 | 7/2003 |
| WO | WO-2004/098637 A1 | 11/2004 |
| WO | WO-2005/019258 A2 | 3/2005 |
| WO | WO-2006/036729 A2 | 4/2006 |
| WO | WO-2008/060371 A1 | 5/2008 |
| WO | WO-2008/157367 A1 | 12/2008 |
| WO | WO-2010/003118 A1 | 1/2010 |
| WO | WO-2010/083034 A1 | 7/2010 |
| WO | WO-2011/109789 A2 | 9/2011 |
| WO | WO-2012/030394 A1 | 3/2012 |
| WO | WO-2013/000234 A1 | 1/2013 |
| WO | WO-2013/012648 A1 | 1/2013 |
| WO | WO-2013/164694 A1 | 11/2013 |
| WO | WO-2014/172584 A1 | 10/2014 |
| WO | WO-2015/027082 A1 | 2/2015 |

OTHER PUBLICATIONS

Alvarez-Larran et al., "JAK2V617F monitoring in polycythemia vera and essential thrombocythemia: Clinical usefulness for predicting myelofibrotic transformation and thrombotic events," *Am J Hematol* vol. 89(5):517-523 (2014).

Barbui et al., "Disease characteristics and clinical outcome in young adults with essential thrombocythemia versus early/prefibrotic primary myelofibrosis," *Blood* vol. 120(3):569-571 (2012).

Barbui et al., "Thrombosis in primary myelofibrosis: incidence and risk factors," *Blood*, vol. 115(4): 778-782 (2010).

Barbui et al., "Masked polycythemia vera diagnosed according to WHO and BCSH classification," American Journal Hematology, vol. 89(2):199-202 (2014).

Barbui et al., "Front-line therapy in polycythemia vera and essential thrombocythemia," *Blood Reviews*, vol. 26: 205-211 (2012).

Barbui et al., "Rethinking the diagnostic criteria of polycythemia vera," *Leukemia*, vol. 28: 1191-1195 (2014).

Barosi et al., "JAK2 V617F mutational status predicts progression to large splenomegaly and leukemic transformation in primary myelofibrosis," Blood, vol. 110(12): 4030-4036 (2007).

Barosi et al., "Therapeutic approaches in myelofibrosis," *Expert Opin Pharmacother*, vol. 12(10): 1597-1611 (2011).

Barosi et al., "Proposed criteria for the diagnosis of post-polycythemia vera and post-essential thrombocythemia myelofibrosis: a consensus statement from the international working group for myelofibrosis research and treatment," *Leukemia*, vol. 22:437-438 (2008).

Baxter et al., "Acquired mutation of the tyrosine kinase JAK2 in human myeloproliferative disorders," *Lancet*, vol. 365:1054-1061 (2005).

Begna et al., "A phase-2 trial of low-dose pomalidomide in myelofibrosis," *Leukemia*, vol. 25:301-304 (2011).

Birgegard G., "Advances and challenges in the management of essential thrombocythemia," Therapeutics Advances Hematology, vol. 6(3): 142-156 (2015).

Bunn, "Drug-induced autoimmune red-cell aplasia," *New England Journal of Medicine*, vol. 346(7): 522-523 (2002).

Campbell et al., "Definition of subtypes of essential thrombocythaemia and relation to polycythaemia vera based on JAK2 V617F mutation status: a prospective study," *Lancet*, vol. 366:1945-1953 (2005).

Campbell et al., *"The Myeloproliferative Disorders," N. Engl J Med*, vol. 355:2452-2466 (2006).

Carbuccia et al., "Mutations of ASXL1 gene in myeloproliferative neoplasms," *Leukemia*, vol. 23:2183-2186 (2009).

Cervantes et al., "New prognostic scoring system for primary myelofibrosis based on a study of the International Working Group for Myelofibrosis Research and Treatment," *Blood*, vol. 113(13):2895-2901 (2009).

Chagraoui et al., "Prominent role of TGF-beta 1 in thrombopoietin-induced myelofibrosis in mice," Blood, vol. 100(10): 3495-3503 (2002).

Chou et al., "Leukocytosis in polycythemia vera and splenomegaly in essential thrombocythemia are independent risk factors for hemorrhage," *European Journal of Haematology*, vol. 90:228-236 (2013).

Dahabreh et al., "Is JAK2 V617F mutation more than a diagnostic index? A meta-analysis of clinical outcomes in essential thrombocythemia," Leukemia Research, vol. 33: 67-73 (2009).

Delanty et al., "Erythropoietin-associated hypertensive posterior leukoencephalopathy," *Neurology*, vol. 49: 686-689 (1997).

Delhommeau et al., "Mutation in TET2 in Myeloid Cancers," N *Engl J Med*, vol. 360(22):2289-2301 (2009).

del Re et al., "In the absence of type III receptor, the transorming growth factor (TGF)-beta type II-B receptor requires the type I receptor to bind TGF-beta2," J Biol Chem, vol. 279(21): 22765-22772 (2004).

Dennler et al, "Direct binding of Smad3 and Smad4 to critical TGF beta-inducible elements in the promoter of human plasminogen activator inhibitor-type 1 gene," EMBO, vol. 17(11): 3091-3100 (1998).

Druker et al., "Efficacy and Safety of a Specific Inhibitor of the BCR-ABL Tyrosine Kinase in Chronic Myeloid Leukemia," *N Engl J Med*, vol. 344(14):1031-1037 (2001).

Elliott et al., "Splenic irradiation in myelofibrosis with myeloid metaplasia: a review, "*Blood Reviews*, vol. 13(3):163-170 (1999).

Emanuel et al., "Myeloproliferative Neoplasm (MPN) Symptom Assessment Form Total Symptom Score: Prospective International Assessment of an Abbreviated Symptom Burden Scoring System Among Patients with MPNs," *J Clin Oncol*, vol. 30(33): 4098-4103 (2012).

Faoro et al., "Long-term analysis of the palliative benefit of 2-chlorodeoxyadenosine for myelofibrosis with myeloid metaplasia," *Eur J Haematol*, vol. 74(2): 117-120 (2005).

Finazzi et al., "Acute leukemia in polycythemia vera: an analysis of 1638 patients enrolled in a prospective observational study," Blood, vol. 105(7):2664-2670 (2005).

Finazzi et al., "How I treat patients with polycythemia vera," *Blood*, vol. 109(12):5104-5111 (2007).

Gangat et al., "Mutations and thrombosis in essential thrombocythemia: prognostic interaction with age and thrombosis history," *Eur J Haematol*, vol. 94: 31-36 (2014).

Gastinne et al., "Adenoviral-mediated TGF-beta1 inhibition in a mouse model of myelofibrosis inhibit bone marrow fibrosis development," Experimental Hematology, vol. 35, Issue 1: 64-74; , p. 67, Retroviral transfer in SCID mice BM cells is highly efficient, p. 68, Histological analysis (2007).

Grobet et al., "A deletion in the bovine myostatin gene causes the double-muscled phenotype in cattle," Nat Genet, vol. 17(1): 71-74 (1997).

Guglielmelli et al., "Safety and efficacy of everolimus, a mTOR inhibitor, as single agent in a phase 1/2 study in patients with myelofibrosis," *Blood*, vol. 118(8):2069-2076 (2011).

(56) References Cited

OTHER PUBLICATIONS

Gupta et al., "Allogeneic hematopoietic cell transplantation for myelofibrosis in the era of JAK inhibitors," Blood, vol. 120(7):1367-1379 (2012).
Harrison et al., "Prodomains regulate the synthesis, extracellular localisation and activity of TGF-beta superfamily ligands," Growth Factors, vol. 29(5): 174-186 (2011).
Hensley et al., "Polycythemia vera: current pharmacotherapy and future directions," Expert Opin Pharmacotherapy, vol. 14:609-617 (2013).
Hirai and Fijita, "A Human Transforming Growth Factor-beta Type II Receptor that Contains an Insertion in the Extracellular Domain," Ex. Cell Res., vol. 223 135-141 (1996).
Horl et al., "European Best Practice Guidelines 17-18 Adverse effects," Nephrol Dial Transplant, vol. 15 (suppl. 4), 51-56 (2000).
Hussein et al., "Conventional cytogenetics in myelofibrosis: literature review and discussion," Eur J Haematology vol. 82:329-338 (2009).
Hussein et al., "International Prognostic Scoring System-independent cytogenetic risk categorization in primary myelofibrosis," Blood, vol. 115(3):496-499 (2010).
Isaka et al., "Gene therapy by transforming growth factor-beta receptor-IgG Fc chimera suppressed extracellular matrix accumulation in experimental glomerulonephritis," Kidney International, vol. 55(2): 467-475 (1999).
James et al., "A unique clonal JAK2 mutation leading to constitutive signaling causes polycythaemia vera," Nature, vol. 434: 1144-1148 (2005).
Klampfl et al., Somatic Mutations of Calreticulin in Myeloproliferative Neoplasms, N Engl J Medicine, vol. 369(25): 2379-2390 (2013).
Komesli et al., "Chimeric extracellular domain of type II transforming growth factor (TGF)-beta receptor fused to the Fc region of human immunoglobulin as a TGF-beta antagonist," Eur. J. Biochem., vol. 254: 505-513 (1998).
Konrad et al., "Alternative splicing of TGF-betas and their high-affinity receptors T beta RI, T beta RII and T beta RIII (betaglycan) reveal new variants in human prostatic cells," BMC Genomics, vol. 8: 318 (2007).
Kontani et al., "Spontaneous elicitation of potent antitumor immunity and eradication of established tumors by administration of DNA encoding soluble transforming growth factor-b II receptor without active antigen-sensitization," Cancer lmmunol. Immunother; vol. 55: 579-487 (2006).
Kralovics et al., "A Gain-of-Function Mutation of JAK2 in Myeloproliferative Disorders," N Engl J Medicine, vol. 352(17): 1779-1790 (2005).
Kvasnicka et al., "Prodromal myeloproliferative neoplasms: The 2008 WHO classification," Am J Hematology, vol. 85:62-69 (2010).
Lasho et al., "SRSF2 mutations in primary myelofibrosis: significant clustering with IDH mutations and independent association with inferior overall and leukemia-free survival," Blood, vol. 120(20):4168-4171 (2012).
Levine et al., "Activating mutation in the tyrosine kinase JAK2 in polycythemia vera, essential thrombocythemia, and myeloid metaplasia with myelofibrosis," Cancer Cell, vol. 7:387-397 (2005).
Levine et al., "Role of JAK2 in the pathogenesis and therapy of myeloproliferative disorders," Nat Rev Cancer, vol. 7:673-683 (2007).
Lin et al. "Expression cloning of the TGF-beta type II receptor, a functional transmembrane serine/threonine kinase," Cell, vol. 68(4): 775-785 (1992).
Lussana et al., "Association of V617F Jak2 mutation with the risk of thrombosis among patients with essential thrombocythaemia or idiopathic myelofibrosis: A systematic review," Thrombosis Research, vol. 124: 409-417 (2009).
Manoharan et al., "The Reticulin Content of Bone Marrow in Acute Leukaemia in Adults," Br J Haematology, vol. 43: 185-190 (1979).

Martinez-Trillos et al., "Efficacy and tolerability of hydroxyurea in the treatment of the hyperproliferative manifestations of myelofibrosis: results in 40 patients," Ann Hematol., vol. 89(12):1233-1237 (2010).
Mascarenhas et al., "Advances in myelofibrosis: a clinical case approach," Haemotologica, vol. 98(10): 1499-1509 (2013).
Mascarenhas et al., "Biology and Clinical Management of Myeloproliferative Neoplasms and Development of the JAK Inhibitor Ruxolitinib," Current Medical Chemistry, vol. 19:4399-4413 (2012).
Mascarenhas et al., "Anti-transforming growth factor-beta therapy in patients with myelofibrosis," Leukemia & Lymphoma. vol. 55(2): 450-452 (2014).
Mascarenhas et al. "Prolonged Low Dose Therapy with a Pan-Deacetylase Inhibitor, Panobinostat (LBH589), in Patients with Myelofibrosis," Blood, The Journal of American Society of Hematology, vol. 118(Suppl.1) (2011).
Massagué, J., "How cells read TGF-beta signals," Nat. Rev. Mol. Cell Biol. 1(3): 169-178 (2000).
McMullin et al., "Amendment to the guideline for diagnosis and investigation of polycythaemia/erythrocytosis," British Journal Haematology, vol. 138:821-823 (2007).
Mehta et al., "Epidemiology of myeloproliferative neoplasms in the United States," Leukemia & Lymphoma, vol. 55:595-600 (2014).
Mesa et al., "Phase1/-2 study of pomalidomide in myelofibrosis," Am J. Hemtatol, vol. 85:129-130 (2010).
Mesa, R.A., "How I treat symptomatic splenomegaly in patients with myelofibrosis," Blood, vol. 113(22):5394-5400 (2009).
Mesa, R.A., "The evolving treatment paradigm in myelofibrosis," Leukemia & Lymphoma. vol. 54(2):242-251 (2013).
Murphy, Scott, "Diagnostic Criteria and Prognosis in Polycythemia Vera and Essential Thrombocythemia," Seminars in Hematology, vol. 36(1), Suppl. 2: 9-13 (1999).
Nangalia et al., "Somatic CALR Mutations in Myeloproliferative Neoplasms with Nonmutated JAK2," The New England Journal of Medicine, vol. 369(25): 2391-2405 (2013).
Nikawa, Jun-ichi. "A cDNA encoding the human transforming growth factor beta receptor suppresses the growth defect of yeast mutant," Gene, vol. 149: 367-372 (1994).
Oh et al., "Novel mutations in the inhibitory adaptor protein LNK drive JAK-STAT signaling in patients with myeloproliferative neoplasms," Blood, vol. 116(6):988- 992 (2010).
Passamonti et al., "Life Expectancy and Prognostic Factors for Survival in Patients with Polycythemia Vera and Essential Thrombocythemia," Am J Med, vol. 117:755-761 (2004).
Passamonti et al.. "Clinical Relevance of JAK2 (V617F) Mutant Allele Burden," Haematologica, vol. 94 (6 pages) (2009).
Passamnoti et al., "A dynamic prognostic model to predict survival in primary myelofibrosis: a study by the IWG-MRT (International Working Group for Myeloproliferative Neoplasms Research and Treatment)," Blood, vol. 115(9): 1703-1708 (2010).
Passamonti et al., "A prospective study of 338 patients with polycythemia vera: the impact of JAK2 (V617F) allele burden and leukocytosis on fibrotic or leukemic disease transformation and vascular complications," Leukemia, vol. 24:1574-1579 (2010).
Passamonti et al., "A prognostic model to predict survival in 867 World Health Organization-defined essential thrombocythemia at diagnosis: a study by the International Working Group on Myelofibrosis Research and Treatment," Blood, vol. 120(6):1197-1201 (2012).
Passamonti F., "How I treat polycythemia vera," Blood, vol. 120(2):275-284 (2012).
Patnaik et al., "Age and platelet count are IPSS-independent prognostic factors in young patients with primary myelofibrosis and complement IPSS in predicting very long or very short survival," European Journal of Haemotology, vol. 84:105-108 (2010).
Pikman et al., "MPLW515L Is a Novel Somatic Activating Mutation in Myelofibrosis with Myeloid Metaplasia," PLOS Medicine, vol. 3:e270 (2006).
Quintas-Cardama et al., "Janus kinase inhibitors for the treatment of myeloproliferative neoplasias and beyond," Nature Reviews Drug Discovery, vol. 10:127-140 (2011).

(56) References Cited

OTHER PUBLICATIONS

R&D Systems, Recombinant Human TGF-β RBII Fc Chimera, Catalog No. 341-BR (2015).

R&D Systems, Recombinant Human TGF-βRI Isoform 2 Fc Chimera Catalog No. 1003-RT (2015).

Radaev et al., "Ternary complex and transforming growth factor-beta1 reveals isoform-specific ligand recognition and receptor recruitment in the superfamily," J Biol Chem, vol. 285(19):14806-14814 (2010).

Rotunno et al., "Impact of calreticulin mutations on clinical and hematological phenotype and outcome in essential thrombocythemia," Blood, vol. 123(10):1552-1555 (2014).

Rotzer et al., "Type III TGF-beta receptor-independent signaling of TGFB2 via TBRII-B, an alternatively spliced TGF-B type II receptor," The EMBO Journal, vol. 20(3): 480-490 (2001).

Rumi et al., "CALR exon 9 mutations are somatically acquired events in familial cases of essential thrombocythemia or primary myelofibrosis," Blood, vol. 123(15):2416-2419 (2014).

Scherber et al., "The Myeloproliferative Neoplasm Symptom Assessment Form (MPN-SAF): International Prospective Validation and Reliability Trial in 402 patients," Blood, vol. 118(2):401-408 (2011).

Schuelke et al., "Myostatin mutation associated with gross muscle hypertrophy in a child," N Engl J Med vol. 350(26): 2682-26888 (2004).

Scott et al., "JAK2 Exon 12 Mutations in Polycythemia Vera and Idiopathic Erthrocytosis," New England Journal of Medicine, vol. 356(5):459-468 (2007).

Sever et al., "Therapeutic options for patients for polycythemia vera and essential thrombocythemia refractory/resistant to hydroxyurea," Leukemia & Lymphoma, vol. 55(12):2685-2690 (2014).

Shi et al., "Latent TGF-beta structure and activation," Nature, vol. 474(7351): 343-349 (2011).

Singibarti, G., "Erythropoietin and Autologous Transfusion: Adverse events of erythropoietin in long-term and in acute/short-term treatment," Journal Clin Investig, vol. 72(suppl 6), S36-S43 (1994).

Sonbol et al., "Comprehensive review of JAK inhibitors in myeloproliferative neoplasms," Therapeutic Advances in Hematology, (vol. 4(1): 15-35 (2013).

Spivak, J.L., "Polycythemia vera: myths, mechanisms, and management," Blood, vol. 100(13):4272-4290 (2002).

Stuart et al., "Polycythemia Vera," Am Fam Physician 69:2139-2144 (2004).

Suzuki et al., "Cloning of an isoform of mouse TGF-beta type II receptor gene," FEBS Letters, vol. 335: 19-22 (1994).

Talarico et al., "Myeloproliferative disorders: A practical review," Patient Care, vol. 30:37-57 (1998).

Tefferi et al., "Proposals and rationale for revision of the World Health Organization diagnostic criteria for polycythemia vera, essential thrombocythemia, and primary myelofibrosis: recommendations from an ad hoc international expert panel," Blood, vol. 110(4):1092-1097 (2007).

Tefferi et al., "CALR and ASXL1 mutations-based molecular prognostication in primary myelofibrosis: an international study of 570 patients," Leukemia, vol. 28:1494-1500 (2014).

Tefferi, A., "Primary myelofibrosis: 2012 update on diagnosis, risk stratification, and management," Am J Hematology, vol. 86(12): 1017-1026 (2011).

Tefferi, A., "How I treat myelofibrosis," Blood 117(13):3494-3504 (2011).

Tefferi, A., "Mutations galor in myeloproliferative neoplasms: Would the real Spartacus please stand up?," Leukemia, vol. 25: 1059-1063 (2011).

Tefferi et al., "CALR vs JAK2 vs MPL-mutated or triple-negative myelofibrosis: clinical, cytogenetic and molecular comparisons," Leukemia, vol. 28: 1472-1477 (2014).

Tefferi et al., "CME Information: Primary myelofibrosis: 2014 update on diagnosis, risk-stratification and management," Am J Hematol, vol. 89(9):915-925 (2014).

Tefferi et al., "The JAK2V617F tyrosine kinase mutation in myelofibrosis with myeloid metaplasia: lineage specificity and clinical correlates," British Journal Haematology, vol. 131:320-328 (2005).

Tefferi et al., "Lenalidomide therapy in del(5)(q31)-associated myelofibrosis: cytogenetic and JAK2V617F molecular remissions," Leukemia, vol. 21(8): 1827-1828 (2007).

Tefferi et al., "Thrombosis in Myeloproliferative Disorders: Prevalence, Prognostic Factors, and the Role of Leukocytes and JAK2V617F," Seminars in Thrombosis and Hemostasis, vol. 33:313-320 (2007).

Tefferi et al., "Transfusion-dependency at presentation and its acquisition in the first year of diagnosis are both equally detrimental for survival in primary myelofibrosis-prognostic relevance is independent of IPSS or karyotype," American Journal of Hematology, vol. 85:14-17 (2009).

Tefferi et al., "Predictors of greater than 80% 2-year mortality in primary myelofibrosis: a Mayo Clinic study of 884 karyotypically annotated patients," Blood, vol. 118:4595-4598 (2011).

Tefferi et al., "IDH mutations in primary myelofibrosis predict leukemic transformation and shortened survival: clinical evidence for leukemogenic collaboration with JAK2V617F," Leukemia, vol. 26: 475-480 (2012).

Tefferi et al., "Survival and prognosis among 1545 patients with contemporary polycythemia vera: an international study," Leukemia, vol. 27:1874-1881 (2013).

Tefferi et al., "Calreticulin mutations and long-term survival in essential thrombocythemia," Leukemia, vol. 28: 2300-2303 (2014).

Thapaliya et al., "International working group for myelofibrosis research and treatment response assessment and long-term follow-up of 50 myelofibrosis patients treated with thalidomide-prednisone based regiments," Am J Hematology, vol. 86(1):96-98 (2011).

Thiele et al., "European consensus on grading bone marrow fibrosis and assessment of cellularity," Haematologica, vol. 90:1128-1132 (2005).

Thiele et al., WHO Classification of Tumours of Haematopoietic and Lymphoid Tissues. IARC Lyon: World Health Organization, 44-47 (2008).

Tibes et al., "Emerging drugs for polycythemia vera," Expert Opinion, vol. 18:393-404 (2013).

Vannucchi A.M., "Insights into the pathogenesis and management of thrombosis in polycythemia vera and essential thrombocythemia," Intern Emerg Med, vol. 5: 177-184 (2010).

Vannucchi et al., "A pathobiologic pathway linking thrombopoietin, GATA-1, and TGF-beta1 in the development of myelofibrosis," Blood, vol. 105(9): 3493-3501 (2005).

Vannucchi et al., "The mTOR Inhibitor, RAD001, Inhibits the Growth of Cells From Patients with Myeloproliferative Neoplasms," Blood. vol. 114(22):2914 (2009).

Vannucchi et al., "Management of Myelofibrosis," American Society of Hematology, Current Issues in Myeloproliferative Neoplasms:222-230 (2011).

Wrana et al., "TGF beta signals through a heteromeric protein kinase receptor complex," Cell vol. 71(6): 1003-1014 (1992).

Wynn, Thomas A., "Common and unique mechanisms regulate fibrosis in various fibroproliferative diseases," The Journal of Clinical Investigation, vol. 117(3):524-529 (2007).

Xing et al., "Transgenic expression of JAK2V617F causes myeloproliferative disorders in mice," Blood, vol. 111(10): 5109-5117 (2008).

Xu et al., JAK2V617F: prevalence in a large Chinese hospital population, Blood, vol. 109(1):339-342 (2007).

Xin et al., "Suppressin of Cyclosporine a Nephrotoxicity in Vivo by Transforming Growth Factor β Receptor-Immunoglobulin G. Chimeric Protein," Transplantation, vol. 77(9): 1433-1442 (2004).

Yan et al., "A Model of Myelofibrosis and Osteosclerosis in Mice Induced by Overexpressing Thrombopoietin (mpl Ligand): Reversal of Disease by Bone Marrow Transplantation," Blood, vol. 88(2): 402-409 (1996).

(56) References Cited

OTHER PUBLICATIONS

Yavorkovsky et al., "Correspondence: Classifying Chronic Myelomonocytic Leukemia," Journal of Clinical Oncology, vol. 19(17):3790-3792 (2001).
Zahr et al., "Bone marrow fibrosis in myelofibrosis: pathogenesis, prognosis and targeted strategies," Haematologica, vol. 101(6): 660-671 (2016).
Zauli et al., "Reduced responsiveness of bone marrow megakaryocyte progenitors to platelet-derived transforming growth factor beta 1, produced in normal amount, in patients with essential thromboycythamia," Br J Haematol, vol. 83(1): 14-20 (1993).
Zwaagstra et al., "Engineering and Therapeutic Application of Single-Chain Bivalent TGF-? Family Traps," Molecular Cancer Therapeutics, vol. 11(7): 1477-1487 (2012).
Ziakas P., "Effect of JAK2 V617F on thrombotic risk in patients with essential thrombocythemia: measuring the uncertain," Haematologica, vol. 93(9): 1412-1414 (2008).

* cited by examiner

```
  1  mgrgllrglw plhivlwtri astipphvqk svnndmivtd nngavkfpql
 51  ckfcdvrfst cdnqkscmsn csitsicekp qevcvavwrk ndenitletv
101  chdpklpyhd filedaaspk cimkekkkpg etffmcscss decndniifs
151  eeyntsnpdl llvifqvtgi slippigvai sviiifycyr vnrqqklsst
201  wetgktrklm efsehcaiil eddrsdisst canninhnte llpieldtlv
251  gkgrfaevyk aklkqntseq fetvavkifp yeeyaswkte kdifsdinlk
301  henilqflta eerktelgkq ywlitafhak gnlqeyltrh viswedlrkl
351  gsslargiah lhsdhtpcgr pkmpivhrdl kssnilvknd ltcclcdfgl
401  slrldptlsv ddlansgqvg tarymapevl esrmnlenve sfkqtdvysm
451  alvlwemtsr cnavgevkdy eppfgskvre hpcvesmkdn vlrdrgrpei
501  psfwlnhqgi qmvcetltec wdhdpearlt aqcvaerfse lehldrlsgr
551  scseekiped gslnttk           (SEQ ID NO: 5)
```

FIGURE 1

```
  1  mgrgllrqlw plhivlwtri astipphvqk sdvemeaqkd eiicpscnrt
 51  ahplrhinnd mivtdnngav kfpqlckfcd vrfstcdnqk scmsncsits
101  icekpqevcv avwrkndeni tletvchdpk lpyhdfiled aaspkcimke
151  kkkpgetffm cscssdecnd niifseeynt snpdlllvif qvtgisllpp
201  lgvaisviii fycyrvnrqq klsstwetgk trklmefseh caiileddrs
251  disstcanni nhntellpie ldtlvgkgrf aevykaklkq ntseqfetva
301  vkifpyeeya swtekdifs dinlkhenil qfltaeerkt elgkqywlit
351  afhakgnlqe yltrhviswe dlrklgssla rgiahlhsdh tpcgrpkmpi
401  vhrdlkssni lvkndltccl cdfglslrld ptlsvddlan sgqvgtarym
451  apevlesrmn lenvesfkqt dvysmalvlw emtsrcnavg evkdyeppfg
501  skvrehpcve smkdnvlrdr grpeipsfwl nhqgiqmvce tltecwdhdp
551  earltaqcva erfselehld rlsgrscsee kipedgslnt tk
     (SEQ ID NO: 6)
```

FIGURE 2

|                    | Native Leader Sequence | Splice Insertion (25 aa) |
|---|---|---|

```
                          Native Leader Sequence              Splice Insertion (25 aa)

1         10        20          30                                35
Native TβRII short      [MGRGLLRGLWPLHIVLWTRIAS]TIPPHVQKS---------------------VNNDMIV...

30                                 35
TβRII_short(23-X)                                       TIPPHVQKS---------------------VNNDMIV...

30                                 35
TβRII_short(29-X)                                       QKS---------------------------VNNDMIV...

35
TβRII_short(35-X)                                                                          DMIV...

1         10        20         30        40        50        60
Native TβRII long       [MGRGLLRGLWPLHIVLWTRIAS]TIPPHVQKSDVEMEAQKDEIICPSCNRTAHPLRHINNDMIV...

30        40        50        60
TβRII_long(23-X)                                        TIPPHVQKSDVEMEAQKDEIICPSCNRTAHPLRHINNDMIV...

30        40        50        60
TβRII_long(29-X)                                        QKSDVEMEAQKDEIICPSCNRTAHPLRHINNDMIV...

60
TβRII_long(60-X)                                                                           DMIV...
```

METHODS FOR TREATING JANUS KINASE-ASSOCIATED DISORDERS BY ADMINISTERING SOLUBLE TRANSFORMING GROWTH FACTOR BETA TYPE II RECEPTOR

RELATED APPLICATIONS

This application claims the benefit of priority from U.S. Provisional Application No. 62/201,058, filed Aug. 4, 2015 and U.S. Provisional Application No. 62/263,603, filed Dec. 4, 2015. The specifications of each of the foregoing applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Sep. 28, 2016, is named PHPH-090-101_SL.txt and is 141,993 bytes in size.

BACKGROUND OF THE INVENTION

Myeloproliferative disorders (MPDs), or neoplasms (MPNs), are a group of conditions generally characterized by chronic increases in some or all of the blood cells (platelets, white blood cells, and red blood cells) [Talarico et al. (1998) *Patient Care* 30:37-57; Yavorkovsky et al. (2001) *J Clin Oncol* 19:3790-3792; and Campbell et at (2006) *N Engl J Med* 355:2452-2-466]. This group of blood disorders includes polycythemia vera (PV), essential thrombocythemia (ET), myelofibrosis (e.g., primary myelofibrosis, post-polycythemia vera myelofibrosis, and post-essential thrombocythemia myelofibrosis), and chronic myeloid leukemia (CML). PV is characterized by increased production of all 3 types of blood cells, whereas ET is manifest in the elevation of platelets. Myelofibrosis (MF) is a disease in which fibrous (scar-like) tissues develop in the bone marrow as a result of abnormal production of red cells, white cells, and/or platelets. CML is characterized by the increased and unregulated growth of predominantly myeloid cells in the bone marrow and the accumulation of these cells in the peripheral blood.

It is generally thought that MPDs arise from a transformation in a hematopoietic stem cell. Indeed, CML is now defined by its causative molecular lesion, the BCR-ABL fusion gene, which most commonly results from the Philadelphia translocation (Ph). Accordingly, CML is characterized as a BCR-ABL positive (+) myeloproliferative disorder. Discovery of this defined molecular defect lead to the development of the drug imatinib mesylate (Gleevec; Novartis, Basel, Switzerland) to treat CML [Druker et al. (2001) *N Engl J Med* 344:1031-1037].

The other three myeloproliferative neoplasms (PV, ET, and MF) are characterized as BCR-ABL-negative myeloproliferative disorder. Recently, several groups identified a gain-of-function mutation of tyrosine kinase JAK2 (JAK2V617F) as a major molecular defect in approximately 90% patients with PV, approximately 50% of patients with ET, and approximately 50-60% of patients with MF [Baxter et al. (2005) *Lancet* 365:1054-1061; James et al (2005) *Nature* 434:1144-1148; Kralovics (2005) *N. Engl. J. Med.* 352:1770-1790]. Interestingly, recent studies have demonstrated that nearly 1% of blood samples collected from hospital patients test positive for the JAK2V617F mutation [Xu et al. (2007) *Blood* 109:339-342]. Most of these JAKV617F-positive patients do not meet the criteria for diagnosis of MPDs but developed vascular diseases, including thrombosis, coronary heart disease, arteriosclerosis, cerebral ischemia, and cerebral infarction at a higher rate than JAKV617F-negative patients. These data suggest that MPDs and pre-MPDs conditions may represent a more profound public health problem than originally anticipated and further emphasizes the pathologic importance of the JAK2V617F as well as other Janus kinase mutations.

Allogeneic hematopoietic stem cell transplantation is the only known cure for BCR-ABL-negative MPDs [Gupta et al. (2012) *Blood* 120:1367-1379]. However, stem cell treatment-related mortality is high and only a minority of patients qualify for transplantation. While the development and use of JAK inhibitors represents a significant therapeutic advancement, there are clear limitations to their use in the treatment of BCR-ABL-negative MPDs. In particular, JAK inhibitors appear to be useful for reducing splenomegaly in myelofibrosis patients; however, their effects on the disease are otherwise largely palliative [Gupta et al. (2012) *Blood* 120:1367-1379]. In particular, JAK inhibitors have little to no effect on many manifestations (complications) of the disease including, for example, cytopenia, transfusion dependence, accelerated or blast phase disease, and fibrosis. Moreover, JAK inhibitors have been shown to promote or worsen thrombocytopenia, anemia, and neutropenia in some patients.

Thus, there is a high, unmet need for effective therapies treating MPDs and Janus kinase-associated disorders. Accordingly, it is an object of the present disclosure to provide methods for treating, preventing, or reducing the progression rate and/or severity of MPDs or Janus kinase-associated disorders or one or more complications of MPDs or Janus kinase-associated disorders.

SUMMARY OF THE INVENTION

In part, the present disclosure relates to the discovery that a TGFβ type II receptor (TβRII) antagonist (inhibitor) can be used to treat myelofibrosis, particularly ameliorating various complications of the disease, including for example, fibrosis, splenomegaly, and inflammatory complications. In particular, the data presented herein shows that a TβRII polypeptide decreases fibrosis, splenomegaly, and inflammation in a JAK2V617F model of myelofibrosis. These data suggest that TβRII antagonists may be used to treat myelofibrosis (e.g., primary myelofibrosis, post-polycythemia vera myelofibrosis, and post-essential thrombocytopenia myelofibrosis) as well as other myeloproliferative disorders including, for example, polycythemia vera and essential thrombocytopenia. Moreover, data from the JAK2V617F model suggests that TβRII antagonists may be used treated Janus kinase-associated disorders, particularly disorders associated with elevated or constitutive Janus kinase activity (e.g., elevated or constitutive JAK2 activity). Accordingly, in certain aspects, the disclosure relates to compositions and methods for treating, preventing, or reducing the progression rate and/or severity of myeloproliferative disorders (e.g., myelofibrosis, polycythemia vera, and essential thrombocytopenia) or Janus kinase-associated disorders one or more complications of a myeloproliferative disorder (e.g., fibrosis, splenomegaly, and inflammation) or Janus kinase-associated disorder, by administering to a patient in need thereof an effective amount of one or more TβRII antagonists, optionally in combination of one or more other supportive therapies or active agents for treating myeloproliferative disorders or Janus kinase-associated disorders. While TβRII polypeptides may affect myeloproliferative disorders and Janus kinase-associated disorders through a mechanism other than TβRII antagonism [e.g., inhibition of one or more of TGFβ1, TGFβ2, and TGFβ3 may be an indicator of the tendency of an agent to inhibit the activities of a spectrum of additional agents, including, perhaps, other members of the TGF-beta superfamily, and such collective inhibition may lead to the desired effect on, for example, myeloproliferative disorders and Janus kinase-associated disorders], the disclosure nonetheless demonstrates that desirable therapeutic agents may be selected on the basis of TβRII antagonism. Therefore, while not wishing to be bound to a particular mechanism of action, it is expected that other TβRII antagonists [e.g., antagonists of the TβRII receptor, antagonists of one or more TβRII-binding ligand (e.g., TGFβ1, TGFβ2, and TGFβ3), antagonists of one or more TβRII-associated type I receptor (e.g., ALK5), antagonists of one or more TβRII-associated co-receptor (betaglycan), antagonists of one or more TβRII downstream signaling components (e.g., Smads), or combination of such antagonists] will useful in the treatment of myeloproliferative disorders or Janus kinase-associated disorders, particularly in treating, preventing, or reducing the progression rate and/or severity of one or more myeloproliferative disorder or Janus kinase-associated disorder complications. Such agents are collectively referred to herein as "TβRII antagonists" or "TβRII inhibitors".

Accordingly, in certain aspects, the disclosure relates to methods for treating a Janus kinase-associated disorder, comprising administering to a patient in need thereof an effective amount of a TβRII antagonist. In certain aspects, the disclosure relates to methods for preventing a Janus kinase-associated disorder, comprising administering to a patient in need thereof an effective amount of a TβRII antagonist. In certain aspects, the disclosure relates to methods for reducing the progression rate of a Janus kinase-associated disorder, comprising administering to a patient in need thereof an effective amount of a TβRII antagonist. In certain aspects, the disclosure relates to methods for reducing the severity of a Janus kinase-associated disorder, comprising administering to a patient in need thereof an effective amount of a TβRII antagonist. In certain aspects, the disclosure relates to methods for treating one or more complications of a Janus kinase-associated disorder, comprising administering to a patient in need thereof an effective amount of a TβRII antagonist. In certain aspects, the disclosure relates to methods for preventing one or more complications of a Janus kinase-associated disorder, comprising administering to a patient in need thereof an effective amount of a TβRII antagonist. In certain aspects, the disclosure relates to methods for reducing the progression rate of one or more complications of a Janus kinase-associated disorder, comprising administering to a patient in need thereof an effective amount of a TβRII antagonist. In certain aspects, the disclosure relates to methods for reducing the severity of one or more complications of a Janus kinase-associated disorder, comprising administering to a patient in need thereof an effective amount of a TβRII antagonist. In some embodiments, the disclosure relates to methods for treating, preventing, or reducing the progression rate and/or severity of one or more complications of a Janus kinase-associated disorder selected from the group consisting of: ineffective hematopoiesis, extramedullary hematopoiesis (e.g., splenic extramedullary hematopoiesis, hepatic extramedullary hematopoiesis, pulmonary extramedullary hematopoiesis, and lymphatic extramedullary hematopoiesis), inflammatory complications, pancytopenia, fibrosis (e.g., bone marrow fibrosis, spleen fibrosis, and liver fibrosis), splenomegaly, hepatomegaly, thrombocytopenia, anemia, poikilocytosis, progressive hepatosplenomegaly, fatigue, weight loss, night sweats, fever, pruritus, bone pain, early satiety, abdominal pain or discomfort, arthralgias, myalgias, parasthesias, cachexia, splenic infarct, bleeding, inflammation, neutropenia, elevated cytokine levels, coagulopathy, IL-6-mediated inflammation or inflammatory complication, osteosclerosis, and osteomyelofibrosis. In some embodiments, a Janus kinase-associated disorder is associated with one or more gain-of-function Janus kinase mutations. In some embodiments, a Janus kinase-associated disorder is associated with one or more gain-of-function Janus kinase mutations in one or more Janus kinases selected from the group consisting of: JAK1, JAK2, and JAK3. In some embodiments, a Janus kinase-associated disorder is associated with one or more gain-of-function Janus kinase mutations in JAK2. In some embodiments, a Janus kinase-associated disorder is associated with elevated kinase activity (e.g., elevated kinase activity as compared to, for example, healthy subjects of the same age and sex) of one or more Janus kinases. In some embodiments, a Janus kinase-associated disorder is associated with constitutive kinase activity of one or more Janus kinases. In some embodiments, a Janus kinase-associated disorder is associated with elevated or constitutive kinase activity of one or more Janus kinases selected from the group consisting of: JAK1, JAK2, or JAK3. In some embodiments, a Janus kinase-associated disorder is associated with elevated or constitutive kinase activity of JAK2. In some embodiments, a Janus kinase-associated disorder is a JAK2-associated disorder. In some embodiments, a Janus kinase-associated disorder is a JAK2V617F-associated disorder. In certain aspects, the disclosure relates to methods of treating, preventing, or reducing the progression rate and/or severity of a Janus kinase-associated disorder or one or more complications of a Janus kinase-associated disorder wherein the patient has myelofibrosis. In some embodiments, a patient with a Janus kinase-associated disorder has primary myelofibrosis. In some embodiments, a patient with a Janus kinase-associated disorder has post-polycythemia vera myelofibrosis. In some embodiments, a patient with a Janus kinase-associated disorder has post-essential thrombocythemia myelofibrosis. In some embodiments, the disclosure relates to methods for treating, preventing, or reducing the progression rate and/or severity of one or more complications of a Janus kinase-associated disorder in a patient having myelofibrosis selected from the group consisting of: ineffective hematopoiesis, extramedullary hematopoiesis (e.g., splenic extramedullary hematopoiesis, hepatic extramedullary hematopoiesis, pulmonary extramedullary hematopoiesis, and lymphatic extramedullary hematopoiesis), inflammatory complications, pancytopenia, fibrosis (e.g., bone marrow fibrosis, spleen fibrosis, and liver fibrosis), splenomegaly, hepatomegaly, thrombocytopenia, anemia, poikilocytosis, progressive hepatosplenomegaly, fatigue, weight loss, night sweats, fever, pruritus, bone pain, early satiety, abdominal pain or discomfort, arthralgias, myalgias, parasthesias, cachexia, splenic infarct, bleeding, inflammation, neutropenia, elevated cytokine levels, coagulopathy, IL-6-mediated inflammation or inflammatory complication, osteosclerosis, osteomyelofibrosis, and bleeding. In some embodiments, a patient with a Janus kinase-associated disorder has low risk myelofibrosis according to the International Prognostic Scoring System (IPSS). In some embodiments, a patient with a Janus kinase-associated disorder has intermediate-1 risk myelofibrosis according to the IPSS. In some embodiments, a patient with a Janus kinase-associated disorder has intermediate-2 risk myelofibrosis according to the IPSS. In some embodiments, a patient with a Janus kinase-associated disorder has high risk myelofibrosis according to the IPSS. In some embodiments, a patient with a Janus kinase-associated disorder has low risk myelofibrosis according to the dynamic IPSS (DIPSS). In some embodiments, a patient with a Janus kinase-associated disorder has intermediate-1 risk myelofibrosis according to the DIPSS. In some embodiments, a patient with a Janus kinase-associated disorder has intermediate-2 risk myelofibrosis according to the DIPSS. In some embodiments, a patient with a Janus kinase-associated disorder has high risk myelofibrosis according to the DIPSS. In some embodiments, a patient with a Janus kinase-associated disorder has low risk myelofibrosis according to the DIPSS-plus. In some embodiments, a patient with a Janus kinase-associated disorder has intermediate-1 risk myelofibrosis according to the DIPSS-plus. In some embodiments, a patient with a Janus kinase-associated disorder has intermediate-2 risk myelofibrosis according to the DIPSS-plus. In some embodiments, a patient with a Janus kinase-associated disorder has high risk myelofibrosis according to the DIPSS-plus. In certain aspects, the disclosure relates to methods of treating, preventing, or reducing the progression rate and/or severity of a Janus kinase-associated disorder or one or more complications of a Janus kinase-associated disorder wherein the patient has polycythemia vera. In some embodiments, the disclosure relates to method for treating, preventing, or reducing the progression rate and/or severity of one or more complications of a Janus kinase-associated disorder in a patient having polycythemia vera selected from the group consisting of: fatigue, pruritus, night sweats, bone pain, fever, and weight loss, splenomegaly, hepatomegaly, abdominal pain, early satiety, nausea, abdominal organ compression, portal hypertension, vascular events, thromboembolic events, hemorrhages, thrombosis, macrovascular complications, headaches, dizziness, visual disturbances, distal paresthesia, acrocyanosis, erythromelalgia, excessive proliferation of erythroid cells, excessive proliferation of myeloid cells, excessive proliferation of megakaryocytic cells, high red blood cell levels, high white blood cell levels, high platelet levels, elevated inflammatory cytokines, inflammatory complications, and IL-6-mediated inflammatory complications. In some embodiments, a patient with a Janus kinase-associated disorder has low risk polycythemia vera. In some embodiments, a patient with a Janus kinase-associated disorder has low risk polycythemia vera and no history of thrombosis. In some embodiments, a patient with a Janus kinase-associated disorder has low risk polycythemia vera and has or previously had a history of thrombosis. In some embodiments, a patient with a Janus kinase-associated disorder has high risk polycythemia vera. In some embodiments, a patient with a Janus kinase-associated disorder has high risk polycythemia vera and no history of thrombosis. In some embodiments, a patient with a Janus kinase-associated disorder has high risk polycythemia vera and has or previously had a history of thrombosis. In some embodiments, a patient with a Janus kinase-associated disorder has high risk polycythemia vera and is refractory to treatment with hydroxyurea. In some embodiments, a patient with a Janus kinase-associated disorder has high risk polycythemia vera and is intolerant to treatment with hydroxyurea. In certain aspects, the disclosure relates to methods of treating, preventing, or reducing the progression rate and/or severity of a Janus kinase-associated disorder or one or more complications of a Janus kinase-associated disorder wherein the patient has essential thrombocythemia. In some embodiments, the disclosure relates to method for treating, preventing, or reducing the progression rate and/or severity of one or more complications of a Janus kinase-associated disorder in a patient having essential thrombocythemia selected from the group consisting of: thrombocytosis, low white blood cell counts, low hemoglobin levels, low lactate dehydrogenase (LDH) levels, fatigue, night sweats, nausea, numbness, visions disturbances, weight loss, microvascular complications, headache, chest pain, dizziness, erythromelalgia, splenomegaly, hepatomegaly, inflammatory complication, IL-6 inflammatory complication, elevated inflammatory cytokine levels, elevated IL-6 levels, and hemorrhage. In some embodiments, a patient with a Janus kinase-associated disorder has low risk essential thrombocythemia. In some embodiments, a patient with a Janus kinase-associated disorder has low risk essential thrombocythemia and no history of thrombosis. In some embodiments, a patient with a Janus kinase-associated disorder has low risk essential thrombocythemia and has or previously had a history of thrombosis. In some embodiments, a patient with a Janus kinase-associated disorder has high risk essential thrombocythemia. In some embodiments, a patient with a Janus kinase-associated disorder has high risk essential thrombocythemia and no history of thrombosis. In some embodiments, a patient with a Janus kinase-associated disorder has high risk essential thrombocythemia and has or previously had a history of thrombosis. In some embodiments, a patient with a Janus kinase-associated disorder has high risk essential thrombocythemia and is refractory to treatment with hydroxyurea. In some embodiments, a patient with a Janus kinase-associated disorder has high risk essential thrombocythemia and is intolerant to treatment with hydroxyurea. In certain aspects, the disclosure relates to methods of treating, preventing, or reducing the progression rate and/or severity of a Janus kinase-associated disorder or one or more complications of a Janus kinase-associated disorder wherein the patient has fibrosis. In some embodiments, the disclosure relates to methods for treating, preventing, or reducing the progression rate and/or severity fibrosis in a Janus kinase-associated disorder patient. In some embodiments, the disclosure relates to methods for treating, preventing, or reducing the progression rate and/or severity fibrosis in a Janus kinase-associated disorder patient wherein the fibrosis is in one or more organs/tissues selected from the group consisting of: spleen, liver, lung, lymph node, and bone marrow. In some embodiments, the disclosure relates to methods for treating, preventing, or reducing the rate progression and/or severity of spleen fibrosis in a Janus kinase-associated disorder patient. In some embodiments, the disclosure relates to methods for treating, preventing, or reducing the rate progression and/or severity of bone marrow fibrosis in a Janus kinase-associated disorder patient. In some embodiments, a patient with a Janus kinase-associated disorder has grade 0 bone marrow fibrosis in accordance with the Bauermeister scoring system. In some embodiments, a patient with a Janus kinase-associated disorder has grade 1 bone marrow fibrosis in accordance with the Bauermeister scoring system. In some embodiments, a patient with a Janus kinase-associated disorder has grade 2 bone marrow fibrosis in accordance with the Bauermeister scoring system. In some embodiments, a patient with a Janus kinase-associated disorder has grade 3 bone marrow fibrosis in accordance with the Bauermeister scoring system. In some embodiments, a patient with a Janus kinase-associated disorder has grade 4 bone marrow fibrosis in accordance with the Bauermeister scoring system. In some embodiments, methods of the disclosure relate to reducing bone marrow fibrosis by at least 1 grade in accordance with the Bauermeister scoring system (e.g., grade reduction from 4 to 3, 4 to 2, 4 to 1, 4 to 0, 3 to 2, 3 to 1, 3 to 0, 2 to 1, 2 to 0, or 1 to 0 bone marrow fibrosis) in a patient with a Janus kinase-associated disorder. In some embodiments, methods of the disclosure relate to preventing or delaying grade progression (e.g., preventing or delaying grade progression of bone marrow fibrosis from 0 to 1, 0 to 2, 0 to 3, 0 to 4, 1 to 2, 1 to 3, 1 to 4, 2 to 3, 2 to 4, or 3 to 4) of bone marrow fibrosis according to the Bauermeister scoring system in a patient with a Janus kinase-associated disorder. In some embodiments, a patient with a Janus kinase-associated disorder has grade 1 bone marrow fibrosis in accordance with the European consensus scoring system. In some embodiments, a patient with a Janus kinase-associated disorder has grade 2 bone marrow fibrosis in accordance with the European consensus scoring system. In some embodiments, a patient with a Janus kinase-associated disorder has grade 3 bone marrow fibrosis in accordance with the European consensus scoring system. In some embodiments, methods of the disclosure relate to reducing bone marrow fibrosis by at least 1 grade in accordance with the European consensus scoring system (e.g., grade reduction from 3 to 2, 3 to 1, 3 to 0, 2 to 1, 2 to 0, or 1 to 0 bone marrow fibrosis) in a patient with a Janus kinase-associated disorder. In some embodiments, methods of the disclosure relate to preventing or delaying grade progression (e.g., preventing or delaying grade progression of bone marrow fibrosis from 0 to 1, 0 to 2, 0 to 3, 1 to 2, 1 to 3, 2 to 3) of bone marrow fibrosis according to the European consensus scoring system in a patient with a Janus kinase-associated disorder. In some embodiments, the disclosure relates to methods for preventing, or reducing the progression rate and/or severity fibrosis in a Janus kinase-associated disorder patient wherein the TβRII antagonist is administered prior to onset of fibrosis. In some embodiments, the disclosure relates to methods for treating or reducing the progression rate and/or severity fibrosis in a Janus kinase-associated disorder patient wherein the TβRII antagonist is administered after the onset of fibrosis. In certain aspects, the disclosure relates to methods of treating, preventing, or reducing the progression rate and/or severity of a Janus kinase-associated disorder or one or more complications of a Janus kinase-associated disorder wherein the patient has organ/tissue enlargement (e.g., increased organ/tissue size and/or weight as compared to, for example, healthy subjects of the same age and sex). In some embodiments, the disclosure relates to methods for treating, preventing, or reducing the progression rate and/or severity of organ/tissue enlargement in a Janus kinase-associated disorder patient. In some embodiments, the disclosure relates to methods for treating, preventing, or reducing the progression rate and/or severity of organ/tissue enlargement in a Janus kinase-associated disorder patient wherein the one or more organs/tissues are selected from the group consisting of: spleen, liver, lung(s), and lymph nodes. In some embodiments, the disclosure relates to methods for treating, preventing, or reducing the progression rate and/or severity of spleen enlargement in a Janus kinase-associated disorder patient. In some embodiments, the disclosure relates to methods for treating, preventing, or reducing the progression rate and/or severity of liver enlargement in a Janus kinase-associated disorder patient. In certain aspects, the disclosure relates to methods of treating, preventing, or reducing the progression rate and/or severity of a Janus kinase-associated disorder or one or more complications of a Janus kinase-associated disorder wherein the patient has organ/tissue inflammation (e.g., increased organ/tissue inflammation as compared to, for example, healthy subjects of the same age and sex). In some embodiments, the disclosure relates to methods for treating, preventing, or reducing the progression rate and/or severity of organ/tissue inflammation in a Janus kinase-associated disorder patient. In some embodiments, the disclosure relates to methods for treating, preventing, or reducing the progression rate and/or severity of organ/tissue inflammation in a Janus kinase-associated disorder patient wherein the one or more organs/tissues is selected from the group consisting of: spleen, liver, lung(s), and lymph nodes. In some embodiments, the disclosure relates to methods for treating, preventing, or reducing the progression rate and/or severity of spleen inflammation in a Janus kinase-associated disorder patient. In some embodiments, the disclosure relates to methods for treating, preventing, or reducing the progression rate and/or severity of liver inflammation in a Janus kinase-associated disorder patient. In certain aspects, the disclosure relates to methods of treating, preventing, or reducing the progression rate and/or severity of a Janus kinase-associated disorder or one or more complications of a Janus kinase-associated disorder wherein the patient has splenomegaly. In some embodiments, the disclosure relates to methods for treating, preventing, or reducing the progression rate and/or severity of splenomegaly in a Janus kinase-associated disorder patient. In certain aspects, the disclosure relates to methods of treating, preventing, or reducing the progression rate and/or severity of a Janus kinase-associated disorder or one or more complications of a Janus kinase-associated disorder wherein the patient has hepatomegaly. In some embodiments, the disclosure relates to methods for treating, preventing, or reducing the progression rate and/or severity of hepatomegaly in a Janus kinase-associated disorder patient. In certain aspects, the disclosure relates to methods of treating, preventing, or reducing the progression rate and/or severity of a Janus kinase-associated disorder or one or more complications of a Janus kinase-associated disorder wherein the patient has extramedullary hematopoiesis. In some embodiments, the disclosure relates to methods for treating, preventing, or reducing the progression rate and/or severity of extramedullary hematopoiesis in a Janus kinase-associated disorder patient. In some embodiments, the disclosure relates to methods for treating, preventing, or reducing the progression rate and/or severity of extramedullary hematopoiesis in a Janus kinase-associated disorder patient wherein the one or more organs/tissues is selected from the group consisting of: spleen, liver, lymph nodes, and lung(s). In certain aspects, the disclosure relates to methods of treating, preventing, or reducing the progression rate and/or severity of a Janus kinase-associated disorder or one or more complications of a Janus kinase-associated disorder wherein the patient has elevated inflammatory cytokine levels (e.g., elevated inflammatory cytokine levels as compared to, for example, healthy subjects of the same age and sex). In some embodiments, the disclosure relates to methods for reducing inflammatory cytokine levels in one or more organs/tissues (e.g., serum cytokine levels) in a Janus kinase-associated disorder patient. In some embodiments, the disclosure relates to methods for reducing IL-6 levels in one or more organs/tissues in a Janus kinase-associated disorder patient. In certain aspects, the disclosure relates to methods of treating, preventing, or reducing the progression rate and/or severity of a Janus kinase-associated disorder or one or more complications of a Janus kinase-associated disorder wherein the patient has low red blood cell levels (e.g., low red blood cell levels as compared to, for example, healthy subjects of the same age and sex). In some embodiments, the disclosure relates to methods for increasing red blood cell levels in a Janus kinase-associated disorder patient. In certain aspects, the disclosure relates to methods of treating, preventing, or reducing the progression rate and/or severity of a Janus kinase-associated disorder or one or more complications of a Janus kinase-associated disorder wherein the patient has low hemoglobin levels (e.g., low hemoglobin levels as compared to, for example, healthy subjects of the same age and sex). In some embodiments, the disclosure relates to methods for increasing hemoglobin levels in a Janus kinase-associated disorder patient. In certain aspects, the disclosure relates to methods of treating, preventing, or reducing the progression rate and/or severity of a Janus kinase-associated disorder or one or more complications of a Janus kinase-associated disorder wherein the patient has anemia. In some embodiments, the disclosure relates to methods for treating, preventing, or reducing the progression rate and/or severity of anemia in a Janus kinase-associated disorder patient. In certain aspects, the disclosure relates to methods of treating, preventing, or reducing the progression rate and/or severity of a Janus kinase-associated disorder or one or more complications of a Janus kinase-associated disorder wherein the patient has been administered one or more blood cell transfusions prior to the start of TβRII antagonist treatment. In some embodiments, a patient with a Janus kinase-associated disorder is blood cell transfusion-dependent. In some embodiments, the disclosure relates to methods for decreasing blood cell transfusion burden in a patient with a Janus kinase-associated disorder. In some embodiments, the disclosure relates to methods for decreasing blood cell transfusion burden in a patient with a Janus kinase-associated disorder wherein the method decreases blood cell transfusion by greater than about 30%, 40%, 50%, 60%, 70%, 80%, 90%, or 100% for 4 to 8 weeks relative to the equal time prior to the start of TβRII antagonist treatment. In some embodiments, the disclosure relates to methods for decreasing blood cell transfusion burden in a patient with a Janus kinase-associated disorder wherein the method decreases blood cell transfusion by greater than about 50% for 4 to 8 weeks relative to the equal time prior to the start of TβRII antagonist treatment. In certain aspects, a patient with a Janus kinase-associated disorder has iron overload. In some embodiments, the disclosure relates to methods for treating, preventing, or reducing the progression rate and/or severity of iron overload in a Janus kinase-associated disorder patient. In some embodiments, the disclosure relates to methods for treating, preventing, or reducing the progression rate and/or severity of spleen (splenic) iron overload in a Janus kinase-associated disorder patient. In some embodiments, the disclosure relates to methods for treating, preventing, or reducing the progression rate and/or severity of liver (hepatic) iron overload in a Janus kinase-associated disorder. In some embodiments, the disclosure relates to methods for treating, preventing, or reducing the progression rate and/or severity of heart (cardiac) iron overload in a Janus kinase-associated disorder. In certain aspects, the disclosure relates to methods for reducing allele burden in a Janus kinase-associated disorder patient. In some embodiments, the disclosure relates to methods for reducing allele burden of one or more Janus kinase alleles in a Janus kinase-associated disorder patient. In some embodiments, the disclosure relates to methods for reducing allele burden of one or more Janus kinase alleles selected from the group consisting of: JAK1, JAK2, and JAK3, in a Janus kinase-associated disorder patient. In some embodiments, the disclosure relates to methods for reducing allele burden of one or more JAK2 alleles in a Janus kinase-associated disorder patient. In some embodiments, the disclosure relates to methods for reducing allele burden of one or more Janus kinase alleles that are associated with one or more mutations resulting in elevated (e.g., elevated Janus kinase activity compared to, for example, healthy subjects of the same age and sex) or constitutive activation of one or more Janus kinases in a Janus kinase-associated disorder patient. In some embodiments, the disclosure relates to methods for reducing allele burden of JAK2V617F in a Janus kinase-associated disorder patient. In certain aspects, the disclosure relates to methods of treating, preventing, or reducing the progression rate and/or severity of a Janus kinase-associated disorder or one or more complications of a Janus kinase-associated disorder wherein the patient has been treated with a Janus kinase inhibitor. In some embodiments, the disclosure relates to methods of treating, preventing, or reducing the progression rate and/or severity of a Janus kinase-associated disorder or one or more complications of a Janus kinase-associated disorder wherein the patient is intolerant to treatment with a Janus kinase inhibitor (e.g., ruxolitinib). In some embodiments, the disclosure relates to methods of treating, preventing, or reducing the progression rate and/or severity of a Janus kinase-associated disorder or one or more complications of a Janus kinase-associated disorder wherein the patient is refractory to treatment with a Janus kinase inhibitor (e.g., ruxolitinib). In some embodiments, a patient with a Janus kinase-associated disorder has been treated with a Janus kinase inhibitor that inhibits at least JAK2. In some embodiments, a patient with a Janus kinase-associated disorder has been treated with a Janus kinase inhibitor selected from the group consisting of: ruxolitinib, fedratinib (SAR302503), monoelotinib (CYT387), pacritinib, lestaurtinib, AZD-1480, BMS-911543, NS-018, LY2784544, SEP-701, XL019, and AT-9283. In some embodiments, a patient with a Janus kinase-associated disorder has been treated with ruxolitinib. In certain aspects, the disclosure relates to methods of treating, preventing, or reducing the progression rate and/or severity of a Janus kinase-associated disorder or one or more complications of a Janus kinase-associated disorder wherein the patient has been treated with hydroxyurea. In some embodiments, the disclosure relates to methods of treating, preventing, or reducing the progression rate and/or severity of a Janus kinase-associated disorder or one or more complications of a Janus kinase-associated disorder wherein the patient is intolerant of treatment with hydroxyurea. In some embodiments, the disclosure relates to methods of treating, preventing, or reducing the progression rate and/or severity of a Janus kinase-associated disorder or one or more complications of a Janus kinase-associated disorder wherein the patient is refractory to treatment with hydroxyurea.

Accordingly, in certain aspects, the disclosure relates to methods for treating a myeloproliferative disorder, comprising administering to a patient in need thereof an effective amount of a TβRII antagonist. In certain aspects, the disclosure relates to methods for preventing a myeloproliferative disorder, comprising administering to a patient in need thereof an effective amount of a TβRII antagonist. In certain aspects, the disclosure relates to methods for reducing the progression rate of a myeloproliferative disorder, comprising administering to a patient in need thereof an effective amount of a TβRII antagonist. In certain aspects, the disclosure relates to methods for reducing the severity of a myeloproliferative disorder, comprising administering to a patient in need thereof an effective amount of a TβRII antagonist. In certain aspects, the disclosure relates to methods for treating one or more complications of a myeloproliferative disorder, comprising administering to a patient in need thereof an effective amount of a TβRII antagonist. In certain aspects, the disclosure relates to methods for preventing one or more complications of a myeloproliferative disorder, comprising administering to a patient in need thereof an effective amount of a TβRII antagonist. In certain aspects, the disclosure relates to methods for reducing the progression rate of one or more complications of a myeloproliferative disorder, comprising administering to a patient in need thereof an effective amount of a TβRII antagonist. In certain aspects, the disclosure relates to methods for reducing the severity of one or more complications of a myeloproliferative disorder, comprising administering to a patient in need thereof an effective amount of a TβRII antagonist. In certain aspects, the disclosure relates to methods for treating myelofibrosis (e.g., primary myelofibrosis, post-polycythemia vera myelofibrosis, or post-essential thrombocytopenia myelofibrosis), comprising administering to a patient in need thereof an effective amount of a TβRII antagonist. In certain aspects, the disclosure relates to methods for preventing myelofibrosis (e.g., primary myelofibrosis, post-polycythemia vera myelofibrosis, or post-essential thrombocytopenia myelofibrosis), comprising administering to a patient in need thereof an effective amount of a TβRII antagonist. In certain aspects, the disclosure relates to methods for reducing the progression rate of myelofibrosis (e.g., primary myelofibrosis, post-polycythemia vera myelofibrosis, or post-essential thrombocytopenia myelofibrosis), comprising administering to a patient in need thereof an effective amount of a TβRII antagonist. In certain aspects, the disclosure relates to methods for reducing the severity of myelofibrosis (e.g., primary myelofibrosis, post-polycythemia vera myelofibrosis, or post-essential thrombocytopenia myelofibrosis), comprising administering to a patient in need thereof an effective amount of a TβRII antagonist. In certain aspects, the disclosure relates to methods for treating one or more complications of myelofibrosis (e.g., primary myelofibrosis, post-polycythemia vera myelofibrosis, or post-essential thrombocytopenia myelofibrosis), comprising administering to a patient in need thereof an effective amount of a TβRII antagonist. In certain aspects, the disclosure relates to methods for preventing one or more complications of myelofibrosis (e.g., primary myelofibrosis, post-polycythemia vera myelofibrosis, or post-essential thrombocytopenia myelofibrosis), comprising administering to a patient in need thereof an effective amount of a TβRII antagonist. In certain aspects, the disclosure relates to methods for reducing the progression rate of one or more complications of myelofibrosis (e.g., primary myelofibrosis, post-polycythemia vera myelofibrosis, or post-essential thrombocytopenia myelofibrosis), comprising administering to a patient in need thereof an effective amount of a TβRII antagonist. In certain aspects, the disclosure relates to methods for reducing the severity of one or more complications of myelofibrosis (e.g., primary myelofibrosis, post-polycythemia vera myelofibrosis, or post-essential thrombocytopenia myelofibrosis), comprising administering to a patient in need thereof an effective amount of a TβRII antagonist. In certain aspects, the disclosure relates to methods for treating polycythemia vera, comprising administering to a patient in need thereof an effective amount of a TβRII antagonist. In certain aspects, the disclosure relates to methods for preventing polycythemia vera, comprising administering to a patient in need thereof an effective amount of a TβRII antagonist. In certain aspects, the disclosure relates to methods for reducing the progression rate of polycythemia vera, comprising administering to a patient in need thereof an effective amount of a TβRII antagonist. In certain aspects, the disclosure relates to methods for reducing the severity of polycythemia vera, comprising administering to a patient in need thereof an effective amount of a TβRII antagonist. In certain aspects, the disclosure relates to methods for treating one or more complications of polycythemia vera, comprising administering to a patient in need thereof an effective amount of a TβRII antagonist. In certain aspects, the disclosure relates to methods for preventing one or more complications of polycythemia vera, comprising administering to a patient in need thereof an effective amount of a TβRII antagonist. In certain aspects, the disclosure relates to methods for reducing the progression rate of one or more complications of polycythemia vera, comprising administering to a patient in need thereof an effective amount of a TβRII antagonist. In certain aspects, the disclosure relates to methods for reducing the severity of one or more complications of polycythemia vera, comprising administering to a patient in need thereof an effective amount of a TβRII antagonist. In certain aspects, the disclosure relates to methods for treating essential thrombocythemia, comprising administering to a patient in need thereof an effective amount of a TβRII antagonist. In certain aspects, the disclosure relates to methods for preventing essential thrombocythemia, comprising administering to a patient in need thereof an effective amount of a TβRII antagonist. In certain aspects, the disclosure relates to methods for reducing the progression rate of essential thrombocythemia, comprising administering to a patient in need thereof an effective amount of a TβRII antagonist. In certain aspects, the disclosure relates to methods for reducing the severity of essential thrombocythemia, comprising administering to a patient in need thereof an effective amount of a TβRII antagonist. In certain aspects, the disclosure relates to methods for treating one or more complications of essential thrombocythemia, comprising administering to a patient in need thereof an effective amount of a TβRII antagonist. In certain aspects, the disclosure relates to methods for preventing one or more complications of essential thrombocythemia, comprising administering to a patient in need thereof an effective amount of a TβRII antagonist. In certain aspects, the disclosure relates to methods for reducing the progression rate of one or more complications of essential thrombocythemia, comprising administering to a patient in need thereof an effective amount of a TβRII antagonist. In certain aspects, the disclosure relates to methods for reducing the severity of one or more complications of essential thrombocythemia, comprising administering to a patient in need thereof an effective amount of a TβRII antagonist. In certain aspects, the disclosure relates to methods of treating, preventing, or reducing the progression rate and/or severity of myelofibrosis or one or more complications of myelofibrosis, wherein the patient has low risk myelofibrosis according to the International Prognostic Scoring System (IPSS). In certain aspects, the disclosure relates to methods of treating, preventing, or reducing the progression rate and/or severity of myelofibrosis or one or more complications of myelofibrosis, wherein the patient has intermediate-1 risk myelofibrosis according to the IPSS. In certain aspects, the disclosure relates to methods of treating, preventing, or reducing the progression rate and/or severity of myelofibrosis or one or more complications of myelofibrosis, wherein the patient has intermediate-2 risk myelofibrosis according to the IPSS. In certain aspects, the disclosure relates to methods of treating, preventing, or reducing the progression rate and/or severity of myelofibrosis or one or more complications of myelofibrosis, wherein the patient has high-risk myelofibrosis risk myelofibrosis according to the IPSS. In certain aspects, the disclosure relates to methods of treating, preventing, or reducing the progression rate and/or severity of myelofibrosis or one or more complications of myelofibrosis, wherein the patient has low risk myelofibrosis according to the dynamic IPSS (DIPSS). In certain aspects, the disclosure relates to methods of treating, preventing, or reducing the progression rate and/or severity of myelofibrosis or one or more complications of myelofibrosis, wherein the patient has intermediate-1 risk myelofibrosis according to the DIPSS. In certain aspects, the disclosure relates to methods of treating, preventing, or reducing the progression rate and/or severity of myelofibrosis or one or more complications of myelofibrosis, wherein the patient has intermediate-2 risk myelofibrosis according to the DIPSS. In certain aspects, the disclosure relates to methods of treating, preventing, or reducing the progression rate and/or severity of myelofibrosis or one or more complications of myelofibrosis, wherein the patient has high-risk myelofibrosis risk myelofibrosis according to the DIPSS. In certain aspects, the disclosure relates to methods of treating, preventing, or reducing the progression rate and/or severity of myelofibrosis or one or more complications of myelofibrosis, wherein the patient has low risk myelofibrosis according to the DIPSS-plus. In certain aspects, the disclosure relates to methods of treating, preventing, or reducing the progression rate and/or severity of myelofibrosis or one or more complications of myelofibrosis, wherein the patient has intermediate-1 risk myelofibrosis according to the DIPSS-plus. In certain aspects, the disclosure relates to methods of treating, preventing, or reducing the progression rate and/or severity of myelofibrosis or one or more complications of myelofibrosis, wherein the patient has intermediate-2 risk myelofibrosis according to the DIPSS-plus. In certain aspects, the disclosure relates to methods of treating, preventing, or reducing the progression rate and/or severity of myelofibrosis or one or more complications of myelofibrosis, wherein the patient has high-risk myelofibrosis risk myelofibrosis according to the DIPSS-plus. In certain aspects, a TβRII antagonists may be used to prevent or delay risk progression of myelofibrosis in accordance with any of the recognized risk stratification models for myelofibrosis (e.g., IPSS, DIPPS, and DIPPS-plus). For example, in some embodiments, a TβRII antagonist may be used to prevent or delay myelofibrosis risk progression from low risk to intermediate-1 risk in accordance with IPSS, DIPPS, or DIPPS-plus. In other embodiments, a TβRII antagonist may be used to prevent or delay myelofibrosis risk progression from intermediate-1 risk to intermediate-2 risk in accordance with IPSS, DIPPS, or DIPPS-plus. In still other embodiments, a TβRII antagonist may be used to prevent or delay myelofibrosis risk progression from intermediate-2 risk to high risk in accordance with IPSS, DIPPS, or DIPPS-plus. In certain aspects, a TβRII antagonists may be used to promote or increase myelofibrosis risk regression in accordance with any of the recognized risk stratification models for myelofibrosis (e.g., IPSS, DIPPS, and DIPPS-plus). For example, in some embodiments, a TβRII antagonist may be used to promote or increase myelofibrosis risk regression from high risk to intermediate-2 risk in accordance with IPSS, DIPPS, or DIPPS-plus. In other embodiments, a TβRII antagonist may be used to promote or increase myelofibrosis risk regression from intermediate-2 risk to intermediate-1 risk in accordance with IPSS, DIPPS, or DIPPS-plus. In still other embodiments, a TβRII antagonist may be used to promote or increase myelofibrosis risk regression from intermediate-1 risk to low risk in accordance with IPSS, DIPPS, or DIPPS-plus. In certain aspects, the disclosure relates to methods of treating, preventing, or reducing the progression rate and/or severity of polycythemia vera or one or more complications of polycythemia vera, wherein the patient has low risk polycythemia vera. In some embodiments, the patient has low risk polycythemia vera and no history of thrombosis. In some embodiments, the patient has low risk polycythemia vera and has or previously had thrombosis. In certain aspects, the disclosure relates to methods of treating, preventing, or reducing the progression rate and/or severity of polycythemia vera or one or more complications of polycythemia vera, wherein the patient has high risk polycythemia vera. In some embodiments, the patient has high risk polycythemia vera and no history of thrombosis. In some embodiments, the patient has high risk polycythemia vera and has or previously had thrombosis. In some embodiments, the patient has high risk polycythemia vera and is refractory or intolerant to treatment with hydroxyurea. In certain aspects, the disclosure relates to methods of treating, preventing, or reducing the progression rate and/or severity of essential thrombocytopenia or one or more complications of essential thrombocytopenia, wherein the patient has low risk essential thrombocytopenia. In some embodiments, the patient has low risk essential thrombocytopenia and no history of thrombosis. In some embodiments, the patient has low risk essential thrombocytopenia and has or previously had thrombosis. In certain aspects, the disclosure relates to methods of treating, preventing, or reducing the progression rate and/or severity of essential thrombocytopenia or one or more complications of essential thrombocytopenia, wherein the patient has high risk essential thrombocytopenia. In some embodiments, the patient has high risk essential thrombocytopenia and no history of thrombosis. In some embodiments, the patient has high risk essential thrombocytopenia and has or previously had thrombosis. In some embodiments, the patient has high risk essential thrombocytopenia and is refractory or intolerant to treatment with hydroxyurea. In certain aspects, the disclosure relates to methods of using TβRII antagonists to treat, prevent, or reduce the progression rate and/or severity of a myeloproliferative disorder (e.g., myelofibrosis, polycythemia vera, and essential thrombocythemia) or one or more complications of a myeloproliferative disorder wherein the patient comprises one or more gene mutations or other molecular markers associated with a myeloproliferative disorder. For example, in some embodiments, a TβRII antagonist may be used to treat, prevent, or reduce the progression rate and/or severity of a myeloproliferative disorder or one or more complications of a myeloproliferative disorder wherein the a myeloproliferative disorder is associated with one or more mutations in one or more genes selected from the group consisting of: IDH1, IDH2, EZH2, SRSF2, ASXL1, JAK1, JAK2, JAK3, TYK2, MPL, CALR, TET2, THPO, and LNK. In some embodiments, the myeloproliferative disorder is associated with one or more gene mutations in a Janus kinase (JAK) (e.g., JAK1, JAK2, and/or JAK3). In some embodiments, the myeloproliferative disorder is associated with one or more JAK2 mutations. In some embodiments, a myeloproliferative disorder is associated with one or more gain-of-function Janus kinase mutations. In some embodiments, a myeloproliferative disorder is associated with one or more gain-of-function Janus kinase mutations in one or more Janus kinases selected from the group consisting of: JAK1, JAK2, and JAK3. In some embodiments, a myeloproliferative disorder is associated with one or more gain-of-function Janus kinase mutations in JAK2. In some embodiments, a myeloproliferative disorder is associated with elevated kinase activity (e.g., elevated kinase activity as compared to, for example, healthy subjects of the same age and sex) of one or more Janus kinases. In some embodiments, a myeloproliferative disorder is associated with constitutive kinase activity of one or more Janus kinases. In some embodiments, a myeloproliferative disorder is associated with elevated or constitutive kinase activity of one or more Janus kinases selected from the group consisting of: JAK1, JAK2, or JAK3. In some embodiments, a myeloproliferative disorder is associated with elevated or constitutive kinase activity of JAK2. In some embodiments, a myeloproliferative disorder is a JAK2-associated disorder. In some embodiments, the myeloproliferative disorder is associated with one or more genetic markers selected from the group consisting of: nullizygosity for JAK2 46/1 haplotype, JAK2V617F, CALR+ASXL1−, CALR−ASKL1+, CALR+ASKL1+, and CALR−ASKL1−. In some embodiments, the myeloproliferative disorder is associated with the JAK2V617F mutation. In some embodiments, the method reduces the myeloproliferative disease-associated allele burden in the patient. In some embodiments, the method reduces the allele burden of one or more JAK2 mutations. In some embodiments, the method reduces the allele burden of JAK2V617F. In some embodiments, the method reduces allele burden of one or more mutations in one or more genes selected from the group consisting of: IDH1, IDH2, EZH2, SRSF2, ASXL1, JAK1, JAK2, JAK3, TYK2, MPL, CALR, TET2, THPO, and LNK. In some embodiments, the method reduces allele burden of one or more genetic markers selected from the group consisting of: nullizygosity for JAK2 46/1 haplotype, CALR+ASXL1−, CALR−ASKL1+, CALR+ASKL1+, and CALR−ASKL1−. In certain aspects, the disclosure relates to methods of using a TβRII antagonist to treat, prevent, or reduce the progression rate and/or severity of a myeloproliferative disorder (e.g., myelofibrosis, polycythemia vera, and essential thrombocythemia) or one or more complications of a myeloproliferative disorder wherein the myelofibrosis is associated with one or more elevated serum markers selected from the group consisting of: increased serum IL-8 levels, increased serum IL-2R levels, and increased serum free light chain levels. In certain aspects, the disclosure relates to methods of using a TβRII antagonist to treat, prevent, or reduce the progression rate and/or severity of a myeloproliferative disorder (e.g., myelofibrosis, polycythemia vera, and essential thrombocythemia) or one or more complications of a myeloproliferative disorder wherein the patient has been treated with a Janus kinase inhibitor. In some embodiments, the patient has been treated with a JAK2 inhibitor. In some embodiments, the patient has been treated with a Janus kinase inhibitor selected from the group consisting of: ruxolitinib, fedratinib (SAR302503), monoelotinib (CYT387), pacritinib, lestaurtinib, AZD-1480, BMS-911543, NS-018, LY2784544, SEP-701, XL019, and AT-9283. In some embodiments, the patient has been treated with ruxolitinib. In some embodiments, a TβRII antagonist may be used to treat, prevent, or reduce the progression rate and/or severity of a myeloproliferative disorder or one or more complications of a myeloproliferative disorder wherein the patient is intolerant of a Janus kinase inhibitor. In some embodiments, a TβRII antagonist may be used to treat, prevent, or reduce the progression rate and/or severity of a myeloproliferative disorder or one or more complications of a myeloproliferative disorder wherein the patient has an inadequate response to a Janus kinase inhibitor. In certain aspects, the disclosure relates to methods of using a TβRII antagonist to treat, prevent, or reduce the progression rate and/or severity of a myeloproliferative disorder (e.g., myelofibrosis, polycythemia vera, and essential thrombocythemia) or one or more complications of a myeloproliferative disorder wherein the patient has been treated with hydroxyurea. In some embodiments, a TβRII antagonist may be used to treat, prevent, or reduce the progression rate and/or severity of a myeloproliferative disorder or one or more complications of a myeloproliferative disorder wherein the patient is intolerant of hydroxyurea. In some embodiments, a TβRII antagonist may be used to treat, prevent, or reduce the progression rate and/or severity of a myeloproliferative disorder or one or more complications of a myeloproliferative disorder wherein the patient has an inadequate response to hydroxyurea.

As described herein myeloproliferative disorders are clonal neoplastic diseases of hematopoiesis that are associated with various clinical complications which may manifest during disease progression in a patient. The examples of the disclosure demonstrate that a TβRII antagonist may be used to mitigate a number of these clinical complications, indicating that TβRII antagonists may be used to more broadly treat various complications of myeloproliferative disorders (e.g., myelofibrosis, polycythemia vera, and essential thrombocytopenia) as opposed to many of the current myeloproliferative disorder therapies, which only treat one or a limited number of complications of the disease. Therefore, in certain aspects, a TβRII antagonist may be used to treat, prevent, or reduce the progression rate and/or severity of one or more constitutional symptoms (e.g., fatigue, weight loss, night sweats, fever, pruritus, early satiety, abdominal pain or discomfort, arthralgias, myalgias, paresthesias, nausea, abdominal organ compression, headache, and cachexia) in a patient with a myeloproliferative disorder (e.g., myelofibrosis, polycythemia vera, and essential thrombocytopenia). In certain aspects, a TβRII antagonist may be used to treat, prevent, or reduce the progression rate and/or severity of bone pain in a patient with a myeloproliferative disorder (e.g., myelofibrosis, polycythemia vera, and essential thrombocytopenia). In certain aspects, a TβRII antagonist may be used to treat, prevent, or reduce the progression rate and/or severity of vision disturbances in a patient with a myeloproliferative disorder (e.g., myelofibrosis, polycythemia vera, and essential thrombocytopenia). In certain aspects, the disclosure relates to methods of treating, preventing, or reducing the progression rate and/or severity of a myeloproliferative disorder (e.g., myelofibrosis, polycythemia vera, and essential thrombocytopenia) or one or more complications of a myeloproliferative disorder wherein the patient has fibrosis. In some embodiments, the disclosure relates to methods for treating, preventing, or reducing the progression rate and/or severity fibrosis in a myeloproliferative disorder patient. In some embodiments, the disclosure relates to methods for treating, preventing, or reducing the progression rate and/or severity fibrosis in a myeloproliferative disorder patient wherein the fibrosis is in one or more organs/tissues selected from the group consisting of: spleen, liver, lung, lymph node, and bone marrow. In some embodiments, the disclosure relates to methods for treating, preventing, or reducing the rate progression and/or severity of spleen fibrosis in a myeloproliferative disorder patient. In some embodiments, the disclosure relates to methods for treating, preventing, or reducing the rate progression and/or severity of bone marrow fibrosis in a myeloproliferative disorder patient. In some embodiments, a patient with a myeloproliferative disorder has grade 0 bone marrow fibrosis in accordance with the Bauermeister scoring system. In some embodiments, a patient with a myeloproliferative disorder has grade 1 bone marrow fibrosis in accordance with the Bauermeister scoring system. In some embodiments, a patient with a myeloproliferative disorder has grade 2 bone marrow fibrosis in accordance with the Bauermeister scoring system. In some embodiments, a patient with a myeloproliferative disorder has grade 3 bone marrow fibrosis in accordance with the Bauermeister scoring system. In some embodiments, a patient with a myeloproliferative disorder has grade 4 bone marrow fibrosis in accordance with the Bauermeister scoring system. In some embodiments, methods of the disclosure relate to reducing bone marrow fibrosis by at least 1 grade in accordance with the Bauermeister scoring system (e.g., grade reduction from 4 to 3, 4 to 2, 4 to 1, 4 to 0, 3 to 2, 3 to 1, 3 to 0, 2 to 1, 2 to 0, or 1 to 0 bone marrow fibrosis) in a patient with a myeloproliferative disorder. In some embodiments, methods of the disclosure relate to preventing or delaying grade progression (e.g., preventing or delaying grade progression of bone marrow fibrosis from 0 to 1, 0 to 2, 0 to 3, 0 to 4, 1 to 2, 1 to 3, 1 to 4, 2 to 3, 2 to 4, or 3 to 4) of bone marrow fibrosis according to the Bauermeister scoring system in a patient with a myeloproliferative disorder. In some embodiments, a patient with a myeloproliferative disorder has grade 1 bone marrow fibrosis in accordance with the European consensus scoring system. In some embodiments, a patient with a myeloproliferative disorder has grade 2 bone marrow fibrosis in accordance with the European consensus scoring system. In some embodiments, a patient with a myeloproliferative disorder has grade 3 bone marrow fibrosis in accordance with the European consensus scoring system. In some embodiments, methods of the disclosure relate to reducing bone marrow fibrosis by at least 1 grade in accordance with the European consensus scoring system (e.g., grade reduction from 3 to 2, 3 to 1, 3 to 0, 2 to 1, 2 to 0, or 1 to 0 bone marrow fibrosis) in a patient with a myeloproliferative disorder. In some embodiments, methods of the disclosure relate to preventing or delaying grade progression (e.g., preventing or delaying grade progression of bone marrow fibrosis from 0 to 1, 0 to 2, 0 to 3, 1 to 2, 1 to 3, 2 to 3) of bone marrow fibrosis according to the European consensus scoring system in a patient with a myeloproliferative disorder. In some embodiments, the disclosure relates to methods for preventing, or reducing the progression rate and/or severity fibrosis in a myeloproliferative disorder wherein the TβRII antagonist is administered prior to onset of fibrosis. In some embodiments, the disclosure relates to methods for treating or reducing the progression rate and/or severity fibrosis in a myeloproliferative disorder patient wherein the TβRII antagonist is administered after the onset of fibrosis. In certain aspects, a TβRII antagonist may be used to treat, prevent, or reduce the progression rate and/or severity of organ/tissue (e.g., spleen, liver, lymph nodes, and lungs) inflammation (e.g., increased inflammation as compared to, for example, healthy subjects of the same age and sex) and/or enlargement (e.g., increased organ/tissue size and/or weight as compared to, for example, healthy subjects of the same age and sex) in a patient with a myeloproliferative disorder (e.g., myelofibrosis, polycythemia vera, and essential thrombocytopenia). In some embodiments, a TβRII antagonist may be used to treat, prevent, or reduce the progression rate and/or severity of splenomegaly in a patient with a myeloproliferative disorder (e.g., myelofibrosis, polycythemia vera, and essential thrombocytopenia). In some embodiments, a TβRII antagonist may be used to treat, prevent, or reduce the progression rate and/or severity of hepatomegaly in a patient with a myeloproliferative disorder (e.g., myelofibrosis, polycythemia vera, and essential thrombocytopenia). In certain aspects, a TβRII antagonist may be used to treat, prevent, or reduce the progression rate and/or severity of splenic infarct in a patient with a myeloproliferative disorder (e.g., myelofibrosis, polycythemia vera, and essential thrombocytopenia). In certain aspects, a TβRII antagonist may be used to treat, prevent, or reduce the progression rate and/or severity of one or more inflammatory complications in a patient with a myeloproliferative disorder (e.g., myelofibrosis, polycythemia vera, and essential thrombocytopenia). In some embodiments, a TβRII antagonist may be used to reduce inflammatory cytokine levels in a patient with a myeloproliferative disorder (e.g., myelofibrosis, polycythemia vera, and essential thrombocytopenia). In some embodiments, a TβRII antagonist may be used to reduce IL6 levels in a patient with a myeloproliferative disorder (e.g., myelofibrosis, polycythemia vera, and essential thrombocytopenia). In some embodiments, a TβRII antagonist may be used to treat, prevent, or reduce the progression rate and/or severity of one or more IL6-associated complications in a patient with a myeloproliferative disorder (e.g., myelofibrosis, polycythemia vera, and essential thrombocytopenia). In certain aspects, a TβRII antagonist may be used to treat, prevent, or reduce the progression rate and/or severity of extramedullary hematopoiesis (e.g., splenic extramedullary hematopoiesis, hepatic extramedullary hematopoiesis, pulmonary extramedullary hematopoiesis, and lymphatic extramedullary hematopoiesis) in a patient with a myeloproliferative disorder (e.g., myelofibrosis, polycythemia vera, and essential thrombocytopenia). In certain aspects, a TβRII antagonist may be used to treat, prevent, or reduce the progression rate and/or severity of vascular complications in a patient with a myeloproliferative disorder (e.g., myelofibrosis, polycythemia vera, and essential thrombocytopenia). In certain aspects, a TβRII antagonist may be used to treat, prevent, or reduce the progression rate and/or severity of thrombosis in a patient with a myeloproliferative disorder (e.g., myelofibrosis, polycythemia vera, and essential thrombocytopenia). In certain aspects, a TβRII antagonist may be used to treat, prevent, or reduce the progression rate and/or severity of hemorrhaging in a patient with a myeloproliferative disorder (e.g., myelofibrosis, polycythemia vera, and essential thrombocytopenia). In certain aspects, a TβRII antagonist may be used to treat, prevent, or reduce the progression rate and/or severity of ineffective erythropoiesis in a patient with a myeloproliferative disorder (e.g., myelofibrosis). In certain aspects, a TβRII antagonist may be used to treat, prevent, or reduce the progression rate and/or severity of ineffective erythropoiesis in a patient with a myeloproliferative disorder (e.g., myelofibrosis). In certain aspects, TβRII antagonist may be used to treat, prevent, or reduce the progression rate and/or severity of pancytopenia in a patient with a myeloproliferative disorder (e.g., myelofibrosis). In certain aspects, a TβRII antagonist may be used to treat, prevent, or reduce the progression rate and/or severity of pancytopenia in a patient with a myeloproliferative disorder (e.g., myelofibrosis). In certain aspects, a TβRII antagonist may be used to treat, prevent, or reduce the progression rate and/or severity of thrombocytopenia in a patient with a myeloproliferative disorder (e.g., myelofibrosis). In certain aspects, a TβRII antagonist may be used to treat, prevent, or reduce the progression rate and/or severity of anemia in a patient with a myeloproliferative disorder (e.g., myelofibrosis). In certain aspects, a TβRII antagonist may be used to treat, prevent, or reduce the progression rate and/or severity of poikilocytosis in a patient with a myeloproliferative disorder (e.g., myelofibrosis). In certain aspects, a TβRII antagonist may be used to treat, prevent, or reduce the progression rate and/or severity of neutropenia in a patient with a myeloproliferative disorder (e.g., myelofibrosis). In certain aspects, a TβRII antagonist may be used to treat, prevent, or reduce the progression rate and/or severity of osteosclerosis in a patient with a myeloproliferative disorder (e.g., myelofibrosis). In certain aspects, a TβRII antagonist may be used to treat, prevent, or reduce the progression rate and/or severity of osteomyelofibrosis in a patient with a myeloproliferative disorder (e.g., myelofibrosis). In certain aspects, a TβRII antagonist may be used to treat, prevent, or reduce the progression rate and/or severity of excessive proliferation of one or more blood cells (e.g., erythroid cells, myeloid cells, and megakaryocytic cells) in a patient with a myeloproliferative disorder (e.g., polycythemia vera). In certain aspects, a TβRII antagonist may be used to reduce levels of red blood cells in a patient with a myeloproliferative disorder (e.g., polycythemia vera). In certain aspects, a TβRII antagonist may be used to reduce levels of white blood cells in a patient with a myeloproliferative disorder (e.g., polycythemia vera). In certain aspects, a TβRII antagonist may be used to reduce levels of platelets in a patient with a myeloproliferative disorder (e.g., polycythemia vera and essential thrombocythemia). In certain aspects, the disclosure relates to increasing red blood cell levels in a patient with a myeloproliferative disorder (e.g., myelofibrosis) by administering an effective amount of a TβRII antagonist. In certain aspects, disclosure relates to increasing hemoglobin levels in a patient with a myeloproliferative disorder (e.g., myelofibrosis) by administering an effective amount of a TβRII antagonist. In certain aspects, a patient with a myeloproliferative disorder (e.g., myelofibrosis) to be treated in accordance with the methods described herein has anemia. In some embodiments, a TβRII antagonist may be used to treat, prevent, or reduce the progression rate and/or severity of anemia in a patient with a myeloproliferative disorder (e.g., myelofibrosis). In certain aspects, the disclosure relates to methods using a TβRII antagonist to treat, prevent, or reduce the progression rate and/or severity of a myeloproliferative disorder (e.g., myelofibrosis) or a complication of a myeloproliferative disorder in a patient that has been administered one or more blood cell transfusions (whole or red blood cell transfusions). In some embodiments, the disclosure relates to methods using a TβRII antagonist to treat, prevent, or reduce the progression rate and/or severity of a myeloproliferative disorder (e.g., myelofibrosis) or a complication of a myeloproliferative disorder in patient that is blood cell transfusion-dependent. In certain aspects, a TβRII antagonist may be used to decrease (reduce) blood cell transfusion burden in a patient with a myeloproliferative disorder (e.g., myelofibrosis). For example, a TβRII antagonist may be used to decrease blood cell transfusion by greater than about 30%, 40%, 50%, 60%, 70%, 80%, 90%, or 100% for 4 to 8 weeks relative to the equal time prior to the start of the TβRII antagonist treatment in a patient with a myeloproliferative disorder (e.g., myelofibrosis). In some embodiments, a TβRII antagonist may be used to decrease blood cell transfusion by greater than about 50% for 4 to 8 weeks relative to the equal time prior to the start of the TβRII antagonist treatment in a patient with a myeloproliferative disorder (e.g., myelofibrosis). In certain aspects, a TβRII antagonist may be used to decrease iron overload in a patient with a myeloproliferative disorder (e.g., myelofibrosis). For example, a TβRII antagonist may be used to decrease iron overload in an organ and/or tissue in a patient with a myeloproliferative disorder (e.g., myelofibrosis). In some embodiments, a TβRII antagonist may be used to decrease iron overload in the spleen of a patient with a myeloproliferative disorder (e.g., myelofibrosis). In some embodiments, a TβRII antagonist may be used to decrease iron overload in the liver of a patient with a myeloproliferative disorder (e.g., myelofibrosis). In some embodiments, a TβRII antagonist may be used to decrease iron overload in the heart of a patient with a myeloproliferative disorder (e.g., myelofibrosis).

In part, the present disclosure relates to methods of treating, preventing, or reducing the severity or progression rate of a JAK2 kinase-associated disorder, comprising administering to a patient in need thereof an effective amount of a TβRII antagonist. In some embodiments, the patient has is a JAK2V617F mutation-associated disorder. In certain aspects, the disclosure relates to methods for treating, preventing, or reducing the progression rate and/or severity of one or more complications of a JAK2 kinase-associated disorder comprising administering to a patient in need thereof an effective amount of a TβRII antagonist. For example, in some embodiments, the one or more complications of a JAK2 kinase-associated disorder are selected from the group consisting of: ineffective hematopoiesis, extramedullary hematopoiesis (e.g., splenic extramedullary hematopoiesis, hepatic extramedullary hematopoiesis, pulmonary extramedullary hematopoiesis, and lymphatic extramedullary hematopoiesis), inflammatory complications, pancytopenia, fibrosis (e.g., bone marrow fibrosis, spleen fibrosis, and liver fibrosis), splenomegaly, hepatomegaly, thrombocytopenia, anemia, poikilocytosis, progressive hepatosplenomegaly, fatigue, weight loss, night sweats, fever, pruritus, bone pain, early satiety, abdominal pain or discomfort, arthralgias, myalgias, parasthesias, cachexia, splenic infarct, bleeding, inflammation, neutropenia, elevated cytokine levels, coagulopathy, IL-6-mediated inflammation or inflammatory complication, osteosclerosis, and osteomyelofibrosis. In certain aspects, the disclosure relates to methods of using a TβRII antagonist to treat, prevent, or reduce the progression rate and/or severity of a JAK2 kinase-associated disorder or one or more complications of a JAK2 kinase-associated disorder (e.g., a JAK2 gain-of-function associated disorder) wherein the patient further comprises one or more additional gene mutations or other molecular markers associated with a myeloproliferative disorder. For example, in some embodiments, a TβRII antagonist may be used to treat, prevent, or reduce the progression rate and/or severity of a JAK2 kinase-associated disorder or one or more complications of a JAK2 kinase-associated disorder wherein the a myeloproliferative disorder is further associated with one or more mutations in one or more genes selected from the group consisting of: IDH1, IDH2, EZH2, SRSF2, ASXL1, TYK2, MPL, CALR, TET2, THPO, and LNK. In some embodiments, the a JAK2 kinase-associated disorder is further associated with one or more genetic markers selected from the group consisting of: nullizygosity for JAK2 46/1 haplotype, JAK2V617F, CALR+ASXL1−, CALR−ASKL1+, CALR+ASKL1+, and CALR−ASKL1−. In some embodiments, the method reduces the JAK2-associated disorder allele burden in the patient. In some embodiments, the method reduces the allele burden of one or more JAK2 mutations. In some embodiments, the method reduces the allele burden of JAK2V617F. In some embodiments, the method reduces allele burden of one or more mutations in one or more genes selected from the group consisting of: IDH1, IDH2, EZH2, SRSF2, ASXL1, JAK1, JAK3, TYK2, MPL, CALR, TET2, THPO, and LNK. In some embodiments, the method reduces allele burden of one or more genetic markers selected from the group consisting of: nullizygosity for JAK2 46/1 haplotype, CALR+ASXL1−, CALR-ASKL1+, CALR+ASKL1+, and CALR-ASKL1−. In certain aspects, the disclosure relates to methods of using a TβRII antagonist to treat, prevent, or reduce the progression rate and/or severity of a JAK2 kinase-associated disorder or one or more complications of a JAK2 kinase-associated disorder wherein the a JAK2 kinase-associated disorder is further associated with one or more elevated serum markers selected from the group consisting of: increased serum IL-8 levels, increased serum IL-2R levels, and increased serum free light chain levels. In certain aspects, the disclosure relates to methods of using a TβRII antagonist to treat, prevent, or reduce the progression rate and/or severity of a JAK2 kinase-associated disorder or one or more complications of a JAK2 kinase-associated disorder wherein the patient has been treated with a Janus kinase inhibitor. In some embodiments, the patient has been treated with a JAK2 inhibitor. In some embodiments, the patient has been treated with a Janus kinase inhibitor selected from the group consisting of: ruxolitinib, fedratinib (SAR302503), monoelotinib (CYT387), pacritinib, lestaurtinib, AZD-1480, BMS-911543, NS-018, LY2784544, SEP-701, XL019, and AT-9283. In some embodiments, the patient has been treated with ruxolitinib. In some embodiments, a TβRII antagonist may be used to treat, prevent, or reduce the progression rate and/or severity of a JAK2 kinase-associated disorder or one or more complications of a JAK2 kinase-associated disorder wherein the patient is intolerant of a Janus kinase inhibitor. In some embodiments, a TβRII antagonist may be used to treat, prevent, or reduce the progression rate and/or severity of a JAK2 kinase-associated disorder or one or more complications of a JAK2 kinase-associated disorder wherein the patient has an inadequate response to a Janus kinase inhibitor. In certain aspects, the disclosure relates to methods of using a JAK2 kinase-associated disorder to treat, prevent, or reduce the progression rate and/or severity of a JAK2 kinase-associated disorder or one or more complications of a JAK2 kinase-associated disorder wherein the patient has been treated with hydroxyurea. In some embodiments, a TβRII antagonist may be used to treat, prevent, or reduce the progression rate and/or severity of a JAK2 kinase-associated disorder or one or more complications of a JAK2 kinase-associated disorder wherein the patient is intolerant of hydroxyurea. In some embodiments, a TβRII antagonist may be used to treat, prevent, or reduce the progression rate and/or severity of a JAK2 kinase-associated disorder or one or more complications of a JAK2 kinase-associated disorder wherein the patient has an inadequate response to hydroxyurea.

In any of the methods and uses described herein, a patient with a myeloproliferative disorder (e.g., myelofibrosis, polycythemia vera, and essential thrombocytopenia) and/or a patient with a Janus kinase-associated disorder (e.g., a JAK2 kinase-associated disorder) may further be administered one or more additional active agents and/or supportive therapies (in addition to administration of one or more TβRII antagonists) for treating, preventing, or reducing, the progression rate and/or severity of a myeloproliferative disorder and/or a Janus kinase-associated disorder or one or more complications of a myeloproliferative disorder and/or a Janus kinase-associated disorder. For example, in some embodiments, a patient may be further administered one or more supportive therapies or active agents selected from the group consisting of: blood transfusion (whole blood or red blood cell transfusion), erythropoiesis-stimulating agents [e.g., ESAs such as erythropoietin (EPO) and derivatives thereof], androgens (e.g., testosterone enanthate and fluoxymesterone), prednisone, danazol, thalidomide, prednisone, lenalidomide, iron-chelating agents, deferoxamine, deferiprone, deferasirox, hydroxyurea, cladribine ruxolitinib, SAR302503, CYT387, pacritinib, AZD-1480, BMS-911543, NS-018, LY2784544, lestaurtinib, SEP-701, AT-9283, Janus kinase inhibitors (e.g., inhibitors of one or more of JAK1, JAK2, and JAK3), splenectomy, radiotherapy, aspirin, immunomodulating drugs, PI3K/mTOR inhibitors, epigenetic factors modulators, pomalidonmide, rapamycin, sirolimus, deforolimus, everolimus, temsirolimus, NVP-BEZ235, BGT226, SF1126, PK1-587, INK128, AZD8055, AZD2014, histone deacetylase inhibitors, givinostat, panobinostat, pracinostat, corticosteroids, gamma-interferon, cyclophosphamide, azathioprine, methotrexate, penicillamine, cyclosporine, colchicine, antithymocyte globulin, mycophenolate mofetil, hydroxychloroquine, calcium channel blockers, nifedipine, angiotensin converting enzyme inhibitors, para-aminobenzoic acid, dimethyl sulfoxide, interleukin-5 (IL-5) inhibitors, pan caspase inhibitors, lectins, colchicine, azathioprine, cyclophosphamide, prednisone, thalidomide, pentoxifylline, and theophylline.

In certain aspects, the disclosure relates to methods for treating, preventing, or reducing the progression rate and/or severity of a myeloproliferative disorder (e.g., myelofibrosis, polycythemia vera, and essential thrombocytopenia) and/or a patient with a Janus kinase-associated disorder (e.g., a JAK2 kinase-associated disorder) or one or more complications of a myeloproliferative disorder and/or a Janus kinase-associated disorder, comprising administering to a patient in need thereof: a) a Janus kinase inhibitor; and b) a TβRII antagonists, wherein the Janus kinase inhibitor and TβRII antagonist are administered in an effective amount. In some embodiments, a TβRII antagonist is administered prior to treatment with the Janus kinase inhibitor. In other embodiments, a TβRII antagonist is administered after treatment with the Janus kinase inhibitor. In even other embodiments, a TβRII antagonist is administered concurrently with the Janus kinase inhibitor. A Janus kinase inhibitor to be used in accordance with the methods described herein may be an agent that inhibits one or more Janus kinases selected from the group consisting of: JAK1, JAK2, and JAK3. For example, a Janus kinase inhibitor may be an agent that inhibits signaling of one or more of JAK1, JAK2, and JAK3 in a cell-based assay. In some embodiments, a Janus kinase inhibitor to be used in accordance with the methods described herein is selected from the group consisting of: ruxolitinib, fedratinib (SAR302503), monoelotinib (CYT387), pacritinib, lestaurtinib, AZD-1480, BMS-911543, NS-018, LY2784544, SEP-701, XL019, and AT-9283. In some preferred embodiments, a Janus kinase inhibitor to be used in accordance with the methods described herein is ruxolitinib.

In certain aspects, a TβRII antagonist, or combination of antagonists, to be used in accordance with methods and uses described herein is an agent that inhibits at least TGFβ1 (e.g., a TGFβ1 antagonist). Effects on TGFβ1 inhibition may be determined, for example, using a cell-based assay including those described herein (e.g., Smad signaling assay). Therefore, in some embodiments, a TβRII antagonist, or combination of antagonists, of the disclosure may bind to at least TGFβ1. Ligand binding activity may be determined, for example, using a binding affinity assay including those described herein. In some embodiments, a TβRII antagonist, or combination of antagonists, of the disclosure binds to at least TGFβ1 with a $K_D$ of at least $1 \times 10^{-7}$M (e.g., at least $1 \times 10^{-8}$M, at least $1 \times 10^{-9}$M, at least $1 \times 10^{-10}$ M, at least $1\times10^{-11}$M, or at least $1\times10^{-12}$M). As described herein, various TβRII antagonists that inhibit TGFβ1 can be used in accordance with the methods and uses described herein including, for example, ligand traps (e.g., TβRII polypeptides and variants thereof), antibodies, small molecules, nucleotide sequences, and combinations thereof. In certain embodiments, a TβRII antagonist, or combination of antagonists, that inhibits TGFβ1 may further inhibit one or more of: TGFβ2, TGFβ3, TβRII, ALK5, and betaglycan. In some embodiments, a TβRII antagonist, or combination of antagonists, that inhibits TGFβ1 further inhibits TGFβ3. In some embodiments, a TβRII antagonist, or combination of antagonists, that inhibits TGFβ1 does not inhibit or does not substantially inhibit TGFβ2. In some embodiments, a TβRII antagonist, or combination of antagonists, that inhibits TGFβ1 further inhibits TGFβ3 but does not inhibit or does not substantially inhibit TGFβ2.

In certain aspects, a TβRII antagonist, or combination of antagonists, to be used in accordance with methods and uses described herein is an agent that inhibits at least TGFβ2 (e.g., a TGFβ2 antagonist). Effects on TGFβ2 inhibition may be determined, for example, using a cell-based assay including those described herein (e.g., Smad signaling assay). Therefore, in some embodiments, a TβRII antagonist, or combination of antagonists, of the disclosure may bind to at least TGFβ2. Ligand binding activity may be determined, for example, using a binding affinity assay including those described herein. In some embodiments, a TβRII antagonist, or combination of antagonists, of the disclosure binds to at least TGFβ2 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). As described herein, various TβRII antagonists that inhibit TGFβ2 can be used in accordance with the methods and uses described herein including, for example, ligand traps (e.g., TβRII polypeptides and variants thereof), antibodies, small molecules, nucleotide sequences, and combinations thereof. In certain embodiments, a TβRII antagonist, or combination of antagonists, that inhibits TGFβ2 may further inhibit one or more of: TGFβ1, TGFβ3, TβRII, ALK5, and betaglycan.

In certain aspects, a TβRII antagonist, or combination of antagonists, to be used in accordance with methods and uses described herein is an agent that inhibits at least TGFβ3 (e.g., a TGFβ3 antagonist). Effects on TGFβ3 inhibition may be determined, for example, using a cell-based assay including those described herein (e.g., Smad signaling assay). Therefore, in some embodiments, a TβRII antagonist, or combination of antagonists, of the disclosure may bind to at least TGFβ3. Ligand binding activity may be determined, for example, using a binding affinity assay including those described herein. In some embodiments, a TβRII antagonist, or combination of antagonists, of the disclosure binds to at least TGFβ3 with a $K_D$ of at least $1\times10^{-7}$ M (e.g., at least $1\times10^{-8}$M, at least $1\times10^{-9}$M, at least $1\times10^{-10}$ M, at least $1\times10^{-11}$ M, or at least $1\times10^{-12}$ M). As described herein, various TβRII antagonists that inhibit TGFβ3 can be used in accordance with the methods and uses described herein including, for example, ligand traps (e.g., TβRII polypeptides and variants thereof), antibodies, small molecules, nucleotide sequences, and combinations thereof. In certain embodiments, a TβRII antagonist, or combination of antagonists, that inhibits TGFβ3 may further inhibit one or more of: TGFβ1, TGFβ2, TβRII, ALK5, and betaglycan. In some embodiments, a TβRII antagonist, or combination of antagonists, that inhibits TGFβ3 further inhibits TGFβ1. In some embodiments, a TβRII antagonist, or combination of antagonists, that inhibits TGFβ3 does not inhibit or does not substantially inhibit TGFβ2. In some embodiments, a TβRII antagonist, or combination of antagonists, that inhibits TGFβ3 further inhibits TGFβ1 but does not inhibit or does not substantially inhibit TGFβ2.

In certain aspects, a TβRII antagonist, or combination of antagonists, to be used in accordance with methods and uses described herein is an agent that inhibits at least TβRII (e.g., a TβRII receptor antagonist). Effects on TβRII inhibition may be determined, for example, using a cell-based assay including those described herein (e.g., Smad signaling assay). Therefore, in some embodiments, a TβRII antagonist, or combination of antagonists, of the disclosure may bind to at least TβRII. Ligand binding activity may be determined, for example, using a binding affinity assay including those described herein. In some embodiments, a TβRII antagonist, or combination of antagonists, of the disclosure binds to at least TβRII with a $K_D$ of at least $1\times10^{-7}$ M (e.g., at least $1\times10^{-8}$M, at least $1\times10^{-9}$M, at least $1\times10^{-10}$ M, at least $1\times10^{-11}$ M, or at least $1\times10^{-12}$ M). As described herein, various TβRII antagonists that inhibit TβRII can be used in accordance with the methods and uses described herein including, for example, ligand traps (e.g., TβRII polypeptides and variants thereof), antibodies, small molecules, nucleotide sequences, and combinations thereof. In certain embodiments, a TβRII antagonist, or combination of antagonists, that inhibits TβRII may further inhibit one or more of: TGFβ1, TGFβ2, TGFβ3, ALK5, and betaglycan. In some embodiments, a TβRII antagonist, or combination of antagonists, that inhibits TβRII does not inhibit or does not substantially inhibit TGFβ2.

In certain aspects, a TβRII antagonist, or combination of antagonists, to be used in accordance with methods and uses described herein is an agent that inhibits at least ALK5 (e.g., a ALK5 antagonist). Effects on ALK5 inhibition may be determined, for example, using a cell-based assay including those described herein (e.g., Smad signaling assay). Therefore, in some embodiments, a TβRII antagonist, or combination of antagonists, of the disclosure may bind to at least ALK5. Ligand binding activity may be determined, for example, using a binding affinity assay including those described herein. In some embodiments, an ALK5 antagonist, or combination of antagonists, of the disclosure binds to at least ALK5 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). As described herein, various TβRII antagonists that inhibit ALK5 can be used in accordance with the methods and uses described herein including, for example, ligand traps (e.g., TβRII polypeptides and variants thereof), antibodies, small molecules, nucleotide sequences, and combinations thereof. In certain embodiments, a TβRII antagonist, or combination of antagonists, that inhibits ALK5 may further inhibit one or more of: TGFβ1, TGFβ2, TGFβ3, TβRII, and betaglycan. In some embodiments, a TβRII antagonist, or combination of antagonists, that inhibits ALK5 does not inhibit or does not substantially inhibit TGFβ2.

In certain aspects, a TβRII antagonist, or combination of antagonists, to be used in accordance with methods and uses described herein is an agent that inhibits at least betaglycan (e.g., a betaglycan antagonist). Effects on betaglycan inhibition may be determined, for example, using a cell-based assay including those described herein (e.g., Smad signaling assay). Therefore, in some embodiments, a TβRII antagonist, or combination of antagonists, of the disclosure may bind to at least betaglycan. Ligand binding activity may be determined, for example, using a binding affinity assay including those described herein. In some embodiments, a betaglycan antagonist, or combination of antagonists, of the disclosure binds to at least betaglycan with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). As described herein, various TβRII antagonists that inhibit betaglycan can be used in accordance with the methods and uses described herein including, for example, ligand traps (e.g., TβRII polypeptides and variants thereof), antibodies, small molecules, nucleotide sequences, and combinations thereof. In certain embodiments, a TβRII antagonist, or combination of antagonists, that inhibits betaglycan may further inhibit one or more of: TGFβ1, TGFβ2, TGFβ3, TβRII, and ALK5. In some embodiments, a TβRII antagonist, or combination of antagonists, that inhibits betaglycan does not inhibit or does not substantially inhibit TGFβ2.

In certain aspects, the disclosure provides TβRII polypeptides and the use of such TβRII polypeptides as selective antagonists for TGFβ1 and/or TGFβ3. As described herein, polypeptides comprising part or all of the TβRII extracellular domain (ECD), with or without additional mutations, bind to and/or inhibit TGFβ1 and/or TGFβ3 with varying affinities. Thus, in certain aspects, the disclosure provides TβRII polypeptides for use in selectively inhibiting TGFβ superfamily associated disorders.

In certain aspects, the disclosure provides polypeptides comprising mutations and/or truncations in the extracellular domain of TβRII. In certain aspects, the disclosure provides a TβRII fusion polypeptide comprising a first amino acid sequence from the extracellular domain of TβRII and a heterologous amino acid sequence, wherein the first amino acid sequence comprises or consists of an amino acid sequence at least 80%, at least 85%, at least 90%, at least 95%, at least 96%, at least 97%, at least 98%, at least 99% identical or identical to a) a sequence beginning at any of positions 23 to 35 of SEQ ID NO: 5 and ending at any of positions 153 to 159 of SEQ ID NO: 5 orb) a sequence beginning at any of positions 23 to 60 of SEQ ID NO: 6 and ending at any of positions 178 to 184 of SEQ ID NO: 6.

In certain aspects the disclosure provides polypeptides comprising a wild-type or altered and/or truncated extracellular domain of TβRII fused to at least a portion of the Fc domain of a human IgG2. Thus in certain aspects, the disclosure provides a TβRII fusion polypeptide comprising a first amino acid sequence from the extracellular domain of TβRII and a heterologous amino acid sequence, wherein the first amino acid sequence comprises or consists of an amino acid sequence at least 80%, at least 85%, at least 90%, at least 95%, at least 96%, at least 97%, at least 98%, at least 99% identical or identical to a) a sequence beginning at any of positions 23 to 35 of SEQ ID NO: 5 and ending at any of positions 153 to 159 of SEQ ID NO: 5 orb) a sequence beginning at any of positions 23 to 60 of SEQ ID NO: 6 and ending at any of positions 178 to 184 of SEQ ID NO: 6, and wherein the polypeptide comprises a second polypeptide sequence that comprises at least a constant domain of a human IgG2 and may optionally comprise or consist of an amino acid sequence that is at least 80%, at least 85%, at least 90%, at least 95%, at least 96%, at least 97%, at least 98%, at least 99% identical to SEQ ID NO: 19, and wherein an linker is optionally positioned between the first polypeptide and the second polypeptide. An example of the is provided as SEQ ID NO: 50 and is encoded by the nucleic acid sequence of SEQ ID NO: 51. In certain embodiments, the disclosure provides polypeptides with an amino acid sequence that comprises or consists of an amino acid sequence that is at least 80%, 85%, 90%, 95%, 96%, 97%. 98%, 99% or 100% identical to the amino acid sequence of SEQ ID NO: 50. In certain embodiments, the disclosure provides polypeptides that are encoded by a nucleic acid sequence that comprises or consists of a nucleic acid sequence that is at least 80%, 85%, 90%, 95%, 96%, 97%, 98%, 99% or 100% identical to the nucleic acid sequence of SEQ ID NO: 51.

In certain aspects the disclosure provides polypeptides comprising a wild-type or altered and/or truncated extracellular domain of TβRII fused to at least a portion of the Fc domain of a human IgG1, IgG3, or IgG4.

In certain aspects the disclosure provides polypeptides comprising a wild-type or altered and/or truncated extracellular domain of TβRII fused to at least a portion of the Fc domain of a human IgG1. Thus in certain aspects, the disclosure provides a TβRII fusion polypeptide comprising a first amino acid sequence from the extracellular domain of TβRII and a heterologous amino acid sequence, wherein the first amino acid sequence comprises, consisting essentially of, or consists of an amino acid sequence at least 80%, at least 85%, at least 90%, at least 95%, at least 96%, at least 97%, at least 98%, at least 99% identical or identical the amino acid sequence of SEQ ID NO: 13, and wherein an linker is optionally positioned between the first polypeptide and the second polypeptide. An example of another TβRII fusion polypeptide provided as SEQ ID NO: 101 and is encoded by the nucleic acid sequence of SEQ ID NO: 102. In certain embodiments, the disclosure provides polypeptides with an amino acid sequence that comprises, consists essentially of, or consists of an amino acid sequence that is at least 80%, 85%, 90%, 95%, 96%, 97%, 98%, 99% or 100% identical to the amino acid sequence of SEQ ID NO: 101. In certain embodiments, the disclosure provides polypeptides with an amino acid sequence that comprises, consists essentially of, or consists of an amino acid sequence that is at least 80%, 85%, 90%, 95%, 96%, 97%, 98%, 99% or 100% identical to the amino acid sequence of SEQ ID NO: 103. In certain embodiments, the disclosure provides an amino acid sequence that is at least 80%, 85%, 90%, 91%, 92%, 93%, 94%, 95%, 96%, 97%, 98%, 99%, or 100% identical to an amino acid sequence that begins at any one of amino acids 25-46 (e.g., 25, 26, 27, 28, 29, 30, 31, 32, 33, 34, 35, 36, 37, 38, 39, 40, 41, 42, 43, 44, 45, or 46) of SEQ ID NO: 101 and ends any one of amino acids 170-186 (e.g., 170, 171, 172, 173, 174, 175, 176, 177, 178, 179, 180, 181, 182, 183, 184, 185, or 186) of SEQ ID NO: 101. In certain embodiments, the disclosure provides polypeptides that are encoded by a nucleic acid sequence that comprises or consists of a nucleic acid sequence that is at least 80%, 85%, 90%, 95%, 96%, 97%, 98%, 99% or 100% identical to the nucleic acid sequence of SEQ ID NO: 102. In certain embodiments, the disclosure provides a nucleic acid sequence that comprises or consists of a nucleic acid sequence that is at least 80%, 85%, 90%, 95%, 96%, 97%, 98%, 99% or 100% identical to the nucleic acid sequence of SEQ ID NO: 102.

In some embodiments, the first amino acid sequence comprises or consists of the sequence beginning at position 23 of SEQ ID NO: 5 and ending at position 159 of SEQ ID NO: 5. In some embodiments, the first amino acid sequence comprises or consists of the sequence beginning at position 29 of SEQ ID NO: 5 and ending at position 159 of SEQ ID NO: 5. In some embodiments, the first amino acid sequence comprises or consists of the sequence beginning at position 35 of SEQ ID NO: 5 and ending at position 159 of SEQ ID NO: 5. In some embodiments, the first amino acid sequence comprises or consists of the sequence beginning at position 23 of SEQ ID NO: 5 and ending at position 153 of SEQ ID NO: 5. In some embodiments, the first amino acid sequence comprises or consists of the sequence beginning at position 29 of SEQ ID NO: 5 and ending at position 153 of SEQ ID NO: 5. In some embodiments, the first amino acid sequence comprises or consists of the sequence beginning at position 35 of SEQ ID NO: 5 and ending at position 153 of SEQ ID NO: 5.

In some embodiments, the first amino acid sequence comprises or consists of the sequence beginning at position 23 of SEQ ID NO: 6 and ending at positions 184 of SEQ ID NO: 6. In some embodiments, the first amino acid sequence comprises or consists of the sequence beginning at position 29 of SEQ ID NO: 6 and ending at position 184 of SEQ ID NO: 6. In some embodiments, the first amino acid sequence comprises or consists of the sequence beginning at position 23 of SEQ ID NO: 6 and ending at position 178 of SEQ ID NO: 6. In some embodiments, the first amino acid sequence comprises or consists of the sequence beginning at position 29 of SEQ ID NO: 6 and ending at position 178 of SEQ ID NO: 6.

In some embodiments, the first amino acid sequence comprises or consists of a sequence that has a D at the position corresponding to position 36 of SEQ ID NO: 47 and/or a K at the position corresponding to position 76 of SEQ ID NO: 47.

In certain aspects, the disclosure provides a TβRII fusion polypeptide comprising a first amino acid sequence at least 80%, at least 85%, at least 90%, at least 95%, at least 96%, at least 97%, at least 98%, at least 99% identical or identical to the sequence of SEQ ID NO: 7 or SEQ ID NO: 13, or active fragment thereof, and a second heterologous portion, wherein the first amino acid sequence has a D at the position corresponding to position 36 of SEQ ID NO: 47 and/or a K at the position corresponding to position 76 of SEQ ID NO: 47.

In some embodiments, the first amino acid sequence comprises an N-terminal truncation of 1-12 amino acids corresponding to amino acids 1-12 of SEQ ID NO: 7 or 1-37 amino acids corresponding to amino acids 1-37 of SEQ ID NO: 13. In some embodiments, the first amino acid sequence comprises an N-terminal truncation of 6 amino acids corresponding to amino acids 1-6 of SEQ ID NO: 7 or SEQ ID NO: 13. In some embodiments, the first amino acid sequence comprises an N-terminal truncation of 12 amino acids corresponding to amino acids 1-12 of SEQ ID NO: 7 or 37 amino acids corresponding to amino acids 1-37 of SEQ ID NO: 13. In some embodiments, the first amino acid sequence comprises a C-terminal truncation of 1-6 amino acids corresponding to amino acids 137-132 of SEQ ID NO: 7 or amino acids 162-157 of SEQ ID NO: 13. In some embodiments, the first amino acid sequence comprises a C-terminal truncation of 6 amino acids corresponding to amino acids 132-137 of SEQ ID NO: 7 or amino acids 157-162 of SEQ ID NO: 13. In some embodiments, the first amino acid sequence comprises an insertion corresponding to SEQ ID NO: 18 between the residues corresponding to positions 117 and 118 of SEQ ID NO: 47.

In some embodiments, the heterologous portion comprises one or more polypeptide portions that enhance one or more of: in vivo stability, in vivo half-life, uptake/administration, tissue localization or distribution, formation of protein complexes, and/or purification. In some embodiments, the heterologous portion comprises a polypeptide portion selected from: an immunoglobulin Fc domain and a serum albumin. In a further embodiment, the immunoglobulin Fc domain is joined to the TβRII polypeptide by a linker.

In some embodiments, the polypeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. In some embodiments, the polypeptide is glycosylated.

In certain aspects, the disclosure provides a TβRII fusion polypeptide comprising a first amino acid sequence consisting of a portion of the extracellular domain of TβRII that comprises an amino acid sequence that is at least 80%, at least 85%, at least 90%, or at least 95% identical to an amino acid sequence selected from SEQ ID NOs: 7-17 and 47-49, and a second heterologous portion. In certain aspects, the disclosure provides a TβRII fusion polypeptide comprising a first amino acid sequence consisting of a portion of the extracellular domain of TβRII that comprises an amino acid sequence that is at least 96% identical to an amino acid sequence selected from SEQ ID NOs: 7-17 and 47-49, and a second heterologous portion. In certain aspects, the disclosure provides a TβRII fusion polypeptide comprising a first amino acid sequence consisting of a portion of the extracellular domain of TβRII that comprises an amino acid sequence that is at least 97% identical to an amino acid sequence selected from SEQ ID NOs: 7-17 and 47-49, and a second heterologous portion. In certain aspects, the disclosure provides a TβRII fusion polypeptide comprising a first amino acid sequence consisting of a portion of the extracellular domain of TβRII that comprises an amino acid sequence that is at least 98% identical to an amino acid sequence selected from SEQ ID NOs: 7-17 and 47-49, and a second heterologous portion. In certain aspects, the disclosure provides a TβRII fusion polypeptide comprising a first amino acid sequence consisting of a portion of the extracellular domain of TβRII that comprises an amino acid sequence that is at least 99% identical to an amino acid sequence selected from SEQ ID NOs: 7-17 and 47-49, and a second heterologous portion. In certain aspects, the disclosure provides a TβRII fusion polypeptide comprising a first amino acid sequence consisting of a portion of the extracellular domain of TβRII that comprises an amino acid sequence is an amino acid sequence selected from SEQ ID NOs: 7-17 and 47-49 and a second heterologous portion.

In certain aspects, the disclosure provides a polypeptide comprising or consisting of an amino acid sequence that is at least 80%, at least 85%, at least 90%, or at least 95% identical to an amino acid sequence selected from SEQ ID NOs: 25, 27, 29, 31, 33, 35, 37, 39, 41 and 43 or the portion thereof with the leader sequence removed, e.g., a polypeptide comprising or consisting of an amino acid sequence that is at least 80%, at least 85%, at least 90%, or at least 95% identical to an amino acid sequence selected from SEQ ID NOs: 53, 54, 55, 56, 57, 58, 59, 60, 61, and 62. In certain aspects, the disclosure provides a polypeptide comprising or consisting of an amino acid sequence that is at least 96% identical to an amino acid sequence selected from SEQ ID NOs: 25, 27, 29, 31, 33, 35, 37, 39, 41 and 43 or the portion thereof with the leader sequence removed, e.g., a polypeptide comprising or consisting of an amino acid sequence that is at least 96% identical to an amino acid sequence selected from SEQ ID NOs: 53, 54, 55, 56, 57, 58, 59, 60, 61, and 62. In certain aspects, the disclosure provides a polypeptide comprising or consisting of an amino acid sequence that is at least 97% identical to an amino acid sequence selected from SEQ ID NOs: 25, 27, 29, 31, 33, 35, 37, 39, 41 and 43 or the portion thereof with the leader sequence removed, e.g., a polypeptide comprising or consisting of an amino acid sequence that is at least 97% identical to an amino acid sequence selected from SEQ ID NOs: 53, 54, 55, 56, 57, 58, 59, 60, 61, and 62. In certain aspects, the disclosure provides a polypeptide comprising or consisting of an amino acid sequence that is at least 98% identical to an amino acid sequence selected from SEQ ID NOs: 25, 27, 29, 31, 33, 35, 37, 39, 41 and 43 or the portion thereof with the leader sequence removed, e.g., a polypeptide comprising or consisting of an amino acid sequence that is at least 98% identical to an amino acid sequence selected from SEQ ID NOs: 53, 54, 55, 56, 57, 58, 59, 60, 61, and 62. In certain aspects, the disclosure provides a polypeptide comprising or consisting of an amino acid sequence that is at least 99% identical to an amino acid sequence selected from SEQ ID NOs: 25, 27, 29, 31, 33, 35, 37, 39, 41 and 43 or the portion thereof with the leader sequence removed, e.g., a polypeptide comprising or consisting of an amino acid sequence that is at least 99% identical to an amino acid sequence selected from SEQ ID NOs: 53, 54, 55, 56, 57, 58, 59, 60, 61, and 62. In certain aspects, the disclosure provides a polypeptide comprising or consisting of an amino acid sequence selected from SEQ ID NOs: 25, 27, 29, 31, 33, 35, 37, 39, 41 and 43 or the portion thereof with the leader sequence removed, e.g., a polypeptide comprising or consisting of an amino acid sequence selected from SEQ ID NOs: 53, 54, 55, 56, 57, 58, 59, 60, 61, and 62.

In certain aspects, the disclosure provides a TβRII polypeptide comprising of an amino acid sequence encoded by a nucleic acid that hybridizes under stringent conditions to a complement of a nucleotide sequence selected from SEQ ID NOs: 26, 28, 30, 32, 34, 36, 38, 40, 42 and 44.

In each of the foregoing, the TβRII polypeptide may be selected that it does not include a full-length TβRII ECD. A TβRII polypeptide may be used as a monomeric protein or in a dimerized form. A TβRII polypeptide may also be fused to a second polypeptide portion to provide improved properties, such as increased half-life or greater ease of production or purification. A fusion may be direct or a linker may be inserted between the TβRII polypeptide and any other portion. A linker may be structured or unstructured and may consist of 1, 2, 3, 4, 5, 10, 15, 20, 30, 50 or more amino acids, optionally relatively free of secondary structure.

In some embodiments, a TβRII polypeptide of the disclosure has a glycosylation pattern characteristic of expression of the polypeptide in CHO cells.

In some embodiments, the disclosure provides a homodimer comprising two TβRII polypeptides of the disclosure.

In some embodiments, the disclosure provides an isolated polynucleotide comprising a coding sequence for the TβRII polypeptides of the disclosure. In some embodiments, the disclosure provides a recombinant polynucleotide comprising a promoter sequence operably linked to the isolated polynucleotide. In some embodiments, the disclosure provides a cell transformed with an isolated polynucleotide or a recombinant polynucleotide of the disclosure. In some embodiments, the cell is a mammalian cell. In some embodiments, the cell is a CHO cell or a human cell. In some embodiments, the cell is an HEK-293 cell.

In certain aspects, the disclosure provides a pharmaceutical preparation comprising the TβRII polypeptides or homodimers of the disclosure and a pharmaceutically acceptable excipient.

In certain aspects, a TβRII antagonist is an antibody, or combination of antibodies. In certain aspects, the antibody binds to at least TβRII. In some embodiments a TβRII antagonist antibody that binds to TβRII inhibits TβRII signaling, optionally as measured in a cell-based assay such as those described herein. In some embodiments, a TβRII antagonist antibody that binds to TβRII inhibits one or more TGF-beta superfamily ligands, TGFβ superfamily type I receptors, or TGFβ superfamily co-receptors from binding to TβRII. In some embodiments, a TβRII antagonist antibody that binds to TβRII inhibits one or more TGF-beta superfamily ligands from binding to TβRII selected from the group consisting of: TGFβ1, TGFβ2, and TGFβ3. In certain aspects, the antibody binds to at least ALK5. In some embodiments a TβRII antagonist antibody that binds to ALK5 inhibits ALK5 signaling, optionally as measured in a cell-based assay such as those described herein. In some embodiments, a TβRII antagonist antibody that binds to ALK5 inhibits one or more TGF-beta superfamily ligands, TGFβ superfamily type II receptors, or TGFβ superfamily co-receptors from binding to ALK5. In some embodiments a TβRII antagonist antibody that binds to ALK5 inhibits one or more TGF-beta superfamily ligands from binding to ALK5 selected from the group consisting of: TGFβ1, TGFβ2, and TGFβ3. In certain aspects, the antibody binds to at least betaglycan. In some embodiments a TβRII antagonist antibody that binds to betaglycan inhibits betaglycan signaling, optionally as measured in a cell-based assay such as those described herein. In some embodiments, a TβRII antagonist antibody that binds to betaglycan inhibits one or more TGF-beta superfamily ligands, TGFβ superfamily type I receptors, or TGFβ superfamily type II receptors from binding to betaglycan. In some embodiments a TβRII antagonist antibody that binds to betaglycan inhibits one or more TGF-beta superfamily ligands from binding to betaglycan selected from the group consisting of: TGFβ1, TGFβ2, and TGFβ3. In certain aspects, a TβRII antagonist antibody binds to at least TGFβ1. In some embodiments, a TβRII antagonist antibody that binds to TGFβ1 inhibits TβRII signaling, optionally as measured in a cell-based assay such as those described herein. In some embodiments, a TβRII antagonist antibody that binds to TGFβ1 inhibits TGFβ1-TβRII, TGFβ1-ALK5, and/or TGFβ1-betaglcyan binding. In certain aspects, a TβRII antagonist antibody binds to at least TGFβ2. In some embodiments, a TβRII antagonist antibody that binds to TGFβ2 inhibits TβRII signaling, optionally as measured in a cell-based assay such as those described herein. In some embodiments, a TβRII antagonist antibody that binds to TGFβ2 inhibits TGFβ2-TβRII, TGFβ1-ALK5, and/or TGFβ1-betaglcyan binding. In certain embodiments, a TβRII antagonist antibody binds to at least TGFβ3. In some embodiments, a TβRII antagonist antibody that binds to TGFβ3 inhibits TβRII signaling, optionally as measured in a cell-based assay such as those described herein. In some embodiments, a TβRII antagonist antibody that binds to TGFβ3 inhibits TGFβ3-TβRII, TGFβ1-ALK5, and/or TGFβ1-betaglcyan binding. In some embodiments, a TβRII antagonist antibody is a multispecific antibody, or a combination of multispecific antibodies, inhibits signaling in a cell-based assay of one or more of: TGFβ1, TGFβ2, TGFβ3, TβRII, ALK5, and betaglycan. In some embodiments, antibody is a chimeric antibody, a humanized antibody, or a human antibody. In some embodiments, the antibody is a single-chain antibody, an F(ab')2 fragment, a single-chain diabody, a tandem single-chain Fv fragment, a tandem single-chain diabody, or a fusion protein comprising a single-chain diabody and at least a portion of an immunoglobulin heavy-chain constant region.

In certain aspects, a TβRII antagonist is a small molecule inhibitor or combination of small molecule inhibitors. In some embodiments, a TβRII antagonist small molecule inhibitor is an inhibitor of at least TβRII. In some embodiments, a TβRII antagonist small molecule inhibitor is an inhibitor of at least ALK5. In some embodiments, a TβRII antagonist small molecule inhibitor is an inhibitor of at least betaglycan. In some embodiments, a TβRII antagonist small molecule inhibitor is an inhibitor of at least TGFβ1. In some embodiments, a TβRII antagonist small molecule inhibitor is an inhibitor of at least TGFβ2. In some embodiments, a TβRII antagonist small molecule inhibitor is an inhibitor of at least TGFβ3.

In certain aspects, a TβRII antagonist is a nucleic acid inhibitor or combination of nucleic acid inhibitors. In some embodiments, a TβRII antagonist nucleic acid inhibitor is an inhibitor of at least TβRII. In some embodiments, a TβRII antagonist nucleic acid inhibitor is an inhibitor of at least ALK5. In some embodiments, a TβRII antagonist nucleic acid inhibitor is an inhibitor of at least betaglycan. In some embodiments, a TβRII antagonist nucleic acid inhibitor is an inhibitor of at least TGFβ1. In some embodiments, a TβRII antagonist nucleic acid inhibitor is an inhibitor of at least TGFβ2. In some embodiments, a TβRII antagonist nucleic acid inhibitor is an inhibitor of at least TGFβ3.

In certain aspects, the disclosure provides a method of modulating the response of a cell to a TGFβ superfamily member, the method comprising exposing the cell to a TβRII polypeptide or homodimer of the disclosure.

In certain aspects, the disclosure provides a method of modulating the response of a cell to a TGFβ superfamily member, the method comprising exposing the cell to a TβRII polypeptide or homodimer of the disclosure.

In certain aspects, the disclosure relates to use of one or more TβRII antagonists, optionally in combination of one or more other supportive therapies or active agents for treating myeloproliferative disorders, in the manufacture of a medicament for treating, preventing, or reducing the progression rate and/or severity of a myeloproliferative disorder (e.g., myelofibrosis, polycythemia vera, and essential thrombocytopenia) one or more complications of a myeloproliferative disorder (e.g., fibrosis, splenomegaly, and inflammation) as described herein. In certain aspects, the disclosure relates to use of one or more TβRII antagonists, optionally in combination of one or more other supportive therapies or active agents for treating a Janus kinase-associated disorder (e.g., a JAK2 kinase-associated disorder), in the manufacture of a medicament for treating, preventing, or reducing the progression rate and/or severity of a Janus kinase-associated disorder (e.g., myelofibrosis, polycythemia vera, and essential thrombocytopenia) one or more complications of a Janus kinase-associated disorders (e.g., fibrosis, splenomegaly, and inflammation) as described herein. In certain aspects, the disclosure relates to one or more TβRII antagonists, optionally in combination of one or more other supportive therapies or active agents for treating myeloproliferative disorders, for use in treating, preventing, or reducing the progression rate and/or severity of a myeloproliferative disorder (e.g., myelofibrosis, polycythemia vera, and essential thrombocytopenia) one or more complications of a myeloproliferative disorder (e.g., fibrosis, splenomegaly, and inflammation) as described herein. In certain aspects, the disclosure relates to one or more TβRII antagonists, optionally in combination of one or more other supportive therapies or active agents for treating Janus kinase-associated disorders, for use in treating, preventing, or reducing the progression rate and/or severity of a Janus kinase-associated disorder (e.g., myelofibrosis, polycythemia vera, and essential thrombocytopenia) one or more complications of a Janus kinase-associated disorder (e.g., fibrosis, splenomegaly, and inflammation) as described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows the amino acid sequence of native precursor for the B (short) isoform of human TGFβ receptor type II (hTβRII) (NP_003233.4). Solid underline indicates the mature extracellular domain (ECD) (residues 23-159), and double underline indicates valine that is replaced in the A (long) isoform. Dotted underline denotes leader (residues 1-22).

FIG. 2 shows the amino acid sequence of native precursor for the A (long) isoform of human TβRII (NP_001020018.1). Solid underline indicates the mature ECD (residues 23-184), and double underline indicates the splice-generated isoleucine substitution. Dotted underline denotes leader (residues 1-22).

FIG. 3 shows N-terminal alignment of hTβRII$_{short}$ truncations and their hTβRII$_{long}$ counterparts. The 25-amino-acid insertion present in hTβRII$_{long}$ truncations is underlined. Note that the splicing process causes the valine flanking the insertion site in the short isoform to be replaced by an isoleucine in the long isoform. Boxed sequence denotes leader. FIG. 3 discloses SEQ ID NOS 107-113 and 110, respectively, in order of appearance.

DETAILED DESCRIPTION OF THE INVENTION

1. Overview

Figure 4A:
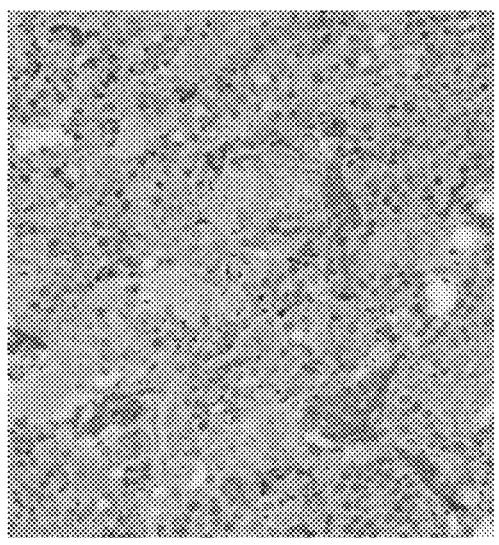
FIGS. 4A, 4B, and 4C show bone biopsy from vehicle treated JAK2V617F mice (FIG. 4B), mTβRII-Fc treated JAK2V617F mice (FIG. 4C), and age matched wild-type mice (FIG. 4A). Fibrosis was reduced in bone marrow samples from mTβRII-Fc treated JAK2V617F mice compared to control JAK2V617F mice.

Proteins described herein are the human forms, unless otherwise specified. NCBI references for the proteins are as follows: human TβRII isoform A (hTβRII$_{long}$), NP_001020018.1 and human TβRII isoform B (hTβRII$_{short}$), NP_003233.4. Sequences of native human TβRII proteins are set forth in FIGS. 1-2.

The TGFβ superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. By manipulating the activity of a member of the TGFβ family, it is often possible to cause significant physiological changes in an organism. For example, the Piedmontese and Belgian Blue cattle breeds carry a loss-of-function mutation in the GDF8 (also called myostatin) gene that causes a marked increase in muscle mass [Grobet et al. (1997) *Nat Genet* 17(1):71-4]. Similarly, in humans, inactive alleles of GDF8 are associated with increased muscle mass and, reportedly, exceptional strength [Schuelke et al. (2004) N Engl J Med 350:2682-8].

TGFβ signals are mediated by heteromeric complexes of type I (e.g. TPRI) and type II (e.g. TβRII) serine/threonine kinase receptors, which phosphorylate and activate downstream SMAD proteins upon ligand stimulation [Massagué (2000) *Nat. Rev. Mol. Cell Biol.* 1:169-178]. These type I and type II receptors are transmembrane proteins, composed of a ligand-binding extracellular domain with cysteine-rich region, a transmembrane domain, and a cytoplasmic domain with predicted serine/threonine specificity. Type I receptors are essential for signaling; and type II receptors are required for binding ligands and for expression of type I receptors. Type I and II receptors form a stable complex after ligand binding, resulting in phosphorylation of type I receptors by type II receptors. TGFβ has three mammalian isoforms, TGFβ1, TGFβ2 and TGFβ3, each with distinct functions in vivo. The binding of TGFβs to TβRII is a crucial step in initiating activation of the TGFβ signaling pathway, leading to phosphorylation of SMAD2, and translocation of the activated SMAD2/SMAD4 complex to the nucleus to modulate gene expression.

TβRII is the known type II receptor for TGFβ and binds with high affinity to TGFβ1 and TGFβ3. Human TβRII occurs naturally in at least two isoforms—A (long) and B (short)—generated by alternative splicing in the extracellular domain (ECD) (FIGS. 2 and 1 and SEQ ID NOS: 6 and 5). The long isoform has a 25-amino-acid insertion and the splicing process causes the valine flanking the insertion site in the short isoform to be replaced by an isoleucine in the long isoform. Soluble receptor ectodomains can function as scavengers or ligand traps to inhibit ligand-receptor interactions. Ligand traps such as soluble TβRII-Fc fusion proteins incorporating the native TβRII extracellular domain (ectodomain) will function as pan-inhibitors against TβRII ligands, including, TGFβ1 and TGFβ3. While in some therapeutic settings this broader spectrum of ligand-binding and signal inhibition may be advantageous, in other settings a more selective molecule may be superior. It is highly desirable for ligand traps such as TβRII ectodomain polypeptides to exhibit selective ligand-binding profiles. Thus, in certain aspects, the disclosure provides TβRII polypeptides as antagonists of TGFβ1 or TGFβ3 for use in treating various TGFβ1- or TGFβ3-associated disorders. While not wishing to be bound to any particular mechanism of action, it is expected that such polypeptides act by binding to TGFβ1 or TGFβ3 and inhibiting the ability of these ligands to form ternary signaling complexes.

Myeloproliferative disorders are a group of conditions characterized, in part, by chronic increases in some or all of blood cells (platelets, white blood cells, and red blood cells). This group of blood disorders includes polycythemia vera (PV), essential thrombocythemia (ET), myelofibrosis (e.g., primary myelofibrosis (PMF), post-polycythemia vera myelofibrosis, and post-essential thrombocythemia myelofibrosis), and chronic myeloid leukemia (CML). It is generally thought that myeloproliferative disorders arise from a transformation in a hematopoietic stem cell. Indeed, CML is defined by its causative molecular lesion, the BCR-ABL fusion, which most commonly results from the Philadelphia translocation. Recently, several groups identified a gain-of-function of tyrosine kinase JAK2 (JAK2V617F) as a major molecular defect in patients with in the BCR-ABL-negative myeloproliferative disorders PV, ET, and myelofibrosis (MF). JAK2V617F mice develop pathology that closely resembles human essential thrombocythemia and polycythemia vera [Xing et al. (2008) *Blood* 111: 5109-5117]. As they age, these JAK2V617F mice also develop primary myelofibrosis-like pathology. As disclosed herein, it has been discovered that TβRII-Fc treatment can reduce splenomegaly, fibrosis, and other morbidities in a JAK2V617F disease model.

The data presented herein demonstrates that a TβRII antagonist may be used to treat or prevent complications resultant from the JAK2V617F mutation, which indicates that such therapeutics may be used to treat myeloproliferative disorders (e.g., polycythemia vera, essential thrombocythaemia, and myelofibrosis) as well as Janus kinase-associated disorder (e.g., a JAK2 kinase-associated disorder). In view of the effects on early stage (e.g., splenomegaly) and reduction/delay of onset of late stage disease pathology (e.g., fibrosis and pro-inflammatory cytokines), TβRII antagonists may be particular well suited for treatment of polycythemia vera and essential thrombocythaemia to prevent/delay the onset or reduce the severity of fibrosis and other late stage disease complications and thus prevent/delay the transition into secondary myelofibrosis disease (post-polycythemia vera myelofibrosis and post-essential thrombocythaemia myelofibrosis, respectively). Also, TβRII antagonists clearly demonstrate positive effects in treated last stage fibrosis and inflammation in myelofibrosis patients.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions. The term "sequence similarity," in all its grammatical forms, refers to the degree of identity or correspondence between nucleic acid or amino acid sequences that may or may not share a common evolutionary origin. However, in common usage and in the instant application, the term "homologous," when modified with an adverb such as "highly," may refer to sequence similarity and may or may not relate to a common evolutionary origin.

"Percent (%) sequence identity" with respect to a reference polypeptide (or nucleotide) sequence is defined as the percentage of amino acid residues (or nucleic acids) in a candidate sequence that are identical to the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid (nucleic acid) sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

"Agonize", in all its grammatical forms, refers to the process of activating a protein and/or gene (e.g., by activating or amplifying that protein's gene expression or by inducing an inactive protein to enter an active state) or increasing a protein's and/or gene's activity.

"Antagonize", in all its grammatical forms, refers to the process of inhibiting a protein and/or gene (e.g., by inhibiting or decreasing that protein's gene expression or by inducing an active protein to enter an inactive state) or decreasing a protein's and/or gene's activity.

The terms "about" and "approximately" as used in connection with a numerical value throughout the specification and the claims denotes an interval of accuracy, familiar and acceptable to a person skilled in the art. In general, such interval of accuracy is ±10%. Alternatively, and particularly in biological systems, the terms "about" and "approximately" may mean values that are within an order of magnitude, preferably <5-fold and more preferably <2-fold of a given value.

Numeric ranges disclosed herein are inclusive of the numbers defining the ranges.

The terms "a" and "an" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; and C; A (alone); B (alone); and C (alone).

Throughout this specification, the word "comprise" or variations such as "comprises" or "comprising" will be understood to imply the inclusion of a stated integer or groups of integers but not the exclusion of any other integer or group of integers.

2. TβRII Antagonists

In part, the data presented herein demonstrates that a TβRII antagonist (inhibitor) can be used to treat a myeloproliferative disorder (e.g., polycythemia vera, essential thrombocythemia, and myelofibrosis) and/or a patient with a Janus kinase-associated disorder (e.g., a JAK2 kinase-associated disorder). In particular, a TβRII polypeptide was shown to be effective in improving various myeloproliferative disease complications including, for example, splenomegaly, high inflammatory cytokine levels, and fibrosis. Accordingly, the disclosure provides, in part, various TβRII antagonists that can be used, alone or in combination with one or more additional active agents and/or supportive therapies, to treat, prevent, reduce the progression rate and/or severity of a myeloproliferative disorder and/or a patient with a Janus kinase-associated disorder or one or more complications of a myeloproliferative disorder and/or a Janus kinase-associated disorder. Although TβRII polypeptides may affect myeloproliferative disease and/or a patient with a Janus kinase-associated disorder through a mechanism other than inhibition of TβRII ligands [e.g., inhibition of one or more of TGFβ1, TGFβ2, and/or TGFβ3 may be an indicator of the tendency of an agent to inhibit the activities of a spectrum of additional agents, including, perhaps, other members of the TGF-beta superfamily and such collective inhibition may lead to the desired effect on, for example, a myeloproliferative disease and/or a Janus kinase-associated disorder], other types of TGFβ antagonists [e.g., antagonists of the TβRII receptor, antagonists of one or more TβRII ligands (e.g., TGFβ1, TGFβ2, and TGFβ3), antagonists of one or more TβRII-associated type I receptors (e.g., ALK5), antagonists of one or more TβRII-associated co-receptor (e.g., betaglycan), antagonists or one or more TβRII downstream signaling components (Smads), or combinations of such antagonists] will be useful in the treatment of myeloproliferative disorders and/or Janus kinase-associated disorders, particularly in the treatment, prevention, or reduction in progression rate and/or severity of one or more complications of a myeloproliferative disorder and/or a Janus kinase-associated disorder. Such antagonists include, for example, for example, TβRII polypeptides and variants thereof, anti-TGFβ antibodies, anti-ALK5 antibodies, anti-betaglycan antibodies, and anti-TβRII antibodies; nucleic acids that inhibit the activity or expression (e.g., transcription, translation, secretion from a cell, or combinations thereof) of one or more of TGFβ1, TGFβ2, TGFβ3, ALK5, betaglycan, and TβRII; as well as small molecules that inhibit the activity or expression (e.g., transcription, translation, secretion from a cell, or combinations thereof) of one or more of TGFβ1, TGFβ2, TGFβ3, ALK5, betaglycan and TβRII.

A. TβRII Polypeptides

In certain aspects, a TβRII antagonist to be used in accordance with the methods and uses disclosed herein is a TβRII polypeptide or variant thereof (TβRII antagonist polypeptide). A TβRII polypeptide, or combination of polypeptides, may inhibit, for example, one or more TβRII ligands (e.g., TGFβ1, TGFβ2, and TGFβ3), TβRII receptor, TβRII-associated type I receptor (e.g., ALK5), and/or TβRII-associated co-receptor (e.g., betaglycan). In some embodiments, the ability for a TβRII polypeptide, or combination of polypeptides, to inhibit signaling (e.g., Smad signaling) is determined in a cell-based assay including, for example, those described herein. A TβRII polypeptide, or combination of polypeptides, may be used alone or in combination with one or more additional supportive therapies or active agents to treat, prevent, or reduce the progression rate and/or severity of a myeloproliferative disorder (e.g., myelofibrosis, polycythemia vera, and essential thrombocythaemia) and/or a Janus kinase-associated disorder or one or more complications of a myeloproliferative disorder and/or a Janus kinase-associated disorder (e.g., a JAK2 kinase-associated disorder).

Naturally occurring TβRII proteins are transmembrane proteins, with a portion of the protein positioned outside the cell (the extracellular portion) and a portion of the protein positioned inside the cell (the intracellular portion). Aspects of the present disclosure encompass variant TβRII polypeptides comprising mutations within the extracellular domain and/or truncated portions of the extracellular domain of TβRII. As described above, human TβRII occurs naturally in at least two isoforms—A (long) and B (short)—generated by alternative splicing in the extracellular domain (ECD) (FIGS. 2 and 1 and SEQ ID NOS: 6 and 5). SEQ ID NO: 7, which corresponds to residues 23-159 of SEQ ID NO: 5, depicts the native full-length extracellular domain of the short isoform of TβRII. SEQ ID NO: 13, which corresponds to residues 23-184 of SEQ ID NO: 6, depicts the native full-length extracellular domain of the long isoform of TβRII. Unless noted otherwise, amino acid position numbering with regard to variants based on the TβRII short and long isoforms refers to the corresponding position in the native precursors, SEQ ID NO: 5 and SEQ ID NO:6, respectively.

In certain embodiments, the disclosure provides variant TβRII polypeptides. A TβRII polypeptide of the disclosure may bind to and inhibit the function of a TGFβ superfamily member, such as but not limited to, TGFβ1 or TGFβ3. TβRII polypeptides may include a polypeptide consisting of, or comprising, an amino acid sequence at least 80% identical, and optionally at least 85%, 90%, 91%, 92%, 93%, 94% 95%, 96%, 97%, 98%, 99%, or 100% identical to a truncated ECD domain of a naturally occurring TβRII polypeptide, whose C-terminus occurs at any of amino acids 153-159 (e.g., 153, 154, 155, 156, 157, 158, or 159) of SEQ ID NO: 5. TβRII polypeptides may include a polypeptide consisting of, or comprising, an amino acid sequence at least 80% identical, and optionally at least 85%, 90%, 91%, 92%, 93%, 94% 95%, 96%, 97%, 98%, 99%, or 100% identical to a truncated ECD domain of a naturally occurring TβRII polypeptide, whose C-terminus occurs at any of amino acids 178-184 (e.g., 178, 179, 180, 181, 182, 183, or 184) of SEQ ID NO: 6. Optionally, a TβRII polypeptide does not include more than 5 consecutive amino acids, or more than 10, 20, 30, 40, 50, 52, 60, 70, 80, 90, 100, 150 or 200 or more consecutive amino acids from a sequence consisting of amino acids 160-567 of SEQ ID NO: 5 or from a sequence consisting of amino acids 185-592 of SEQ ID NO: 6. The unprocessed TβRII polypeptide may either include or exclude any signal sequence, as well as any sequence N-terminal to the signal sequence. As elaborated herein, the N-terminus of the mature (processed) TβRII polypeptide may occur at any of amino acids 23-35 of SEQ ID NO: 5 or 23-60 of SEQ ID NO: 6. Examples of mature TβRII polypeptides include, but are not limited to, amino acids 23-159 of SEQ ID NO: 5 (set forth in SEQ ID NO: 7), amino acids 29-159 of SEQ ID NO: 5 (set forth in SEQ ID NO: 105), amino acids 35-159 of SEQ ID NO: 5 (set forth in SEQ ID NO: 10), amino acids 23-153 of SEQ ID NO: 5 (set forth in SEQ ID NO: 11), amino acids 29-153 of SEQ ID NO: 5 (set forth in SEQ ID NO: 48), amino acids 35-153 of SEQ ID NO: 5 (set forth in SEQ ID NO: 47), amino acids 23-184 of SEQ ID NO: 6 (set forth in SEQ ID NO: 13), amino acids 29-184 of SEQ ID NO: 6 (set forth in SEQ ID NO: 15), amino acids 35-184 of SEQ ID NO:6 (set forth in SEQ ID NO: 10), amino acids 23-178 of SEQ ID NO: 6 (set forth in SEQ ID NO: 16), amino acids 29-178 of SEQ ID NO: 6 (set forth in SEQ ID NO: 49), and amino acids 35-178 of SEQ ID NO: 6 (set forth in SEQ ID NO: 47). Likewise, a TβRII polypeptide may comprise a polypeptide that is encoded by nucleotides 73-465 of SEQ ID NO: 30, nucleotides 73-447 of SEQ ID NO: 34, nucleotides 73-465 of SEQ ID NO: 38, nucleotides 91-465 of SEQ ID NO: 38, or nucleotides 109-465 of SEQ ID NO: 38, or silent variants thereof or nucleic acids that hybridize to the complement thereof under stringent hybridization conditions (generally, such conditions are known in the art but may, for example, involve hybridization in 50% v/v formamide, 5×SSC, 2% w/v blocking agent, 0.1% N-lauroylsarcosine, and 0.3% SDS at 65° C. overnight and washing in, for example, 5×SSC at about 65° C.). It will be understood by one of skill in the art that corresponding variants based on the long isoform of TβRII will include nucleotide sequences encoding the 25-amino acid insertion along with a conservative Val-Ile substitution at the flanking position C-terminal to the insertion. The TβRII polypeptides accordingly may include isolated extracellular portions of TβRII polypeptides, including both the short and the long isoforms, variants thereof (including variants that comprise, for example, no more than 2, 3, 4, 5, 10, 15, 20, 25, 30, or 35 amino acid substitutions in the sequence corresponding to amino acids 23-159 of SEQ ID NO: 5 or amino acids 23-184 of SEQ ID NO: 6), fragments thereof, and fusion proteins comprising any of the foregoing, but in each case preferably any of the foregoing TβRII polypeptides will retain substantial affinity for at least one of TGFβ1 or TGFβ3. Generally, a TβRII polypeptide will be designed to be soluble in aqueous solutions at biologically relevant temperatures, pH levels, and osmolarity.

In some embodiments, the variant TβRII polypeptides of the disclosure comprise one or more mutations in the extracellular domain that confer an altered ligand binding profile. A TβRII polypeptide may include one, two, five or more alterations in the amino acid sequence relative to the corresponding portion of a naturally occurring TβRII polypeptide. In some embodiments, the mutation results in a substitution, insertion, or deletion at the position corresponding to position 70 of SEQ ID NO: 5. In some embodiments, the mutation results in a substitution, insertion, or deletion at the position corresponding to position 110 of SEQ ID NO: 5. Examples include, but are not limited to, an N to D substitution or a D to K substitution in the positions corresponding to positions 70 and 110, respectively, of SEQ ID NO: 5. Examples of such variant TβRII polypeptides include, but are not limited to, the sequences set forth in SEQ ID NO: 8, SEQ ID NO:14, SEQ ID NO: 12 and SEQ ID NO: 17. A TβRII polypeptide may comprise a polypeptide or portion thereof that is encoded by nucleotides 73-483 of SEQ ID NO: 26, nucleotides 73-465 of SEQ ID NO: 42 or silent variants thereof or nucleic acids that hybridize to the complement thereof under stringent hybridization conditions.

In some embodiments, the variant TβRII polypeptides of the disclosure further comprise an insertion of 36 amino acids (SEQ ID NO: 18) between the pair of glutamate residues (positions 151 and 152 of SEQ ID NO: 5, or positions 176 and 177 of SEQ ID NO: 6) located near the C-terminus of the human TβRII ECD, as occurs naturally in the human TβRII isoform C (Konrad et al., BMC Genomics 8:318, 2007).

The disclosure further demonstrates that TβRII polypeptides can be modified to selectively antagonize TβRII ligands. Data presented here show that Fc fusion proteins comprising shorter N-terminally and C-terminally truncated variants of TβRII polypeptides display differential inhibitory effects on cellular signaling mediated by TGFβ1 and TGFβ3. Specifically, N-terminally truncated variants beginning at amino acids 29 or 35 of SEQ ID NO: 5 and carrying, respectively, a 6- or 12-amino acid N-terminal truncation of the extracellular domain, were found to significantly reduced potency for inhibiting TGFβ3 while maintaining an intermediate degree of TGFβ1 inhibition, compared to the full length extracellular domain of the short isoform of TβRII. C-terminally truncated variants, ending at amino acid 153 of SEQ ID NO: 5 and carrying a 6-amino acid C-terminal truncation of the extracellular domain had no substantial effect on ligand binding and may therefore be used interchangeably with full length versions. An N to D substitution at the position corresponding to position 70 of SEQ ID NO: 5, was found to inhibit TGFβ3 potently and negligible effect on TGFβ1. The N70 residue represents a potential glycosylation site. Further, an Fc fusion protein comprising a D to K substitution at the position corresponding to position 110 of SEQ ID NO: 5, was found to significantly reduced potency for inhibiting TGFβ1 while maintaining an intermediate degree of TGFβ3 inhibition compared to the full length extracellular domain of the short isoform of TβRII. The region around position 110 has not been associated with selectivity for the known TβRII ligands TGFβ1, TGFβ2 and TGFβ3. Thus, unexpectedly, TβRII polypeptides that contain mutations in the ECD, such as but not limited to, N70D and D110K (the numbering of the residues corresponds to that of SEQ ID NO: 5) and/or begin between amino acids 29 and 35 and/or terminate between amino acid 153 and amino acid 159 are all expected to be active and exhibit widely different inhibitory potencies towards the different ligands. Any of these truncated variant forms may be desirable to use, depending on the clinical or experimental setting.

In certain embodiments, a TβRII polypeptide binds to TGFβ1, and the TβRII polypeptide does not show substantial binding to TGFβ3. In certain embodiments, a TβRII polypeptide binds to TGFβ3, and the TβRII polypeptide does not show substantial binding to TGFβ1. Binding may be assessed, e.g., using purified proteins in solution or in a surface plasmon resonance system, such as a Biacore™ system.

In certain embodiments, a TβRII polypeptide inhibits TGFβ1 cellular signaling, and the TβRII polypeptide has an intermediate or limited inhibitory effect on TGFβ3. In certain embodiments, a TβRII polypeptide inhibits TGFβ3 cellular signaling, and the TβRII polypeptide has an intermediate or limited inhibitory effect on TGFβ1. Inhibitory effect on cell signaling can be assayed by methods known in the art.

Taken together, an active portion of a TβRII polypeptide may comprise amino acid sequences 23-153, 23-154, 23-155, 23-156, 23-157, or 23-158 of SEQ ID NO: 5, as well as variants of these sequences starting at any of amino acids 24-35 of SEQ ID NO: 5. Similarly, an active portion of a TβRII polypeptide may comprise amino acid sequences 23-178, 23-179, 23-180, 23-181, 23-182, or 23-183 of SEQ ID NO: 6, as well as variants of these sequences starting at any of amino acids 24-60 of SEQ ID NO: 6. Exemplary TβRII polypeptides comprise amino acid sequences 29-159, 35-159, 23-153, 29-153 and 35-153 of SEQ ID NO: 5 or amino acid sequences 29-184, 60-184, 23-178, 29-178 and 60-178 of SEQ ID NO: 6. Variants within these ranges are also contemplated, particularly those having at least 85%, 90%, 91%, 92%, 93%, 94% 95%, 96%, 97%, 98%, 99%, or 100% identity to the corresponding portion of SEQ ID NO: 5 or SEQ ID NO: 6. A TβRII polypeptide may be selected that does not include the sequence consisting of amino acids 160-567 of SEQ ID NO:5 or amino acids 185-592 of SEQ ID NO:6.

As described above, the disclosure provides TβRII polypeptides sharing a specified degree of sequence identity or similarity to a naturally occurring TβRII polypeptide. To determine the percent identity of two amino acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The amino acid residues at corresponding amino acid positions are then compared. When a position in the first sequence is occupied by the same amino acid residue as the corresponding position in the second sequence, then the molecules are identical at that position (as used herein amino acid "identity" is equivalent to amino acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

In one embodiment, the percent identity between two amino acid sequences is determined using the Needleman and Wunsch (J Mol. Biol. (48):444-453 (1970)) algorithm which has been incorporated into the GAP program in the GCG software package. In a specific embodiment, the following parameters are used in the GAP program: either a Blosum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (Devereux, J., et al., Nucleic Acids Res. 12(1):387 (1984)). Exemplary parameters include using a NWSgapdna.CMP matrix and a gap weight of 40, 50, 60, 70, or 80 and a length weight of 1, 2, 3, 4, 5, or 6. Unless otherwise specified, percent identity between two amino acid sequences is to be determined using the GAP program using a Blosum 62 matrix, a GAP weight of 10 and a length weight of 3, and if such algorithm cannot compute the desired percent identity, a suitable alternative disclosed herein should be selected.

In another embodiment, the percent identity between two amino acid sequences is determined using the algorithm of E. Myers and W. Miller (CABIOS, 4:11-17 (1989)) which has been incorporated into the ALIGN program (version 2.0), using a PAM120 weight residue table, a gap length penalty of 12 and a gap penalty of 4.

Another embodiment for determining the best overall alignment between two amino acid sequences can be determined using the FASTDB computer program based on the algorithm of Brutlag et al. (*Comp. App. Biosci.,* 6:237-245 (1990)). In a sequence alignment the query and subject sequences are both amino acid sequences. The result of said global sequence alignment is presented in terms of percent identity. In one embodiment, amino acid sequence identity is performed using the FASTDB computer program based on the algorithm of Brutlag et al. (*Comp. App. Biosci.,* 6:237-245 (1990)). In a specific embodiment, parameters employed to calculate percent identity and similarity of an amino acid alignment comprise: Matrix=PAM 150, k-tuple=2, Mismatch Penalty=1, Joining Penalty=20, Randomization Group Length=0, Cutoff Score=1, Gap Penalty=5 and Gap Size Penalty=0.05.

TβRII polypeptides may additionally include any of various leader sequences at the N-terminus. Such a sequence would allow the peptides to be expressed and targeted to the secretion pathway in a eukaryotic system. See, e.g., Ernst et al., U.S. Pat. No. 5,082,783 (1992). Alternatively, a native TβRII signal sequence may be used to effect extrusion from the cell. Possible leader sequences include native leaders, tissue plasminogen activator (TPA) and honeybee mellitin (SEQ ID NOs. 22-24, respectively). Examples of TβRII-Fc fusion proteins incorporating a TPA leader sequence include SEQ ID NOs: 25, 27, 29, 31, 33, 35, 37, 39, 41, 43, 101 and 103. Processing of signal peptides may vary depending on the leader sequence chosen, the cell type used and culture conditions, among other variables, and therefore actual N-terminal start sites for mature TβRII polypeptides may shift by 1, 2, 3, 4 or 5 amino acids in either the N-terminal or C-terminal direction. Examples of TβRII-Fc fusion proteins include SEQ ID NOs: 25, 27, 29, 31, 33, 35, 37, 39, 41, 43, 50, 53, 54, 55, 56, 57, 58, 59, 60, 61, 62, 101, and 103, as shown herein with the TβRII polypeptide portion underlined (see Examples). It will be understood by one of skill in the art that corresponding variants based on the long isoform of TβRII will include the 25-amino acid insertion along with a conservative Val-Ile substitution at the flanking position C-terminal to the insertion. In certain aspects the disclosure relates to a TβRII polypeptide that comprises amino acid sequence that is at least 80%, 85%, 90%, 91%, 92%, 93%, 94%, 95%, 96%, 97%, 98%, 99%, or 100% identical to the amino acid sequence of SEQ ID NO: 101 as well as uses thereof in accordance with the methods described herein. In certain aspects the disclosure relates to a TβRII polypeptide that comprises an amino acid sequence that is at least 80%, 85%, 90%, 91%, 92%, 93%, 94%, 95%, 96%, 97%, 98%, 99%, or 100% identical to the amino acid sequence of SEQ ID NO: 103 as well as uses thereof in accordance with the methods described herein. In certain aspects the disclosure relates to a TβRII polypeptide that comprises amino acid sequence that is at least 80%, 85%, 90%, 91%, 92%, 93%, 94%, 95%, 96%, 97%, 98%, 99%, or 100% identical to an amino acid sequence that begins at any one of amino acids 25-46 (e.g., 25, 26, 27, 28, 29, 30, 31, 32, 33, 34, 35, 36, 37, 38, 39, 40, 41, 42, 43, 44, 45, or 46) of SEQ ID NO: 101 and ends and any one of amino acids 170-186 (e.g., 170, 171, 172, 173, 174, 175, 176, 177, 178, 179, 180, 181, 182, 183, 184, 185, or 186) of SEQ ID NO: 101 as well as uses thereof in accordance with the methods described herein.

In certain embodiments, the present disclosure contemplates specific mutations of the TβRII polypeptides so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (or asparagine-X-serine) (where "X" is any amino acid) which is specifically recognized by appropriate cellular glycosylation enzymes. The alteration may also be made by the addition of, or substitution by, one or more serine or threonine residues to the sequence of the wild-type TβRII polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a TβRII polypeptide is by chemical or enzymatic coupling of glycosides to the TβRII polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on a TβRII polypeptide may be accomplished chemically and/or enzymatically. Chemical deglycosylation may involve, for example, exposure of the TβRII polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on TβRII polypeptides can be achieved by the use of a variety of endo- and exo-glycosidases as described by Thotakura et al. (1987) Meth. Enzymol. 138:350. The sequence of a TβRII polypeptide may be adjusted, as appropriate, depending on the type of expression system used, as mammalian, yeast, insect and plant cells may all introduce differing glycosylation patterns that can be affected by the amino acid sequence of the peptide. In general, TβRII polypeptides for use in humans will be expressed in a mammalian cell line that provides proper glycosylation, such as HEK293 or CHO cell lines, although other mammalian expression cell lines, yeast cell lines with engineered glycosylation enzymes, and insect cells are expected to be useful as well.

This disclosure further contemplates a method of generating mutants, particularly sets of combinatorial mutants of a TβRII polypeptide, as well as truncation mutants; pools of combinatorial mutants are especially useful for identifying functional variant sequences. The purpose of screening such combinatorial libraries may be to generate, for example, TβRII polypeptide variants which can act as either agonists or antagonist, or alternatively, which possess novel activities all together. A variety of screening assays are provided below, and such assays may be used to evaluate variants. For example, a TβRII polypeptide variant may be screened for ability to bind to a TβRII ligand, to prevent binding of a TβRII ligand to a TβRII polypeptide or to interfere with signaling caused by a TβRII ligand. The activity of a TβRII polypeptide or its variants may also be tested in a cell-based or in vivo assay, particularly any of the assays disclosed in the Examples.

Combinatorially-derived variants can be generated which have a selective or generally increased potency relative to a TβRII polypeptide comprising an extracellular domain of a naturally occurring TβRII polypeptide. Likewise, mutagenesis can give rise to variants which have serum half-lives dramatically different than the corresponding wild-type TβRII polypeptide. For example, the altered protein can be rendered either more stable or less stable to proteolytic degradation or other processes which result in destruction of, or otherwise elimination or inactivation of, a native TβRII polypeptide. Such variants, and the genes which encode them, can be utilized to alter TβRII polypeptide levels by modulating the half-life of the TβRII polypeptides. For instance, a short half-life can give rise to more transient biological effects and can allow tighter control of recombinant TβRII polypeptide levels within the patient. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential TβRII polypeptide sequences. For instance, a mixture of synthetic oligonucleotides can be enzymatically ligated into gene sequences such that the degenerate set of potential TβRII polypeptide nucleotide sequences are expressible as individual polypeptides, or alternatively, as a set of larger fusion proteins (e.g., for phage display).

There are many ways by which the library of potential TβRII polypeptide variants can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, TβRII polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of TβRII polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of TβRII polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include TβRII ligand binding assays and ligand-mediated cell signaling assays.

In certain embodiments, the TβRII polypeptides of the disclosure may further comprise post-translational modifications in addition to any that are naturally present in the TβRII polypeptides. Such modifications include, but are not limited to, acetylation, carboxylation, glycosylation, phosphorylation, lipidation, pegylation (polyethylene glycol) and acylation. As a result, the modified TβRII polypeptides may contain non-amino acid elements, such as polyethylene glycols, lipids, mono- or poly-saccharides, and phosphates. Effects of such non-amino acid elements on the functionality of a TβRII polypeptide may be tested as described herein for other TβRII polypeptide variants. When a TβRII polypeptide is produced in cells by cleaving a nascent form of the TβRII polypeptide, post-translational processing may also be important for correct folding and/or function of the protein. Different cells (such as CHO, HeLa, MDCK, 293, WI38, NIH-3T3 or HEK-293) have specific cellular machinery and characteristic mechanisms for such post-translational activities and may be chosen to ensure the correct modification and processing of the TβRII polypeptides.

In certain aspects, functional variants or modified forms of the TβRII polypeptides include fusion proteins having at least a portion of the TβRII polypeptides and one or more fusion domains. Well-known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$) (SEQ ID NO: 106) fusion partners. As another example, a fusion domain may be selected so as to facilitate detection of the TβRII polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus hemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, a TβRII polypeptide is fused with a domain that stabilizes the TβRII polypeptide in vivo (a "stabilizer" domain). By "stabilizing" is meant anything that increases serum half-life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains.

As specific examples, the present disclosure provides fusion proteins comprising variants of TβRII polypeptides fused to one of three Fc domain sequences (e.g., SEQ ID NOs: 19, 20, and 21 as well as sequences 85%, 90%, 91%, 92%, 93%, 94% 95%, 96%, 97%, 98%, 99%, or 100% identical to SEQ ID NOs: 19, 20, and 21). Optionally, the Fc domain has one or more mutations at residues such as Asp-265, Lys-322, and Asn-434 (numbered in accordance with the corresponding full-length IgG). In certain cases, the mutant Fc domain having one or more of these mutations (e.g., Asp-265 mutation) has reduced ability of binding to the Fcy receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

It is understood that different elements of the fusion proteins may be arranged in any manner that is consistent with the desired functionality. For example, a TβRII polypeptide may be placed C-terminal to a heterologous domain, or, alternatively, a heterologous domain may be placed C-terminal to a TβRII polypeptide. The TβRII polypeptide domain and the heterologous domain need not be adjacent in a fusion protein, and additional domains or amino acid sequences may be included C- or N-terminal to either domain or between the domains.

As used herein, the term "immunoglobulin Fc domain" or simply "Fc" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain.

In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant region is discussed in detail in U.S. Pat. Nos. 5,541,087 and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a $CH_3$ domain of Fc gamma or the homologous domains in any of IgA, IgD, IgE, or IgM.

Furthermore, it is contemplated that substitution or deletion of amino acids within the immunoglobulin heavy chain constant regions may be useful in the practice of the methods and compositions disclosed herein. One example would be to introduce amino acid substitutions in the upper CH2 region to create an Fc variant with reduced affinity for Fc receptors (Cole et al. (1997) J. Immunol. 159:3613).

The application further provides TβRII-Fc fusion proteins with engineered or variant Fc regions. Such antibodies and Fc fusion proteins may be useful, for example, in modulating effector functions, such as, antigen-dependent cytotoxicity (ADCC) and complement-dependent cytotoxicity (CDC). Additionally, the modifications may improve the stability of the antibodies and Fc fusion proteins. Amino acid sequence variants of the antibodies and Fc fusion proteins are prepared by introducing appropriate nucleotide changes into the DNA, or by peptide synthesis. Such variants include, for example, deletions from, and/or insertions into and/or substitutions of, residues within the amino acid sequences of the antibodies and Fc fusion proteins disclosed herein. Any combination of deletion, insertion, and substitution is made to arrive at the final construct, provided that the final construct possesses the desired characteristics. The amino acid changes also may alter post-translational processes of the antibodies and Fc fusion proteins, such as changing the number or position of glycosylation sites.

Antibodies and Fc fusion proteins with reduced effector function may be produced by introducing changes in the amino acid sequence, including, but are not limited to, the Ala-Ala mutation described by Bluestone et al. (see WO 94/28027 and WO 98/47531; also see Xu et al. 2000 Cell Immunol 200; 16-26). Thus, in certain embodiments, antibodies and Fc fusion proteins of the disclosure with mutations within the constant region including the Ala-Ala mutation may be used to reduce or abolish effector function. According to these embodiments, antibodies and Fc fusion proteins may comprise a mutation to an alanine at position 234 or a mutation to an alanine at position 235, or a combination thereof. In one embodiment, the antibody or Fc fusion protein comprises an IgG4 framework, wherein the Ala-Ala mutation would describe a mutation(s) from phenylalanine to alanine at position 234 and/or a mutation from leucine to alanine at position 235. In another embodiment, the antibody or Fc fusion protein comprises an IgG1 framework, wherein the Ala-Ala mutation would describe a mutation(s) from leucine to alanine at position 234 and/or a mutation from leucine to alanine at position 235. The antibody or Fc fusion protein may alternatively or additionally carry other mutations, including the point mutation K322A in the CH2 domain (Hezareh et al. 2001 J Virol. 75: 12161-8).

In particular embodiments, the antibody or Fc fusion protein may be modified to either enhance or inhibit complement dependent cytotoxicity (CDC). Modulated CDC activity may be achieved by introducing one or more amino acid substitutions, insertions, or deletions in an Fc region (see, e.g., U.S. Pat. No. 6,194,551). Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing.

See Caron et al., J. Exp Med. 176:1191-1195 (1992) and Shopes, B. J. Immunol. 148:2918-2922 (1992), WO99/51642, Duncan & Winter Nature 322: 738-40 (1988); U.S. Pat. No. 5,648,260; U.S. Pat. No. 5,624,821; and WO94/29351.

In certain embodiments, the present disclosure makes available isolated and/or purified forms of the TβRII polypeptides, which are isolated from, or otherwise substantially free of (e.g., at least 80%, 90%, 95%, 96%, 97%, 98%, or 99% free of), other proteins and/or other TβRII polypeptide species. TβRII polypeptides will generally be produced by expression from recombinant nucleic acids.

In certain embodiments, the disclosure includes nucleic acids encoding soluble TβRII polypeptides comprising the coding sequence for an extracellular portion of a TβRII protein. In further embodiments, this disclosure also pertains to a host cell comprising such nucleic acids. The host cell may be any prokaryotic or eukaryotic cell. For example, a polypeptide of the present disclosure may be expressed in bacterial cells such as E. coli, insect cells (e.g., using a baculovirus expression system), yeast, or mammalian cells. Other suitable host cells are known to those skilled in the art. Accordingly, some embodiments of the present disclosure further pertain to methods of producing the TβRII polypeptides.

B. Nucleic Acids Encoding TβRII Polypeptides

In certain aspects, the disclosure provides isolated and/or recombinant nucleic acids encoding any of the TβRII polypeptides, including fragments, functional variants and fusion proteins disclosed herein. SEQ ID NO: 26, 28, 30, 32, 34, 36, 38, 40, 42, 44, and 102 encode variants of TβRII extracellular domain fused to an IgG2 Fc or an N-terminally truncated IgG1 Fc domain. The subject nucleic acids may be single-stranded or double stranded. Such nucleic acids may be DNA or RNA molecules. These nucleic acids may be used, for example, in methods for making TβRII polypeptides or as direct therapeutic agents (e.g., in an antisense, RNAi or gene therapy approach).

In certain aspects, the subject nucleic acids encoding TβRII polypeptides are further understood to include nucleic acids that are variants of SEQ ID NOs: 26, 28, 30, 32, 34, 36, 38, 40, 42, 44 and 102. Variant nucleotide sequences include sequences that differ by one or more nucleotide substitutions, additions or deletions, such as allelic variants.

In certain embodiments, the disclosure provides isolated or recombinant nucleic acid sequences that are at least 80%, 85%, 90%, 91%, 92%, 93%, 94% 95%, 96%, 97%, 98%, 99%, or 100% identical to SEQ ID NOs: 26, 28, 30, 32, 34, 36, 38, 40, 42, 44, and 102. One of ordinary skill in the art will appreciate that nucleic acid sequences complementary to SEQ ID NOs: 26, 28, 30, 32, 34, 36, 38, 40, 42, 44, and 102, and variants of SEQ ID NOs: 26, 28, 30, 32, 34, 36, 38, 40, 42, 44, and 102 are also within the scope of this disclosure. In further embodiments, the nucleic acid sequences of the disclosure can be isolated, recombinant, and/or fused with a heterologous nucleotide sequence, or in a DNA library.

In other embodiments, nucleic acids of the disclosure also include nucleotide sequences that hybridize under highly stringent conditions to the nucleotide sequences designated in SEQ ID NOs: 26, 28, 30, 32, 34, 36, 38, 40, 42, 44, and 102 complement sequences of SEQ ID NOs: 26, 28, 30, 32, 34, 36, 38, 40, 42, 44, and 102, or fragments thereof. As discussed above, one of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In some embodiments, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 26, 28, 30, 32, 34, 36, 38, 40, 42, 44, and 102 due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

It will be appreciated by one of skill in the art that corresponding variants based on the long isoform of TβRII will include nucleotide sequences encoding the 25-amino acid insertion along with a conservative Val-Ile substitution at the flanking position C-terminal to the insertion. It will also be appreciated that corresponding variants based on either the long (A) or short (B) isoforms of TβRII will include variant nucleotide sequences comprising an insertion of 108 nucleotides, encoding a 36-amino-acid insertion (SEQ ID NO: 18), at the same location described for naturally occurring TβRII isoform C (see Exemplification).

In certain embodiments, the recombinant nucleic acids of the disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects disclosed herein, the subject nucleic acid is provided in an expression vector comprising a nucleotide sequence encoding a TβRII polypeptide and operably linked to at least one regulatory sequence. Regulatory sequences are art-recognized and are selected to direct expression of the TβRII polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a TβRII polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid included in the disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant TβRII polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual,* 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In certain embodiments, a vector will be designed for production of the subject TβRII polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). In a preferred embodiment, a vector will be designed for production of the subject TβRII polypeptides in HEK-293 cells. As will be apparent, the subject gene constructs can be used to cause expression of the subject TβRII polypeptides in cells propagated in culture, e.g., to produce proteins, including fusion proteins or variant proteins, for purification.

This disclosure also pertains to a host cell transfected with a recombinant gene including a coding sequence (e.g., SEQ ID NOs: 26, 28, 30, 32, 34, 36, 38, 40, 42, 44, and 102) for one or more of the subject TβRII polypeptides. The host cell may be any prokaryotic or eukaryotic cell. For example, a TβRII polypeptide disclosed herein may be expressed in bacterial cells such as *E. coli*, insect cells (e.g., using a baculovirus expression system), yeast, or mammalian cells. Other suitable host cells are known to those skilled in the art.

Accordingly, the present disclosure further pertains to methods of producing the subject TβRII polypeptides. For example, a host cell transfected with an expression vector encoding a TβRII polypeptide can be cultured under appropriate conditions to allow expression of the TβRII polypeptide to occur. The TβRII polypeptide may be secreted and isolated from a mixture of cells and medium containing the TβRII polypeptide. Alternatively, the TβRII polypeptide may be retained cytoplasmically or in a membrane fraction and the cells harvested, lysed and the protein isolated. A cell culture includes host cells, and media. Suitable media for cell culture are well known in the art. The subject TβRII polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the TβRII polypeptides and affinity purification with an agent that binds to a domain fused to the TβRII polypeptide (e.g., a protein A column may be used to purify a TβRII-Fc fusion). In a preferred embodiment, the TβRII polypeptide is a fusion protein containing a domain which facilitates its purification. As an example, purification may be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

In another embodiment, a fusion gene coding for a purification leader sequence, such as a poly-(His)/enterokinase cleavage site sequence at the N-terminus of the desired portion of the recombinant TβRII polypeptide, can allow purification of the expressed fusion protein by affinity chromatography using a $Ni^{2+}$ metal resin. The purification leader sequence can then be subsequently removed by treatment with enterokinase to provide the purified TβRII polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

Examples of categories of nucleic acid compounds that are antagonists of TβRII, TGFβ1, and TGFβ3 include antisense nucleic acids, RNAi constructs and catalytic nucleic acid constructs. A nucleic acid compound may be single or double stranded. A double stranded compound may also include regions of overhang or non-complementarity, where one or the other of the strands is single-stranded. A single-stranded compound may include regions of self-complementarity, meaning that the compound forms a so-called "hairpin" or "stem-loop" structure, with a region of double helical structure. A nucleic acid compound may comprise a nucleotide sequence that is complementary to a region consisting of no more than 1000, no more than 500, no more than 250, no more than 100 or no more than 50, 35, 30, 25, 22, 20 or 18 nucleotides of the full-length TβRII nucleic acid sequence or ligand nucleic acid sequence. The region of complementarity will preferably be at least 8 nucleotides, and optionally at least 10 or at least 15 nucleotides, such as between 15 and 25 nucleotides. A region of complementarity may fall within an intron, a coding sequence, or a noncoding sequence of the target transcript, such as the coding sequence portion. Generally, a nucleic acid compound will have a length of about 8 to about 500 nucleotides or base pairs in length, such as about 14 to about 50 nucleotides. A nucleic acid may be a DNA (particularly for use as an antisense), RNA, or RNA:DNA hybrid. Any one strand may include a mixture of DNA and RNA, as well as modified forms that cannot readily be classified as either DNA or RNA. Likewise, a double-stranded compound may be DNA:DNA, DNA:RNA or RNA:RNA, and any one strand may also include a mixture of DNA and RNA, as well as modified forms that cannot readily be classified as either DNA or RNA. A nucleic acid compound may include any of a variety of modifications, including one or modifications to the backbone (the sugar-phosphate portion in a natural nucleic acid, including internucleotide linkages) or the base portion (the purine or pyrimidine portion of a natural nucleic acid). An antisense nucleic acid compound will preferably have a length of about 15 to about 30 nucleotides and will often contain one or more modifications to improve characteristics such as stability in the serum, in a cell or in a place where the compound is likely to be delivered, such as the stomach in the case of orally delivered compounds and the lung for inhaled compounds. In the case of an RNAi construct, the strand complementary to the target transcript will generally be RNA or modifications thereof. The other strand may be RNA, DNA, or any other variation. The duplex portion of double-stranded or single-stranded "hairpin" RNAi construct will preferably have a length of 18 to 40 nucleotides in length and optionally about 21 to 23 nucleotides in length, so long as it serves as a Dicer substrate. Catalytic or enzymatic nucleic acids may be ribozymes or DNA enzymes and may also contain modified forms. Nucleic acid compounds may inhibit expression of the target by about 50%, 75%, 90%, or more when contacted with cells under physiological conditions and at a concentration where a nonsense or sense control has little or no effect. Preferred concentrations for testing the effect of nucleic acid compounds are 1, 5 and 10 micromolar. Nucleic acid compounds may also be tested for effects on, for example, angiogenesis.

C. Antibody Antagonists

In certain aspects, a TβRII antagonist to be used in accordance with the methods and uses disclosed herein is an antibody (TβRII antagonist antibody) or combination of antibodies. A TβRII antagonist antibody, or combination of antibodies, may inhibit and/or bind to, for example, one or more TβRII ligands (e.g., TGFβ1, TGFβ2, and TGFβ3), TβRII receptor, TβRII-associated type I receptor (e.g., ALK5), and/or TβRII co-receptor (e.g., betaglycan). In some embodiments, the ability for a TβRII antagonist antibody, or combination of antibody, to inhibit signaling (e.g., Smad signaling) and/or bind to a target is determined in an in vitro or cell-based assay including, for example, those described herein. As described herein, a TβRII antagonist antibody, or combination of antagonist antibodies, may be used alone or in combination with one or more additional supportive therapies or active agents to treat, prevent, or reduce the progression rate and/or severity of a myeloproliferative disorder (e.g., myelofibrosis, polycythemia vera, and essential thrombocythaemia) and/or a Janus kinase-associated disorder (e.g., a JAK2 kinase-associated disorder) or one or more complications of a myeloproliferative disorders and/or a Janus kinase-associated disorder.

In certain embodiments, a TβRII antagonist antibody, or combination of antibodies, is an antibody that inhibits at least TGFβ1. Therefore, in some embodiments, a TβRII antagonist antibody, or combination of antibodies, binds to at least TGFβ1. As used herein, a TGFβ1 antibody (anti-TGFβ1 antibody) generally refers to an antibody that is capable of binding to TGFβ1 with sufficient affinity such that the antibody is useful as a diagnostic and/or therapeutic agent in targeting TGFβ1. In certain embodiments, the extent of binding of an anti-TGFβ1 antibody to an unrelated, non-TGFβ1 protein is less than about 10%, 9%, 8%, 7%, 6%, 5%, 4%, 3%, 2%, or less than 1% of the binding of the antibody to TGFβ1 as measured, for example, by a radioimmunoassay (MA). In certain embodiments, an anti-TGFβ1 antibody binds to an epitope of TGFβ1 that is conserved among TGFβ1 from different species. In certain preferred embodiments, an anti-TGFβ1 antibody binds to human TGFβ1. In some embodiments, a TGFβ1 antibody may inhibit TGFβ1 from binding to a type I, type II, and/or co-receptor (e.g., TβRII, ALK5, and/or betaglycan) and thus inhibit TGFβ1 signaling (e.g., Smad signaling). It should be noted that TGFβ1 shares some sequence homology to TGFβ2 and TGFβ3. Therefore antibodies that bind TGFβ1, in some embodiments, may also bind to TGFβ2 and/or TGFβ3. In some embodiments, the disclosure relates to a multispecific antibody (e.g., bi-specific antibody), and uses thereof, that binds to TGFβ1 and further binds to, for example, one or more additional TβRII ligands (e.g., TGFβ2, TGFβ3, or TGFβ2 and TGFβ3), one or more type I and/or type II receptors (e.g., TβRII and ALK5), and/or one or more co-receptors (e.g., betaglycan). In some embodiments, a multispecific antibody that binds to TGFβ1 does not bind or does not substantially bind to TGFβ2 (e.g., binds to TGFβ2 with a $K_D$ of greater than $1 \times 10^{-7}$ M or has relatively modest binding, e.g., about $1 \times 10^{-8}$ M or about $1 \times 10^{-9}$ M). In some embodiments, a multispecific antibody that binds to TGFβ1 further binds to TGFβ3 but does not bind or does not substantially bind to TGFβ2 (e.g., binds to TGFβ2 with a $K_D$ of greater than $1 \times 10^{-7}$ M or has relatively modest binding, e.g., about $1 \times 10^{-8}$ M or about $1 \times 10^{-9}$ M). In some embodiments, the disclosure relates to combinations of antibodies, and uses thereof, wherein the combination of antibodies comprises a TGFβ1 antibody and one or more additional antibodies that bind to, for example, one or more additional TβRII ligands (e.g., TGFβ2, TGFβ3, or TGFβ2 and TGFβ3), one or more type I and/or type II receptors (e.g., TβRII and ALK5), and/or one or more co-receptors (e.g., betaglycan). In some embodiments, a combination of antibodies that comprises a TGFβ1 antibody does not comprise a TGFβ2 antibody. In some embodiments, a combination of antibodies that comprises a TGFβ1 antibody further comprises a TGFβ3 antibody but does not comprise a TGFβ2 antibody.

In certain embodiments, a TβRII antagonist antibody, or combination of antibodies, is an antibody that inhibits at least TGFβ2. Therefore, in some embodiments, a TβRII antagonist antibody, or combination of antibodies, binds to at least TGFβ2. As used herein, a TGFβ2 antibody (anti-TGFβ2 antibody) generally refers to an antibody that is capable of binding to TGFβ2 with sufficient affinity such that the antibody is useful as a diagnostic and/or therapeutic agent in targeting TGFβ2. In certain embodiments, the extent of binding of an anti-TGFβ2 antibody to an unrelated, non-TGFβ2 protein is less than about 10%, 9%, 8%, 7%, 6%, 5%, 4%, 3%, 2%, or less than 1% of the binding of the antibody to TGFβ2 as measured, for example, by a radioimmunoassay (MA). In certain embodiments, an anti-TGFβ2 antibody binds to an epitope of TGFβ2 that is conserved among TGFβ2 from different species. In certain preferred embodiments, an anti-TGFβ2 antibody binds to human TGFβ2. In some embodiments, a TGFβ2 antibody may inhibit TGFβ2 from binding to a type I, type II, and/or co-receptor (e.g., TβRII, ALK5, and/or betaglycan) and thus inhibit TGFβ2 signaling (e.g., Smad signaling). It should be noted that TGFβ2 shares some sequence homology to TGFβ1 and TGFβ3. Therefore antibodies that bind TGFβ2, in some embodiments, may also bind to TGFβ1 and/or TGFβ3. In some embodiments, the disclosure relates to a multispecific antibody (e.g., bi-specific antibody), and uses thereof, that binds to TGFβ2 and further binds to, for example, one or more additional TβRII ligands (e.g., TGFβ1, TGFβ3, or TGFβ1 and TGFβ3), one or more type I and/or type II receptors (e.g., TβRII and ALK5), and/or one or more co-receptors (e.g., betaglycan) In some embodiments, the disclosure relates to combinations of antibodies, and uses thereof, wherein the combination of antibodies comprises a TGFβ2 antibody and one or more additional antibodies that bind to, for example, one or more additional TβRII ligands (e.g., TGFβ1, TGFβ3, or TGFβ1 and TGFβ3), one or more type I and/or type II receptors (e.g., TβRII and ALK5), and/or one or more co-receptors (e.g., betaglycan).

In certain embodiments, a TβRII antagonist antibody, or combination of antibodies, is an antibody that inhibits at least TGFβ3. Therefore, in some embodiments, a TβRII antagonist antibody, or combination of antibodies, binds to at least TGFβ3. As used herein, a TGFβ3 antibody (anti-TGFβ3 antibody) generally refers to an antibody that is capable of binding to TGFβ3 with sufficient affinity such that the antibody is useful as a diagnostic and/or therapeutic agent in targeting TGFβ3. In certain embodiments, the extent of binding of an anti-TGFβ3 antibody to an unrelated, non-TGFβ3 protein is less than about 10%, 9%, 8%, 7%, 6%, 5%, 4%, 3%, 2%, or less than 1% of the binding of the antibody to TGFβ3 as measured, for example, by a radioimmunoassay (MA). In certain embodiments, an anti-TGFβ3 antibody binds to an epitope of TGFβ3 that is conserved among TGFβ3 from different species. In certain preferred embodiments, an anti-TGFβ3 antibody binds to human TGFβ3. In some embodiments, a TGFβ3 antibody may inhibit TGFβ3 from binding to a type I, type II, and/or co-receptor (e.g., TβRII, ALK5, and/or betaglycan) and thus inhibit TGFβ3 signaling (e.g., Smad signaling). It should be noted that TGFβ3 shares some sequence homology to TGFβ2 and TGFβ1. Therefore antibodies that bind TGFβ3, in some embodiments, may also bind to TGFβ2 and/or TGFβ1. In some embodiments, the disclosure relates to a multispecific antibody (e.g., bi-specific antibody), and uses thereof, that binds to TGFβ3 and further binds to, for example, one or more additional TβRII ligands (e.g., TGFβ2, TGFβ1, or TGFβ2 and TGFβ1), one or more type I and/or type II receptors (e.g., TβRII and ALK5), and/or one or more co-receptors (e.g., betaglycan). In some embodiments, a multispecific antibody that binds to TGFβ3 does not bind or does not substantially bind to TGFβ2 (e.g., binds to TGFβ2 with a $K_D$ of greater than $1 \times 10^{-7}$ M or has relatively modest binding, e.g., about $1 \times 10^{-8}$ M or about $1 \times 10^{-9}$ M). In some embodiments, a multispecific antibody that binds to TGFβ3 further binds to TGFβ1 but does not bind or does not substantially bind to TGFβ2 (e.g., binds to TGFβ2 with a $K_D$ of greater than $1 \times 10^{-7}$ M or has relatively modest binding, e.g., about $1 \times 10^{-8}$ M or about $1 \times 10^{-9}$ M). In some embodiments, the disclosure relates to combinations of antibodies, and uses thereof, wherein the combination of antibodies comprises a TGFβ3 antibody and one or more additional antibodies that bind to, for example, one or more additional TβRII ligands (e.g., TGFβ2, TGFβ1, or TGFβ2 and TGFβ1), one or more type I and/or type II receptors (e.g., TβRII and ALK5), and/or one or more co-receptors (e.g., betaglycan). In some embodiments, a combination of antibodies that comprises a TGFβ3 antibody does not comprise a TGFβ2 antibody. In some embodiments, a combination of antibodies that comprises a TGFβ3 antibody further comprises a TGFβ1 antibody but does not comprise a TGFβ2 antibody.

In certain aspects, a TβRII antagonist antibody, or combination of antibodies, is an antibody that inhibits at least TβRII. Therefore, in some embodiments, a TβRII antagonist antibody, or combination of antibodies, binds to at least TβRII. As used herein, a TβRII antibody (anti-TβRII antibody) generally refers to an antibody that binds to TβRII with sufficient affinity such that the antibody is useful as a diagnostic and/or therapeutic agent in targeting TβRII. In certain embodiments, the extent of binding of an anti-TβRII antibody to an unrelated, non-TβRII protein is less than about 10%, 9%, 8%, 7%, 6%, 5%, 4%, 3%, 2%, or less than about 1% of the binding of the antibody to TβRII as measured, for example, by a radioimmunoassay (MA), Biacore, or other protein-protein interaction or binding affinity assay. In certain embodiments, an anti-TβRII antibody binds to an epitope of TβRII that is conserved among TβRII from different species. In certain preferred embodiments, an anti-TβRII antibody binds to human TβRII. In some embodiments, an anti-TβRII antibody may inhibit one or more TβRII ligands [e.g., TGFβ1; TGFβ2; TGFβ3; TGFβ1 and TGFβ3; TGFβ1 and TGFβ2; TGFβ2 and TGFβ3; or TGFβ1, TGFβ2, and TGFβ3] from binding to TβRII. In some embodiments, an anti-TβRII antibody is a multispecific antibody (e.g., bi-specific antibody) that binds to TβRII and one or more TβRII ligands [e.g., TGFβ1, TGFβ2, and TGFβ3], type I receptor (e.g., ALK5), and/or co-receptor (e.g., betaglycan). In some embodiments, the disclosure relates to combinations of antibodies, and uses thereof, wherein the combination of antibodies comprises an anti-TβRII antibody and one or more additional antibodies that bind to, for example, one or more TβRII ligands [e.g., TGFβ1, TGFβ2, and TGFβ3], type I receptors (e.g., ALK5), and/or co-receptor (e.g., betaglycan).

In certain aspects, a TβRII antagonist antibody, or combination of antibodies, is an antibody that inhibits at least ALK5. Therefore, in some embodiments, a TβRII antagonist antibody, or combination of antibodies, binds to at least ALK5. As used herein, an ALK5 antibody (anti-ALK5antibody) generally refers to an antibody that binds to ALK5 with sufficient affinity such that the antibody is useful as a diagnostic and/or therapeutic agent in targeting ALK5. In certain embodiments, the extent of binding of an anti-ALK5 antibody to an unrelated, non-ALK5 protein is less than about 10%, 9%, 8%, 7%, 6%, 5%, 4%, 3%, 2%, or less than about 1% of the binding of the antibody to ALK5 as measured, for example, by a radioimmunoassay (MA), Biacore, or other protein-protein interaction or binding affinity assay. In certain embodiments, an anti-ALK5 antibody binds to an epitope of ALK5 that is conserved among ALK5 from different species. In certain preferred embodiments, an anti-ALK5 antibody binds to human ALK5. In some embodiments, an anti-ALK5 antibody may inhibit one or more TβRII ligands [e.g., TGFβ1; TGFβ2; TGFβ3; TGFβ1 and TGFβ3; TGFβ1 and TGFβ2; TGFβ2 and TGFβ3; or TGFβ1, TGFβ2, and TGFβ3] from binding to ALK5. In some embodiments, an anti-ALK5 antibody is a multispecific antibody (e.g., bi-specific antibody) that binds to ALK5 and one or more TβRII ligands [e.g., TGFβ1, TGFβ2, and TGFβ3], type II receptor (e.g., TβRII), and/or co-receptor (e.g., betaglycan). In some embodiments, the disclosure relates to combinations of antibodies, and uses thereof, wherein the combination of antibodies comprises an anti-ALK5 antibody and one or more additional antibodies that bind to, for example, one or more TβRII ligands [e.g., TGFβ1, TGFβ2, and TGFβ3], type II receptors (e.g., TβRII), and/or co-receptor (e.g., betaglycan).

In certain aspects, a TβRII antagonist antibody, or combination of antibodies, is an antibody that inhibits at least betaglycan. Therefore, in some embodiments, a TβRII antagonist antibody, or combination of antibodies, binds to at least betaglycan. As used herein, a betaglycan antibody (anti-betaglycan antibody) generally refers to an antibody that binds to betaglycan with sufficient affinity such that the antibody is useful as a diagnostic and/or therapeutic agent in targeting betaglycan. In certain embodiments, the extent of binding of an anti-betaglycan antibody to an unrelated, non-betaglycan protein is less than about 10%, 9%, 8%, 7%, 6%, 5%, 4%, 3%, 2%, or less than about 1% of the binding of the antibody to betaglycan as measured, for example, by a radioimmunoassay (MA), Biacore, or other protein-protein interaction or binding affinity assay. In certain embodiments, an anti-betaglycan antibody binds to an epitope of betaglycan that is conserved among betaglycan from different species. In certain preferred embodiments, an anti-betaglycan antibody binds to human betaglycan. In some embodiments, an anti-betaglycan antibody may inhibit one or more TβRII ligands [e.g., TGFβ1; TGFβ2; TGFβ3; TGFβ1 and TGFβ3; TGFβ1 and TGFβ2; TGFβ2 and TGFβ3; or TGFβ1, TGFβ2, and TGFβ3] from binding to betaglycan. In some embodiments, an anti-betaglycan antibody is a multi specific antibody (e.g., bi-specific antibody) that binds to betaglycan and one or more TβRII ligands [e.g., TGFβ1, TGFβ2, and TGFβ3], type I receptor (e.g., ALK5), and/or type II receptors (e.g., TβRII). In some embodiments, the disclosure relates to combinations of antibodies, and uses thereof, wherein the combination of antibodies comprises an anti-betaglycan antibody and one or more additional antibodies that bind to, for example, one or more TβRII ligands [e.g., TGFβ1, TGFβ2, and TGFβ3], type I receptors (e.g., ALK5), and/or type II receptors (e.g., TβRII).

The term antibody is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody fragment refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments. See, e.g., Hudson et al. (2003) Nat. Med. 9:129-134; Pluckthun, in The Pharmacology of Monoclonal Antibodies, vol. 113, Rosenburg and Moore eds., (Springer-Verlag, New York), pp. 269-315 (1994); WO 93/16185; and U.S. Pat. Nos. 5,571,894, 5,587,458, and 5,869,046. Antibodies disclosed herein may be polyclonal antibodies or monoclonal antibodies. In certain embodiments, the antibodies of the present disclosure comprise a label attached thereto and able to be detected (e.g., the label can be a radioisotope, fluorescent compound, enzyme, or enzyme co-factor). In preferred embodiments, the antibodies of the present disclosure are isolated antibodies. Diabodies are antibody fragments with two antigen-binding sites that may be bivalent or bispecific. See, e.g., EP 404,097; WO 1993/01161; Hudson et al. (2003) Nat. Med. 9:129-134 (2003); and Hollinger et al. (1993) Proc. Natl. Acad. Sci. USA 90: 6444-6448. Triabodies and tetrabodies are also described in Hudson et al. (2003) Nat. Med. 9:129-134. Single-domain antibodies are antibody fragments comprising all or a portion of the heavy-chain variable domain or all or a portion of the light-chain variable domain of an antibody. In certain embodiments, a single-domain antibody is a human single-domain antibody. See, e.g., U.S. Pat. No. 6,248,516. Antibody fragments can be made by various techniques, including but not limited to proteolytic digestion of an intact antibody as well as production by recombinant host cells (e.g., *E. coli* or phage), as described herein.

The antibodies herein may be of any class. The class of an antibody refers to the type of constant domain or constant region possessed by its heavy chain. There are five major classes of antibodies: IgA, IgD, IgE, IgG, and IgM, and several of these may be further divided into subclasses (isotypes), for example, IgG$_1$, IgG$_2$, IgG$_3$, IgG$_4$, IgA$_1$, and IgA$_2$. The heavy-chain constant domains that correspond to the different classes of immunoglobulins are called alpha, delta, epsilon, gamma, and mu.

In general, an antibody for use in the methods disclosed herein specifically binds to its target antigen, preferably with high binding affinity. Affinity may be expressed as a K$_D$ value and reflects the intrinsic binding affinity (e.g., with minimized avidity effects). Typically, binding affinity is measured in vitro, whether in a cell-free or cell-associated setting. Any of a number of assays known in the art, including those disclosed herein, can be used to obtain binding affinity measurements including, for example, surface plasmon resonance (Biacore™ assay), radiolabeled antigen binding assay (RIA), and ELISA. In some embodiments, antibodies of the present disclosure bind to their target antigens (e.g. TGFβ1, TGFβ2, TGFβ2, ALK5, betaglycan, and TβRII.) with at least a $K_D$ Of $1\times10^{-7}$ or stronger, $1\times10^{-8}$ or stronger, $1\times10^{-9}$ or stronger, $1\times10^{-10}$ or stronger, $1\times10^{-11}$ or stronger, $1\times10^{-12}$ or stronger, $1\times10^{-13}$ or stronger, or $1\times10^{-14}$ or stronger.

In certain embodiments, $K_D$ is measured by RIA performed with the Fab version of an antibody of interest and its target antigen as described by the following assay. Solution binding affinity of Fabs for the antigen is measured by equilibrating Fab with a minimal concentration of radiolabeled antigen (e.g., $^{125}$I-labeled) in the presence of a titration series of unlabeled antigen, then capturing bound antigen with an anti-Fab antibody-coated plate [see, e.g., Chen et al. (1999) J. Mol. Biol. 293:865-881]. To establish conditions for the assay, multi-well plates (e.g., MICROTITER® from Thermo Scientific) are coated (e.g., overnight) with a capturing anti-Fab antibody (e.g., from Cappel Labs) and subsequently blocked with bovine serum albumin, preferably at room temperature (e.g., approximately 23° C.). In a non-adsorbent plate, radiolabeled antigen are mixed with serial dilutions of a Fab of interest [e.g., consistent with assessment of the anti-VEGF antibody, Fab-12, in Presta et al., (1997) Cancer Res. 57:4593-4599]. The Fab of interest is then incubated, preferably overnight but the incubation may continue for a longer period (e.g., about 65 hours) to ensure that equilibrium is reached. Thereafter, the mixtures are transferred to the capture plate for incubation, preferably at room temperature for about one hour. The solution is then removed and the plate is washed times several times, preferably with polysorbate 20 and PBS mixture. When the plates have dried, scintillant (e.g., MICROSCINT® from Packard) is added, and the plates are counted on a gamma counter (e.g., TOPCOUNT® from Packard).

According to another embodiment, $K_D$ is measured using surface plasmon resonance assays using, for example a BIACORE® 2000 or a BIACORE® 3000 (Biacore, Inc., Piscataway, N.J.) with immobilized antigen CM5 chips at about 10 response units (RU). Briefly, carboxymethylated dextran biosensor chips (CM5, Biacore, Inc.) are activated with N-ethyl-N'-(3-dimethylaminopropyl)-carbodiimide hydrochloride (EDC) and N-hydroxysuccinimide (NETS) according to the supplier's instructions. For example, an antigen can be diluted with 10 mM sodium acetate, pH 4.8, to 5 µg/ml (about 0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20®) surfactant (PBST) at at a flow rate of approximately 25 µl/min. Association rates ($k_{on}$) and dissociation rates ($k_{off}$) are calculated using, for example, a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$ [see, e.g., Chen et al., (1999) J. Mol. Biol. 293:865-881]. If the on-rate exceeds, for example, $10^6$ $M^{-1}$ $s^{-1}$ by the surface plasmon resonance assay above, then the on-rate can be determined by using a fluorescent quenching technique that measures the increase or decrease in fluorescence emission intensity (e.g., excitation=295 nm; emission=340 nm, 16 nm band-pass) of a 20 nM anti-antigen antibody (Fab form) in PBS in the presence of increasing concentrations of antigen as measured in a spectrometer, such as a stop-flow equipped spectrophotometer (Aviv Instruments) or a 8000-series SLM-AMINCO® spectrophotometer (ThermoSpectronic) with a stirred cuvette.

The nucleic acid and amino acid sequences of TβRII, ALK5, betaglycan, TGFβ1, TGFβ2, and TGFβ3, particularly human sequences, are well known in the art and thus antibody antagonists for use in accordance with this disclosure may be routinely made by the skilled artisan based on the knowledge in the art and teachings provided herein.

In certain embodiments, an antibody provided herein is a chimeric antibody. A chimeric antibody refers to an antibody in which a portion of the heavy and/or light chain is derived from a particular source or species, while the remainder of the heavy and/or light chain is derived from a different source or species. Certain chimeric antibodies are described, for example, in U.S. Pat. No. 4,816,567; and Morrison et al., (1984) Proc. Natl. Acad. Sci. USA, 81:6851-6855. In some embodiments, a chimeric antibody comprises a non-human variable region (e.g., a variable region derived from a mouse, rat, hamster, rabbit, or non-human primate, such as a monkey) and a human constant region. In some embodiments, a chimeric antibody is a "class switched" antibody in which the class or subclass has been changed from that of the parent antibody. In general, chimeric antibodies include antigen-binding fragments thereof.

In certain embodiments, a chimeric antibody provided herein is a humanized antibody. A humanized antibody refers to a chimeric antibody comprising amino acid residues from non-human hypervariable regions (HVRs) and amino acid residues from human framework regions (FRs). In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

Humanized antibodies and methods of making them are reviewed, for example, in Almagro and Fransson (2008) Front. Biosci. 13:1619-1633 and are further described, for example, in Riechmann et al., (1988) Nature 332:323-329; Queen et al. (1989) Proc. Nat'l Acad. Sci. USA 86:10029-10033; U.S. Pat. Nos. 5,821,337, 7,527,791, 6,982,321, and 7,087,409; Kashmiri et al., (2005) Methods 36:25-34 [describing SDR (a-CDR) grafting]; Padlan, Mol. Immunol. (1991) 28:489-498 (describing "resurfacing"); Dall'Acqua et al. (2005) Methods 36:43-60 (describing "FR shuffling"); Osbourn et al. (2005) Methods 36:61-68; and Klimka et al. Br. J. Cancer (2000) 83:252-260 (describing the "guided selection" approach to FR shuffling).

Human framework regions that may be used for humanization include but are not limited to: framework regions selected using the "best-fit" method [see, e.g., Sims et al. (1993) J. Immunol. 151:2296]; framework regions derived from the consensus sequence of human antibodies of a particular subgroup of light-chain or heavy-chain variable regions [see, e.g., Carter et al. (1992) Proc. Natl. Acad. Sci. USA, 89:4285; and Presta et al. (1993) J. Immunol., 151: 2623]; human mature (somatically mutated) framework regions or human germline framework regions [see, e.g., Almagro and Fransson (2008) Front. Biosci. 13:1619-1633]; and framework regions derived from screening FR libraries

[see, e.g., Baca et cd., (1997) J. Biol. Chem. 272:10678-10684; and Rosok et cd., (1996) J. Biol. Chem. 271:22611-22618].

In certain embodiments, an antibody provided herein is a human antibody. Human antibodies can be produced using various techniques known in the art. Human antibodies are described generally in van Dijk and van de Winkel (2001) Curr. Opin. Pharmacol. 5: 368-74 and Lonberg (2008) Curr. Opin. Immunol. 20:450-459.

Human antibodies may be prepared by administering an immunogen (e.g a TβRII, ALK5, betaglycan, TGFβ1, TGFβ2, or TGFβ3 polypeptide) to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. For a review of methods for obtaining human antibodies from transgenic animals, see, for example, Lonberg (2005) Nat. Biotechnol. 23:1117-1125; U.S. Pat. Nos. 6,075,181 and 6,150,584 (describing XENOMOUSE™ technology); U.S. Pat. No. 5,770,429 (describing HuMab® technology); U.S. Pat. No. 7,041,870 (describing K-M MOUSE® technology); and U.S. Patent Application Publication No. 2007/0061900 (describing VelociMouse® technology). Human variable regions from intact antibodies generated by such animals may be further modified, for example, by combining with a different human constant region.

Human antibodies provided herein can also be made by hybridoma-based methods. Human myeloma and mouse-human heteromyeloma cell lines for the production of human monoclonal antibodies have been described [see, e.g., Kozbor J. Immunol., (1984) 133: 3001; Brodeur et al. (1987) Monoclonal Antibody Production Techniques and Applications, pp. 51-63, Marcel Dekker, Inc., New York; and Boerner et al. (1991) J. Immunol., 147: 86]. Human antibodies generated via human B-cell hybridoma technology are also described in Li et al., (2006) Proc. Natl. Acad. Sci. USA, 103:3557-3562. Additional methods include those described, for example, in U.S. Pat. No. 7,189,826 (describing production of monoclonal human IgM antibodies from hybridoma cell lines) and Ni, Xiandai Mianyixue (2006) 26(4):265-268 (2006) (describing human-human hybridomas). Human hybridoma technology (Trioma technology) is also described in Vollmers and Brandlein (2005) Histol. Histopathol., 20(3):927-937 (2005) and Vollmers and Brandlein (2005) Methods Find Exp. Clin. Pharmacol., 27(3):185-91.

Human antibodies provided herein may also be generated by isolating Fv clone variable-domain sequences selected from human-derived phage display libraries. Such variable-domain sequences may then be combined with a desired human constant domain. Techniques for selecting human antibodies from antibody libraries are described herein.

For example, antibodies of the present disclosure may be isolated by screening combinatorial libraries for antibodies with the desired activity or activities. A variety of methods are known in the art for generating phage-display libraries and screening such libraries for antibodies possessing the desired binding characteristics. Such methods are reviewed, for example, in Hoogenboom et al. (2001) in Methods in Molecular Biology 178:1-37, O'Brien et al., ed., Human Press, Totowa, N.J. and further described, for example, in the McCafferty et al. (1991) Nature 348:552-554; Clackson et al., (1991) Nature 352: 624-628; Marks et al. (1992) J. Mol. Biol. 222:581-597; Marks and Bradbury (2003) in Methods in Molecular Biology 248:161-175, Lo, ed., Human Press, Totowa, N.J.; Sidhu et al. (2004) J. Mol. Biol. 338(2):299-310; Lee et al. (2004) J. Mol. Biol. 340(5):1073-1093; Fellouse (2004) Proc. Natl. Acad. Sci. USA 101(34): 12467-12472; and Lee et al. (2004) J. Immunol. Methods 284(1-2): 119-132.

In certain phage display methods, repertoires of VH and VL genes are separately cloned by polymerase chain reaction (PCR) and recombined randomly in phage libraries, which can then be screened for antigen-binding phage as described in Winter et al. (1994) Ann. Rev. Immunol., 12: 433-455. Phage typically display antibody fragments, either as single-chain Fv (scFv) fragments or as Fab fragments. Libraries from immunized sources provide high-affinity antibodies to the immunogen (e.g., a TβRII, TGFβ1, TGFβ2, or TGFβ3 polypeptide) without the requirement of constructing hybridomas. Alternatively, the naive repertoire can be cloned (e.g., from human) to provide a single source of antibodies directed against a wide range of non-self and also self-antigens without any immunization as described by Griffiths et al. (1993) EMBO J, 12: 725-734. Finally, naive libraries can also be made synthetically by cloning un-rearranged V-gene segments from stem cells and using PCR primers containing random sequence to encode the highly variable CDR3 regions and to accomplish rearrangement in vitro, as described by Hoogenboom and Winter (1992) J. Mol. Biol., 227: 381-388. Patent publications describing human antibody phage libraries include, for example: U.S. Pat. No. 5,750,373, and U.S. Patent Publication Nos. 2005/0079574, 2005/0119455, 2005/0266000, 2007/0117126, 2007/0160598, 2007/0237764, 2007/0292936, and 2009/0002360.

In certain embodiments, an antibody provided herein is a multispecific antibody, for example, a bispecific antibody. Multispecific antibodies (typically monoclonal antibodies) have binding specificities for at least two different epitopes (e.g., two, three, four, five, or six or more) on one or more (e.g., two, three, four, five, six or more) antigens.

Engineered antibodies with three or more functional antigen binding sites, including "octopus antibodies," are also included herein (see, e.g., US 2006/0025576A1).

In certain embodiments, the antibodies disclosed herein are monoclonal antibodies. Monoclonal antibody refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. Thus, the modifier "monoclonal" indicates the character of the antibody as being obtained from a substantially homogeneous population of antibodies and is not to be construed as requiring production of the antibody by any particular method. For example, the monoclonal antibodies to be used in accordance with the present methods may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

For example, by using immunogens derived from TβRII, anti-protein/anti-peptide antisera or monoclonal antibodies can be made by standard protocols [see, e.g., Antibodies: A Laboratory Manual (1988) ed. by Harlow and Lane, Cold Spring Harbor Press]. A mammal, such as a mouse, hamster, or rabbit can be immunized with an immunogenic form of the TβRII polypeptide, an antigenic fragment which is capable of eliciting an antibody response, or a fusion protein. Techniques for conferring immunogenicity on a protein or peptide include conjugation to carriers or other techniques well known in the art. An immunogenic portion of a TβRII polypeptide can be administered in the presence of adjuvant. The progress of immunization can be monitored by detection of antibody titers in plasma or serum. Standard ELISA or other immunoassays can be used with the immunogen as antigen to assess the levels of antibody production and/or level of binding affinity.

Following immunization of an animal with an antigenic preparation of TβRII, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique [see, e.g., Kohler and Milstein (1975) Nature, 256: 495-497], the human B cell hybridoma technique [see, e.g., Kozbar et al. (1983) Immunology Today, 4:72], and the EBV-hybridoma technique to produce human monoclonal antibodies [Cole et al. (1985) Monoclonal Antibodies and Cancer Therapy, Alan R. Liss, Inc. pp. 77-96]. Hybridoma cells can be screened immunochemically for production of antibodies specifically reactive with a TβRII polypeptide, and monoclonal antibodies isolated from a culture comprising such hybridoma cells.

In certain embodiments, one or more amino acid modifications may be introduced into the Fc region of an antibody provided herein thereby generating an Fc-region variant. The Fc-region variant may comprise a human Fc-region sequence (e.g., a human IgG1, IgG2, IgG3 or IgG4 Fc region) comprising an amino acid modification (e.g., a substitution, deletion, and/or addition) at one or more amino acid positions.

For example, the present disclosure contemplates an antibody variant that possesses some but not all effector functions, which make it a desirable candidate for applications in which the half-life of the antibody in vivo is important yet for which certain effector functions [e.g., complement-dependent cytotoxicity (CDC) and antibody-dependent cellular cytotoxicity (ADCC)] are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in, for example, Ravetch and Kinet (1991) Annu. Rev. Immunol. 9:457-492. Non-limiting examples of in vitro assays to assess ADCC activity of a molecule of interest are described in U.S. Pat. No. 5,500,362; Hellstrom, I. et al. (1986) Proc. Nat'l Acad. Sci. USA 83:7059-7063; Hellstrom, I et al. (1985) Proc. Nat'l Acad. Sci. USA 82:1499-1502; U.S. Pat. No. 5,821,337; and Bruggemann, M. et al. (1987) J. Exp. Med. 166:1351-1361. Alternatively, non-radioactive assay methods may be employed (e.g., ACTI™, non-radioactive cytotoxicity assay for flow cytometry; CellTechnology, Inc. Mountain View, Calif.; and CytoTox 96® non-radioactive cytotoxicity assay, Promega, Madison, Wis.). Useful effector cells for such assays include peripheral blood mononuclear cells (PBMC) and natural killer (NK) cells. Alternatively, or additionally, ADCC activity of the molecule of interest may be assessed in vivo, for example, in an animal model such as that disclosed in Clynes et al. (1998) Proc. Nat'l Acad. Sci. USA 95:652-656. C1q binding assays may also be carried out to confirm that the antibody is unable to bind C1q and hence lacks CDC activity [see, e.g., C1q and C3c binding ELISA in WO 2006/029879 and WO 2005/100402]. To assess complement activation, a CDC assay may be performed [see, e.g., Gazzano-Santoro et al. (1996) J. Immunol. Methods 202:163; Cragg, M. S. et al. (2003) Blood 101:1045-1052; and Cragg, M. S, and M. J. Glennie (2004) Blood 103:2738-2743]. FcRn binding and in vivo clearance/half-life determinations can also be performed using methods known in the art [see, e.g., Petkova, S. B. et al. (2006) Int. Immunol. 18(12):1759-1769].

Antibodies of the present disclosure with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In certain embodiments, it may be desirable to create cysteine-engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy-chain Fc region. Cysteine engineered antibodies may be generated as described, for example, in U.S. Pat. No. 7,521,541.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore™ binding assay, Biacore AB, Uppsala, Sweden), sandwich assays (e.g., the paramagnetic bead system of IGEN International, Inc., Gaithersburg, Md.), western blots, immunoprecipitation assays, and immunohistochemistry.

In certain embodiments, amino acid sequence variants of the antibodies and/or the binding polypeptides provided herein are contemplated. For example, it may be desirable to improve the binding affinity and/or other biological properties of the antibody and/or binding polypeptide. Amino acid sequence variants of an antibody and/or binding polypeptides may be prepared by introducing appropriate modifications into the nucleotide sequence encoding the antibody and/or binding polypeptide, or by peptide synthesis. Such modifications include, for example, deletions from, and/or insertions into, and/or substitutions of residues within, the amino acid sequences of the antibody and/or binding polypeptide. Any combination of deletion, insertion, and substitution can be made to arrive at the final construct, provided that the final construct possesses the desired characteristics, e.g., target-binding (TβRII, ALK5, betaglycan, TGFβ1, TGFβ2, and/or TGFβ3).

Alterations (e.g., substitutions) may be made in HVRs, for example, to improve antibody affinity. Such alterations may be made in HVR "hotspots," i.e., residues encoded by codons that undergo mutation at high frequency during the somatic maturation process (see, e.g., Chowdhury (2008) Methods Mol. Biol. 207:179-196 (2008)), and/or SDRs (a-CDRs), with the resulting variant VH or VL being tested for binding affinity. Affinity maturation by constructing and reselecting from secondary libraries has been described in the art [see, e.g., Hoogenboom et al., in Methods in Molecular Biology 178:1-37, O'Brien et al., ed., Human Press, Totowa, N.J., (2001)]. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind to the antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two, or three amino acid substitutions.

A useful method for identification of residues or regions of the antibody and/or the binding polypeptide that may be targeted for mutagenesis is called "alanine scanning mutagenesis", as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody or binding polypeptide with antigen is affected. Further substitutions may be introduced at the amino acid locations demonstrating functional sensitivity to the initial substitutions. Alternatively, or additionally, a crystal structure of an antigen-antibody complex can be used to identify contact points between the antibody and antigen. Such contact residues and neighboring residues may be targeted or eliminated as candidates for substitution. Variants may be screened to determine whether they contain the desired properties.

Amino-acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include fusion of the N- or C-terminus of the antibody to an enzyme (e.g., for ADEPT) or a polypeptide which increases the serum half-life of the antibody.

In certain embodiments, an antibody and/or binding polypeptide provided herein may be further modified to contain additional non-proteinaceous moieties that are known in the art and readily available. The moieties suitable for derivatization of the antibody and/or binding polypeptide include but are not limited to water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody and/or binding polypeptide may vary, and if more than one polymer are attached, they can be the same or different molecules. In general, the number and/or type of polymers used for derivatization can be determined based on considerations including, but not limited to, the particular properties or functions of the antibody and/or binding polypeptide to be improved, whether the antibody derivative and/or binding polypeptide derivative will be used in a therapy under defined conditions.

Any of the TβRII antagonist antibodies disclosed herein can be combined with one or more additional TβRII antagonists to achieve the desired effect [to treat, prevent, or reduce the progression rate and/or severity of a myelodysplastic disorder or one or more complications of a myelodysplastic disorder]. For example, a TβRII antagonist antibody can be used in combination with i) one or more additional TβRII antagonist antibodies, ii) one or more TβRII polypeptides including variants thereof; iii) one or more TβRII antagonist small molecules; and iv) one or more TβRII antagonist polynucleotides.

D. Small Molecule Antagonists

In certain aspects, a TβRII antagonist to be used in accordance with the methods and uses disclosed herein is a small molecule (TβRII antagonist small molecule) or combination of small molecules. A TβRII antagonist small molecule, or combination of small molecules, may inhibit, for example, one or more TβRII ligands (e.g., TGFβ1, TGFβ2, and TGFβ3), TβRII receptor, TβRII-associated type I receptor (e.g., ALK5), TβRII-associated co-receptor (e.g., betaglycan), and/or downstream signaling component (e.g., Smads). In some embodiments, the ability for a TβRII antagonist small molecule, or combination of small molecules, to inhibit signaling (e.g., Smad signaling) is determined in a cell-based assay including, for example, those described herein. A TβRII antagonist small molecule, or combination of small molecules, may be used alone or in combination with one or more additional supportive therapies or active agents to treat, prevent, or reduce the progression rate and/or severity of a myeloproliferative disorder (e.g., myelofibrosis, polycythemia vera, and essential thrombocythaemia) and/or a Janus kinase-associated disorder (e.g., a JAK2 kinase-associated disorder) or one or more complications of a myeloproliferative disorder and/or a Janus kinase-associated disorder.

In certain aspects, a TβRII antagonist small molecule, or combination of small molecules, inhibits at least TGFβ1 (e.g., inhibition of Smad signaling). Therefore, in some embodiments, a small molecule inhibitor of TGFβ1 binds to TGFβ1. In some embodiments, a small molecule inhibitor of TGFβ1 inhibits expression (e.g., transcription, translation, secretion, or combinations thereof) of TGFβ1. In some embodiments, a small molecule inhibitor of TGFβ1 further inhibits one or more of TGFβ2, TGFβ3, TβRII, ALK5, and betaglycan. In some embodiments, a small molecule inhibitor of TGFβ1 does not inhibit or does not substantially inhibit TGFβ2. In some embodiments, a small molecule inhibitor of TGFβ1 further inhibits TGFβ3 but does not inhibit or does not substantially inhibit TGFβ2. In certain aspects, a TβRII antagonist small molecule, or combination of small molecules, inhibits at least TGFβ2 (e.g., inhibition of Smad signaling). Therefore, in some embodiments, a small molecule inhibitor of TGFβ2 binds to TGFβ2. In some embodiments, a small molecule inhibitor of TGFβ2 inhibits expression (e.g., transcription, translation, secretion, or combinations thereof) of TGFβ2. In some embodiments, a small molecule inhibitor of TGFβ2 further inhibits one or more of TGFβ3, TGFβ1, TβRII, ALK5, and betaglycan. In certain aspects, a TβRII antagonist small molecule, or combination of small molecules, inhibits at least TGFβ3 (e.g., inhibition of Smad signaling). Therefore, in some embodiments, a small molecule inhibitor of TGFβ3 binds to TGFβ3. In some embodiments, a small molecule inhibitor of TGFβ3 inhibits expression (e.g., transcription, translation, secretion, or combinations thereof) of TGFβ3. In some embodiments, a small molecule inhibitor of TGFβ3 further inhibits one or more of TGFβ2, TGFβ1, TβRII, ALK5, and betaglycan. In some embodiments, a small molecule inhibitor of TGFβ3 does not inhibit or does not substantially inhibit TGFβ2. In some embodiments, a small molecule inhibitor of TGFβ3 further inhibits TGFβ1 but does not inhibit or does not substantially inhibit TGFβ2. In certain aspects, a TβRII antagonist small molecule, or combination of small molecules, inhibits at least TβRII (e.g., inhibition of Smad signaling). Therefore, in some embodiments, a small molecule inhibitor of TβRII binds to TβRII. In some embodiments, a small molecule inhibitor of TβRII inhibits expression (e.g., transcription, translation, secretion, or combinations thereof) of TβRII. In some embodiments, a small molecule inhibitor of TβRII further inhibits one or more of TGFβ1, TGFβ2, TGFβ3, ALK5, and betaglycan. In certain aspects, a TβRII antagonist small molecule, or combination of small molecules, inhibits TGFβ1 from binding to TβRII. In certain aspects, a TβRII antagonist small molecule, or combination of small molecules, inhibits TGFβ2 from binding to TβRII. In certain aspects, a TβRII antagonist small molecule, or combination of small molecules, inhibits TGFβ3 from binding to TβRII. In certain aspects, a TβRII antagonist small molecule, or combination of small molecules, inhibits TGFβ1 and TGFβ3 from binding to TβRII. In certain aspects, a TβRII antagonist small molecule, or combination of small molecules, inhibits TGFβ1, TGFβ2, and TGFβ3 from binding to TβRII. In certain aspects, a TβRII antagonist small molecule, or combination of small molecules, inhibits TGFβ1 from binding to TβRII but does not inhibit or does not substantially inhibit TGFβ2 from binding to TβRII. In certain aspects, a TβRII antagonist small molecule, or combination of small molecules, inhibits TGFβ3 from binding to TβRII but does not inhibit or does not substantially inhibit TGFβ2 from binding to TβRII. In certain aspects, a TβRII antagonist small molecule, or combination of small molecules, inhibits TGFβ1 and TGFβ3 from binding to TβRII but does not inhibit or does not substantially inhibit TGFβ2 from binding to TβRII. In certain aspects, a TβRII antagonist small molecule, or combination of small molecules, inhibits at least ALK5 (e.g., inhibition of Smad signaling). Therefore, in some embodiments, a small molecule inhibitor of ALK5 binds to ALK5. In some embodiments, a small molecule inhibitor of ALK5 inhibits expression (e.g., transcription, translation, secretion, or combinations thereof) of ALK5. In some embodiments, a small molecule inhibitor of ALK5 further inhibits one or more of TGFβ1, TGFβ2, TGFβ3, TβRII, and betaglycan. In certain aspects, a TβRII antagonist small molecule, or combination of small molecules, inhibits TGFβ1 from binding to ALK5. In certain aspects, a TβRII antagonist small molecule, or combination of small molecules, inhibits TGFβ2 from binding to ALK5. In certain aspects, a TβRII antagonist small molecule, or combination of small molecules, inhibits TGFβ3 from binding to ALK5. In certain aspects, a TβRII antagonist small molecule, or combination of small molecules, inhibits TGFβ1 and TGFβ3 from binding to ALK5. In certain aspects, a TβRII antagonist small molecule, or combination of small molecules, inhibits TGFβ1, TGFβ2, and TGFβ3 from binding to ALK5. In certain aspects, a TβRII antagonist small molecule, or combination of small molecules, inhibits TGFβ1 from binding to ALK5 but does not inhibit or does not substantially inhibit TGFβ2 from binding to ALK5. In certain aspects, a TβRII antagonist small molecule, or combination of small molecules, inhibits TGFβ3 from binding to ALK5 but does not inhibit or does not substantially inhibit TGFβ2 from binding to ALK5. In certain aspects, a TβRII antagonist small molecule, or combination of small molecules, inhibits TGFβ1 and TGFβ3 from binding to ALK5 but does not inhibit or does not substantially inhibit TGFβ2 from binding to ALK5. In certain aspects, a TβRII antagonist small molecule, or combination of small molecules, inhibits at least betaglycan (e.g., inhibition of Smad signaling). Therefore, in some embodiments, a small molecule inhibitor of betaglycan binds to betaglycan. In some embodiments, a small molecule inhibitor of betaglycan inhibits expression (e.g., transcription, translation, secretion, or combinations thereof) of betaglycan. In some embodiments, a small molecule inhibitor of betaglycan further inhibits one or more of TGFβ1, TGFβ2, TGFβ3, TβRII, and ALK5. In certain aspects, a TβRII antagonist small molecule, or combination of small molecules, inhibits TGFβ1 from binding to betaglycan. In certain aspects, a TβRII antagonist small molecule, or combination of small molecules, inhibits TGFβ2 from binding to betaglycan. In certain aspects, a TβRII antagonist small molecule, or combination of small molecules, inhibits TGFβ3 from binding to betaglycan. In certain aspects, a TβRII antagonist small molecule, or combination of small molecules, inhibits TGFβ1 and TGFβ3 from binding to betaglycan. In certain aspects, a TβRII antagonist small molecule, or combination of small molecules, inhibits TGFβ1, TGFβ2, and TGFβ3 from binding to betaglycan. In certain aspects, a TβRII antagonist small molecule, or combination of small molecules, inhibits TGFβ1 from binding to betaglycan but does not inhibit or does not substantially inhibit TGFβ2 from binding to betaglycan. In certain aspects, a TβRII antagonist small molecule, or combination of small molecules, inhibits TGFβ3 from binding to betaglycan but does not inhibit or does not substantially inhibit TGFβ2 from binding to betaglycan. In certain aspects, a TβRII antagonist small molecule, or combination of small molecules, inhibits TGFβ1 and TGFβ3 from binding to betaglycan but does not inhibit or does not substantially inhibit TGFβ2 from binding to betaglycan.

TβRII antagonist small molecules can be direct or indirect inhibitors. For example, a TβRII antagonist small molecule, or combination of small molecules, may inhibit the expression (e.g., transcription, translation, cellular secretion, or combinations thereof) of at least one or more of TβRII, ALK5, betaglycan, TGFβ1, TGFβ2, TGFβ3, and/or one or more downstream TβRII signaling factors (Smads). Alternatively, a direct TβRII antagonist small molecule, or combination of small molecules, may directly bind to, for example, one or more of TβRII, ALK5, betaglycan, TGFβ1, TGFβ2, and TGFβ3 or one or more downstream TβRII signaling factors. Combinations of one or more indirect and one or more direct TβRII antagonist small molecule may be used in accordance with the methods disclosed herein.

Binding organic small molecule antagonists of the present disclosure may be identified and chemically synthesized using known methodology (see, e.g., PCT Publication Nos. WO 00/00823 and WO 00/39585). In general, small molecule antagonists of the disclosure are usually less than about 2000 daltons in size, alternatively less than about 1500, 750, 500, 250 or 200 daltons in size, wherein such organic small molecules that are capable of binding, preferably specifically, to a polypeptide as described herein (e.g., TβRII, ALK5, betaglycan, TGFβ1, TGFβ2, and TGFβ3). Such small molecule antagonists may be identified without undue experimentation using well-known techniques. In this regard, it is noted that techniques for screening organic small molecule libraries for molecules that are capable of binding to a polypeptide target are well-known in the art (see, e.g., international patent publication Nos. WO00/00823 and WO00/39585).

Binding organic small molecules of the present disclosure may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, and acid chlorides.

Any of the TβRII antagonist small molecules disclosed herein can be combined with one or more additional TβRII antagonists to achieve the desired. For example, a TβRII antagonist small molecule can be used in combination with i) one or more additional TβRII antagonist small molecules, ii) one or more TβRII antagonist antibodies disclosed herein; iii) one or more TβRII polypeptides including variants thereof; and/or iv) one or more TβRII antagonist polynucleotides.

E. Antagonist Polynucleotides

In certain aspects, a TβRII antagonist to be used in accordance with the methods and uses disclosed herein is a polynucleotide (TβRII antagonist polynucleotide) or combination of polynucleotides. A TβRII antagonist polynucleotide, or combination of polynucleotides, may inhibit, for example, one or more TβRII ligands (e.g., TGFβ1, TGFβ2, and TGFβ3), TβRII receptor, TβRII-associated type I receptor (e.g., ALK5), TβRII-associated co-receptor (e.g., betaglycan), and/or downstream signaling component (e.g., Smads). In some embodiments, the ability for a TβRII antagonist polynucleotide, or combination of polynucleotides, to inhibit signaling (e.g., Smad signaling) is determined in a cell-based assay including, for example, those described herein. A TβRII antagonist polynucleotide, or combination of polynucleotide, may be used alone or in combination with one or more additional supportive therapies or active agents to treat, prevent, or reduce the progression rate and/or severity of a myeloproliferative disorder (e.g., myelofibrosis, polycythemia vera, and essential thrombocythaemia) and/or a Janus kinase-associated disorder (e.g., a JAK2 kinase-associated disorder) or one or more complications of a myeloproliferative disorder and/or a Janus kinase-associated disorder.

In certain aspects, a TβRII antagonist polynucleotide, or combination of polynucleotides, inhibits at least TGFβ1 (e.g., inhibition of Smad signaling). Therefore, in some embodiments, a polynucleotide inhibitor of TGFβ1 binds to TGFβ1. In some embodiments, a polynucleotide inhibitor of TGFβ1 inhibits expression (e.g., transcription, translation, secretion, or combinations thereof) of TGFβ1. In some embodiments, a polynucleotide inhibitor of TGFβ1 further inhibits one or more of TGFβ2, TGFβ3, TβRII, ALK5, and betaglycan. In some embodiments, a polynucleotide inhibitor of TGFβ1 does not inhibit or does not substantially inhibit TGFβ2. In some embodiments, a polynucleotide inhibitor of TGFβ1 further inhibits TGFβ3 but does not inhibit or does not substantially inhibit TGFβ2. In certain aspects, a TβRII antagonist polynucleotide, or combination of polynucleotides, inhibits at least TGFβ2 (e.g., inhibition of Smad signaling). Therefore, in some embodiments, a polynucleotide inhibitor of TGFβ2 binds to TGFβ2. In some embodiments, a polynucleotide inhibitor of TGFβ2 inhibits expression (e.g., transcription, translation, secretion, or combinations thereof) of TGFβ2. In some embodiments, a polynucleotide inhibitor of TGFβ2 further inhibits one or more of TGFβ3, TGFβ1, ALK5, and betaglycan. In certain aspects, a TβRII antagonist polynucleotide, or combination of polynucleotides, inhibits at least TGFβ3 (e.g., inhibition of Smad signaling). Therefore, in some embodiments, a polynucleotide inhibitor of TGFβ3 binds to TGFβ3. In some embodiments, a polynucleotide inhibitor of TGFβ3 inhibits expression (e.g., transcription, translation, secretion, or combinations thereof) of TGFβ3. In some embodiments, a polynucleotide inhibitor of TGFβ3 further inhibits one or more of TGFβ2, TGFβ1, TβRII, ALK5, and betaglycan. In some embodiments, a polynucleotide inhibitor of TGFβ3 does not inhibit or does not substantially inhibit TGFβ2. In some embodiments, a polynucleotide inhibitor of TGFβ3 further inhibits TGFβ1 but does not inhibit or does not substantially inhibit TGFβ2. In certain aspects, a TβRII antagonist polynucleotide, or combination of polynucleotides, inhibits at least TβRII (e.g., inhibition of Smad signaling). Therefore, in some embodiments, a polynucleotide inhibitor of TβRII binds to TβRII. In some embodiments, a polynucleotide inhibitor of TβRII inhibits expression (e.g., transcription, translation, secretion, or combinations thereof) of TβRII. In some embodiments, a polynucleotide inhibitor of TβRII further inhibits one or more of TGFβ1, TGFβ2, TGFβ3, ALK5, and betaglycan. In some embodiments, a TβRII antagonist polynucleotide, or combination of polynucleotides, inhibits TGFβ1 from binding to TβRII. In some embodiments a TβRII antagonist polynucleotide, or combination of polynucleotides, inhibits TGFβ2 from binding to TβRII. In some embodiments, a TβRII antagonist polynucleotide, or combination of polynucleotides, inhibits TGFβ3 from binding to TβRII. In some embodiments, a TβRII antagonist polynucleotide, or combination of polynucleotides, inhibits TGFβ1 and TGFβ3 from binding to TβRII. In some embodiments, a TβRII antagonist polynucleotide, or combination of polynucleotides, inhibits TGFβ1, TGFβ2, and TGFβ3 from binding to TβRII. In some embodiments, a TβRII antagonist polynucleotide, or combination of polynucleotides, inhibits TGFβ1 from binding to TβRII but does not inhibit or does not substantially inhibit TGFβ2 from binding to TβRII. In some embodiments, a TβRII antagonist polynucleotide, or combination of polynucleotides, inhibits TGFβ3 from binding to TβRII but does not inhibit or does not substantially inhibit TGFβ2 from binding to TβRII. In some embodiments, a TβRII antagonist polynucleotide, or combination of polynucleotides, inhibits TGFβ1 and TGFβ3 from binding to TβRII but does not inhibit or does not substantially inhibit TGFβ2 from binding to TβRII. In certain aspects, a TβRII antagonist polynucleotide, or combination of polynucleotides, inhibits at least ALK5 (e.g., inhibition of Smad signaling). Therefore, in some embodiments, a polynucleotide inhibitor of ALK5 binds to ALK5. In some embodiments, a polynucleotide inhibitor of ALK5 inhibits expression (e.g., transcription, translation, secretion, or combinations thereof) of ALK5. In some embodiments, a polynucleotide inhibitor of ALK5 further inhibits one or more of TGFβ1, TGFβ2, TGFβ3, TβRII, and betaglycan. In some embodiments, a TβRII antagonist polynucleotide, or combination of polynucleotides, inhibits TGFβ1 from binding to ALK5. In some embodiments, a TβRII antagonist polynucleotide, or combination of polynucleotides, inhibits TGFβ2 from binding to ALK5. In some embodiments, a TβRII antagonist polynucleotide, or combination of polynucleotides, inhibits TGFβ3 from binding to ALK5. In some embodiments, a TβRII antagonist polynucleotide, or combination of polynucleotides, inhibits TGFβ1 and TGFβ3 from binding to ALK5. In some embodiments, a TβRII antagonist polynucleotide, or combination of polynucleotides, inhibits TGFβ1, TGFβ2, and TGFβ3 from binding to ALK5. In some embodiments, a TβRII antagonist polynucleotide, or combination of polynucleotides, inhibits TGFβ1 from binding to ALK5 but does not inhibit or does not substantially inhibit TGFβ2 from binding to ALK5. In some embodiments, a TβRII antagonist polynucleotide, or combination of polynucleotides, inhibits TGFβ3 from binding to ALK5 but does not inhibit or does not substantially inhibit TGFβ2 from binding to ALK5. In some embodiments, a TβRII antagonist polynucleotide, or combination of polynucleotides, inhibits TGFβ1 and TGFβ3 from binding to ALK5 but does not inhibit or does not substantially inhibit TGFβ2 from binding to ALK5. In certain aspects, a TβRII antagonist polynucleotide, or combination of polynucleotides, inhibits at least betaglycan (e.g., inhibition of Smad signaling). Therefore, in some embodiments, a polynucleotide inhibitor of betaglycan binds to betaglycan. In some embodiments, a polynucleotide inhibitor of betaglycan inhibits expression (e.g., transcription, translation, secretion, or combinations thereof) of betaglycan. In some embodiments, a polynucleotide inhibitor of betaglycan further inhibits one or more of TGFβ1, TGFβ2, TGFβ3, TβRII, and ALK5. In some embodiments, a TβRII antagonist polynucleotide, or combination of polynucleotides, inhibits TGFβ1 from binding to betaglycan. In some embodiments, a TβRII antagonist polynucleotide, or combination of polynucleotides, inhibits TGFβ2 from binding to betaglycan. In some embodiments, a TβRII antagonist polynucleotide, or combination of polynucleotides, inhibits TGFβ3 from binding to betaglycan. In some embodiments, a TβRII antagonist polynucleotide, or combination of polynucleotides, inhibits TGFβ1 and TGFβ3 from binding to betaglycan. In some embodiments, a TβRII antagonist polynucleotide, or combination of polynucleotides, inhibits TGFβ1, TGFβ2, and TGFβ3 from binding to betaglycan. In some embodiments, a TβRII antagonist polynucleotide, or combination of polynucleotides, inhibits TGFβ1 from binding to betaglycan but does not inhibit or does not substantially inhibit TGFβ2 from binding to betaglycan. In some embodiments, a TβRII antagonist polynucleotide, or combination of polynucleotides, inhibits TGFβ3 from binding to betaglycan but does not inhibit or does not substantially inhibit TGFβ2 from binding to betaglycan. In some embodiments, a TβRII antagonist polynucleotide, or combination of polynucleotides, inhibits TGFβ1 and TGFβ3 from binding to betaglycan but does not inhibit or does not substantially inhibit TGFβ2 from binding to betaglycan.

The polynucleotide antagonists of the present disclosure may be an antisense nucleic acid, an RNAi molecule [e.g., small interfering RNA (siRNA), small-hairpin RNA (shRNA), microRNA (miRNA)], an aptamer and/or a ribozyme. The nucleic acid and amino acid sequences of human TβRII, ALK5, betaglycan, TGFβ1, TGFβ2, and TGFβ3 are known in the art and thus polynucleotide antagonists for use in accordance with methods of the present disclosure may be routinely made by the skilled artisan based on the knowledge in the art and teachings provided herein.

For example, antisense technology can be used to control gene expression through antisense DNA or RNA, or through triple-helix formation. Antisense techniques are discussed, for example, in Okano (1991) J. Neurochem. 56:560; Oligodeoxynucleotides as Antisense Inhibitors of Gene Expression, CRC Press, Boca Raton, Fla. (1988). Triple helix formation is discussed in, for instance, Cooney et al. (1988) Science 241:456; and Dervan et al., (1991)Science 251: 1300. The methods are based on binding of a polynucleotide to a complementary DNA or RNA. In some embodiments, the antisense nucleic acids comprise a single-stranded RNA or DNA sequence that is complementary to at least a portion of an RNA transcript of a desired gene. However, absolute complementarity, although preferred, is not required.

A sequence "complementary to at least a portion of an RNA," referred to herein, means a sequence having sufficient complementarity to be able to hybridize with the RNA, forming a stable duplex; in the case of double-stranded antisense nucleic acids of a gene disclosed herein, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with an RNA it may contain and still form a stable duplex (or triplex as the case may be). One skilled in the art can ascertain a tolerable degree of mismatch by use of standard procedures to determine the melting point of the hybridized complex.

Polynucleotides that are complementary to the 5' end of the message, for example, the 5'-untranslated sequence up to and including the AUG initiation codon, should work most efficiently at inhibiting translation. However, sequences complementary to the 3'-untranslated sequences of mRNAs have been shown to be effective at inhibiting translation of mRNAs as well [see, e.g., Wagner, R., (1994) Nature 372:333-335]. Thus, oligonucleotides complementary to either the 5'- or 3'-untranslated, noncoding regions of a gene of the disclosure, could be used in an antisense approach to inhibit translation of an endogenous mRNA. Polynucleotides complementary to the 5'-untranslated region of the mRNA should include the complement of the AUG start codon. Antisense polynucleotides complementary to mRNA coding regions are less efficient inhibitors of translation but could be used in accordance with the methods of the present disclosure. Whether designed to hybridize to the 5'-untranslated, 3'-untranslated, or coding regions of an mRNA of the disclosure, antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides, or at least 50 nucleotides.

In one embodiment, the antisense nucleic acid of the present disclosure is produced intracellularly by transcription from an exogenous sequence. For example, a vector or a portion thereof, is transcribed, producing an antisense nucleic acid (RNA) of a gene of the disclosure. Such a vector would contain a sequence encoding the desired antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding desired genes of the instant disclosure, or fragments thereof, can be by any promoter known in the art to act in vertebrate, preferably human cells. Such promoters can be inducible or constitutive. Such promoters include, but are not limited to, the 5V40 early promoter region [see, e.g., Benoist and Chambon (1981) Nature 29:304-310], the promoter contained in the 3' long terminal repeat of Rous sarcoma virus [see, e.g., Yamamoto et al. (1980) Cell 22:787-797], the herpes thymidine promoter [see, e.g., Wagner et al. (1981) Proc. Natl. Acad. Sci. U.S.A. 78:1441-1445], and the regulatory sequences of the metallothionein gene [see, e.g., Brinster, et al. (1982) Nature 296:39-42].

In some embodiments, the polynucleotide antagonists are interfering RNA or RNAi molecules that target the expression of one or more genes. RNAi refers to the expression of an RNA which interferes with the expression of the targeted mRNA. Specifically, RNAi silences a targeted gene via interacting with the specific mRNA through a siRNA (small interfering RNA). The ds RNA complex is then targeted for degradation by the cell. An siRNA molecule is a double-stranded RNA duplex of 10 to 50 nucleotides in length, which interferes with the expression of a target gene which is sufficiently complementary (e.g. at least 80% identity to the gene). In some embodiments, the siRNA molecule comprises a nucleotide sequence that is at least 85, 90, 95, 96, 97, 98, 99, or 100% identical to the nucleotide sequence of the target gene.

Additional RNAi molecules include short-hairpin RNA (shRNA); also short-interfering hairpin and microRNA (miRNA). The shRNA molecule contains sense and antisense sequences from a target gene connected by a loop. The shRNA is transported from the nucleus into the cytoplasm, and it is degraded along with the mRNA. Pol III or U6 promoters can be used to express RNAs for RNAi. Paddison et al. [Genes & Dev. (2002) 16:948-958, 2002] have used small RNA molecules folded into hairpins as a means to effect RNAi. Accordingly, such short hairpin RNA (shRNA) molecules are also advantageously used in the methods described herein. The length of the stem and loop of functional shRNAs varies; stem lengths can range anywhere from about 25 to about 30 nt, and loop size can range between 4 to about 25 nt without affecting silencing activity. While not wishing to be bound by any particular theory, it is believed that these shRNAs resemble the double-stranded RNA (dsRNA) products of the DICER RNase and, in any event, have the same capacity for inhibiting expression of a specific gene. The shRNA can be expressed from a lentiviral vector. An miRNA is a single-stranded RNA of about 10 to 70 nucleotides in length that are initially transcribed as pre-miRNA characterized by a "stem-loop" structure and which are subsequently processed into mature miRNA after further processing through the RISC.

Molecules that mediate RNAi, including without limitation siRNA, can be produced in vitro by chemical synthesis (Hohjoh, FEBS Lett 521:195-199, 2002), hydrolysis of dsRNA (Yang et al., Proc Natl Acad Sci USA 99:9942-9947, 2002), by in vitro transcription with T7 RNA polymerase (Donzeet et al., Nucleic Acids Res 30:e46, 2002; Yu et al., Proc Natl Acad Sci USA 99:6047-6052, 2002), and by hydrolysis of double-stranded RNA using a nuclease such as *E. coli* RNase III (Yang et al., Proc Natl Acad Sci USA 99:9942-9947, 2002).

According to another aspect, the disclosure provides polynucleotide antagonists including but not limited to, a decoy DNA, a double-stranded DNA, a single-stranded DNA, a complexed DNA, an encapsulated DNA, a viral DNA, a plasmid DNA, a naked RNA, an encapsulated RNA, a viral RNA, a double-stranded RNA, a molecule capable of generating RNA interference, or combinations thereof.

In some embodiments, the polynucleotide antagonists of the disclosure are aptamers. Aptamers are nucleic acid molecules, including double-stranded DNA and single-stranded RNA molecules, which bind to and form tertiary structures that specifically bind to a target molecule, such as a TβRII, TGFβ1, TGFβ2, and TGFβ3 polypeptide. The generation and therapeutic use of aptamers are well established in the art. See, e.g., U.S. Pat. No. 5,475,096. Additional information on aptamers can be found in U.S. Patent Application Publication No. 20060148748. Nucleic acid aptamers are selected using methods known in the art, for example via the Systematic Evolution of Ligands by Exponential Enrichment (SELEX) process. SELEX is a method for the in vitro evolution of nucleic acid molecules with highly specific binding to target molecules as described in, e.g., U.S. Pat. Nos. 5,475,096, 5,580,737, 5,567,588, 5,707, 796, 5,763,177, 6,011,577, and 6,699,843. Another screening method to identify aptamers is described in U.S. Pat. No. 5,270,163. The SELEX process is based on the capacity of nucleic acids for forming a variety of two- and three-dimensional structures, as well as the chemical versatility available within the nucleotide monomers to act as ligands (form specific binding pairs) with virtually any chemical compound, whether monomeric or polymeric, including other nucleic acid molecules and polypeptides. Molecules of any size or composition can serve as targets. The SELEX method involves selection from a mixture of candidate oligonucleotides and step-wise iterations of binding, partitioning and amplification, using the same general selection scheme, to achieve desired binding affinity and selectivity. Starting from a mixture of nucleic acids, which can comprise a segment of randomized sequence, the SELEX method includes steps of contacting the mixture with the target under conditions favorable for binding; partitioning unbound nucleic acids from those nucleic acids which have bound specifically to target molecules; dissociating the nucleic acid-target complexes; amplifying the nucleic acids dissociated from the nucleic acid-target complexes to yield a ligand enriched mixture of nucleic acids. The steps of binding, partitioning, dissociating and amplifying are repeated through as many cycles as desired to yield highly specific high affinity nucleic acid ligands to the target molecule.

Typically, such binding molecules are separately administered to the animal [see, e.g., O'Connor (1991) J. Neurochem. 56:560], but such binding molecules can also be expressed in vivo from polynucleotides taken up by a host cell and expressed in vivo [see, e.g., Oligodeoxynucleotides as Antisense Inhibitors of Gene Expression, CRC Press, Boca Raton, Fla. (1988)].

Any of the TβRII antagonist polynucleotides can be combined with one or more additional TβRII antagonists to achieve the desired effect. For example, a TβRII antagonist polynucleotide can be used in combination with i) one or more additional TβRII antagonist polynucleotides, ii) one or more TβRII polypeptides including variants thereof; iii) one or more TβRII antagonist antibodies; and/or iv) one or more TβRII antagonist small molecules.

5. Screening Assays

In certain aspects, the present invention relates to the use of TβRII polypeptides (e.g., soluble TβRII polypeptides) to identify compounds (agents) which are agonist or antagonists of the TGFβ-TβRII signaling pathway. Compounds identified through this screening can be tested to assess their ability to modulate TGFβ signaling activity in vitro. Optionally, these compounds can further be tested in animal models to assess their ability to modulate tissue growth in vivo.

There are numerous approaches to screening for therapeutic agents for modulating tissue growth by targeting TGFβ and TβRII polypeptides. In certain embodiments, high-throughput screening of compounds can be carried out to identify agents that perturb TGFβ or TβRII-mediated cell signaling. In certain embodiments, the assay is carried out to screen and identify compounds that specifically inhibit or reduce binding of a TβRII polypeptide to TGFβ. Alternatively, the assay can be used to identify compounds that enhance binding of a TβRII polypeptide to TGFβ. In a further embodiment, the compounds can be identified by their ability to interact with a TGFβ or TβRII polypeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between a TβRII polypeptide and TGFβ.

Merely to illustrate, in an exemplary screening assay of the present invention, the compound of interest is contacted with an isolated and purified TβRII polypeptide which is ordinarily capable of binding to TGFβ. To the mixture of the compound and TβRII polypeptide is then added a composition containing a TβRII ligand. Detection and quantification of TβRII/TGFβ complexes provides a means for determining the compound's efficacy at inhibiting (or potentiating) complex formation between the TβRII polypeptide and TGFβ. The efficacy of the compound can be assessed by generating dose response curves from data obtained using various concentrations of the test compound. Moreover, a control assay can also be performed to provide a baseline for comparison. For example, in a control assay, isolated and a purified TGFβ is added to a composition containing the TβRII polypeptide, and the formation of TβRII/TGFβ complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the TβRII polypeptide and TGFβ may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled TβRII polypeptide or TGFβ, by immunoassay, or by chromatographic detection.

In certain embodiments, the present invention contemplates the use of fluorescence polarization assays and fluorescence resonance energy transfer (FRET) assays in measuring, either directly or indirectly, the degree of interaction between a TβRII polypeptide and its binding protein. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments of the invention.

Moreover, the present invention contemplates the use of an interaction trap assay, also known as the "two hybrid assay," for identifying agents that disrupt or potentiate interaction between a TβRII polypeptide and its binding protein. See for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present invention contemplates the use of reverse two hybrid systems to identify compounds (e.g., small molecules or peptides) that dissociate interactions between a TβRII polypeptide and its binding protein. See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368.

In certain embodiments, the subject compounds are identified by their ability to interact with a TβRII or TGFβ polypeptide of the invention. The interaction between the compound and the TβRII or TGFβ polypeptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to a TGFβ or TβRII polypeptide. This may include a solid-phase or fluid-phase binding event. Alternatively, the gene encoding a TGFβ or TβRII polypeptide can be transfected with a reporter system (e.g., β-galactosidase, luciferase, or green fluorescent protein) into a cell and screened against the library preferably by a high-throughput screening or with individual members of the library. Other mechanism-based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

In certain aspects, the present invention provides methods and agents for modulating (stimulating or inhibiting) TGFβ-mediated cell signaling. Therefore, any compound identified can be tested in whole cells or tissues, in vitro or in vivo, to confirm their ability to modulate TGFβ signaling. Various methods known in the art can be utilized for this purpose.

6. Exemplary Therapeutic Uses

The myeloproliferative neoplasms (MPNs) arise from aberrant hematopoietic stem cell proliferation and include myelofibrosis (PMF), polycythemia vera (PV) and essential thrombocythemia (ET) [Mesa, R. A. (2013 *Leuk Lymphoma* 54(2):242-251]. ET and PV are capable of evolving into myelofibrosis (post ET-related myelofibrosis and post PV-related myelofibrosis, respectively) [Thiele et al. (2008) WHO Classification of Tumours of Haematopoietic and Lymphoid Tissues. IARC Lyon: World Health Organization, 44-7; and Cervantes et al. (2009) *Blood* 113(13):2895-901]. Despite certain idiosyncratic features, these myelofibrotic diseases have remarkable phenotypic and clinical commonalities, such as their proclivity to develop thrombotic and hemorrhagic complications and to progress to acute myeloid leukemia [Spivak, J. L. (2002) *Blood* 100:4272-4290; Finazzi et al. (2007) *Blood* 190:5104-5111; and Passamnoti et al. (2010) *Blood* 115:1703-1708]. Prior to the Food and Drug Administration (FDA) approval of ruxolitinib (e.g., Jakafi), there were no approved treatments for the treatment of MF other than hematopoietic stem cell transplant (HSCT). Improved understanding of the disease biology has led to an increase in clinical trials evaluating potential new classes of therapeutics. However, a significant unmet need still remain for the treatment of myeloproliferative disorders.

In certain aspects, the present disclosure provides methods for treating, preventing, or reducing the progression rate and/or severity of a myeloproliferative disorder (e.g., BCR-ABL-negative myeloproliferative neoplasms including primary myelofibrosis, polycythemia vera, masked polycythemia, essential thrombocythemia, post-polycythemia vera myelofibrosis, and post-essential thrombocythaemia myelofibrosis) or one or more complications of a myeloproliferative disorder (e.g., fibrosis, splenomegaly, inflammation, anemia, and extramedullary hematopoiesis) comprising administering to a patient in need thereof an effective amount of one or more TβRII antagonists (e.g., a TβRII polypeptide comprising, consisting essential of, or consisting of the amino acid sequence that is at least 85%, 90%, 91%, 92%, 93%, 94% 95%, 96%, 97%, 98%, 99%, or 100% identical to the amino acid sequence of any one of SEQ ID NOs: 5-17, 25, 27, 29, 31, 33, 35, 37, 39, 41, 43, 47-49, 53-62, 101, and 103-105), optionally in combination with one or more additional supportive therapies and/or active agents for treating a myeloproliferative disorder (e.g., a Janus kinase inhibitor such as ruxolitinib).

In certain aspects, the present disclosure provides methods of treating, preventing, or reducing the progression rate and/or severity of a Janus kinase-associated disorder (e.g., a JAK2 kinase-associated disorder) or one or more complications of a Janus kinase-associated disorder comprising administering to a patient in need thereof an effective amount of one or more TβRII antagonists (e.g., a TβRII polypeptide comprising, consisting essential of, or consisting of the amino acid sequence that is at least 85%, 90%, 91%, 92%, 93%, 94% 95%, 96%, 97%, 98%, 99%, or 100% identical to the amino acid sequence of any one of SEQ ID NOs: 5-17, 25, 27, 29, 31, 33, 35, 37, 39, 41, 43, 47-49, 53-62, 101, and 103-105), optionally in combination with one or more additional supportive therapies and/or active agents for treating a Janus kinase-associated disorder (e.g., a Janus kinase inhibitor such as ruxolitinib). Janus kinase-associated disorders that may be treated or prevented by the methods of the disclosure include, for example, myeloproliferative disorders (e.g. primary myelofibrosis, polycythemia vera, masked polycythemia vera essential thrombocythaemia, post-polycythemia vera myelofibrosis, post-essential thrombocythaemia myelofibrosis, and CML), other hematological disorders associated with a Janus kinase-associated disorder, and other clonal disorders associated with a Janus kinase-associated disorder as well as complications arising therefrom.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" as used herein includes amelioration or elimination of the condition once it has been established. In either case, prevention or treatment may be discerned in the diagnosis provided by a physician or other health care provider and the intended result of administration of the therapeutic agent.

In general, treatment or prevention of a disease or condition as described in the present disclosure is achieved by administering a TβRII antagonist in an effective amount. An effective amount of an agent refers to an amount effective, at dosages and for periods of time necessary, to achieve the desired therapeutic or prophylactic result. A therapeutically effective amount of an agent of the present disclosure may vary according to factors such as the disease state, age, sex, and weight of the individual, and the ability of the agent to elicit a desired response in the individual. A prophylactically effective amount refers to an amount effective, at dosages and for periods of time necessary, to achieve the desired prophylactic result.

Myelofibrosis is a clonal neoplastic disorder of hematopoiesis, generally characterized by progressive bone marrow fibrosis resulting in increasingly ineffective hematopoiesis, extramedullary hematopoiesis, a variety of inflammatory complications, and shortened survival [Mascarenhas et al. (2012) Curr Med Chem 19:4399-4413; and Vannucchi et al. (2011) Hematol Am Soc Hematol Educ Prog 2011:222-230]. It is one of the myeloproliferative disorders of the bone marrow in which excess cells are produced. Production of cytokines such fibroblast growth factor by the abnormal hematopoietic cell clone leads to replacement of the hematopoietic tissue of the bone marrow by connective tissue via collagen fibrosis. The decrease in hematopoietic tissue impairs the patient's ability to generate new blood cells, resulting in progressive pancytopenia, a shortage of all blood types. However, the proliferation and fibroblasts and deposition of collagen is a secondary phenomenon, and the fibroblasts themselves are not part of the abnormal cell clone. As a result of progressive scarring, or fibrosis, of the bone marrow, patients develop extramedullary hematopoiesis as the haemopoetic cells are forced to migrate to other areas, particularly the liver and spleen. This causes an enlargement of these organs. In the liver, the condition is call hepatomegaly. Enlargement of the spleen is called splenomegaly, which also contributes pancytopenia, particularly thrombocytopenia and anemia. There are also reports of extramedullary hematopoiesis occurring in the lungs and lymph nodes. Another complication of extramedullary hematopoiesis is poikilocytosis, of the presence of abnormally shaped red blood cells. Common clinical manifestations of myelofibrosis include progressive hepatosplenomegaly, abnormal blood counts, and debilitating symptoms such as fatigue, weight loss, night sweats, fever, pruritus, bone pain, early satiety, abdominal pain or discomfort, arthralgias, myalgias, parasthesias, cachexia, splenic infarct and bleeding. Until recently, the only treatment with a clearly demonstrated impact on disease progression has been allogeneic hematopoietic stem cell transplantation alloHSCT, but treatment-related mortality is high and only a minority of patients qualify for this intensive therapy [Gupta et al. (2012) Blood 120: 1367-1379].

In certain aspects, a TβRII antagonist may be used, alone or in combination with one or more supportive therapies or active agents, to treat, prevent, or reduce the progression rate and/or severity of myelofibrosis (e.g., primary myelofibrosis, post-polycythemia vera myelofibrosis, and post-essential thrombocythemia myelofibrosis). In particular, TβRII antagonists may be used, alone or in combination with one or more supportive therapies or active agents, to treat, prevent, or reduce the progression rate and/or severity of one or more complications of myelofibrosis including, for example, ineffective hematopoiesis, anemia, inflammation, fibrosis (e.g., bone marrow fibrosis, spleen fibrosis, and liver fibrosis), pancytopenia, neutropenia, elevated cytokines, coagulopathy, an inflammatory complication, IL-6-mediated inflammation or inflammatory complication, thrombocytopenia, extramedullary hematopoiesis (e.g., splenic extramedullary hematopoiesis, hepatic extramedullary hematopoiesis, pulmonary extramedullary hematopoiesis, and lymphatic extramedullary hematopoiesis), hepatomegaly, splenomegaly, osteosclerosis, osteomyelofibrosis, poikilocytosis, fatigue, weight loss, night sweats, fever, pruritus, bone pain, early satiety, abdominal pain or discomfort, arthralgias, myalgias, parasthesias, cachexia, splenic infarct, and bleeding.

Current diagnosis of primary myelofibrosis (PMF) is based on World Health Organization (WHO)-criteria and involves a composite assessment of clinical and laboratory features [Tefferi A et al. (2007) Blood. 110:1092-1097]. There are three WHO diagnostic primary criteria: 1) megakaryocyte proliferation and atypia (small to large megakaryocytes with aberrant nuclear/cytoplasmic ratio and hyperchromatic and irregularly folded nuclei and dense clustering) accompanied by either reticulin and/or collagen fibrosis or, in the absence of reticulin fibrosis, the megakaryocyte changes must be accompanied by increased marrow cellularity, granulocytic proliferation, and often decreased erythropoiesis (i.e., pre-fibrotic primary myelofibrosis), 2) not meeting WHO criteria for chronic myelogenous leukemia, polycythemia vera, myelodysplastic syndrome, or other myeloid neoplasm, and 3) demonstration of JAK2V617F or other clonal marker or no evidence of reactive bone marrow fibrosis. In addition, there are four WHO diagnostic minor criteria: 1) leukoerythroblastosis, 2) increased serum LDH levels, 3) anemia, and 4) palpable splenomegaly. Peripheral blood leukoerythroblastosis (i.e., presence of nucleated red cells, immature granulocytes, and dacryocytes) is a typical but not invariable feature of PMF; prefibrotic PMF might not display overt leukoerythroblastosis [Kvasnicka et al. (2010) Am J Hematol. 85:62-69]. Bone marrow fibrosis in PMF is usually associated with JAK2V617F or mutant CALR, or MPL, trisomy 9, or del(13q) [Hussein et al. (2009) Eur J Haematol. 82:329-338]. The presence of these genetic markers, therefore, strongly supports a diagnosis of PMF, in the presence of a myeloid neoplasm associated with bone marrow fibrosis. In certain aspects, the disclosure relates to methods and uses of TβRII antagonists to treat, prevent, or reduce the progression rate and/or severity of primary myelofibrosis, particularly treating, preventing, or reducing the progression rate and/or severity of one or more complications of primary myelofibrosis.

Current diagnosis of post-polycythemia vera myelofibrosis (post-PV MF) and post-essential thrombocythemia myelofibrosis (post-ET MF) are based on the criteria published by the International Working Group for MPN Research and Treatment (IWG-MRT) [Barosi G et al. (2008) Leukemia. 22:437-438]. There are two IWG-MRT primary criteria for post-PV MF: 1) documentation of previous diagnosis of polycythemia vera as defined by the WHO criteria, and 2) bone marrow fibrosis grade 2-3 (on 0-3 scale) or grade 3-4 (on 0-4 scale). Grade 2-3 according to the European classification: diffuse, often coarse fiber network with no evidence of collagenization (negative trichrome stain) or diffuse, coarse fiber network with areas of collagenization (positive trichrome stain) [Thiele et al. (2005) Haematologica. 90:1128-1132]. Grade 3-4 according to the standard classification: diffuse and dense increase in reticulin with extensive intersections, occasionally with only focal bundles of collagen and/or focal osteosclerosis or diffuse and dense increase in reticulin with extensive intersections with coarse bundles of collagen, often associated with significant osteosclerosis [Manoharan et al. (1979) Br J Haematol 43:185-190]. In addition, there are four IWG-MRT diagnostic secondary criteria, of which two must be detected in a patient along with the IWG-MRT primary criteria for a post-PV MF diagnosis: 1) anemia or sustained loss of requirement for phlebotomy in the absence of cytoreductive therapy, 2) a leukoerythroblastic peripheral blood picture, 3) increasing splenomegaly defined as either an increase in palpable splenomegaly of ≥5 cm or the appearance of a newly palpable splenomegaly, 4) development of ≥1 of three constitutional symptoms: >10% weight loss in six months, night sweats, unexplained fever. There are two IWG-MRT primary criteria for post-ET MF: 1) documentation of a previous diagnosis of polycythemia vera as defined by the WHO criteria, 2) bone marrow fibrosis grade 2-3 (on 0-3 scale) or grade 3-4 (on 0-4 scale). In addition, there are five IWG-MRT diagnostic secondary criteria, of which two must be detected in a patient along with the IWG-MRT primary criteria for a post-ET MF diagnosis: 1) anemia and a ≥2 g/dL decrease from baseline hemoglobin levels, 2) a leukoerythroblastic peripheral blood picture, 3) increasing splenomegaly defined as either an increase in palpable splenomegaly of ≥5 cm or the appearance of a newly palpable splenomegaly, 4) increased lactate dehydrogenase, and 5) development of ≥1 of three constitutional symptoms: >10% weight loss in six months, night sweats, unexplained fever. In certain aspects, the disclosure relates to methods and uses of TβRII antagonists to treat, prevent, or reduce the progression rate and/or severity of post-polycythemia vera myelofibrosis, particularly treating, preventing, or reducing the progression rate and/or severity of one or more complications of post-polycythemia vera myelofibrosis. In certain aspects, the disclosure relates to methods and uses of TβRII antagonists to treat, prevent, or reduce the progression rate and/or severity of post-essential thrombocythemia myelofibrosis, particularly treating, preventing, or reducing the progression rate and/or severity of one or more complications of post-essential thrombocythemia myelofibrosis.

Robust prognostic modeling in myelofibrosis started with the development of the International Prognostic Scoring System (IPSS) in 2009 [Cervantes F et al. (2009) Blood 113:2895-2901]. The IPSS for myelofibrosis is applicable to patients being evaluated at time of initial diagnosis and uses five independent predictors of inferior survival: age ≥65 years, hemoglobin <10 g/dL, leukocyte count >25×109/L, circulating blasts ≥1%, and presence of constitutional symptoms. The presence of 0, 1, 2, and ≥3 adverse factors defines low, intermediate-1, intermediate-2, and high-risk disease, respectively. The corresponding median survivals were 11.3, 7.9, 4, and 2.3 years, respectively. In certain aspects, the disclosure relates to methods and uses of TβRII antagonists to treat, prevent, or reduce the progression rate and/or severity of myelofibrosis in a patient that has low, intermediate-1, intermediate-2, and/or high-risk myelofibrosis according to the IPSS. In some embodiments, the disclosure relates to methods and uses of TβRII antagonists to prevent or delay myelofibrosis risk progression according to the IPSS (e.g., prevents or delays risk progression from low to intermediate-1 risk, intermediate-1 to intermediate-2 risk, and/or intermediate-2 to high risk according to the IPSS). In some embodiments, the disclosure relates to methods and uses of TβRII antagonists to promote or increase myelofibrosis risk regression according to the IPSS (e.g., promotes or increase regression from high to intermediate-2 risk, intermediate-2 to intermediate-1 risk, and/or intermediate-1 to low risk according to the IPSS).

The IWG-MRT subsequently developed a dynamic prognostic model (dynamic international prognostic scoring system [DIPSS]) that uses the same prognostic variables used in IPSS but can be applied at any time during the disease course [Passamonti F et al. (2010) Blood. 115:1703-1708]. DIPSS assigns two, instead of one, adverse points for hemoglobin <10 g/dL and risk categorization is accordingly modified: low (0 adverse points), intermediate-1 (1 or 2 points), intermediate-2 (3 or 4 points), and high (5 or 6 points). The corresponding median survivals were not reached, 14.2, 4, and 1.5 years. In certain aspects, the disclosure relates to methods and uses of TβRII antagonists to treat, prevent, or reduce the progression rate and/or severity of myelofibrosis in a patient that has low, intermediate-1, intermediate-2, and/or high-risk myelofibrosis according to the DIPSS. In some embodiments, the disclosure relates to methods and uses of TβRII antagonists to prevent or delay myelofibrosis risk progression according to the DIPSS (e.g., prevents or delays risk progression from low to intermediate-1 risk, intermediate-1 to intermediate-2 risk, and/or intermediate-2 to high risk according to the DIPSS). In some embodiments, the disclosure relates to methods and uses of TβRII antagonists to promote or increase myelofibrosis risk regression according to the DIPSS (e.g., promotes or increase regression from high to intermediate-2 risk, intermediate-2 to intermediate-1 risk, and/or intermediate-1 to low risk according to the DIPSS).

IPSS- and DIPSS-independent risk factors for survival in myelofibrosis were subsequently identified and included unfavorable karyotype (i.e., complex karyotype or sole or two abnormalities that include +8, −7/7q−, i(17q), inv(3), −5/5q−, 12p−, or 11q23 rearrangement) [Hussein et al. (2010) Blood. 115:496-499], red cell transfusion need [Tefferi et al. (2009) Am J Hematol. 85:14-17], and platelet count <100×109/L [Patnaik et al. (2010) Eur J Haematol. 84:105-108]. Accordingly, DIPSS was modified into DIPSS-plus by incorporating these three additional DIPSS-independent risk factors: platelet count <100×109/L, red cell transfusion need, and unfavorable karyotype. The four DIPSS-plus risk categories based on the aforementioned eight risk factors are low (no risk factors), intermediate-1 (one risk factor), intermediate-2 (two or three risk factors), and high (four or more risk factors) with respective median survivals of 15.4, 6.5, 2.9, and 1.3 years. In certain aspects, the disclosure relates to methods and uses of TβRII antagonists to treat, prevent, or reduce the progression rate and/or severity of myelofibrosis in a patient that has low, intermediate-1, intermediate-2, and/or high-risk myelofibrosis according to the DIPSS-plus. In some embodiments, the disclosure relates to methods and uses of TβRII antagonists to prevent or delay myelofibrosis risk progression according to the DIPS S-plus (e.g., prevents or delays risk progression from low to intermediate-1 risk, intermediate-1 to intermediate-2 risk, and/or intermediate-2 to high risk according to the DIPSS-plus). In some embodiments, the disclosure relates to methods and uses of TβRII antagonists to promote or increase myelofibrosis risk regression according to the DIPSS-plus (e.g., promotes or increase regression from high to intermediate-2 risk, intermediate-2 to intermediate-1 risk, and/or intermediate-1 to low risk according to the DIPS S-plus).

Since the publication of DIPSS-plus, several studies that suggest additional prognostic information have been published. For example, a >80% 2-year mortality in myelofibrosis was predicted by monosomal karyotype, inv(3)/i(17q) abnormalities, or any two of circulating blasts >9%, leukocytes ≥40×109/L or other unfavorable karyotype [Tefferi et al. (2011) Blood. 118:4595-4598.]. Similarly, inferior survival in myelofibrosis has been associated with nullizygosity for JAK2 46/1 haplotype, low JAK2V617F allele burden, or presence of IDH, EZH2, SRSF2, or ASXL1 mutations [Tefferi, Ayalew (2014) Am. J. Hematol. 89:916-925]. In contrast, the presence or absence of JAK2V617F, MPL, or TET2 mutations did not appear to affect survival. Survival in myelofibrosis was also affected by increased serum IL-8 and IL-2R levels as well as serum free light chain levels, both independent of DIPSS-plus. Most recently, Tefferi et al. studied 254 patients with myelofibrosis and reported mutational frequencies of 58% for JAK2, 25% CALR, 8% MPL, and 9% wild-type for all three mutations (i.e., triple-negative) [Tefferi et al. (2014) Leukemia. prepublished as DOI 10.1038/leu.2014.3]. CALR mutational frequency in JAK2/MPL-unmutated cases was 74%. CALR mutations were associated with younger age, higher platelet count, and lower DIPSS-plus score. CALR-mutated patients were also less likely to be anemic, require transfusions, or display leukocytosis. Spliceosome mutations were infrequent in CALR-mutated patients. In a subsequent international study of 570 patients, the authors reported the longest survival in CALR+ASXL1− patients (median 10.4 years) and shortest in CALR−ASXL1+patients (median 2.3 years) [Tefferi et al. (2014) Leukemia. prepublished as DOI 10.1038/leu.2014.57]. CALR+ASXL1+ and CALR−ASXL1− patients had similar survival and were grouped together in an intermediate risk category (median survival 5.8 years). As is becoming evident for overall survival, leukemia-free survival is also significantly compromised in patients carrying certain mutations including IDH and SRSF2 [Tefferi et al. (2012) Leukemia. 26:475-480; Lasho et al. (2012) Blood. 120:4168-4171]. In addition, mutations in LNK and THPO have also been associated with myelofibrosis.

In certain aspects, the disclosure relates to methods and uses of TβRII antagonists to treat, prevent, or reduce the progression rate and/or severity of myelofibrosis in a patient that has one or more of: monosomal karyotype, inv(3)/i(17q) abnormalities, circulating blasts >9% and/or leukocytes ≥40×109/L, nullizygosity for JAK2 46/1 haplotype, JAK2V617F mutation, IDH1 mutation, IDH2 mutation, EZH2 mutation, SRSF2 mutation, ASXL1 mutation, increased serum IL-8 levels, increased serum IL-2R levels, increased free light chain levels, JAK1 mutation, JAK2 mutation, JAK3 mutation, TYK2 mutation, MPL mutation, CALR mutation, CALR+ASXL1−, CALR−ASKL1+, CALR+ASKL1+, CALR−ASKL1−, TET2 mutation, THPO mutation, and LNK mutation.

In general, PV is characterized by an increased red blood cell mass [Vardiman et al. (2009) Blood. 114:937-951; Stuart et al. (2004) Am Fam Physician 69:2139-2144; Hensley et al. (2013) Expert Opin Pharmacother 14:609-617; Passamonti F. (2012) Blood 120:275-2845; and Vannucchi A. M. (2010) Intern Emerg Med. 5:177-184]. Patients with PV typically have excessive proliferation of not only erythroid but also myeloid and megakaryocytic components in the bone marrow, resulting in high red blood cell, white blood cell (WBC), and platelet counts. PV patients generally have a reduced quality of life and are at risk of transformation to secondary MF and acute myeloid leukemia (AML). Therapeutic options are limited (e.g., low-dose aspirin, phlebotomy, and hydroxyurea) and are mainly palliative, focusing on preventing the occurrence of thrombosis and improving symptoms associated with elevated erythroid, myeloid, and/or megakaryocytic levels.

PV has a much higher prevalence than MF (44-57 per 100,000 persons vs 4-6 per 100,000, respectively), and PV patients have a higher risk of death than the general population [Mehta et al. (2014) Leuk Lymphoma 55:595-600; and Passamonti et al. (2004) Am J Med. 117:755-761]. PV affects more men than women, with the median age of diagnosis being 60 years; however, approximately 20-25% of patients are younger than 40 years [Tibes et al. (2013) Expert Opin Emerg Drugs. 18:393-404]. The median survival in patients with PV is around 14 years, but it is much lower in those older than 60 years and/or with a history of thrombosis (around 8 years) [Tefferi et al. (2013) Leukemia 27:1874-1881].

The understanding of the pathogenesis of PV has greatly improved after the discovery of activating mutations in JAK2 in most patients with PV [Levine R L, Pardanani A, Tefferi et al. (2007) Nat Rev Cancer 7:673-683; Tefferi A. (2011) Leukemia 25:1059-1063; and Sever et al. (2014) Leuk Lymphoma 55:2685-2690]. The classical JAK2 V617F mutation present in approximately 96% of patients with PV and JAK2 exon 12 mutations in approximately 3% of patients with PV. Over-activation of JAK2 autonomously activates downstream pathways, including JAK-STAT, leading to unregulated hematopoiesis. These findings have been instrumental in shaping criteria for diagnosis and treatment. The presence of the JAK2V617F mutation is a major criterion in the diagnosis of PV, and several JAK2 inhibitors are in development as targeted molecular therapies for PV [Hensley et al. (2013) Expert Opin Pharmacother 14:609-617].

PV diagnosis is currently based on the 2008 World Health Organization (WHO) diagnostic criteria [Vardiman et al. (2009) Blood. 114:937-951]. The WHO diagnostic criteria emphasize laboratory values, morphologic features, and genetic data, with erythrocytosis being the first major criterion. According to the WHO, evidence of erythrocytosis includes elevated hemoglobin (Hgb) levels (>18.5 g/dL in men and >16.5 g/dL in women), but other groups, such as the British Committee for Standards in Haematology and the Polycythemia Vera Study Group, emphasize the use of elevated hematocrit (Hct) value (>48% in women and >52% in men) or red cell mass measurement, respectively [McMullin et al. (2007) Br J Haematol 138:821-822; and Murphy S. (1999) Semin Hematol 36:9-13]. Recently, some investigators have proposed revising the WHO criteria, especially following the identification of masked PV (mPV) in a subgroup of patients with PV [Barbui T et al. (2014) Leukemia 28:1191-1195; and Barbui et al. (2014) Am J Hematol 89:199-202] Unlike patients with overt PV, patients with mPV tend to have normal or borderline Hgb and Hct values but are usually positive for JAK2 mutations, have bone marrow features consistent with PV, and have low serum erythropoietin levels. It has been proposed that a revision to the current WHO diagnostic criteria with emphasis on a lower Hgb threshold and/or the use of Hct threshold values may be helpful in accurately diagnosing those with mPV and could allow for appropriate and prompt treatment of these patients.

In the current risk stratification model, age ≥60 years of age and history of thrombosis are the two risk factors used to classify patients with PV into low (0 risk factors) and high (one or two risk factors) risk groups. In certain aspects, the disclosure relates to methods and uses of TβRII antagonists to treat, prevent, or reduce the progression rate and/or severity of PV or one or more complications of PV in a patient that has low or high risk PV. In some embodiments, the disclosure relates to methods and uses of TβRII antagonists to prevent or delay PV risk progression (e.g., prevent or delay risk progression from low to high risk PV). In some embodiments, the disclosure relates to methods and uses of TβRII antagonists to promote or increase PV risk regression (e.g., promotes or increases regression from high to low risk PV). In some embodiments, the disclosure relates to methods and uses of TβRII antagonists to prevent or delay PV progression into myelofibrosis (post-PV myelofibrosis). PV also carries a risk of transformation into acute leukemia [Vannucchi A. M. (2010) *Intern Emerg Med.* 5:177-184]. The incidence of transformation to AML in patients with PV ranges from 5 to 15% after 10 years of disease, with progressive risk over time [Finazzi et al. (2005) *Blood* 105:2664-2670]. Advanced age, female sex, and the use of alkylating drugs, radiation, or a combination of cytoreductive drugs are associated with a higher risk of leukemic transformation. In some embodiments, the disclosure relates to methods and uses of TβRII antagonists to prevent or delay PV progression into AML.

Symptomatic burden in PV is generally severe and present in most patients with the disease [Scherber et al. (2011) *Blood* 118:401-408; and Hensley et al. (2013) *Expert Opin Pharmacother* 14:609-617]. The most common complaints are fatigue (reported by 88% of patients), pruritus (62%), night sweats (52%), bone pain (50%), fever (18%), and weight loss (31%), with pruritus and fatigue being the most prevalent and troublesome symptoms. Pruritus presents as generalized burning, pricking, tingling, or itching and is frequently reported after water contact (aquagenic pruritus), large temperature shifts, alcohol consumption, or exercise may induce comparable symptoms. Fatigue has been identified as the consequence of elevated circulating cytokines (e.g., tumor necrosis factor alpha, interleukin-1, and interleukin-6). Additionally, approximately 35 to 45% of patients develop splenomegaly, although its presence is usually indicative of advanced disease [Tefferi et al. (2013) *Leukemia* 27:1874-1881]. Splenomegaly usually results in secondary symptoms, including abdominal pain, early satiety, weight loss, and nausea, and complications can lead to abdominal organ compression and portal hypertension. PV-associated constitutional symptoms and symptoms associated with splenomegaly are present in 70% of patients and compromise quality of life [Scherber et al. (2011) *Blood* 118:401-408; Hensley et al. (2013) *Expert Opin Pharmacother* 14:609-617; and Abelsson et al. (2013) *Leuk Lymphoma* 54:2226-2230], as assessed by tools such as the European Organisation for Research and Treatment of Cancer Quality of Life Questionnaire Core 30 and/or the MPN-Symptom Assessment Form (SAF) questionnaires. The MPN-SAF Total Symptom Score is a ten-item scoring instrument focusing on fatigue, concentration, early satiety, inactivity, night sweats, itching, bone pain, abdominal discomfort, weight loss, and fevers. Based on these tools, the symptom burden in patients with PV at diagnosis has been found to be comparable to or worse than that observed in patients with newly diagnosed primary MF.

Some of the most frequent complications of PV are vascular and thromboembolic events and hemorrhages [Vannucchi A. M. (2010) *Intern Emerg Med.* 5:177-184]. Thrombosis is a prominent symptom observed in up to 39% of patients with PV at diagnosis [Tefferi et al. (2007) *Semin Thromb Hemost* 33:313-320; and Barbui T et al. (2012) *Blood Rev* 26:205-211]. The most frequent types of major thrombosis include stroke, transient ischemic attack, myocardial infarction, peripheral arterial thrombosis, deep venous thrombosis, portal vein thrombosis, and thrombosis of the hepatic veins causing Budd-Chiari syndrome. In addition to macrovascular complications, patients may experience microvascular symptoms (e.g., headaches, dizziness, visual disturbances, distal paresthesia, acrocyanosis), with erythromelalgia being the most characteristic disturbance and consisting of congestion, redness, and burning pain in the extremities. In cases of extreme thrombocytosis (e.g., $>1500 \times 10^9/L$), patients may be at risk for developing acquired von Willebrand syndrome, which causes a bleeding diathesis [Chou Y S et al. (2013) *Eur J Haematol* 90:228-236]. Hemorrhage is also a significant cause of morbidity and mortality in patients with PV, with a cumulative incidence of 39.6% (6.2% per person-year). Additionally, overall survival has been found to be significantly shorter among patients with hemorrhage than among those without this complication (median overall survival, around 95 months).

In certain aspects, a TβRII antagonist (e.g., a TβRII polypeptide comprising, consisting essential of, or consisting of an amino acid sequence that is at least 85%, 90%, 91%, 92%, 93%, 94% 95%, 96%, 97%, 98%, 99%, or 100% identical to the amino acid sequence of any one of SEQ ID NOs: 5-17, 25, 27, 29, 31, 33, 35, 37, 39, 41, 43, 47-49, 53-62, 101, and 103-105) may be used, alone or in combination with one or more supportive therapies or active agents (e.g., a Janus kinase inhibitor such as ruxolitinib), to treat, prevent, or reduce the progression rate and/or severity of polycythemia vera. In particular, TβRII antagonists may be used, alone or in combination with one or more supportive therapies or active agents, to treat, prevent, or reduce the progression rate and/or severity of one or more complications of polycythemia vera. Complications of polycythemia vera that may be treated in accordance with the methods disclosed herein include, for example, excessive proliferation of erythroid cells, excessive proliferation of myeloid cells, excessive proliferation of megakaryocytic cells, high red blood cell levels, high white blood cell levels, high platelet levels, fatigue, pruritus, night sweats, bone pain, fever, and weight loss, elevated inflammatory cytokines (e.g., IL-6), inflammatory complications, IL-6-mediated inflammatory complications, splenomegaly, abdominal pain, early satiety, weight loss, nausea, abdominal organ compression, portal hypertension, constitutional symptoms, vascular complications, thrombosis, microvascular complications, and macrovascular complications.

The new World Health Organization (WHO) diagnostic criteria for essential thrombocythemia (ET) issued in 2008 made an important distinction between true ET and early myelofibrosis and thus helped to identify a more homogenous population for diagnosis, which are characterized, in part, by longer survival and less transformation to overt MF. Thrombocytosis is a prerequisite for the diagnosis of ET, but such events may also manifest in PV and PMF patients, although more seldom [Birgegard G. (2015) Ther Adv Hematol 6(3):142-156]. In addition, ET is characterized by lower white blood cell counts, lower hemoglobin levels, low lactate dehydrogenase (LDH) levels in plasma and, importantly, a better prognosis, that early myelofibrosis patients [Barbui et al. (2012) Blood 120: 569-571.]. A recent prognostic model for WHO-classified ET indicates that expected survival from diagnosis is 13.7 years for high risk patients, 24.5 years for an intermediate group and >25 years for low risk patients [Passamonti et al. (2012) Blood 120: 1197-1201]. The distinction between true ET and early MF, so far, has no great consequences for the pharmacological treatment, since this is directed by risk stratification for thrombohemorrhagic events, but it is of course important in communications with the patients and may soon be very important for treatment decisions with the new drugs under development.

The detection of driver mutations in ET and other myelofibrosis conditions has greatly increased understanding of the pathophysiology of the disease. As discussed previously, a breakthrough in myelofibrosis research was made when a mutation in the pseudokinase domain of the JAK2 gene was discovered to be present in a large percentage of myelofibrosis patients. Interestingly, while around 95% of PV patients carry the JAK2V617F mutation, only around 50% of ET patients are JAK2 mutation positive [Campbell et al. (2005) Lancet 366:1945-1953]. Moreover, JAK2V617F+ET patients manifest a slightly different phenotypic pattern than JAK2V617F−ET patients, presenting with higher Hb and WBC levels, lower serum erythropoietin, and lower platelets. Several studies demonstrate that there is an increased risk of thrombosis in JAK2V617F+ET patients compared to JAK2V617F−ET patients [Ziakas P. (2008) Haematologica 93:1412-1414; Dahabreh et al. (2009) Leuk Res 33: 67-73; and Lussana et al. (2009) Thromb Res 124: 409-417]. A recent study showed that progression of JAK2V617F allele burden, particularly at high stable levels, was significantly correlated to development of MF [Alvarez-Larran A et al. (2014b) Am J Hematol 89: 517-523].

A recent addition to the mutational pattern in myelofibrosis is the detection of a driver mutation of CALR, a highly conserved multifunctional endoplasmic reticulum protein with partly unknown functions. The mutation is found in ET and PMF patients, but almost exclusively in ones that do not have mutations in either JAK2 or MPL [Klampfl et al. (2013) N Engl J Med 369: 2379-2390; Nangalia et al. (2013) N Engl J Med 369: 2391-2405]. The frequency is around 20% in both ET and PMF, which means that about 85% of ET patients can now be diagnosed with a molecular marker. Interestingly, the CALR mutation in ET produces a phenotype profile with clear differences from JAK2V617F+patients. Compared with JAK2V617F+patients, CALR+patients are younger, more commonly male, have higher platelet levels, and lower leukocyte levels [Gangat et al. (2014) Eur J Haematol 94: 31-36; Rotunno et al. (2014) Blood 123: 1552-1555; Rumi et al. (2014) Blood 123: 2416-2419; Tefferi et al. (2014c) Leukemia 28: 2300-2303]. In addition, the difference in thrombotic rate is quite marked: the 10-year cumulative incidence being 5.1% (JAK2V617F+patients), and 14.5% (CALR+patients), respectively, and correspondingly, the 15-year rate 10.5% (JAK2V617F+patients) and 25.1% (CALR+patients).

In the current risk stratification model, age ≥60 years of age and history of thrombosis are the two risk factors used to classify patients with ET into low (0 risk factors) and high (one or two risk factors) risk groups. In certain aspects, the disclosure relates to methods and uses of TβRII antagonists to treat, prevent, or reduce the progression rate and/or severity of ET or one or more complications of ET in a patient that has low or high risk ET. In some embodiments, the disclosure relates to methods and uses of TβRII antagonists to prevent or delay ET risk progression (e.g., prevent or delay risk progression from low to high risk ET). In some embodiments, the disclosure relates to methods and uses of TβRII antagonists to promote or increase ET risk regression (e.g., promotes or increases regression from high to low risk ET). In some embodiments, the disclosure relates to methods and uses of TβRII antagonists to prevent or delay ET progression into myelofibrosis (post-ET myelofibrosis). ET also carries a risk of transformation into acute leukemia [Vannucchi A. M. (2010) Intern Emerg Med. 5:177-184]. In some embodiments, the disclosure relates to methods and uses of TβRII antagonists to prevent or delay ET progression into AML.

Studies have shown that ET patients have a significant symptom burden with an effect on quality of life. In an international effort, a symptom assessment tool specific to the MPN population was developed and validated [Emanuel et al. (2012) J Clin Oncol 30: 4098-4103; and Scherber et al. (2011) Blood 118: 401-408]. Symptoms/complications of ET include, for example: fatigue, night sweats, nausea, numbness, visions disturbances, and weight loss, as well as resulting from microvascular complications like headache, chest pain, dizziness and erythromelalgia. Additionally, about 20% of ET patients have experienced thrombosis before or at diagnosis. Mild splenomegaly is also frequently observed in ET patients.

In certain aspects, a TβRII antagonist (e.g., a TβRII polypeptide comprising, consisting essential of, or consisting of an amino acid sequence that is at least 85%, 90%, 91%, 92%, 93%, 94% 95%, 96%, 97%, 98%, 99%, or 100% identical to the amino acid sequence of any one of SEQ ID NOs: 5-17, 25, 27, 29, 31, 33, 35, 37, 39, 41, 43, 47-49, 53-62, 101, and 103-105) may be used, alone or in combination with one or more supportive therapies or active agents (e.g., a Janus kinase inhibitor such as ruxolitinib), to treat, prevent, or reduce the progression rate and/or severity of essential thrombocythemia. In particular, TβRII antagonists may be used, alone or in combination with one or more supportive therapies or active agents, to treat, prevent, or reduce the progression rate and/or severity of one or more complications of essential thrombocythemia. Complications of essential thrombocythemia that may be treated in accordance with the methods disclosed herein include, for example, thrombocytosis, fatigue, night sweats, nausea, numbness, visions disturbances, weight loss, microvascular complications, macrovascular complications, headache, chest pain, dizziness, erythromelalgia, thrombosis, splenomegaly, elevated inflammatory cytokines, inflammatory complication, IL-6 inflammatory complication, elevated inflammatory cytokine levels, elevated IL-6 levels, vasculature complications, and hemorrhage.

As discussed above, the discovery of a Janus kinase 2 (JAK2) gain-of-function mutation, JAK2V617F, has led to significant improvements in the understanding of the biology underlying myelofibrosis, as well as the development of ruxolitinib, a JAK2 inhibitor which is the first drug approved by the FDA for the treatment of myelofibrosis [Baxter et al. (2005) Lancet 365:1054-1061; James C. et al. (2005) Nature 434:1144-1148; Kralovics et al. (2005) N Engl J Med. 352:1779-1790; and Levine et al. (2005) Cancer Cell 7:387-397]. JAK2V617F is present in the majority of myelofibrosis (50-60%) and PV (95%) patients and about half ET (~50%) patients [Baxter et al. (2005) Lancet 365:1054-1061; James C. et al. (2005) Nature 434:1144-1148; Kralovics et al. (2005) N Engl J Med. 352:1779-1790; Levine et al. (2005) Cancer Cell 7:387-397; and Quintas-Cardama et al. (2011) Nat Rev Drug Discov 10:127-140]. Additional mutations relevant to the JAKSTAT pathway have been identified in patients with myeloproliferative disorders including, for example, MPL, CALR, LNK, TET2, IDH1, IDH2, THPO, and ASXL1 [Pikman et al. (2006) PLoS Med 3:e270; Oh et al. (2010) Blood 116:988-992; Delhommeau et al. (2009) N Engl J Med 360:2289-2301; and Carbuccia et al. (2009) Leukemia 23:2183-2186]. JAK2V617F and other mutations may occur in the same patient at the same time, and multiple clones with different mutational profiles can occur in a single patient. The presence of JAK2V617F has been correlated to worsening of symptoms and progression stage of myeloproliferative disease to advanced stages [Barosi et al. (2007) Blood 110:4030-4036; and Tefferi et al. (2005) Br J Haematol 131:320-328]

With the discovery of these genetic markers, newer therapeutic strategies are focusing, in part, on achieving a reduction in myeloproliferative disease-associated allele burden.

In the context of myeloproliferative diseases, allele burden is generally defined as the ratio of mutant copy number (e.g., JAK2V617F) to total gene copy number a given patient (e.g., JAK2V617F/JAK2V617F+wild-type JAK2]). In some studies, patients with lower allele burden have demonstrated a better prognosis than those with higher allele burdens. Several MF studies have linked high allele burden to progression of disease, for example, one study has shown higher allele burden of certain mutant genes is associated with progressing to AML which is consistent with the observation that a majority of patients with leukemia are homozygous for JAK2V617F [Barosi et al. (2007) *Blood* 110:4030-4036; and Passamonti et al. (2010) *Leukemia* 24:1574-1579]. In addition, studies have consistently demonstrated a link between increasing allele burden and worsening splenomegaly and increased myelopoiesis [Passamonti et al. 2009) *Haematologica* 94:7-10].

In certain aspects, the present disclosure provides methods for treating, preventing, or reducing the progression rate and/or severity of a myeloproliferative disorder [e.g., myelofibrosis (e.g., primary myelofibrosis, post-polycythemia vera myelofibrosis, and post-essential thrombocythemia myelofibrosis), polycythemia vera (e.g., masked polycythemia vera), and essential thrombocythemia] or one or more complications of a myeloproliferative disorder (e.g., fibrosis, splenomegaly, inflammation, anemia, and extramedullary hematopoiesis) by administering to a patient in need thereof and effective amount of a TβRII antagonist (e.g., a TβRII polypeptide comprising, consisting essential of, or consisting of an amino acid sequence that is at least 85%, 90%, 91%, 92%, 93%, 94% 95%, 96%, 97%, 98%, 99%, or 100% identical to the amino acid sequence of any one of SEQ ID NOs: 5-17, 25, 27, 29, 31, 33, 35, 37, 39, 41, 43, 47-49, 53-62, 101, and 103-105), optionally in combination with one or more additional supportive therapies and/or active agents for treating a myeloproliferative disorder (e.g., a Janus kinase inhibitor such as ruxolitinib) wherein the patient has one or more myeloproliferative-associated alleles (e.g., JAK2, MPL, CALR, LNK, TET2, IDH1, IDH2, THPO, and ASXL1). In some embodiments, the method reduces allele burden of one or more myeloproliferative-associated alleles (e.g., JAK2, MPL, CALR, LNK, TET2, IDH1, IDH2, THPO, and ASXL1) in the patient. In some embodiments, the patient has one or more myeloproliferative-associated JAK2 alleles. In some embodiments, the method reduces allele burden of one or more myeloproliferative-associated JAK2 alleles. In some embodiments, the patient has the JAK2V617F myeloproliferative-associated allele. In some embodiments, the method reduces JAK2V617F myeloproliferative-associated allele burden.

In certain aspects, the present disclosure provides methods for reducing myeloproliferative-associated allele burden in a patient having a myeloproliferative disorder [e.g., myelofibrosis (e.g., primary myelofibrosis, post-polycythemia vera myelofibrosis, and post-essential thrombocythemia myelofibrosis), polycythemia vera (e.g., masked polycythemia vera), and essential thrombocythemia] by administering to a patient in need thereof and effective amount of a TβRII antagonist (e.g., a TβRII polypeptide comprising, consisting essential of, or consisting of an amino acid sequence that is at least 85%, 90%, 91%, 92%, 93%, 94% 95%, 96%, 97%, 98%, 99%, or 100% identical to the amino acid sequence of any one of SEQ ID NOs: 5-17, 25, 27, 29, 31, 33, 35, 37, 39, 41, 43, 47-49, 53-62, 101, and 103-105), optionally in combination with one or more additional supportive therapies and/or active agents for treating a myeloproliferative disorder (e.g., a Janus kinase inhibitor such as ruxolitinib). In some embodiments, the patient has one or more myeloproliferative-associated alleles selected from the group consisting of: JAK2, MPL, CALR, LNK, TET2, IDH1, IDH2, THPO, and ASXL1). In some embodiments, the patient has one or more JAK2 myeloproliferative-associated alleles. In some embodiments, the patient has the JAK2V617F myeloproliferative-associated allele.

In accordance with the methods described herein, a TβRII antagonist (e.g., a TβRII polypeptide comprising, consisting essential of, or consisting of an amino acid sequence that is at least 85%, 90%, 91%, 92%, 93%, 94% 95%, 96%, 97%, 98%, 99%, or 100% identical to the amino acid sequence of any one of SEQ ID NOs: 5-17, 25, 27, 29, 31, 33, 35, 37, 39, 41, 43, 47-49, 53-62, 101, and 103-105) can be administered to the subject alone, or in combination with one or more additional active agents or supportive therapies, for example, active agents or supportive therapies that are useful for treating myeloproliferative disorders (e.g., primary myelofibrosis polycythemia vera, masked polycythemia, essential thrombocythemia, post-polycythemia vera myelofibrosis, and post-essential thrombocythaemia myelofibrosis) as well as one or more complications thereof a myeloproliferative disorders.

As used herein, "in combination with", "combinations of", "combined with", or "conjoint" administration refers to any form of administration such that additional therapies (e.g., second, third, fourth, etc.) are still effective in the body (e.g., multiple compounds are simultaneously effective in the patient, which may include synergistic effects of those compounds). Effectiveness may not correlate to measurable concentration of the agent in blood, serum, or plasma. For example, the different therapeutic compounds can be administered either in the same formulation or in separate formulations, either concomitantly or sequentially, and on different schedules. Thus, an individual who receives such treatment can benefit from a combined effect of different therapies. One or more TβRII antagonists of the disclosure can be administered concurrently with, prior to, or subsequent to, one or more other additional agents or supportive therapies. In general, each therapeutic agent will be administered at a dose and/or on a time schedule determined for that particular agent. The particular combination to employ in a regimen will take into account compatibility of the TβRII antagonist of the present disclosure with the therapy and/or the desired effect.

The management of anemia can be one of the most challenging aspects of treating patients with myelofibrosis [Tefferi A. (2011) Blood 117(13):3949-3504; Barosi et al. (2011) Expert Opin Pharmacother 12(10):1597-1611]. Blood transfusion (whole blood or red blood cell transfusion) is a standard therapy for symptomatically anemic myelofibrosis patients. In addition to transfusion, there are a variety of conventional agents used to treat anemia in these patients. For example, erythropoiesis-stimulating agents [e.g., ESAs such as erythropoietin (EPO) and derivatives thereof], androgens (e.g., testosterone enanthate and fluoxymesterone), prednisone, danazol, thalidomide, prednisone, and lenalidomide are commonly used to treat anemia in myelofibrosis patients. In general, ESAs are used in patients with moderate, non-transfusion-dependent anemia and low serum erythropoietin levels. Response rates vary from 20-60% with no clear support for darbepoetin-alpha versus conventional recombinant erythropoietin. ESAs responses are usually short-lived (around 1 year). If ESAs do not work or have poor efficacy, danazol or androgen preparations are typically used to treat anemic patients with a response rate around 20%. Low-dose thalidomide in association with tapering prednisone has produced responses in anemia in approximately 20-40% of patients [Thapaliya et al. (2011) Am J Hematol 86(1):86-98]. However, thalidomide treatment is often poorly tolerated with peripheral neuropathies, constipation, and somnolence leading to discontinuation of the drug in most patients. In myelofibrosis patients with del(5q31)-associated anemia, lenalidomide is the recommended first line therapy because significant improvement, with resolution of anemia and occasionally evidenced of molecular remission, has been reported [Tefferi et al. (2007) Leukemia 21(8):1827-1828].

In certain aspects, the disclosure relates to methods and uses of TβRII antagonists to treat, prevent, or reduce the progression rate and/or severity of myelofibrosis in a patient that has anemia. In some embodiments, the disclosure relates to methods and uses of TβRII antagonists to treat, prevent, or reduce the progression rate and/or severity of anemia in a myelofibrosis patient. In some embodiments, the disclosure relates to a method of treating, preventing, or reducing the progression rate and/or severity myelofibrosis or one or more complications of myelofibrosis (e.g., anemia) in a patient in need thereof that comprises administration of one or more TβRII antagonists conjointly with one or more additional active agents selected from the group consisting of: an erythropoiesis-stimulating agent [e.g., ESAs such as erythropoietin (EPO) and derivatives thereof], androgen (e.g., testosterone enanthate and fluoxymesterone), prednisone, danazol, thalidomide, prednisone, and lenalidomide. In some embodiments, the disclosure relates to a method of treating, preventing, or reducing the progression rate and/or severity of anemia in a myelofibrosis patient in need thereof of comprises administration of one or more TβRII antagonists conjointly with one or more additional active agents selected from the group consisting of: an erythropoiesis-stimulating agent [e.g., ESAs such as erythropoietin (EPO) and derivatives thereof], androgen (e.g., testosterone enanthate and fluoxymesterone), prednisone, danazol, thalidomide, prednisone, and lenalidomide. In some embodiments, the disclosure relates a method of treating, preventing, or reducing the progression rate and/or severity anemia in a myelofibrosis patient in need thereof of comprises administration of one or more TβRII antagonists conjointly with a blood transfusion (whole blood or red blood cell transfusion).

One or more TβRII antagonists of the disclosure may be used in combination with an EPO receptor activator to achieve an increase in red blood cells, particularly at lower dose ranges. This may be beneficial in reducing the known off-target effects and risks associated with high doses of EPO receptor activators. The primary adverse effects of ESAs include, for example, an excessive increase in the hematocrit or hemoglobin levels and polycythemia. Elevated hematocrit levels can lead to hypertension (more particularly aggravation of hypertension). Other adverse effects of ESAs which have been reported, some of which relate to hypertension, are headaches, influenza-like syndrome, obstruction of shunts, myocardial infarctions and cerebral convulsions due to thrombosis, hypertensive encephalopathy, and red cell blood cell aplasia. See, e.g., Singibarti (1994) J. Clin Investig 72 (suppl 6), S36-S43; Horl et al. (2000) Nephrol Dial Transplant 15 (suppl 4), 51-56; Delanty et al. (1997) Neurology 49, 686-689; and Bunn (2002) N Engl J Med 346(7), 522-523). In certain embodiments, the present disclosure provides methods of treating or preventing anemia in a myelofibrosis patient by administering to the patient a therapeutically effective amount of one or more TβRII antagonists and an EPO receptor activator. In certain embodiments, a TβRII antagonist of the disclosure may be used in combination with EPO receptor activators to reduce the required dose of these activators in patients that are susceptible to adverse effects of ESAs. These methods may be used for therapeutic and prophylactic treatments of a patient.

When monitoring hemoglobin and/or hematocrit levels in humans, a level of less than normal for the appropriate age and gender category may be indicative of anemia, although individual variations are taken into account. For example, a hemoglobin level from 10-12.5 g/dl, and typically about 11.0 g/dl is considered to be within the normal range in healthy adults, although, in terms of therapy, a lower target level may cause fewer cardiovascular side effects. See, e.g., Jacobs et al. (2000) Nephrol Dial Transplant 15, 15-19. Alternatively, hematocrit levels (percentage of the volume of a blood sample occupied by the cells) can be used as a measure of anemia. Hematocrit levels for healthy individuals range from about 41-51% for adult males and from 35-45% for adult females. In certain embodiments, a patient may be treated with a dosing regimen (e.g., TβRII antagonist optionally in combination with one or more additional active agents or supportive therapies) intended to restore the patient to a target level of red blood cells, hemoglobin, and/or hematocrit or allow the reduction or elimination of red blood cell transfusions (reduce transfusion burden) while maintaining an acceptable level of red blood cells, hemoglobin and/or hematocrit. As hemoglobin and hematocrit levels vary from person to person, optimally, the target hemoglobin and/or hematocrit level can be individualized for each patient.

In patients who receive frequent transfusions of whole blood or red blood cells, normal mechanisms of iron homeostasis can be overwhelmed, eventually leading to toxic and potentially fatal accumulation of iron in vital tissues such as heart, liver, and endocrine glands. Regular red blood cell transfusions require exposure to various donor units of blood and hence a higher risk of alloimmunization. Difficulties with vascular access, availability of and compliance with iron chelation, and high cost are some of the reasons why it can be beneficial to limit the number of red blood cell transfusions.

In certain aspects, one or more TβRII antagonists, optionally combined with an EPO receptor activator, may be used in combination with one or more iron-chelating agents to treat, prevent, or reduce the progression rate and/or severity of iron overload in a myelofibrosis patient. In some embodiments, one or more TβRII antagonists, optionally combined with an EPO receptor activator, may be used in combination with one or more iron-chelating agents to treat, prevent, or reduce the progression rate and/or severity of tissue iron overload [e.g., spleen (splenic), liver (hepatic), heart (cardiac) iron overload] in a myelofibrosis patient. Effective iron-chelating agents should be able to selectively bind and neutralize ferric iron, the oxidized form of non-transferrin bound iron which likely accounts for most iron toxicity through catalytic production of hydroxyl radicals and oxidation products [see, e.g., Esposito et al. (2003) Blood 102:2670-2677]. These agents are structurally diverse, but all possess oxygen or nitrogen donor atoms able to form neutralizing octahedral coordination complexes with individual iron atoms in stoichiometries of 1:1 (hexadentate agents), 2:1 (tridentate), or 3:1 (bidentate) [Kalinowski et al. (2005) Pharmacol Rev 57:547-583]. In general, effective iron-chelating agents also are relatively low molecular weight (e.g., less than 700 daltons), with solubility in both water and lipids to enable access to affected tissues. Specific examples of iron-chelating molecules include deferoxamine, a hexadentate agent of bacterial origin requiring daily parenteral administration, and the orally active synthetic agents deferiprone (bidentate) and deferasirox (tridentate). Combination therapy consisting of same-day administration of two iron-chelating agents shows promise in patients unresponsive to chelation monotherapy and also in overcoming issues of poor patient compliance with dereroxamine alone [Cao et al. (2011) Pediatr Rep 3(2):e17; and Galanello et al. (2010) Ann NY Acad Sci 1202:79-86].

In the management of patients with a myeloproliferative disorder (e.g., myelofibrosis, polycythemia vera, and essential thrombocytopenia), cytoreductive agents have been the treatment of choice for most patients with symptomatic splenomegaly. Hydroxycarbamide (hydroxyurea, HC) is the most commonly used cytoreductive agent, which usually produces modest responses at higher doses. However, HC can often exacerbate cytopenias and therefore is often not well tolerated. Reductions in spleen size from 25%-50% have been reported in up to 35% of the patients treated with HC [Martinez-Trillos et al. (2010) Ann Hematol. 89(12): 1233-1237]. In patients who do not respond to HC, busulfan or melphalan may be used, especially in older patients, since there is evidence that these agents can increase the frequency of leukemic transformation. Spleen responses with low-dose thalidomide are low (<20%). However, lenalidomide has been shown to result in a 33% response rate in a study that included some patients who had failed prior thalidomide therapy. In cases of massive refractory splenomegaly, monthly intravenous cladribine courses have produced responses up to 50%, with severe but reversible cytopenias being the primary toxicity [Faoro et al. (2005) Eur J Haematol 74(2):117-120]. Ruxolitinib has proven superior to HC in recent studies and thus is becoming first line agent to control symptomatic or progressive splenomegaly. Other JAK inhibitors (e.g., SAR302503, CYT387, pacritinib, AZD-1480, BMS-911543, NS-018, LY2784544, lestaurtinib, SEP-701, and AT-9283) are being evaluated for use in treating MF, ET, and PV and thus may be useful in reducing splenomegaly such patients.

While the management of myeloproliferative disease-associated splenomegaly with splenectomy is well established, the procedure is associated with morbidity and mortality rates of approximately 31% and 9%, respectively [Mesa R A. (2009) Blood 113(22):5394-5400]. Hepatic extramedullary hematopoiesis, which sometimes leads to rapid hepatic enlargement, is an unusual but well recognized complication following splenectomy, as is the increased thrombotic risk. As a result, splenectomy is generally restricted to selected patients with refractory hemolysis or anemia, symptomatic splenomegaly, significant splenic infarction, severe portal hypertension, and/or severe hypercatabolic symptoms. Radiotherapy can be an alternative to splenectomy in patients with symptomatic splenomegaly and an adequate platelet count. However, studies have shown that 44% of patients experienced cytopenias, following radiotherapy, of which 13% were fatal [Elliott M A et al. (1999) Blood Rev. 13(3):163-170]. Low-dose radiotherapy remains a preferred treatment for nonsplenic extramedullary hematopoiesis, including involvement of the peritoneum and pleura with resultant ascites and pleural effusions.

In certain aspects, the present disclosure provides methods for treating, preventing, or reducing the progression rate and/or severity of a myeloproliferative disorder (e.g., primary myelofibrosis, polycythemia vera, masked polycythemia, essential thrombocythemia, post-polycythemia vera myelofibrosis, and post-essential thrombocythemia myelofibrosis) or one or more complications of a myeloproliferative disorder comprising administering to a patient in need thereof an effective amount of a TβRII antagonist (e.g., a TβRII polypeptide comprising, consisting essential of, or consisting of an amino acid sequence that is at least 85%, 90%, 91%, 92%, 93%, 94% 95%, 96%, 97%, 98%, 99%, or 100% identical to the amino acid sequence of any one of SEQ ID NOs: 5-17, 25, 27, 29, 31, 33, 35, 37, 39, 41, 43, 47-49, 53-62, 101, and 103-105) in combination with one or more active agents or supportive therapies for treating splenomegaly and/or extramedullary hematopoiesis. Active agents or supportive therapies for treating splenomegaly and/or extramedullary hematopoiesis include, for example, cytoreductive agents, thalidomide (e.g., Immunoprin, Talidex, Talizer, and Thalomid), lenalidomide (e.g., Revlimid), hydroxyurea (e.g., Apo-Hydroxyurea, Droxia, and Hydrea), busulfan (e.g., Myleran and Busulfex IV), melphalan (e.g., Alkeran and Sarcolysin), cladribine (e.g., Leustatin, Litak, and Movectro), splenectomy, radiotherapy, JAK inhibitors (e.g., ruxolitinib, SAR302503, CYT387, pacritinib, AZD-1480, BMS-911543, NS-018, LY2784544, lestaurtinib, SEP-701, and AT-9283).

Patients with myeloproliferative disorders (e.g., primary myelofibrosis polycythemia vera, masked polycythemia, essential thrombocythemia, post-polycythemia vera myelofibrosis, and post-essential thrombocythaemia myelofibrosis) suffer from an increased risk of major cardiovascular events [Barbui et al. (2010) Blood 115(4):778-782]. Fatal and nonfatal thromboses were reported in 7.2% PMF patients included in a multi-institutional series, with a rate of 1.75% patient-years not dissimilar from that reported in ET (1%-3% patient-year). Risk factors for thrombosis were age >60 years and a JAK2V617F mutational status, particularly if the latter was associated with leukocytosis. Hydroxyurea and low-dose aspirin is generally prescribed to treat or prevent thrombosis in MF patients.

In certain aspects, the present disclosure provides methods for treating, preventing, or reducing the progression rate and/or severity of a myeloproliferative disorder (e.g., primary myelofibrosis, polycythemia vera, masked polycythemia, essential thrombocythemia, post-polycythemia vera myelofibrosis, and post-essential thrombocythemia myelofibrosis) or one or more complications of a myeloproliferative disorder comprising administering to a patient in need thereof an effective amount of a TβRII antagonist (e.g., a TβRII polypeptide comprising, consisting essential of, or consisting of an amino acid sequence that is at least 85%, 90%, 91%, 92%, 93%, 94% 95%, 96%, 97%, 98%, 99%, or 100% identical to the amino acid sequence of any one of SEQ ID NOs: 5-17, 25, 27, 29, 31, 33, 35, 37, 39, 41, 43, 47-49, 53-62, 101, and 103-105) in combination with one or more active agents or supportive therapies for treating thrombosis. Active agents or supportive therapies for treating thrombosis include, for example, hydroxyurea (e.g., Apo-Hydroxyurea, Droxia, and Hydrea) and aspirin In certain aspects, the present disclosure provides methods for treating, preventing, or reducing the progression rate and/or severity of a myeloproliferative disorder (e.g., primary myelofibrosis, polycythemia vera, masked polycythemia, essential thrombocythemia, post-polycythemia vera myelofibrosis, and post-essential thrombocythemia myelofibrosis) or one or more complications of a myeloproliferative disorder comprising administering to a patient in need thereof an effective amount of a TβRII antagonist (e.g., a TβRII polypeptide comprising, consisting essential of, or consisting of an amino acid sequence that is at least 85%, 90%, 91%, 92%, 93%, 94% 95%, 96%, 97%, 98%, 99%, or 100% identical to the amino acid sequence of any one of SEQ ID NOs: 5-17, 25, 27, 29, 31, 33, 35, 37, 39, 41, 43, 47-49, 53-62, 101, and 103-105) in combination with one or more JAK inhibitors. JAK inhibitors that may be used in accordance with the methods of the disclosure include, for example, ruxolitinib, fedratinib (SAR302503), monoelotinib (CYT387), pacritinib, lestaurtinib, AZD-1480, BMS-911543, NS-018, LY2784544, SEP-701, XL019, and AT-9283.

In addition to JAK2 inhibition, several other treatment strategies are under investigation for the treatment of myeloproliferative disorders, including immunomodulating drugs (IMiDs), inhibitors of the mammalian target of rapamycin (mTOR) pathway, and epigenetic factors modulators [Mascarenhas et al. (2013) Haematologica 98(10):1499-1509].

Pomalidomide is a second-generation immunomodulatory drug under evaluation in a range of doses for treatment of MF, PV, and ET [Begna et al. (2011) Leukemia 25:301-304; and Mesa et al. (2010) Am J Hematol 85:129-130]. A phase 2 trial evaluating low-dose pomalidomide and prednisone in 58 patients reported anemia responses in 24% of the JAK2V617F-positive patients. Anemia responses were absent in those without the mutation, and predicted by pomalidomide-induced basophilia and the absence of marked splenomegaly. An analysis of 82 evaluable patients with MF enrolled in three consecutive phase 1 and 2 clinical trials from 2007 to 2010 demonstrated an anemia response in 27% of patients according to IWG-MRT criteria. Anemia response occurred most often in the first 6 months of treatment, in the presence of JAK2V617F, and in the absence of marked splenomegaly.

In certain aspects, the present disclosure provides methods for treating, preventing, or reducing the progression rate and/or severity of a myeloproliferative disorder (e.g., primary myelofibrosis, polycythemia vera, masked polycythemia, essential thrombocythemia, post-polycythemia vera myelofibrosis, and post-essential thrombocythemia myelofibrosis) or one or more complications of a myeloproliferative disorder comprising administering to a patient in need thereof an effective amount of a TβRII antagonist (e.g., a TβRII polypeptide comprising, consisting essential of, or consisting of an amino acid sequence that is at least 85%, 90%, 91%, 92%, 93%, 94% 95%, 96%, 97%, 98%, 99%, or 100% identical to the amino acid sequence of any one of SEQ ID NOs: 5-17, 25, 27, 29, 31, 33, 35, 37, 39, 41, 43, 47-49, 53-62, 101, and 103-105) in combination with one or more immunomodulatory agents. Immunomodulatory agents that may be used in accordance with the methods of the disclosure include, for example, pomalidomide (e.g., Pomalyst and Imnovid).

In addition to JAK/STAT, other related pathways, such as the phosphatidylinositol 3-kinase/mammalian target of rapamycin (PI3K/mTOR) pathway, have been found to be dysregulated in myeloproliferative disorder patients [Tefferi A. (2011) Am J Hematol 86(12):1017-1026]. In several studies, it has been shown that the proliferation of JAK2V617F positive cells decreased when treated with the mTOR inhibitor everolimus [Guglielmelli et al. (2011) Blood 118(8):2069-2076; and Vannucchi et al. (2009) Blood 114(22):2914]. Results from a Phase I/II study of 39 high- or intermediate-risk patients with PMF or post-PV/ET MF treated with everolimus have also been reported. Of 30 evaluable patients, 69% and 80% experienced complete resolution of systemic symptoms and pruritus, respectively. The response rate was 60% when European Myelofibrosis Network criteria were applied (eight major, seven moderate, and three minor responses) or 23% when International Working Group for Myelofibrosis Research and Treatment criteria were used (one partial response, six clinical improvements). These results provide proof of concept that targeting the mTOR pathway may be clinically relevant in patients with myeloproliferative neoplasms.

In certain aspects, the present disclosure provides methods for treating, preventing, or reducing the progression rate and/or severity of a myeloproliferative disorder (e.g., primary myelofibrosis, polycythemia vera, masked polycythemia, essential thrombocythemia, post-polycythemia vera myelofibrosis, and post-essential thrombocythemia myelofibrosis) or one or more complications of a myeloproliferative disorder comprising administering to a patient in need thereof an effective amount of a TβRII antagonist (e.g., a TβRII polypeptide comprising, consisting essential of, or consisting of an amino acid sequence that is at least 85%, 90%, 91%, 92%, 93%, 94% 95%, 96%, 97%, 98%, 99%, or 100% identical to the amino acid sequence of any one of SEQ ID NOs: 5-17, 25, 27, 29, 31, 33, 35, 37, 39, 41, 43, 47-49, 53-62, 101, and 103-105) in combination with one or more mTOR inhibitors. mTOR inhibitors that may be used in accordance with the methods of the disclosure include, for example, rapamycin, sirolimus, deforolimus, everolimus, temsirolimus, NVP-BEZ235, BGT226, SF1126, PK1-587, INK128, AZD8055, and AZD2014.

Histone deacetylase (HDAC) inhibition has an inhibitory effect on the JAK-STAT pathway, and HDAC inhibitors givinostat (ITF2357), panobinostat (LBH589) and pracinostat (SB939) are all currently under investigation for MF [Quintas-Cardama et al. (2011) Therapy Blood 118 (Suppl. 1); Mascarenhas et al. (2011) Blood. 118 (Suppl. 1); and Rambaldi et al. (2011) Blood 118 (Suppl. 1)]. It has been reported that treatment with pracinostat results in a reduction in spleen size in 27% of patients, and IWG criteria anemia responses in approximately 10% of MF patients. Panobinostat in doses of 20, 25 and 30 mg three times daily also demonstrated encouraging activity in results from a phase 1/2 trial. Durable (>6 months) responses in splenomegaly, decreases in leukoerythroblastosis, and responses in anemia were reported by IWG criteria. Givinostat also shows promise based on results of a randomized phase 2 trial in patients with PV that did not respond to hydroxyurea. A complete or partial response was observed in approximately 50% of patients, and the combination was generally well tolerated.

In certain aspects, the present disclosure provides methods for treating, preventing, or reducing the progression rate and/or severity of a myeloproliferative disorder (e.g., primary myelofibrosis, polycythemia vera, masked polycythemia, essential thrombocythemia, post-polycythemia vera myelofibrosis, and post-essential thrombocythemia myelofibrosis) or one or more complications of a myeloproliferative disorder comprising administering to a patient in need thereof an effective amount of a TβRII antagonist (e.g., a TβRII polypeptide comprising, consisting essential of, or consisting of an amino acid sequence that is at least 85%, 90%, 91%, 92%, 93%, 94% 95%, 96%, 97%, 98%, 99%, or 100% identical to the amino acid sequence of any one of SEQ ID NOs: 5-17, 25, 27, 29, 31, 33, 35, 37, 39, 41, 43, 47-49, 53-62, 101, and 103-105) in combination with one or more histone deacetylase inhibitors. Histone deacetylase inhibitors that may be used in accordance with the methods of the disclosure include, for example, givinostat, panobinostat, and pracinostat.

The present disclosure contemplates the use of TβRII antagonists in combination with one or more therapies for treating fibrotic disorders. For example, TβRII antagonist can be administered in combination with (i.e., together with) cytotoxins, immunosuppressive agents, radiotoxic agents, and/or therapeutic antibodies. Particular co-therapeutics contemplated by the present invention include, but are not limited to, steroids (e.g., corticosteroids, such as Prednisone), immune-suppressing and/or anti-inflammatory agents (e.g., gamma-interferon, cyclophosphamide, azathioprine, methotrexate, penicillamine, cyclosporine, colchicine, antithymocyte globulin, mycophenolate mofetil, and hydroxychloroquine), cytotoxic drugs, calcium channel blockers (e.g., nifedipine), angiotensin converting enzyme inhibitors (ACE) inhibitors, para-aminobenzoic acid (PABA), dimethyl sulfoxide, transforming growth factor beta (TGFβ) inhibitors, interleukin-5 (IL-5) inhibitors, and pan caspase inhibitors. Additional anti-fibrotic agents that may be used in combination with TβRII antagonist include, but are not limited to, lectins (as described in, for example, U.S. Pat. No. 7,026,283, the entire contents of which is incorporated herein by reference), as well as the anti-fibrotic agents described by Wynn et al (2007, J Clin Invest 117: 524-529, the entire contents of which is incorporated herein by reference). For example, additional anti-fibrotic agents and therapies include, but are not limited to, various anti-inflammatory/immunosuppressive/cytotoxic drugs (including colchicine, azathioprine, cyclophosphamide, prednisone, thalidomide, pentoxifylline and theophylline), TGFβ signaling modifiers (including relaxin, SMAD7, HGF, and BMP7, as well as TGFβ1, TβRI, TβRII, EGR-I, and CTGF inhibitors), cytokine and cytokine receptor antagonists (inhibitors of IL-10, IL-5, IL-6, IL-13, IL-21, IL-4R, IL-13RαI, GM-CSF, TNF-α, oncostatin M, WlSP-I, and PDGFs), cytokines and chemokincs (IFN-γ, IFN-α/β, IL-12, IL-10, HGF, CXCL10, and CXCL11), chemokine antagonists (inhibitors of CXCL1, CXCL2, CXCL12, CCL2, CCL3, CCL6, CCL17, and CCL18), chemokine receptor antagonists (inhibitors of CCR2, CCR3, CCR5, CCR7, CXCR2, and CXCR4), TLR antagonists (inhibitors of TLR3, TLR4, and TLR9), angiogenesis antagonists (VEGF-specific antibodies and adenosine deaminase replacement therapy), anti-hypertensive drugs (beta blockers and inhibitors of ANG 11, ACE, and aldosterone), vasoactive substances (ET-1 receptor antagonists and bosetan), inhibitors of the enzymes that synthesize and process collagen (inhibitors of prolyl hydroxylase), B cell antagonists (rituximab), integrin/adhesion molecule antagonists (molecules that block αIβ1 and αvβ6 integrins, as well as inhibitors of integrin-linked kinase, and antibodies specific for ICAM-I and VCAM-I), proapoptotic drugs that target myofibroblasts, MMP inhibitors (inhibitors of MMP2, MMP9, and MMP12), and TlMP inhibitors (antibodies specific for TIMP-1).

In certain embodiments, the subject methods may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present disclosure recognizes that the effectiveness of conventional cancer therapies (e.g., chemotherapy, radiation therapy, phototherapy, immunotherapy, and surgery) can be enhanced through the use of a subject antagonist therapeutic agent.

When a therapeutic agent disclosed herein is administered in combination with another conventional anti-neoplastic agent, either concomitantly or sequentially, such therapeutic agent may enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells. According to the present disclosure, the TβRII antagonists described herein may be used in combination with other compositions and procedures for the treatment of diseases. For example, a tumor may be treated conventionally with surgery, radiation or chemotherapy combined with the TβRII antagonist, and then the TβRII antagonist may be subsequently administered to the patient to extend the dormancy of micrometastases and to stabilize any residual primary tumor.

In certain aspects of the invention, other therapeutic agents useful for combination therapy with a TβRII antagonist and one or more cancer therapies: e.g., surgery, cytotoxic agents, radiological treatments involving irradiation or administration of radioactive substances, chemotherapeutic agents, anti-hormonal agents, growth inhibitory agents, anti-neoplastic compositions, and treatment with anti-cancer agents listed herein and known in the art, or combinations thereof.

The term "cytotoxic agent" as used herein refers to a substance that inhibits or prevents the function of cells and/or causes destruction of cells. The term is intended to include radioactive isotopes (e.g., At211, 1131, 1125, Y90, Re186, Re188, Sm153, Bi212, P32 and radioactive isotopes of Lu), chemotherapeutic agents e.g. methotrexate, adriamicin, *vinca* alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® docetaxel (Rhone-Poulenc Rorer, Antony, France); chlorambucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY1 17018, onapristone, and FARESTON® toremifene; anti-progesterones; estrogen receptor down-regulators (ERDs); agents that function to suppress or shut down the ovaries, for example, luteinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestane, fadrozole, RIVIS OR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROC AL® etidronate, NE-58095, ZOMET A® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

7. Pharmaceutical Compositions

The therapeutic agents described herein (e.g., a TβRII polypeptide comprising, consisting essential of, or consisting of the amino acid sequence of any one of SEQ ID NOs: 7-17, 25, 27, 29, 31, 33, 35, 37, 39, 41, 43, 47-50, 52-62, 101, and 103-105) may be formulated into pharmaceutical compositions. Pharmaceutical compositions for use in accordance with the present disclosure may be formulated in conventional manner using one or more physiologically acceptable carriers or excipients. Such formulations will generally be substantially pyrogen-free, in compliance with most regulatory requirements.

In certain embodiments, the therapeutic method of the disclosure includes administering the composition systemically, or locally as an implant or device. When administered, the therapeutic composition for use in this disclosure is in a pyrogen-free, physiologically acceptable form. Therapeutically useful agents other than the TβRII signaling antagonists which may also optionally be included in the composition as described above, may be administered simultaneously or sequentially with the subject compounds (e.g., TβRII polypeptides) in the methods disclosed herein.

Typically, protein therapeutic agents disclosed herein will be administered parentally, and particularly intravenously or subcutaneously. Pharmaceutical compositions suitable for parenteral administration may comprise one or more TβRII antagonist in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions and formulations may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration Further, the composition may be encapsulated or injected in a form for delivery to a target tissue site. In certain embodiments, compositions of the present invention may include a matrix capable of delivering one or more therapeutic compounds (e.g., TβRII polypeptides) to a target tissue site, providing a structure for the developing tissue and optimally capable of being resorbed into the body. For example, the matrix may provide slow release of the TβRII antagonist. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalcium phosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., TβRII polypeptides). The various factors include, but are not limited to, the patient's age, sex, and diet, the severity disease, time of administration, and other clinical factors. Optionally, the dosage may vary with the type of matrix used in the reconstitution and the types of compounds in the composition. The addition of other known growth factors to the final composition, may also affect the dosage. Progress can be monitored by periodic assessment of bone growth and/or repair, for example, X-rays (including DEXA), histomorphometric determinations, and tetracycline labeling.

In certain embodiments, the present invention also provides gene therapy for the in vivo production of TβRII antagonist. Such therapy would achieve its therapeutic effect by introduction of the TβRII polynucleotide sequences into cells or tissues having the disorders as listed above. Delivery of TβRII polynucleotide sequences can be achieved using a recombinant expression vector such as a chimeric virus or a colloidal dispersion system. Preferred for therapeutic delivery of TβRII polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the TβRII polynucleotide. In a preferred embodiment, the vector is targeted to bone or cartilage.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for TβRII antagonist polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

The disclosure provides formulations that may be varied to include acids and bases to adjust the pH; and buffering agents to keep the pH within a narrow range.

EXEMPLIFICATION

The invention now being generally described, it will be more readily understood by reference to the following examples, which are included merely for purposes of illustration of certain embodiments of the present invention, and are not intended to limit the invention.

Example 1. Generation of Receptor Fusion Protein Variants

TβRII ECD Variants

Human TβRII occurs naturally in at least two isoforms A (long) and B (short) generated by alternative splicing in the extracellular domain (ECD) (FIGS. 1 and 2). TβRII binds with high affinity to TGFβ1 and TGFβ3. While in some therapeutic settings this spectrum of ligand binding may be advantageous, in other settings a more selective molecule may be superior. As detailed below, Applicants generated and have envisioned various TβRII polypeptides and Fc fusion proteins comprising an extracellular domain of the TβRII long or short isoforms ($T\beta RII_{long}$ or $T\beta RII_{short}$) as well as variants thereof.

The wild-type $hT\beta RII_{long}$(23-184) sequence is shown below (SEQ ID NO: 13), in which the 25 amino-acid insertion is underlined. Note that splicing results in a conservative amino acid substitution (Val→Ile) at the flanking position C-terminal to the insertion. Sequence relationships among several $hT\beta RII_{short}$ variants and their $hT\beta RII_{long}$ counterparts are indicated in FIG. 3.

```
                                                     (SEQ ID NO: 13)
  1 TIPPHVQKSD VEMEAQKDEI ICPSCNRTAH PLRHINNDMI VTDNNGAVKF

51 PQLCKFCDVR FSTCDNQKSC MSNCSITSIC EKPQEVCVAV WRKNDENITL

101 ETVCHDPKLP YHDFILEDAA SPKCIMKEKK KPGETFFMCS CSSDECNDNI

151 IFSEEYNTSN PD
```

Applicant generated a hTβRII$_{long}$(23-184)-Fc fusion protein in which the hTβRII$_{long}$(23-184) domain was fused at the C-terminus (via a minimal linker) to a human IgG1 Fc domain and fused at the N-terminus to a TPA leader sequence, which has the following amino acid sequence (SEQ ID NO: 101):

```
                                                    (SEQ ID NO: 101)
  1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG THTCPPCPAP

201 ELLGGPSVFL FPPKPKDTLM ISRTPEVTCV VVDVSHEDPE VKFNWYVDGV

251 EVHNAKTKPR EEQYNSTYRV VSVLTVLHQD WLNGKEYKCK VSNKALPAPI

301 EKTISKAKGQ PREPQVYTLP PSREEMTKNQ VSLTCLVKGF YPSDIAVEWE

351 SNGQPENNYK TTPPVLDSDG SFFLYSKLTV DKSRWQQGNV FSCSVMHEAL

401 HNHYTQKSLS LSPGK
```

The N-terminal leader sequence and C-terminal Fc domain are represented by a single underline and the linker domain is indicated by double underline. A nucleotide sequence encoding the hTβRII$_{long}$(23-184)-Fc fusion protein has the following nucleotide sequence (SEQ ID NO: 102):

```
                                                    (SEQ ID NO: 102)
  1 ATGGATGCAA TGAAGAGAGG GCTCTGCTGT GTGCTGCTGC TGTGTGGAGC AGTCTTCGTT

61 TCGCCCGGCG CCACGATCCC ACCGCACGTT CAGAAGTCGG ATGTGGAAAT GGAGGCCCAG

121 AAAGATGAAA TCATCTGCCC CAGCTGTAAT AGGACTGCCC ATCCACTGAG ACATATTAAT

181 AACGACATGA TAGTCACTGA CAACAACGGT GCAGTCAAGT TTCCACAACT GTGTAAATTT

241 TGTGATGTGA GATTTTCCAC CTGTGACAAC CAGAAATCCT GCATGAGCAA CTGCAGCATC

301 ACCTCCATCT GTGAGAAGCC ACAGGAAGTC TGTGTGGCTG TATGGAGAAA GAATGACGAG

361 AACATAACAC TAGAGACAGT TTGCCATGAC CCCAAGCTCC CCTACCATGA CTTTATTCTG

421 GAAGATGCTG CTTCTCCAAA GTGCATTATG AAGGAAAAAA AAAAGCCTGG TGAGACTTTC

481 TTCATGTGTT CCTGTAGCTC TGATGAGTGC AATGACAACA TCATCTTCTC AGAAGAATAT

541 AACACCAGCA ATCCTGACAC CGGTGGTGGA ACTCACACAT GCCCACCGTG CCCAGCACCT

601 GAACTCCTGG GGGGACCGTC AGTCTTCCTC TTCCCCCCAA AACCCAAGGA CACCCTCATG

661 ATCTCCCGGA CCCCTGAGGT CACATGCGTG GTGGTGGACG TGAGCCACGA AGACCCTGAG

721 GTCAAGTTCA ACTGGTACGT GGACGGCGTG GAGGTGCATA ATGCCAAGAC AAAGCCGCGG

781 GAGGAGCAGT ACAACAGCAC GTACCGTGTG GTCAGCGTCC TCACCGTCCT GCACCAGGAC

841 TGGCTGAATG GCAAGGAGTA CAAGTGCAAG GTCTCCAACA AAGCCCTCCC AGCCCCCATC

901 GAGAAAACCA TCTCCAAAGC CAAAGGGCAG CCCCGAGAAC CACAGGTGTA CACCCTGCCC

961 CCATCCCGGG AGGAGATGAC CAAGAACCAG GTCAGCCTGA CCTGCCTGGT CAAAGGCTTC
```

```
1021 TATCCCAGCG ACATCGCCGT GGAGTGGGAG AGCAATGGGC AGCCGGAGAA CAACTACAAG

1081 ACCACGCCTC CCGTGCTGGA CTCCGACGGC TCCTTCTTCC TCTATAGCAA GCTCACCGTG

1141 GACAAGAGCA GGTGGCAGCA GGGGAACGTC TTCTCATGCT CCGTGATGCA TGAGGCTCTG

1201 CACAACCACT ACACGCAGAA GAGCCTCTCC CTGTCTCCGG GTAAATGA
```

A processed version of the hTβRII$_{long}$(23-184)-Fc fusion protein has the following amino acid sequence (SEQ ID NO: 103):

```
                                                (SEQ ID NO: 103)
    TIPPHV QKSDVEMEAQ KDEIICPSCN

RTAHPLRHIN NDMIVTDNNG AVKFPQLCKF CDVRFSTCDN

QKSCMSNCSI TSICEKPQEV CVAVWRKNDE NITLETVCHD

PKLPYHDFIL EDAASPKCIM KEKKKPGETF FMCSCSSDEC

NDNIIFSEEY NTSNPDTGGG THTCPPCPAP ELLGGPSVFL

FPPKPKDTLM ISRTPEVTCV VVDVSHEDPE VKFNWYVDGV

EVHNAKTKPR EEQYNSTYRV VSVLTVLHQD WLNGKEYKCK

VSNKALPAPI EKTISKAKGQ PREPQVYTLP PSREEMTKNQ

VSLTCLVKGF YPSDIAVEWE SNGQPENNYK TTPPVLDSDG

SFFLYSKLTV DKSRWQQGNV FSCSVMHEAL HNHYTQKSLS

LSPGK
```

For use in certain animal models described herein, Applicants generated an Fc fusion protein comprising the mature, full-length ECD from the mouse TβRII isoform 1, which is designated herein as mTβRII-Fc. The mouse TβRII isoform 1 is homologous to the human TβRII isoform A (long form) and thus is a mouse equivalent version of the hTβRII$_{long}$(23-184)-Fc fusion protein above described. As with the human version, it was determined that mTβRII-Fc binds with high affinity (picomolar) to TGFβ1 and TGFβ3, but does not bind to TGFβ2. In addition, it was determined that the hTβRII$_{long}$(23-184)-Fc fusion protein and mTβRII-Fc are potent inhibitors of TGFβ1 and TGFβ3 activity, but does not inhibit TGFβ2 activity, in a cell-based assay as described below.

Applicants also envision five corresponding variants (SEQ ID NO: 14-17) based on the wild-type hTβRII$_{long}$(23-184) sequence shown in (SEQ ID NO: 13) and Fc fusion proteins thereof.

(1) The hTβRII$_{long}$(23-184/D135K) amino acid sequence shown below (SEQ ID NO: 14), in which the substituted residue is double underlined.

```
                                                (SEQ ID NO: 14)
  1 TIPPHVQKSD VEMEAQKDEI ICPSCNRTAH PLRHINNDMI VTDNNGAVKF

51 PQLCKFCDVR FSTCDNQKSC MSNCSITSIC EKPQEVCVAV WRKNDENITL

101 ETVCHDPKLP YHKFILEDAA SPKCIMKEKK KPGETFFMCS CSSDECNDNI

151 IFSEEYNTSN PD
```

(2) The N-terminally truncated hTβRII$_{long}$(29-184) amino acid sequence shown below (SEQ ID NO: 15).

```
                                                (SEQ ID NO: 15)
  1 QKSDVEMEAQ KDEIICPSCN RTAHPLRHIN NDMIVTDNNG AVKFPQLCKF

51 CDVRFSTCDN QKSCMSNCSI TSICEKPQEV CVAVWRKNDE NITLETVCHD

101 PKLPYHDFIL EDAASPKCIM KEKKKPGETF FMCSCSSDEC NDNIIFSEEY

151 NTSNPD
```

(3) The N-terminally truncated hTβRII$_{long}$(60-184) amino acid sequence shown below (SEQ ID NO: 104).

```
                                                (SEQ ID NO: 104)
  1 DMIVTDNNGA VKFPQLCKFC DVRFSTCDNQ KSCMSNCSIT SICEKPQEVC

51 VAVWRKNDEN ITLETVCHDP KLPYHDFILE DAASPKCIMK EKKKPGETFF

101 MCSCSSDECN DNIIFSEEYN TSNPD
```

(4) The C-terminally truncated hTβRII$_{long}$(23-178) amino acid sequence shown below (SEQ ID NO: 16).

```
                                                       (SEQ ID NO: 16)
  1 TIPPHVQKSD VEMEAQKDEI ICPSCNRTAH PLRHINNDMI VTDNNGAVKF

51 PQLCKFCDVR FSTCDNQKSC MSNCSITSIC EKPQEVCVAV WRKNDENITL

101 ETVCHDPKLP YHDFILEDAA SPKCIMKEKK KPGETFFMCS CSSDECNDNI

151 IFSEEY
```

(5) The C-terminally truncated hTβRII$_{long}$(23-178/N95D) amino acid sequence shown below (SEQ ID NO: 17), in which the substituted residue is double underlined.

```
                                                       (SEQ ID NO: 17)
  1 TIPPHVQKSD VEMEAQKDEI ICPSCNRTAH PLRHINNDMI VTDNNGAVKF

51 PQLCKFCDVR FSTCDNQKSC MSDCSITSIC EKPQEVCVAV WRKNDENITL

101 ETVCHDPKLP YHDFILEDAA SPKCIMKEKK KPGETFFMCS CSSDECNDNI

151 IFSEEY
```

The wild-type hTβRII$_{short}$(23-159) sequence shown below (SEQ ID NO: 7) served as the basis for five receptor ECD variants listed below (SEQ ID NO: 8-12). A wild type hTβRII$_{short}$(23-159) was fused to an Fc portion of IgG2 to generate a novel, base Fc fusion construct. See SEQ ID Nos. 50, 51 and 52, below.

```
                                                        (SEQ ID NO: 7)
  1 TIPPHVQKSV NNDMIVTDNN GAVKFPQLCK FCDVRFSTCD NQKSCMSNCS

51 ITSICEKPQE VCVAVWRKND ENITLETVCH DPKLPYHDFI LEDAASPKCI

101 MKEKKKPGET FFMCSCSSDE CNDNIIFSEE YNTSNPD
```

(1) The hTβRII$_{short}$(23-159/D110K) amino acid sequence shown below (SEQ ID NO: 8), in which the substituted residue is underlined.

```
                                                        (SEQ ID NO: 8)
  1 TIPPHVQKSV NNDMIVTDNN GAVKFPQLCK FCDVRFSTCD NQKSCMSNCS

51 ITSICEKPQE VCVAVWRKND ENITLETVCH DPKLPYHKFI LEDAASPKCI

101 MKEKKKPGET FFMCSCSSDE CNDNIIFSEE YNTSNPD
```

(2) The N-terminally truncated hTβRII$_{short}$(29-159) amino acid sequence shown below (SEQ ID NO: 9).

```
                                                        (SEQ ID NO: 9)
  1 QKSVNNDMIV TDNNGAVKFP QLCKFCDVRF STCDNQKSCM SNCSITSICE

51 KPQEVCVAVW RKNDENITLE TVCHDPKLPY HDFILEDAAS PKCIMKEKKK

101 PGETFFMCSC SSDECNDNII FSEEYNTSNP D
```

(3) The N-terminally truncated hTβRII$_{short}$(35-159) amino acid sequence shown below (SEQ ID NO: 10).

```
                                                       (SEQ ID NO: 10)
  1 DMIVTDNNGA VKFPQLCKFC DVRFSTCDNQ KSCMSNCSIT SICEKPQEVC

51 VAVWRKNDEN ITLETVCHDP KLPYHDFILE DAASPKCIMK EKKKPGETFF

101 MCSCSSDECN DNIIFSEEYN TSNPD
```

(4) The C-terminally truncated hTβRII$_{short}$(23-153) amino acid sequence shown below (SEQ ID NO: 11).

```
                                                  (SEQ ID NO: 11)
  1 TIPPHVQKSV NNDMIVTDNN GAVKFPQLCK FCDVRFSTCD NQKSCMSNCS

51 ITSICEKPQE VCVAVWRKND ENITLETVCH DPKLPYHDFI LEDAASPKCI

101 MKEKKKPGET FFMCSCSSDE CNDNIIFSEE Y
```

(5) The C-terminally truncated hTβRII$_{short}$(23-153/N70D) amino acid sequence shown below (SEQ ID NO: 12), in which the substituted residue is underlined.

```
                                                  (SEQ ID NO: 12)
  1 TIPPHVQKSV NNDMIVTDNN GAVKFPQLCK FCDVRFSTCD NQKSCMSDCS

51 ITSICEKPQE VCVAVWRKND ENITLETVCH DPKLPYHDFI LEDAASPKCI

101 MKEKKKPGET FFMCSCSSDE CNDNIIFSEE Y
```

Additional TβRII ECD variants include:
(A) The N- and C-terminally truncated hTβRII$_{short}$(35-153) or hTβRII$_{long}$(60-178) amino acid sequence shown below (SEQ ID NO: 47).

```
                                                  (SEQ ID NO: 47)
  1 DMIVTDNNGA VKFPQLCKFC DVRFSTCDNQ KSCMSNCSIT SICEKPQEVC

51 VAVWRKNDEN ITLETVCHDP KLPYHDFILE DAASPKCIMK EKKKPGETFF

101 MCSCSSDECN DNIIFSEEY
```

(B) The N- and C-terminally truncated hTβRII$_{short}$(29-153) amino acid sequence shown below (SEQ ID NO: 48).

```
                                                  (SEQ ID NO: 48)
  1 QKSVNNDMIV TDNNGAVKFP QLCKFCDVRF STCDNQKSCM SNCSITSICE

51 KPQEVCVAVW RKNDENITLE TVCHDPKLPY HDFILEDAAS PKCIMKEKKK

101 PGETFFMCSC SSDECNDNII FSEEY
```

(C) The N- and C-terminally truncated hTβRII$_{long}$(29-178) amino acid sequence shown below (SEQ ID NO: 49).

```
                                                  (SEQ ID NO: 49)
  1 QKSDVEMEAQ KDEIICPSCN RTAHPLRHIN NDMIVTDNNG AVKFPQLCKF

51 CDVRFSTCDN QKSCMSNCSI TSICEKPQEV CVAVWRKNDE NITLETVCHD

101 PKLPYHDFIL EDAASPKCIM KEKKKPGETF FMCSCSSDEC NDNIIFSEEY
```

Any of the above variants (e.g., SEQ ID NO: 8-12, 14-17, and 47-49) could incorporate an insertion of 36 amino acids (SEQ ID NO: 18) between the pair of glutamate residues (positions 151 and 152 of SEQ ID NO: 5, or positions 176 and 177 of SEQ ID NO: 6) located near the C-terminus of the hTβRII ECD, as occurs naturally in the hTβRII isoform C [Konrad et al. (2007) BMC Genomics 8:318].

```
                              (SEQ ID NO: 18)
    GRCKIRHIGS NNRLQRSTCQ NTGWESAHVM KTPGFR
```

As an example, the paired glutamate residues flanking the optional insertion site are denoted below (underlined) for the hTβRII$_{short}$(29-159) variant (SEQ ID NO: 105).

```
                                                  (SEQ ID NO: 105)
  1 QKSVNNDMIV TDNNGAVKFP QLCKFCDVRF STCDNQKSCM SNCSITSICE

51 KPQEVCVAVW RKNDENITLE TVCHDPKLPY HDFILEDAAS PKCIMKEKKK

101 PGETFFMCSC SSDECNDNII FSEEYNTSNP D
```

In part, Applicants sought polypeptides with enhanced or reduced selectivity for TGFβ1 or TGFβ3 by generating fusion proteins comprising variants of human TβRII ECD. The wild-type hTβRII$_{short}$(23-159) sequence shown below (SEQ ID NO: 7) served as the basis for five receptor ECD variants listed below (SEQ ID NO: 8-12). A wild type hTβRII$_{short}$(23-159) was fused to an Fc portion of IgG2 to generate a novel, base Fc fusion construct. See SEQ ID Nos. 50, 51 and 52, below.

Applicants envision five corresponding variants (SEQ ID NO: 14-17) based on the wild-type hTβRII$_{long}$(23-184) sequence shown below (SEQ ID NO: 13), in which the 25 amino-acid insertion is underlined. Note that splicing results in a conservative amino acid substitution (Val→Ile) at the flanking position C-terminal to the insertion. Sequence relationships among several hTβRII$_{short}$ variants and their hTβRII$_{long}$ counterparts are indicated in FIG. 3.

Fc Domain Variants hTβRII-hFc fusion proteins were generated in which five hTβRII$_{short}$ variants described above were each fused at their C-terminus (via a minimal linker) to a human IgG2 Fc domain, which has the following amino acid sequence (SEQ ID NO: 19):

Leader Sequence Variants

The following three leader sequences were considered:

```
(1) Native:
                                          (SEQ ID NO: 22)
MGRGLLRGLWPLHIVLWTRIAS (2) Tissue plasminogen activator (TPA):
                                          (SEQ ID NO: 23)
MDAMKRGLCCVLLLCGAVFVSP (3) Honey bee melittin (HBML):
                                          (SEQ ID NO: 24)
MKFLVNVALVFMVVYISYIYA
```

Expression of hTβRII-hFc Fusion Proteins

The selected hTβRII-hFc protein variants incorporate the TPA leader and have the unprocessed amino-acid sequences shown in SEQ ID NOs: 25, 29, 33, 37, 41, and 101 (see Example 3). Corresponding nucleotide sequences for these variants are SEQ ID NOs: 26, 30, 34, 38, 42, and 102. Selected hTβRII-hFc variants, each with a G2Fc domain (SEQ ID NO: 19), were expressed in HEK-293 cells and purified from conditioned media by filtration and protein

```
                                              (SEQ ID NO: 19)
  1 VECPPCPAPP VAGPSVFLFP PKPKDTLMIS RTPEVTCVVV DVSHEDPEVQ

51 FNWYVDGVEV HNAKTKPREE QFNSTFRVVS VLTVVHQDWL NGKEYKCKVS

101 NKGLPAPIEK TISKTKGQPR EPQVYTLPPS REEMTKNQVS LTCLVKGFYP

151 SDIAVEWESN GQPENNYKTT PPMLDSDGSF FLYSKLTVDK SRWQQGNVFS

201 CSVMHEALHN HYTQKSLSLS PGK
```

Applicants envision hTβRII($_{short\ and\ long}$)-hFC fusion proteins comprising Fc domains, including full-length human IgG2 Fc domain above, the IgG1 Fc (hG1Fc) (SEQ ID NO: 20, below) and N-terminally truncated human IgG1 Fc (hG1Fc$_{short}$) (SEQ ID NO: 21, below). Optionally, a polypeptide unrelated to an Fc domain could be attached in place of the Fc domain.

A chromatography. Purity of samples for reporter gene assays was evaluated by SDS-PAGE and Western blot analysis.

Applicants envision additional hTβRII-hFc protein variants with the unprocessed amino-acid sequences shown in SEQ ID NOs: 27, 31, 35, 39, 43, and 101 and corresponding nucleotide sequences shown in SEQ ID NOs: 28, 32, 36, 40, 44, and 101.

```
                                              (SEQ ID NO: 20)
  1 GGPKSCDKTH TCPPCPAPEL LGGPSVFLFP PKPKDTLMIS RTPEVTCVVV

51 DVSHEDPEVK FNWYVDGVEV HNAKTKPREE QYNSTYRVVS VLTVLHQDWL

101 NGKEYKCKVS NKALPAPIEK TISKAKGQPR EPQVYTLPPS REEMTKNQVS

151 LTCLVKGFYP SDIAVEWESN GQPENNYKTT PPVLDSDGSF FLYSKLTVDK

201 SRWQQGNVFS CSVMHEALHN HYTQKSLSLS PGK (SEQ ID NO: 21)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLYSKLTV DKSRWQQGNV

201 FSCSVMHEAL HNHYTQKSLS LSPGK
```

The amino acid sequence of the wild-type short construct hTβRII$_{short}$(23-159)-hG2Fc (SEQ ID NO: 50 is shown below.

```
                                              (SEQ ID NO: 50)
TIPPHVQKSV NNDMIVTDNN GAVKFPQLCK FCDVRFSTCD
NQKSCMSNCS ITSICEKPQE VCVAVWRKND ENITLETVCH
DPKLPYHDFI LEDAASPKCI MKEKKKPGET FFMCSCSSDE
CNDNIIFSEE YNTSNPDTGG GVECPPCPAP PVAGPSVFLF
PPKPKDTLMI SRTPEVTCVV VDVSHEDPEV QFNWYVDGVE
VHNAKTKPRE EQFNSTFRVV SVLTVVHQDW LNGKEYKCKV
SNKGLPAPIE KTISKTKGQP REPQVYTLPP SREEMTKNQV
SLTCLVKGFY PSDIAVEWES NGQPENNYKT TPPMLDSDGS
FFLYSKLTVD KSRWQQGNVF SCSVMHEALH NHYTQKSLSL
SPGK
```

This protein was expressed from a construct including a TPA leader sequence, as shown below (SEQ ID NO:52). Dotted underline denotes leader, and solid underline denotes linker.

```
                                              (SEQ ID NO: 52)
  1 MDAMKRGLCC VLLLCGAVFV SPGATIPPHV QKSVNNDMIV TDNNGAVKFP
 51 QLCKFCDVRF STCDNQKSCM SNCSITSICE KPQEVCVAVW RKNDENITLE
101 TVCHDPKLPY HDFILEDAAS PKCIMKEKKK PGETFFMCSC SSDECNDNII
151 FSEEYNTSNP DTGGGVECPP CPAPPVAGPS VFLFPPKPKD TLMISRTPEV
201 TCVVVDVSHE DPEVQFNWYV DGVEVHNAKT KPREEQFNST FRVVSVLTVV
251 HQDWLNGKEY KCKVSNKGLP APIEKTISKT KGQPREPQVY TLPPSREEMT
301 KNQVSLTCLV KGFYPSDIAV EWESNGQPEN NYKTTPPMLD SDGSFFLYSK
351 LTVDKSRWQQ GNVFSCSVMH EALHNHYTQK SLSLSPGK
```

The nucleic acid sequence encoding SEQ ID NO:52 is shown below:

```
                                              (SEQ ID NO: 51)
  1 ATGGATGCAA TGAAGAGAGG GCTCTGCTGT GTGCTGCTGC TGTGTGGAGC
 51 AGTCTTCGTT TCGCCCGGCG CCACGATCCC ACCGCACGTT CAGAAGTCGG
101 TTAATAACGA CATGATAGTC ACTGACAACA ACGGTGCAGT CAAGTTTCCA
151 CAACTGTGTA AATTTTGTGA TGTGAGATTT TCCACCTGTG ACAACCAGAA
201 ATCCTGCATG AGCAACTGCA GCATCACCTC CATCTGTGAG AAGCCACAGG
251 AAGTCTGTGT GGCTGTATGG AGAAAGAATG ACGAGAACAT AACACTAGAG
301 ACAGTTTGCC ATGACCCCAA GCTCCCCTAC CATGACTTTA TTCTGGAAGA
351 TGCTGCTTCT CCAAAGTGCA TTATGAAGGA AAAAAAAAAG CCTGGTGAGA
401 CTTTCTTCAT GTGTTCCTGT AGCTCTGATG AGTGCAATGA ACACATCATC
451 TTCTCAGAAG AATATAACAC CAGCAATCCT GACACCGGTG GTGGAGTCGA
501 GTGCCCACCG TGCCCAGCAC CACCTGTGGC AGGACCGTCA GTCTTCCTCT
551 TCCCCCCAAA ACCCAAGGAC ACCCTCATGA TCTCCCGGAC CCCTGAGGTC
601 ACGTGCGTGG TGGTGGACGT GAGCCACGAA GACCCCGAGG TCCAGTTCAA
651 CTGGTACGTG GACGGCGTGG AGGTGCATAA TGCCAAGACA AAGCCACGGG
701 AGGAGCAGTT CAACAGCACG TTCCGTGTGG TCAGCGTCCT CACCGTCGTG
```

```
 751  CACCAGGACT GGCTGAACGG CAAGGAGTAC AAGTGCAAGG TCTCCAACAA

801  AGGCCTCCCA GCCCCCATCG AGAAAACCAT CTCCAAAACC AAAGGGCAGC

851  CCCGAGAACC ACAGGTGTAC ACCCTGCCCC CATCCCGGGA GGAGATGACC

901  AAGAACCAGG TCAGCCTGAC CTGCCTGGTC AAAGGCTTCT ACCCCAGCGA

951  CATCGCCGTG GAGTGGGAGA GCAATGGGCA GCCGGAGAAC AACTACAAGA

1001  CCACACCTCC CATGCTGGAC TCCGACGGCT CCTTCTTCCT CTACAGCAAG

1051  CTCACCGTGG ACAAGAGCAG GTGGCAGCAG GGGAACGTCT TCTCATGCTC

1101  CGTGATGCAT GAGGCTCTGC ACAACCACTA CACGCAGAAG AGCCTCTCCC

1151  TGTCTCCGGG TAAA
```

Example 2. Differential Ligand Inhibition by Receptor Fusion Protein Variants in Cell-Based Assay A reporter gene assay in A549 cells was used to determine the ability of hTβRII-hFc variants to inhibit activity of TGFβ1, TGFβ2, and TGFβ3. This assay is based on a human lung carcinoma cell line transfected with a pGL3(CAGA)12 reporter plasmid (Dennler et al, 1998, EMBO 17: 3091-3100) as well as a *Renilla* reporter plasmid (pRLCMV) to control for transfection efficiency. The CAGA motif is present in the promoters of TGFβ-responsive genes (for example, PAI-1), so this vector is of general use for factors signaling through SMAD2 and SMAD3.

On the first day of the assay, A549 cells (ATCC®: CCL-185™) were distributed in 48-well plates at $6.5 \times 10^4$ cells per well. On the second day, a solution containing 10 pGL3(CAGA)12, 100 ng pRLCMV, 30 μl X-tremeGENE 9 (Roche Applied Science), and 970 μl OptiMEM (Invitrogen) was preincubated for 30 min, then added to Eagle's minimum essential medium (EMEM, ATCC®) supplemented with 0.1% BSA, which was applied to the plated cells (500 μl/well) for incubation overnight at room temperature. On the third day, medium was removed, and cells were incubated overnight at 37° C. with a mixture of ligands and inhibitors prepared as described below.

Serial dilutions of test articles were made in a 48-well plate in a 200 μl volume of assay buffer (EMEM+0.1% BSA). An equal volume of assay buffer containing the test ligand was added to obtain a final ligand concentration equal to the EC50 determined previously. Human TGFβ1, human TGFβ2, and human TGFβ3 were obtained from PeproTech. Test solutions were incubated at 37° C. for 30 minutes, then 250 μl of the mixture was added to all wells. Each concentration of test article was determined in duplicate. After incubation with test solutions overnight, cells were rinsed with phosphate-buffered saline, then lysed with passive lysis buffer (Promega E1941) and stored overnight at −70° C. On the fourth and final day, plates were warmed to room temperature with gentle shaking. Cell lysates were transferred in duplicate to a chemiluminescence plate (96-well) and analyzed in a luminometer with reagents from a Dual-Luciferase Reporter Assay system (Promega E1980) to determine normalized luciferase activity.

This assay was used to screen receptor fusion protein variants for potential inhibitory effects on cell signaling by TβRII ligands. Consistent with previous reports concerning wild-type TβRII$_{short}$-Fc and TβRII$_{long}$-Fc [del Re et al. (2004) *J Biol Chem* 279:22765], none of the variants tested were able to inhibit TGFβ2, even at high concentrations. However, hTβRII-hFc variants unexpectedly showed differential inhibition of cellular signaling mediated by TGFβ1 and TGFβ3. Compared with wild-type TβRII$_{short}$(23-159)-G2Fc, the TβRII$_{short}$(23-159/D110K)-G2Fc variant exhibited loss of inhibition of TGFβ1 but maintained intermediate inhibition of TGFβ3 (see table below). Position 110 is located in the "hook" region of TβRII [Radaev et al. (2010) *J Biol Chem* 285:14806] but has not been suggested to confer selectivity among the recognized TβRII ligands TGFβ1, TGFβ2, and TGFβ3. Thus, this variant displays a profile of differential ligand inhibition in which some TGFβ3 inhibition is maintained the variant has little to no effect on TGFβ1 activity.

| Construct | | $IC_{50}$ (nM) hTGFβ1 (640 pg/ml) | $IC_{50}$ (nM) hTGFβ3 (270 pg/ml) |
|---|---|---|---|
| Full-length wild-type ECD | $T\beta RII_{short}$ (23-159)-G2Fc | 1.73 | 0.14 |
| Full-length ECD with D110K substitution | $T\beta RII_{short}$ (23-159/D110K)-G2Fc | ND (>73.6) | ~6.9 |

ND, not determined

In a second experiment, potencies of variants with N-terminally truncated TβRII ECD were compared with that of full-length wild-type TβRII ECD. As shown in the table below, $T\beta RII_{short}$(29-159)-G2Fc and $T\beta RII_{short}$(35-159)-G2Fc displayed a greatly diminished ability to inhibit TGFβ3 but maintains some TGFβ1 inhibitor effects.

| Construct | | $IC_{50}$ (nM) hTGFβ1 (640 pg/ml) | $IC_{50}$ (nM) hTGFβ3 (270 pg/ml) |
|---|---|---|---|
| Full-length wild-type ECD | $T\beta RII_{short}$ (23-159)-G2Fc | 0.52 | 0.37 |
| N'Δ6 ECD | $T\beta RII_{short}$ (29-159)-G2Fc | 2.05 | ND (>7.5) |
| N'Δ12 ECD | $T\beta RII_{short}$ (35-159)-G2Fc | 2.51 | ND (>7.5) |

ND, not determined

In a third experiment, we determined the effect on potency of a N70D substitution in a C-terminally truncated TβRII ECD. This aspartate residue represents a potential glycosylation site. As shown in the table below, TβRII$_{short}$(23-153/N70D)-G2Fc displayed greatly diminished ability to inhibit TGFβ1 and virtually undiminished ability to inhibit TGFβ3 compared to TβRII$_{short}$(23-153)-G2Fc. Thus, the C-terminally truncated variant with N70D substitution exhibits a profile of differential ligand inhibition in which TGFβ3 is inhibited most potently but greatly diminished potency for TGFβ1 inhibition.

|  |  | IC$_{50}$ (nM) | |
| --- | --- | --- | --- |
| Construct | | hTGFβ1 (640 pg/ml) | hTGFβ3 (270 pg/ml) |
| Full-length wild-type ECD | TβRII$_{short}$ (23-159)-G2Fc | ND | ND |
| C'Δ6 ECD | TβRII$_{short}$ (23-153)-G2Fc | 2.62 | 0.14 |
| C'Δ6 ECD with N70D substitution | TβRII$_{short}$ (23-153/N70D)-G2Fc | 17.7 | 0.28 |

Together, these results demonstrate that Applicants have generated truncations and mutations of the TβRII ECD that exhibit widely different ligand binding profiles. Activity profiles of these variants can be summarized in the following table.

Summary of Ligand Selectivity

| | | Degree of Ligand Inhibition | | |
| --- | --- | --- | --- | --- |
| Construct | | Potent | Moderate | Negligible |
| Full-length wild-type ECD | TβRII$_{short}$ (23-159)-G2Fc | TGFβ1 TGFβ3 | — | TGFβ2 |
| Full-length ECD with D110K substitution | TβRII$_{short}$ (23-159/D110K)-G2Fc | — | TGFβ3 | TGFβ1 TGFβ2 |
| N'Δ6 ECD | TβRII$_{short}$ (29-159)-G2Fc | — | TGFβ1 | TGFβ2 TGFβ3 |
| N'Δ12 ECD | TβRII$_{short}$ (35-159)-G2Fc | — | TGFβ1 | TGFβ2 TGFβ3 |
| C'Δ6 ECD with N70D substitution | TβRII$_{short}$(23-153/N70D)-G2Fc | TGFβ3 | — | TGFβ1 TGFβ2 |

We predict that the TβRII$_{long}$ ECD counterparts of these TβRII$_{short}$ ECD variants will exhibit similar ligand selectivity. In addition, a C'46 truncated ECD (such as SEQ ID NOs: 11 and 16 for the TβRII$_{short}$ and TβRII$_{long}$ isoforms, respectively) can be used as a base sequence for TβRII$_{short}$ or TβRII$_{long}$ in which to introduce mutations and N-terminal truncations.

Example 3. Exemplary hTβRII-hFc Nucleic Acids and Proteins

This example summarizes nucleic acid constructs that can be used to express TβRII constructs in HEK-293 or CHO cells, according to the methods provided herein in order to provide the proteins isolated from cell culture. In each case the mature protein isolated from cell culture will have the leader sequence (dotted underline in each sequence below) removed.

Item 1 shows the amino acid sequence of hTβRII$_{short}$(23-159/D110K)-hG2Fc (SEQ ID NO: 25). Double underline indicates D110K substitution. Dotted underline denotes leader, and solid underline denotes linker.

```
                                                    (SEQ ID NO: 25)
  1  MDAMKRGLCC VLLLCGAVFV SPGATIPPHV QKSVNNDMIV TDNNGAVKFP

51  QLCKFCDVRF STCDNQKSCM SNCSITSICE KPQEVCVAVW RKNDENITLE

101  TVCHDPKLPY HKFILEDAAS PKCIMKEKKK PGETFFMCSC SSDECNDNII

151  FSEEYNTSNP DTGGGVECPP CPAPPVAGPS VFLFPPKPKD TLMISRTPEV

201  TCVVVDVSHE DPEVQFNWYV DGVEVHNAKT KPREEQFNST FRVVSVLTVV

251  HQDWLNGKEY KCKVSNKGLP APIEKTISKT KGQPREPQVY TLPPSREEMT

301  KNQVSLTCLV KGFYPSDIAV EWESNGQPEN NYKTTPPMLD SDGSFFLYSK

351  LTVDKSRWQQ GNVFSCSVMH EALHNHYTQK SLSLSPGK
```

Item 2 shows a nucleotide sequence encoding hTβRII$_{short}$(23-159/D110K)-hG2Fc (SEQ ID NO: 26). Double underline indicates D110K substitution. Dotted underline denotes leader, and solid underline denotes linker.

```
                                                    (SEQ ID NO: 26)
  1  ATGGATGCAA TGAAGAGAGG GCTCTGCTGT GTGCTGCTGC TGTGTGGAGC

51  AGTCTTCGTT TCGCCCGGCG CCACGATCCC ACCGCACGTT CAGAAGTCGG

101  TTAATAACGA CATGATAGTC ACTGACAACA ACGGTGCAGT CAAGTTTCCA
```

-continued

```
 151   CAACTGTGTA AATTTTGTGA TGTGAGATTT TCCACCTGTG ACAACCAGAA
 201   ATCCTGCATG AGCAACTGCA GCATCACCTC CATCTGTGAG AAGCCACAGG
 251   AAGTCTGTGT GGCTGTATGG AGAAAGAATG ACGAGAACAT AACACTAGAG
 301   ACAGTTTGCC ATGACCCCAA GCTCCCCTAC CATAAGTTTA TTCTGGAAGA
 351   TGCTGCTTCT CCAAAGTGCA TTATGAAGGA AAAAAAAAG CCTGGTGAGA
 401   CTTTCTTCAT GTGTTCCTGT AGCTCTGATG AGTGCAATGA CAACATCATC
 451   TTCTCAGAAG AATATAACAC CAGCAATCCT GACACCGGTG GTGGAGTCGA
 501   GTGCCCACCG TGCCCAGCAC CACCTGTGGC AGGACCGTCA GTCTTCCTCT
 551   TCCCCCCAAA ACCCAAGGAC ACCCTCATGA TCTCCCGGAC CCCTGAGGTC
 601   ACGTGCGTGG TGGTGGACGT GAGCCACGAA GACCCCGAGG TCCAGTTCAA
 651   CTGGTACGTG GACGGCGTGG AGGTGCATAA TGCCAAGACA AAGCCACGGG
 701   AGGAGCAGTT CAACAGCACG TTCCGTGTGG TCAGCGTCCT CACCGTCGTG
 751   CACCAGGACT GGCTGAACGG CAAGGAGTAC AAGTGCAAGG TCTCCAACAA
 801   AGGCCTCCCA GCCCCCATCG AGAAAACCAT CTCCAAAACC AAAGGGCAGC
 851   CCCGAGAACC ACAGGTGTAC ACCCTGCCCC CATCCCGGGA GGAGATGACC
 901   AAGAACCAGG TCAGCCTGAC CTGCCTGGTC AAAGGCTTCT ACCCCAGCGA
 951   CATCGCCGTG GAGTGGGAGA GCAATGGGCA GCCGGAGAAC AACTACAAGA
1001   CCACACCTCC CATGCTGGAC TCCGACGGCT CCTTCTTCCT CTACAGCAAG
1051   CTCACCGTGG ACAAGAGCAG GTGGCAGCAG GGGAACGTCT TCTCATGCTC
1101   CGTGATGCAT GAGGCTCTGC ACAACCACTA CACGCAGAAG AGCCTCTCCC
1151   TGTCTCCGGG TAAA
```

Item 3 shows the amino acid sequence of hTβRII$_{short}$(23-159/D110K)-hG1Fc$_{short}$ (SEQ ID NO: 27). Double underline indicates D110K substitution. Dotted underline denotes leader, and solid underline denotes linker.

```
                                                (SEQ ID NO: 27)
  1   MDAMKRGLCC VLLLCGAVFV SPGATIPPHV QKSVNNDMIV TDNNGAVKFP
 51   QLCKFCDVRF STCDNQKSCM SNCSITSICE KPQEVCVAVW RKNDENITLE
101   TVCHDPKLPY HKFILEDAAS PKCIMKEKKK PGETFFMCSC SSDECNDNII
151   FSEEYNTSNP DTGGGTHTCP PCPAPELLGG PSVFLFPPKP KDTLMISRTP
201   EVTCVVVDVS HEDPEVKFNW YVDGVEVHNA KTKPREEQYN STYRVVSVLT
251   VLHQDWLNGK EYKCKVSNKA LPAPIEKTIS KAKGQPREPQ VYTLPPSREE
301   MTKNQVSLTC LVKGFYPSDI AVEWESNGQP ENNYKTTPPV LDSDGSFFLY
351   SKLTVDKSRW QQGNVFSCSV MHEALHNHYT QKSLSLSPGK
```

Item 4 shows a nucleotide sequence encoding hTβRII$_{short}$(23-159/D110K)-hG1Fc$_{short}$ (SEQ ID NO: 28). Double underline indicates D110K substitution. Dotted underline denotes leader, and solid underline denotes linker.

```
                                                        (SEQ ID NO: 28)
   1    ATGGATGCAA TGAAGAGAGG GCTCTGCTGT GTGCTGCTGC TGTGTGGAGC
  51    AGTCTTCGTT TCGCCCGGCG CCACGATCCC ACCGCACGTT CAGAAGTCGG
 101    TTAATAACGA CATGATAGTC ACTGACAACA ACGGTGCAGT CAAGTTTCCA
 151    CAACTGTGTA AATTTTGTGA TGTGAGATTT TCCACCTGTG ACAACCAGAA
 201    ATCCTGCATG AGCAACTGCA GCATCACCTC CATCTGTGAG AAGCCACAGG
 251    AAGTCTGTGT GGCTGTATGG AGAAAGAATG ACGAGAACAT AACACTAGAG
 301    ACAGTTTGCC ATGACCCCAA GCTCCCCTAC CATAAGTTTA TTCTGGAAGA
 351    TGCTGCTTCT CCAAAGTGCA TTATGAAGGA AAAAAAAAG CCTGGTGAGA
 401    CTTTCTTCAT GTGTTCCTGT AGCTCTGATG AGTGCAATGA CAACATCATC
 451    TTCTCAGAAG AATATAACAC CAGCAATCCT GACACCGGTG GTGGAACTCA
 501    CACATGCCCA CCGTGCCCAG CACCTGAACT CCTGGGGGGA CCGTCAGTCT
 551    TCCTCTTCCC CCCAAAACCC AAGGACACCC TCATGATCTC CCGGACCCCT
 601    GAGGTCACAT GCGTGGTGGT GGACGTGAGC CACGAAGACC CTGAGGTCAA
 651    GTTCAACTGG TACGTGGACG GCGTGGAGGT GCATAATGCC AAGACAAAGC
 701    CGCGGGAGGA GCAGTACAAC AGCACGTACC GTGTGGTCAG CGTCCTCACC
 751    GTCCTGCACC AGGACTGGCT GAATGGCAAG GAGTACAAGT GCAAGGTCTC
 801    CAACAAAGCC CTCCCAGCCC CCATCGAGAA AACCATCTCC AAAGCCAAAG
 851    GGCAGCCCCG AGAACCACAG GTGTACACCC TGCCCCCATC CCGGGAGGAG
 901    ATGACCAAGA ACCAGGTCAG CCTGACCTGC CTGGTCAAAG GCTTCTATCC
 951    CAGCGACATC GCCGTGGAGT GGGAGAGCAA TGGGCAGCCG GAGAACAACT
1001    ACAAGACCAC GCCTCCCGTG CTGGACTCCG ACGGCTCCTT CTTCCTCTAT
1051    AGCAAGCTCA CCGTGGACAA GAGCAGGTGG CAGCAGGGGA ACGTCTTCTC
1101    ATGCTCCGTG ATGCATGAGG CTCTGCACAA CCACTACACG CAGAAGAGCC
1151    TCTCCCTGTC CCCGGGTAAA
```

Item 5 shows the amino acid sequence of hTβRII$_{short}$(29-159)-hG2Fc (SEQ ID NO: 29). Dotted underline denotes leader, and solid underline denotes linker.

```
                                                        (SEQ ID NO: 29)
   1    MDAMKRGLCC VLLLCGAVFV SPGAQKSVNN DMIVTDNNGA VKFPQLCKFC
  51    DVRFSTCDNQ KSCMSNCSIT SICEKPQEVC VAVWRKNDEN ITLETVCHDP
 101    KLPYHDFILE DAASPKCIMK EKKKPGETFF MCSCSSDECN DNIIFSEEYN
 151    TSNPDTGGGV ECPPCPAPPV AGPSVFLFPP KPKDTLMISR TPEVTCVVVD
 201    VSHEDPEVQF NWYVDGVEVH NAKTKPREEQ FNSTFRVVSV LTVVHQDWLN
 251    GKEYKCKVSN KGLPAPIEKT ISKTKGQPRE PQVYTLPPSR EEMTKNQVSL
 301    TCLVKGFYPS DIAVEWESNG QPENNYKTTP PMLDSDGSFF LYSKLTVDKS
 351    RWQQGNVFSC SVMHEALHNH YTQKSLSLSP GK
```

Item 6 shows a nucleotide sequence encoding hTβRII$_{short}$ (29-159)-hG2Fc (SEQ ID NO: 30). Dotted underline denotes leader, and solid underline denotes linker.

```
                                                    (SEQ ID NO: 30)
   1    ATGGATGCAA TGAAGAGAGG GCTCTGCTGT GTGCTGCTGC TGTGTGGAGC

51    AGTCTTCGTT TCGCCCGGCG CCCAGAAGTC GGTTAATAAC GACATGATAG

101    TCACTGACAA CAACGGTGCA GTCAAGTTTC CACAACTGTG TAAATTTTGT

151    GATGTGAGAT TTTCCACCTG TGACAACCAG AAATCCTGCA TGAGCAACTG

201    CAGCATCACC TCCATCTGTG AGAAGCCACA GGAAGTCTGT GTGGCTGTAT

251    GGAGAAAGAA TGACGAGAAC ATAACACTAG AGACAGTTTG CCATGACCCC

301    AAGCTCCCCT ACCATGACTT TATTCTGGAA GATGCTGCTT CTCCAAAGTG

351    CATTATGAAG GAAAAAAAA AGCCTGGTGA GACTTTCTTC ATGTGTTCCT

401    GTAGCTCTGA TGAGTGCAAT GACAACATCA TCTTCTCAGA AGAATATAAC

451    ACCAGCAATC CTGACACCGG TGGTGGAGTC GAGTGCCCAC CGTGCCCAGC

501    ACCACCTGTG GCAGGACCGT CAGTCTTCCT CTTCCCCCCA AAACCCAAGG

551    ACACCCTCAT GATCTCCCGG ACCCCTGAGG TCACGTGCGT GGTGGTGGAC

601    GTGAGCCACG AAGACCCCGA GGTCCAGTTC AACTGGTACG TGGACGGCGT

651    GGAGGTGCAT AATGCCAAGA CAAAGCCACG GGAGGAGCAG TTCAACAGCA

701    CGTTCCGTGT GGTCAGCGTC CTCACCGTCG TGCACCAGGA CTGGCTGAAC

751    GGCAAGGAGT ACAAGTGCAA GGTCTCCAAC AAAGGCCTCC CAGCCCCCAT

801    CGAGAAAACC ATCTCCAAAA CCAAAGGGCA GCCCCGAGAA CCACAGGTGT

851    ACACCCTGCC CCCATCCCGG GAGGAGATGA CCAAGAACCA GGTCAGCCTG

901    ACCTGCCTGG TCAAAGGCTT CTACCCCAGC GACATCGCCG TGGAGTGGGA

951    GAGCAATGGG CAGCCGGAGA ACAACTACAA GACCACACCT CCCATGCTGG

1001    ACTCCGACGG CTCCTTCTTC CTCTACAGCA AGCTCACCGT GGACAAGAGC

1051    AGGTGGCAGC AGGGGAACGT CTTCTCATGC TCCGTGATGC ATGAGGCTCT

1101    GCACAACCAC TACACGCAGA AGAGCCTCTC CCTGTCTCCG GGTAAA
```

Item 7 shows the amino acid sequence of hTβRII$_{short}$(29-159)-hG1Fc$_{short}$ (SEQ ID NO: 31). Dotted underline denotes leader, and solid underline denotes linker.

```
                                                    (SEQ ID NO: 31)
   1    MDAMKRGLCC VLLLCGAVFV SPGAQKSVNN DMIVTDNNGA VKFPQLCKFC

51    DVRFSTCDNQ KSCMSNCSIT SICEKPQEVC VAVWRKNDEN ITLETVCHDP

101    KLPYHDFILE DAASPKCIMK EKKKPGETFF MCSCSSDECN DNIIFSEEYN

151    TSNPDTGGGT HTCPPCPAPE LLGGPSVFLF PPKPKDTLMI SRTPEVTCVV

201    VDVSHEDPEV KFNWYVDGVE VHNAKTKPRE EQYNSTYRVV SVLTVLHQDW

251    LNGKEYKCKV SNKALPAPIE KTISKAKGQP REPQVYTLPP SREEMTKNQV

301    SLTCLVKGFY PSDIAVEWES NGQPENNYKT TPPVLDSDGS FFLYSKLTVD

351    KSRWQQGNVF SCSVMHEALH NHYTQKSLSL SPGK
```

Item 8 shows a nucleotide sequence encoding hTβRII$_{short}$ (29-159)-hG1Fc$_{short}$ (SEQ ID NO: 32). Dotted underline denotes leader, and solid underline denotes linker.

```
                                                       (SEQ ID NO: 32)
   1  ATGGATGCAA TGAAGAGAGG GCTCTGCTGT GTGCTGCTGC TGTGTGGAGC

51  AGTCTTCGTT TCGCCCGGCG CCCAGAAGTC GGTTAATAAC GACATGATAG

101  TCACTGACAA CAACGGTGCA GTCAAGTTTC CACAACTGTG TAAATTTTGT

151  GATGTGAGAT TTTCCACCTG TGACAACCAG AAATCCTGCA TGAGCAACTG

201  CAGCATCACC TCCATCTGTG AGAAGCCACA GGAAGTCTGT GTGGCTGTAT

251  GGAGAAAGAA TGACGAGAAC ATAACACTAG AGACAGTTTG CCATGACCCC

301  AAGCTCCCCT ACCATGACTT TATTCTGGAA GATGCTGCTT CTCCAAAGTG

351  CATTATGAAG GAAAAAAAAA AGCCTGGTGA GACTTTCTTC ATGTGTTCCT

401  GTAGCTCTGA TGAGTGCAAT GACAACATCA TCTTCTCAGA AGAATATAAC

451  ACCAGCAATC CTGACACCGG TGGTGGAACT CACACATGCC CACCGTGCCC

501  AGCACCTGAA CTCCTGGGGG GACCGTCAGT CTTCCTCTTC CCCCCAAAAC

551  CCAAGGACAC CCTCATGATC TCCCGGACCC CTGAGGTCAC ATGCGTGGTG

601  GTGGACGTGA GCCACGAAGA CCCTGAGGTC AAGTTCAACT GGTACGTGGA

651  CGGCGTGGAG GTGCATAATG CCAAGACAAA GCCGCGGGAG GAGCAGTACA

701  ACAGCACGTA CCGTGTGGTC AGCGTCCTCA CCGTCCTGCA CCAGGACTGG

751  CTGAATGGCA AGGAGTACAA GTGCAAGGTC TCCAACAAAG CCCTCCCAGC

801  CCCCATCGAG AAAACCATCT CCAAAGCCAA AGGGCAGCCC CGAGAACCAC

851  AGGTGTACAC CCTGCCCCCA TCCCGGGAGG AGATGACCAA GAACCAGGTC

901  AGCCTGACCT GCCTGGTCAA AGGCTTCTAT CCCAGCGACA TCGCCGTGGA

951  GTGGGAGAGC AATGGGCAGC CGGAGAACAA CTACAAGACC ACGCCTCCCG

1001  TGCTGGACTC CGACGGCTCC TTCTTCCTCT ATAGCAAGCT CACCGTGGAC

1051  AAGAGCAGGT GGCAGCAGGG GAACGTCTTC TCATGCTCCG TGATGCATGA

1101  GGCTCTGCAC AACCACTACA CGCAGAAGAG CCTCTCCCTG TCCCCGGGTA

1151  AA
```

Item 9 shows the amino acid sequence of hTβRII$_{short}$(35-159)-hG2Fc (SEQ ID NO: 33). Dotted underline denotes leader, and solid underline denotes linker.

```
                                                       (SEQ ID NO: 33)
   1  MDAMKRGLCC VLLLCGAVFV SPGADMIVTD NNGAVKFPQL CKFCDVRFST

51  CDNQKSCMSN CSITSICEKP QEVCVAVWRK NDENITLETV CHDPKLPYHD

101  FILEDAASPK CIMKEKKKPG ETFFMCSCSS DECNDNIIFS EEYNTSNPDT

151  GGGVECPPCP APPVAGPSVF LFPPKPKDTL MISRTPEVTC VVVDVSHEDP

201  EVQFNWYVDG VEVHNAKTKP REEQFNSTFR VVSVLTVVHQ DWLNGKEYKC

251  KVSNKGLPAP IEKTISKTKG QPREPQVYTL PPSREEMTKN QVSLTCLVKG

301  FYPSDIAVEW ESNGQPENNY KTTPPMLDSD GSFFLYSKLT VDKSRWQQGN

351  VFSCSVMHEA LHNHYTQKSL SLSPGK
```

Item 10 shows a nucleotide sequence encoding hT$\beta$RII$_{short}$ (35-159)-hG2Fc (SEQ ID NO: 34). Dotted underline denotes leader, and solid underline denotes linker.

```
                                                     (SEQ ID NO: 34)
   1 ATGGATGCAA TGAAGAGAGG GCTCTGCTGT GTGCTGCTGC TGTGTGGAGC

51 AGTCTTCGTT TCGCCCGGCG CCGACATGAT AGTCACTGAC AACAACGGTG

101 CAGTCAAGTT TCCACAACTG TGTAAATTTT GTGATGTGAG ATTTTCCACC

151 TGTGACAACC AGAAATCCTG CATGAGCAAC TGCAGCATCA CCTCCATCTG

201 TGAGAAGCCA CAGGAAGTCT GTGTGGCTGT ATGGAGAAAG AATGACGAGA

251 ACATAACACT AGAGACAGTT TGCCATGACC CCAAGCTCCC CTACCATGAC

301 TTTATTCTGG AAGATGCTGC TTCTCCAAAG TGCATTATGA AGGAAAAAAA

351 AAAGCCTGGT GAGACTTTCT TCATGTGTTC CTGTAGCTCT GATGAGTGCA

401 ATGACAACAT CATCTTCTCA GAAGAATATA ACACCAGCAA TCCTGACACC

451 GGTGGTGGAG TCGAGTGCCC ACCGTGCCCA GCACCACCTG TGGCAGGACC

501 GTCAGTCTTC CTCTTCCCCC CAAAACCCAA GGACACCCTC ATGATCTCCC

551 GGACCCCTGA GGTCACGTGC GTGGTGGTGG ACGTGAGCCA CGAAGACCCC

601 GAGGTCCAGT TCAACTGGTA CGTGGACGGC GTGGAGGTGC ATAATGCCAA

651 GACAAAGCCA CGGGAGGAGC AGTTCAACAG CACGTTCCGT GTGGTCAGCG

701 TCCTCACCGT CGTGCACCAG GACTGGCTGA ACGGCAAGGA GTACAAGTGC

751 AAGGTCTCCA ACAAAGGCCT CCCAGCCCCC ATCGAGAAAA CCATCTCCAA

801 AACCAAAGGG CAGCCCCGAG AACCACAGGT GTACACCCTG CCCCCATCCC

851 GGGAGGAGAT GACCAAGAAC CAGGTCAGCC TGACCTGCCT GGTCAAAGGC

901 TTCTACCCCA GCGACATCGC CGTGGAGTGG GAGAGCAATG GGCAGCCGGA

951 GAACAACTAC AAGACCACAC CTCCCATGCT GGACTCCGAC GGCTCCTTCT

1001 TCCTCTACAG CAAGCTCACC GTGGACAAGA GCAGGTGGCA GCAGGGGAAC

1051 GTCTTCTCAT GCTCCGTGAT GCATGAGGCT CTGCACAACC ACTACACGCA

1101 GAAGAGCCTC TCCCTGTCTC CGGGTAAA
```

Item 11 shows the amino acid sequence of hT$\beta$RII$_{short}$(35-159)-hG1Fc$_{short}$ (SEQ ID NO: 35). Dotted underline denotes leader, and solid underline denotes linker.

```
                                                     (SEQ ID NO: 35)
   1 MDAMKRGLCC VLLLCGAVFV SPGADMIVTD NNGAVKFPQL CKFCDVRFST

51 CDNQKSCMSN CSITSICEKP QEVCVAVWRK NDENITLETV CHDPKLPYHD

101 FILEDAASPK CIMKEKKKPG ETFFMCSCSS DECNDNIIFS EEYNTSNPDT

151 GGGTHTCPPC PAPELLGGPS VFLFPPKPKD TLMISRTPEV TCVVVDVSHE

201 DPEVKFNWYV DGVEVHNAKT KPREEQYNST YRVVSVLTVL HQDWLNGKEY

251 KCKVSNKALP APIEKTISKA KGQPREPQVY TLPPSREEMT KNQVSLTCLV

301 KGFYPSDIAV EWESNGQPEN NYKTTPPVLD SDGSFFLYSK LTVDKSRWQQ

351 GNVFSCSVMH EALHNHYTQK SLSLSPGK
```

Item 12 shows a nucleotide sequence encoding hTβRII$_{short}$ (35-159)-hG1Fc$_{short}$. (SEQ ID NO: 36). Dotted underline denotes leader, and solid underline denotes linker.

```
                                                       (SEQ ID NO: 36)
   1 ATGGATGCAA TGAAGAGAGG GCTCTGCTGT GTGCTGCTGC TGTGTGGAGC

51 AGTCTTCGTT TCGCCCGGCG CCGACATGAT AGTCACTGAC AACAACGGTG

101 CAGTCAAGTT TCCACAACTG TGTAAATTTT GTGATGTGAG ATTTTCCACC

151 TGTGACAACC AGAAATCCTG CATGAGCAAC TGCAGCATCA CCTCCATCTG

201 TGAGAAGCCA CAGGAAGTCT GTGTGGCTGT ATGGAGAAAG AATGACGAGA

251 ACATAACACT AGAGACAGTT TGCCATGACC CCAAGCTCCC CTACCATGAC

301 TTTATTCTGG AAGATGCTGC TTCTCCAAAG TGCATTATGA AGGAAAAAAA

351 AAAGCCTGGT GAGACTTTCT TCATGTGTTC CTGTAGCTCT GATGAGTGCA

401 ATGACAACAT CATCTTCTCA GAAGAATATA ACACCAGCAA TCCTGACACC

451 GGTGGTGGAA CTCACACATG CCCACCGTGC CCAGCACCTG AACTCCTGGG

501 GGGACCGTCA GTCTTCCTCT TCCCCCCAAA ACCCAAGGAC ACCCTCATGA

551 TCTCCCGGAC CCCTGAGGTC ACATGCGTGG TGGTGGACGT GAGCCACGAA

601 GACCCTGAGG TCAAGTTCAA CTGGTACGTG GACGGCGTGG AGGTGCATAA

651 TGCCAAGACA AAGCCGCGGG AGGAGCAGTA CAACAGCACG TACCGTGTGG

701 TCAGCGTCCT CACCGTCCTG CACCAGGACT GGCTGAATGG CAAGGAGTAC

751 AAGTGCAAGG TCTCCAACAA AGCCCTCCCA GCCCCCATCG AGAAAACCAT

801 CTCCAAAGCC AAAGGGCAGC CCGAGAACCA CAGGTGTAC ACCCTGCCCC

851 CATCCCGGGA GGAGATGACC AAGAACCAGG TCAGCCTGAC CTGCCTGGTC

901 AAAGGCTTCT ATCCCAGCGA CATCGCCGTG GAGTGGGAGA GCAATGGGCA

951 GCCGGAGAAC AACTACAAGA CCACGCCTCC CGTGCTGGAC TCCGACGGCT

1001 CCTTCTTCCT CTATAGCAAG CTCACCGTGG ACAAGAGCAG GTGGCAGCAG

1051 GGGAACGTCT TCTCATGCTC CGTGATGCAT GAGGCTCTGC ACAACCACTA

1101 CACGCAGAAG AGCCTCTCCC TGTCCCCGGG TAAA
```

Item 13 shows the amino acid sequence of hTβRII$_{short}$(23-153)-hG2Fc (SEQ ID NO: 37). Dotted underline denotes leader, and solid underline denotes linker.

```
                                                       (SEQ ID NO: 37)
   1 MDAMKRGLCC VLLLCGAVFV SPGATIPPHV QKSVNNDMIV TDNNGAVKFP

51 QLCKFCDVRF STCDNQKSCM SNCSITSICE KPQEVCVAVW RKNDENITLE

101 TVCHDPKLPY HDFILEDAAS PKCIMKEKKK PGETFFMCSC SSDECNDNII

151 FSEEYTGGGV ECPPCPAPPV AGPSVFLFPP KPKDTLMISR TPEVTCVVVD

201 VSHEDPEVQF NWYVDGVEVH NAKTKPREEQ FNSTFRVVSV LTVVHQDWLN

251 GKEYKCKVSN KGLPAPIEKT ISKTKGQPRE PQVYTLPPSR EEMTKNQVSL

301 TCLVKGFYPS DIAVEWESNG QPENNYKTTP PMLDSDGSFF LYSKLTVDKS

351 RWQQGNVFSC SVMHEALHNH YTQKSLSLSP GK
```

Item 14 shows a nucleotide sequence encoding hTβRII$_{short}$ (23-153)-hG2Fc (SEQ ID NO: 38). Dotted underline denotes leader, and solid underline denotes linker.

```
                                                          (SEQ ID NO: 38)
   1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 TTAATAACGA CATGATAGTC ACTGACAACA ACGGTGCAGT CAAGTTTCCA

151 CAACTGTGTA AATTTTGTGA TGTGAGATTT TCCACCTGTG ACAACCAGAA

201 ATCCTGCATG AGCAACTGCA GCATCACCTC CATCTGTGAG AAGCCACAGG

251 AAGTCTGTGT GGCTGTATGG AGAAAGAATG ACGAGAACAT AACACTAGAG

301 ACAGTTTGCC ATGACCCCAA GCTCCCCTAC CATGACTTTA TTCTGGAAGA

351 TGCTGCTTCT CCAAAGTGCA TTATGAAGGA AAAAAAAAAG CCTGGTGAGA

401 CTTTCTTCAT GTGTTCCTGT AGCTCTGATG AGTGCAATGA CAACATCATC

451 TTCTCAGAAG AATATACCGG TGGTGGAGTC GAGTGCCCAC CGTGCCCAGC

501 ACCACCTGTG GCAGGACCGT CAGTCTTCCT CTTCCCCCCA AAACCCAAGG

551 ACACCCTCAT GATCTCCCGG ACCCCTGAGG TCACGTGCGT GGTGGTGGAC

601 GTGAGCCACG AAGACCCCGA GGTCCAGTTC AACTGGTACG TGGACGGCGT

651 GGAGGTGCAT AATGCCAAGA CAAAGCCACG GGAGGAGCAG TTCAACAGCA

701 CGTTCCGTGT GGTCAGCGTC CTCACCGTCG TGCACCAGGA CTGGCTGAAC

751 GGCAAGGAGT ACAAGTGCAA GGTCTCCAAC AAAGGCCTCC CAGCCCCCAT

801 CGAGAAAACC ATCTCCAAAA CCAAAGGGCA GCCCCGAGAA CCACAGGTGT

851 ACACCCTGCC CCCATCCCGG GAGGAGATGA CCAAGAACCA GGTCAGCCTG

901 ACCTGCCTGG TCAAAGGCTT CTACCCCAGC GACATCGCCG TGGAGTGGGA

951 GAGCAATGGG CAGCCGGAGA ACAACTACAA GACCACACCT CCCATGCTGG

1001 ACTCCGACGG CTCCTTCTTC CTCTACAGCA AGCTCACCGT GGACAAGAGC

1051 AGGTGGCAGC AGGGGAACGT CTTCTCATGC TCCGTGATGC ATGAGGCTCT

1101 GCACAACCAC TACACGCAGA AGAGCCTCTC CCTGTCTCCG GGTAAA
```

Item 15 shows the amino acid sequence of hTβRII$_{short}$(23-153)-hG1Fc$_{short}$ (SEQ ID NO: 39). Dotted underline denotes leader, and solid underline denotes linker.

```
                                                          (SEQ ID NO: 39)
   1 MDAMKRGLCC VLLLCGAVFV SPGATIPPHV QKSVNNDMIV TDNNGAVKFP

51 QLCKFCDVRF STCDNQKSCM SNCSITSICE KPQEVCVAVW RKNDENITLE

101 TVCHDPKLPY HDFILEDAAS PKCIMKEKKK PGETFFMCSC SSDECNDNII

151 FSEEYTGGGT HTCPPCPAPE LLGGPSVFLF PPKPKDTLMI SRTPEVTCVV

201 VDVSHEDPEV KFNWYVDGVE VHNAKTKPRE EQYNSTYRVV SVLTVLHQDW

251 LNGKEYKCKV SNKALPAPIE KTISKAKGQP REPQVYTLPP SREEMTKNQV

301 SLTCLVKGFY PSDIAVEWES NGQPENNYKT TPPVLDSDGS FFLYSKLTVD

351 KSRWQQGNVF SCSVMHEALH NHYTQKSLSL SPGK
```

Item 16 shows a nucleotide sequence encoding hTβRII$_{short}$(23-153)-hG1Fc$_{short}$ (SEQ ID NO: 40). Dotted underline denotes leader, and solid underline denotes linker.

```
                                                         (SEQ ID NO: 40)
   1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 TTAATAACGA CATGATAGTC ACTGACAACA ACGGTGCAGT CAAGTTTCCA

151 CAACTGTGTA AATTTTGTGA TGTGAGATTT TCCACCTGTG ACAACCAGAA

201 ATCCTGCATG AGCAACTGCA GCATCACCTC CATCTGTGAG AAGCCACAGG

251 AAGTCTGTGT GGCTGTATGG AGAAAGAATG ACGAGAACAT AACACTAGAG

301 ACAGTTTGCC ATGACCCCAA GCTCCCCTAC CATGACTTTA TTCTGGAAGA

351 TGCTGCTTCT CCAAAGTGCA TTATGAAGGA AAAAAAAAAG CCTGGTGAGA

401 CTTTCTTCAT GTGTTCCTGT AGCTCTGATG AGTGCAATGA CAACATCATC

451 TTCTCAGAAG AATATACCGG TGGTGGAACT CACACATGCC CACCGTGCCC

501 AGCACCTGAA CTCCTGGGGG GACCGTCAGT CTTCCTCTTC CCCCCAAAAC

551 CCAAGGACAC CCTCATGATC TCCCGGACCC CTGAGGTCAC ATGCGTGGTG

601 GTGGACGTGA GCCACGAAGA CCCTGAGGTC AAGTTCAACT GGTACGTGGA

651 CGGCGTGGAG GTGCATAATG CCAAGACAAA GCCGCGGGAG GAGCAGTACA

701 ACAGCACGTA CCGTGTGGTC AGCGTCCTCA CCGTCCTGCA CCAGGACTGG

751 CTGAATGGCA AGGAGTACAA GTGCAAGGTC TCCAACAAAG CCCTCCCAGC

801 CCCCATCGAG AAAACCATCT CCAAAGCCAA AGGGCAGCCC CGAGAACCAC

851 AGGTGTACAC CCTGCCCCCA TCCCGGGAGG AGATGACCAA GAACCAGGTC

901 AGCCTGACCT GCCTGGTCAA AGGCTTCTAT CCCAGCGACA TCGCCGTGGA

951 GTGGGAGAGC AATGGGCAGC CGGAGAACAA CTACAAGACC ACGCCTCCCG

1001 TGCTGGACTC CGACGGCTCC TTCTTCCTCT ATAGCAAGCT CACCGTGGAC

1051 AAGAGCAGGT GGCAGCAGGG GAACGTCTTC TCATGCTCCG TGATGCATGA

1101 GGCTCTGCAC AACCACTACA CGCAGAAGAG CCTCTCCCTG TCCCCGGGTA

1151 AA
```

Item 17 shows the amino acid sequence of hTβRII$_{short}$(23-153/N70D)-hG2Fc (SEQ ID NO: 41). Double underline indicates N70D substitution. Dotted underline denotes leader, and solid underline denotes linker.

```
                                                         (SEQ ID NO: 41)
   1 MDAMKRGLCC VLLLCGAVFV SPGATIPPHV QKSVNNDMIV TDNNGAVKDP

51 QLCKFCDVRF STCDNQKSCM SDCSITSICE KPQEVCVAVW RKNDENITLE

101 TVCHDPKLPY HDFILEDAAS PKCIMKEKKK PGETFFMCSC SSDECNDNII

151 FSEEYTGGGV ECPPCPAPPV AGPSVFLFPP KPKDTLMISR TPEVTCVVVD

201 VSHEDPEVQF NWYVDGVEVH NAKTKPREEQ FNSTFRVVSV LTVVHQDWLN

251 GKEYKCKVSN KGLPAPIEKT ISKTKGQPRE PQVYTLPPSR EEMTKNQVSL

301 TCLVKGFYPS DIAVEWESNG QPENNYKTTP PMLDSDGSFF LYSKLTVDKS

351 RWQQGNVFSC SVMHEALHNH YTQKSLSLSP GK
```

Item 18 shows a nucleotide sequence encoding hTβRII$_{short}$ (23-153/N70D)-hG2Fc (SEQ ID NO: 42). Double underline indicates N70D substitution. Dotted underline denotes leader, and solid underline denotes linker.

```
                                                       (SEQ ID NO: 42)
   1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 TTAATAACGA CATGATAGTC ACTGACAACA ACGGTGCAGT CAAGTTTCCA

151 CAACTGTGTA AATTTTGTGA TGTGAGATTT TCCACCTGTG ACAACCAGAA

201 ATCCTGCATG AGCGACTGCA GCATCACCTC CATCTGTGAG AAGCCACAGG

251 AAGTCTGTGT GGCTGTATGG AGAAAGAATG ACGAGAACAT AACACTAGAG

301 ACAGTTTGCC ATGACCCCAA GCTCCCCTAC CATGACTTTA TTCTGGAAGA

351 TGCTGCTTCT CCAAAGTGCA TTATGAAGGA AAAAAAAAAG CCTGGTGAGA

401 CTTTCTTCAT GTGTTCCTGT AGCTCTGATG AGTGCAATGA CAACATCATC

451 TTCTCAGAAG AATATACCGG TGGTGGAGTC GAGTGCCCAC CGTGCCCAGC

501 ACCACCTGTG GCAGGACCGT CAGTCTTCCT CTTCCCCCCA AAACCCAAGG

551 ACACCCTCAT GATCTCCCGG ACCCCTGAGG TCACGTGCGT GGTGGTGGAC

601 GTGAGCCACG AAGACCCCGA GGTCCAGTTC AACTGGTACG TGGACGGCGT

651 GGAGGTGCAT AATGCCAAGA CAAAGCCACG GGAGGAGCAG TTCAACAGCA

701 CGTTCCGTGT GGTCAGCGTC CTCACCGTCG TGCACCAGGA CTGGCTGAAC

751 GGCAAGGAGT ACAAGTGCAA GGTCTCCAAC AAAGGCCTCC CAGCCCCCAT

801 CGAGAAAACC ATCTCCAAAA CCAAAGGGCA GCCCCGAGAA CCACAGGTGT

851 ACACCCTGCC CCCATCCCGG GAGGAGATGA CCAAGAACCA GGTCAGCCTG

901 ACCTGCCTGG TCAAAGGCTT CTACCCCAGC GACATCGCCG TGGAGTGGGA

951 GAGCAATGGG CAGCCGGAGA ACAACTACAA GACCACACCT CCCATGCTGG

1001 ACTCCGACGG CTCCTTCTTC CTCTACAGCA AGCTCACCGT GGACAAGAGC

1051 AGGTGGCAGC AGGGGAACGT CTTCTCATGC TCCGTGATGC ATGAGGCTCT

1101 GCACAACCAC TACACGCAGA AGAGCCTCTC CCTGTCTCCG GGTAAA
```

Item 19 shows the amino acid sequence of hTβRII$_{short}$(23-153/N70D)-hG1Fc$_{short}$ (SEQ ID NO: 43). Double underline indicates N70D substitution. Dotted underline denotes leader, and solid underline denotes linker.

```
                                                       (SEQ ID NO: 43)
   1 MDAMKRGLCC VLLLCGAVFV SPGATIPPHV QKSVNNDMIV TDNNGAVKFP

51 QLCKFCDVRF STCDNQKSCM SDCSITSICE KPQEVCVAVW RKNDENITLE

101 TVCHDPKLPY HDFILEDAAS PKCIMKEKKK PGETFFMCSC SSDECNDNII

151 FSEEYTGGGT HTCPPCPAPE LLGGPSVFLF PPKPKDTLMI SRTPEVTCVV

201 VDVSHEDPEV KFNWYVDGVE VHNAKTKPRE EQYNSTYRVV SVLTVLHQDW

251 LNGKEYKCKV SNKALPAPIE KTISKAKGQP REPQVYTLPP SREEMTKNQV

301 SLTCLVKGFY PSDIAVEWES NGQPENNYKT TPPVLDSDGS FFLYSKLTVD

351 KSRWQQGNVF SCSVMHEALH NHYTQKSLSL SPGK
```

Item 20 shows a nucleotide sequence encoding hTβRII$_{short}$ (23-153/N70D)-hG1Fc$_{short}$ (SEQ ID NO: 44). Double underline indicates N70D substitution. Dotted underline denotes leader, and solid underline denotes linker.

```
                                                     (SEQ ID NO: 44)
   1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 TTAATAACGA CATGATAGTC ACTGACAACA ACGGTGCAGT CAAGTTTCCA

151 CAACTGTGTA AATTTTGTGA TGTGAGATTT TCCACCTGTG ACAACCAGAA

201 ATCCTGCATG AGCGACTGCA GCATCACCTC CATCTGTGAG AAGCCACAGG

251 AAGTCTGTGT GGCTGTATGG AGAAAGAATG ACGAGAACAT AACACTAGAG

301 ACAGTTTGCC ATGACCCCAA GCTCCCCTAC CATGACTTTA TTCTGGAAGA

351 TGCTGCTTCT CCAAAGTGCA TTATGAAGGA AAAAAAAAAG CCTGGTGAGA

401 CTTTCTTCAT GTGTTCCTGT AGCTCTGATG AGTGCAATGA CAACATCATC

451 TTCTCAGAAG AATATACCGG TGGTGGAACT CACACATGCC CACCGTGCCC

501 AGCACCTGAA CTCCTGGGGG GACCGTCAGT CTTCCTCTTC CCCCCAAAAC

551 CCAAGGACAC CCTCATGATC TCCCGGACCC CTGAGGTCAC ATGCGTGGTG

601 GTGGACGTGA GCCACGAAGA CCCTGAGGTC AAGTTCAACT GGTACGTGGA

651 CGGCGTGGAG GTGCATAATG CCAAGACAAA GCCGCGGGAG GAGCAGTACA

701 ACAGCACGTA CCGTGTGGTC AGCGTCCTCA CCGTCCTGCA CCAGGACTGG

751 CTGAATGGCA AGGAGTACAA GTGCAAGGTC TCCAACAAAG CCCTCCCAGC

801 CCCCATCGAG AAAACCATCT CCAAAGCCAA AGGGCAGCCC CGAGAACCAC

851 AGGTGTACAC CCTGCCCCCA TCCCGGGAGG AGATGACCAA GAACCAGGTC

901 AGCCTGACCT GCCTGGTCAA AGGCTTCTAT CCCAGCGACA TCGCCGTGGA

951 GTGGGAGAGC AATGGGCAGC CGGAGAACAA CTACAAGACC ACGCCTCCCG

1001 TGCTGGACTC CGACGGCTCC TTCTTCCTCT ATAGCAAGCT CACCGTGGAC

1051 AAGAGCAGGT GGCAGCAGGG GAACGTCTTC TCATGCTCCG TGATGCATGA

1101 GGCTCTGCAC AACCACTACA CGCAGAAGAG CCTCTCCCTG TCCCCGGGTA

1151 AA
```

Item 21 shows the mature amino acid sequence (i.e., without the leader sequence) of hTβRII$_{short}$(23-159/D110K)-hG2Fc (SEQ ID NO: 53). Double underline indicates D110K substitution. Single underline denotes linker.

```
                                       (SEQ ID NO: 53)
               TIPPHV QKSVNNDMIV

TDNNGAVKFP QLCKFCDVRF STCDNQKSCM SNCSITSICE

KPQEVCVAVW RKNDENITLE TVCHDPKLPY HKFILEDAAS

PKCIMKEKKK PGETFFMCSC SSDECNDNII FSEEYNTSNP

DTGGGVECPP CPAPPVAGPS VFLFPPKPKD TLMISRTPEV

TCVVVDVSHE DPEVQFNWYV DGVEVHNAKT KPREEQFNST

FRVVSVLTVV HQDWLNGKEY KCKVSNKGLP APIEKTISKT

KGQPREPQVY TLPPSREEMT KNQVSLTCLV KGFYPSDIAV

EWESNGQPEN NYKTTPPMLD SDGSFFLYSK LTVDKSRWQQ

GNVFSCSVMH EALHNHYTQK SLSLSPGK
```

Item 22 shows the mature amino acid sequence (i.e., without the leader sequence) of hTβRII$_{short}$(23-159/D110K)-hG1Fc$_{short}$ (SEQ ID NO: 54). Double underline indicates D110K substitution. Single underline denotes linker.

```
                                       (SEQ ID NO: 54)
               TIPPHV QKSVNNDMIV

TDNNGAVKFP QLCKFCDVRF STCDNQKSCM SNCSITSICE
```

-continued

```
KPQEVCVAVW RKNDENITLE TVCHDPKLPY HKFILEDAAS

PKCIMKEKKK PGETFFMCSC SSDECNDNII FSEEYNTSNP

DTGGGTHTCP PCPAPELLGG PSVFLFPPKP KDTLMISRTP

EVTCVVVDVS HEDPEVKFNW YVDGVEVHNA KTKPREEQYN

STYRVVSVLT VLHQDWLNGK EYKCKVSNKA LPAPIEKTIS

KAKGQPREPQ VYTLPPSREE MTKNQVSLTC LVKGFYPSDI

AVEWESNGQP ENNYKTTPPV LDSDGSFFLY SKLTVDKSRW

QQGNVFSCSV MHEALHNHYT QKSLSLSPGK
```

Item 23 shows the mature amino acid sequence (i.e., without the leader sequence) of hTβRII$_{short}$(29-159)-hG2Fc (SEQ ID NO: 55). Single underline denotes linker.

```
                    (SEQ ID NO: 55)
           QKSVNN DMIVTDNNGA

VKFPQLCKFC DVRFSTCDNQ KSCMSNCSIT SICEKPQEVC

VAVWRKNDEN ITLETVCHDP KLPYHDFILE DAASPKCIMK

EKKKPGETFF MCSCSSDECN DNIIFSEEYN TSNPDTGGGV

ECPPCPAPPV AGPSVFLFPP KPKDTLMISR TPEVTCVVVD

VSHEDPEVQF NWYVDGVEVH NAKTKPREEQ FNSTFRVVSV

LTVVHQDWLN GKEYKCKVSN KGLPAPIEKT ISKTKGQPRE

PQVYTLPPSR EEMTKNQVSL TCLVKGFYPS DIAVEWESNG

QPENNYKTTP PMLDSDGSFF LYSKLTVDKS RWQQGNVFSC

SVMHEALHNH YTQKSLSLSP GK
```

Item 24 shows the mature amino acid sequence (i.e., without the leader sequence) of hTβRII$_{short}$(29-159)-hG1Fc$_{short}$ (SEQ ID NO: 56). Single underline denotes linker.

```
                    (SEQ ID NO: 56)
           QKSVNN DMIVTDNNGA

VKFPQLCKFC DVRFSTCDNQ KSCMSNCSIT SICEKPQEVC

VAVWRKNDEN ITLETVCHDP KLPYHDFILE DAASPKCIMK

EKKKPGETFF MCSCSSDECN DNIIFSEEYN TSNPDTGGGT

HTCPPCPAPE LLGGPSVFLF PPKPKDTLMI SRTPEVTCVV

VDVSHEDPEV KFNWYVDGVE VHNAKTKPRE EQYNSTYRVV

SVLTVLHQDW LNGKEYKCKV SNKALPAPIE KTISKAKGQP

REPQVYTLPP SREEMTKNQV SLTCLVKGFY PSDIAVEWES

NGQPENNYKT TPPVLDSDGS FFLYSKLTVD KSRWQQGNVF

SCSVMHEALH NHYTQKSLSL SPGK
```

Item 25 shows the mature amino acid sequence (i.e., without the leader sequence) of hTβRII$_{short}$(35-159)-hG2Fc (SEQ ID NO: 57). Single underline denotes linker.

```
                    (SEQ ID NO: 57)
           DMIVTD NNGAVKFPQL

CKFCDVRFST CDNQKSCMSN CSITSICEKP QEVCVAVWRK
```

-continued

```
NDENITLETV CHDPKLPYHD FILEDAASPK CIMKEKKKPG

ETFFMCSCSS DECNDNIIFS EEYNTSNPDT GGGVECPPCP

APPVAGPSVF LFPPKPKDTL MISRTPEVTC VVVDVSHEDP

EVQFNWYVDG VEVHNAKTKP REEQFNSTFR VVSVLTVVHQ

DWLNGKEYKC KVSNKGLPAP IEKTISKTKG QPREPQVYTL

PPSREEMTKN QVSLTCLVKG FYPSDIAVEW ESNGQPENNY

KTTPPMLDSD GSFFLYSKLT VDKSRWQQGN VFSCSVMHEA

LHNHYTQKSL SLSPGK
```

Item 26 shows the mature amino acid sequence (i.e., without the leader sequence) of hTβRII$_{short}$(35-159)-hG1Fc$_{short}$ (SEQ ID NO: 58). Single underline denotes linker.

```
                    (SEQ ID NO: 58)
           DMIVTD NNGAVKFPQL

CKFCDVRFST CDNQKSCMSN CSITSICEKP QEVCVAVWRK

NDENITLETV CHDPKLPYHD FILEDAASPK CIMKEKKKPG

ETFFMCSCSS DECNDNIIFS EEYNTSNPDT GGGTHTCPPC

PAPELLGGPS VFLFPPKPKD TLMISRTPEV TCVVVDVSHE

DPEVKFNWYV DGVEVHNAKT KPREEQYNST YRVVSVLTVL

HQDWLNGKEY KCKVSNKALP APIEKTISKA KGQPREPQVY

TLPPSREEMT KNQVSLTCLV KGFYPSDIAV EWESNGQPEN

NYKTTPPVLD SDGSFFLYSK LTVDKSRWQQ GNVFSCSVMH

EALHNHYTQK SLSLSPGK
```

Item 27 shows the mature amino acid sequence (i.e., without the leader sequence) of hTβRII$_{short}$(23-153)-hG2Fc (SEQ ID NO: 59). Single underline denotes linker.

```
                    (SEQ ID NO: 59)
           TIPPHV QKSVNNDMIV

TDNNGAVKFP QLCKFCDVRF STCDNQKSCM SNCSITSICE

KPQEVCVAVW RKNDENITLE TVCHDPKLPY HDFILEDAAS

PKCIMKEKKK PGETFFMCSC SSDECNDNII FSEEYTGGGV

ECPPCPAPPV AGPSVFLFPP KPKDTLMISR TPEVTCVVVD

VSHEDPEVQF NWYVDGVEVH NAKTKPREEQ FNSTFRVVSV

LTVVHQDWLN GKEYKCKVSN KGLPAPIEKT ISKTKGQPRE

PQVYTLPPSR EEMTKNQVSL TCLVKGFYPS DIAVEWESNG

QPENNYKTTP PMLDSDGSFF LYSKLTVDKS RWQQGNVFSC

SVMHEALHNH YTQKSLSLSP GK
```

Item 28 shows the mature amino acid sequence (i.e., without the leader sequence) of hTβRII$_{short}$(23-153)-hG1Fc$_{short}$ (SEQ ID NO: 60). Single underline denotes linker.

```
                    (SEQ ID NO: 60)
           TIPPHV QKSVNNDMIV

TDNNGAVKFP QLCKFCDVRF STCDNQKSCM SNCSITSICE
```

```
KPQEVCVAVW RKNDENITLE TVCHDPKLPY HDFILEDAAS

PKCIMKEKKK PGETFFMCSC SSDECNDNII FSEEYTGGGT

HTCPPCPAPE LLGGPSVFLF PPKPKDTLMI SRTPEVTCVV

VDVSHEDPEV KFNWYVDGVE VHNAKTKPRE EQYNSTYRVV

SVLTVLHQDW LNGKEYKCKV SNKALPAPIE KTISKAKGQP

REPQVYTLPP SREEMTKNQV SLTCLVKGFY PSDIAVEWES

NGQPENNYKT TPPVLDSDGS FFLYSKLTVD KSRWQQGNVF

SCSVMHEALH NHYTQKSLSL SPGK
```

Item 29 shows the mature amino acid sequence (i.e., without the leader sequence) of hTβRII$_{short}$(23-153/N70D)-hG2Fc (SEQ ID NO: 61). Double underline indicates N70D substitution. Single underline denotes linker.

```
                                    (SEQ ID NO: 61)
                            TIPPHV QKSVNNDMIV

TDNNGAVKFP QLCKFCDVRF STCDNQKSCM SDCSITSICE

KPQEVCVAVW RKNDENITLE TVCHDPKLPY HDFILEDAAS

PKCIMKEKKK PGETFFMCSC SSDECNDNII FSEEYTGGGV

ECPPCPAPPV AGPSVFLFPP KPKDTLMISR TPEVTCVVVD

VSHEDPEVQF NWYVDGVEVH NAKTKPREEQ FNSTFRVVSV

LTVVHQDWLN GKEYKCKVSN KGLPAPIEKT ISKTKGQPRE

PQVYTLPPSR EEMTKNQVSL TCLVKGFYPS DIAVEWESNG

QPENNYKTTP PMLDSDGSFF LYSKLTVDKS RWQQGNVFSC

SVMHEALHNH YTQKSLSLSP GK
```

Item 30 shows the mature amino acid sequence (i.e., without the leader sequence) of hTβRII$_{short}$(23-153/N70D)-hG1Fc$_{short}$ (SEQ ID NO: 62). Double underline indicates N70D substitution. Single underline denotes linker.

```
                                    (SEQ ID NO: 62)
                            TIPPHV QKSVNNDMIV

TDNNGAVKFP QLCKFCDVRF STCDNQKSCM SDCSITSICE

KPQEVCVAVW RKNDENITLE TVCHDPKLPY HDFILEDAAS

PKCIMKEKKK PGETFFMCSC SSDECNDNII FSEEYTGGGT

HTCPPCPAPE LLGGPSVFLF PPKPKDTLMI SRTPEVTCVV

VDVSHEDPEV KFNWYVDGVE VHNAKTKPRE EQYNSTYRVV

SVLTVLHQDW LNGKEYKCKV SNKALPAPIE KTISKAKGQP

REPQVYTLPP SREEMTKNQV SLTCLVKGFY PSDIAVEWES

NGQPENNYKT TPPVLDSDGS FFLYSKLTVD KSRWQQGNVF

SCSVMHEALH NHYTQKSLSL SPGK
```

Example 4. Effects of TβRII-Fc in a JAK2V617F Animal Model

Myeloproliferative disorders are a group of conditions characterized, in part, by blood cells abnormalities (e.g., abnormal levels of one or more of platelets, white blood cells, and red blood cells). This group of disorders includes polycythemia vera (PV), essential thrombocythemia (ET), and myelofibrosis (MF). Recently, several groups identified a gain-of-function mutation of tyrosine kinase JAK2 (JAK2V617F) as a major molecular defect in patients with PV, ET, and MF [e.g., Kralovics et al (2005) N Engl J Med 2005; 352:1779-1790]. The mutation results in constitutive activation of JAK2, which has been associated with development or worsening of myeloproliferative disease. Recently a JAK2 inhibitor (ruxolitinib) has been approved for treatment of MF and PV.

A JAK2V617F myeloproliferative disease model has been developed that closely resembles human neoplasms [Xing et al. (2008) Blood 111: 5109-5117]. In particular, JAK2V617F mice develop pathology that closely resembles human PV or ET at a young age, and the disease progresses with advanced age, resulting in myelofibrosis. Applicants have evaluated the effects of a TβRII$_{long}$-Fc fusion protein in this JAK2V617F model of myeloproliferative disease.

Transgenic JAK2V617F mutant mice [the A line as described in Xing et al. (2008) Blood 111: 5109-5117] and age-matched wild-type (control) mice (C57BL/6 mice) were used in these studies. To understand the onset and progression of myelofibrosis disease, the complete blood counts and degree of fibrosis in JAK2V617F mice was compared, at various ages, to data obtained from control animals. Red blood cell (RBC) and platelet levels were elevated in JAK2V617F mice at all ages compared to wild-type, with a trend toward increased levels in mutant animals between 2 to 5 months followed by a progressive decrease between 8 to 14 months. Fibrosis was detectable in bone marrow of JAK2V617F mice starting around 5 months, which worsened with age. JAK2V617F mice also displayed splenomegaly, which also worsened with age. Interestingly, serum levels of TGFβ1, TGFβ2, and various bone metabolic cytokines (e.g., OPG, OPN, aFGF, and Trance) were more elevated in younger JAK2V617F mice (2-5 months) than in older JAK2V617F mice, which coincides with the observed increase in RBC and platelet levels. Peak serum levels of these proteins were observed at the onset of fibrosis (around 5 months). Similarly, inflammatory cytokines (e.g., IL-6, IL-1b, and TNFα) were elevated at older ages. Accordingly, JAK2V617F mice display PV or ET pathology at an early age (approximately 2-5 months of age) and develop MF pathology as they age (after approximately 5-8 months of age).

Figure 4B:
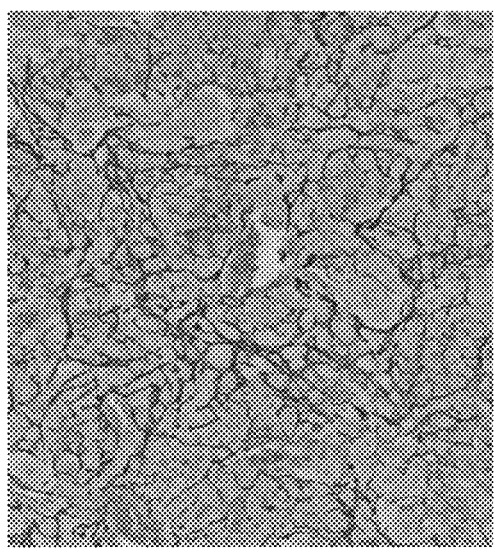
Figure 4C:
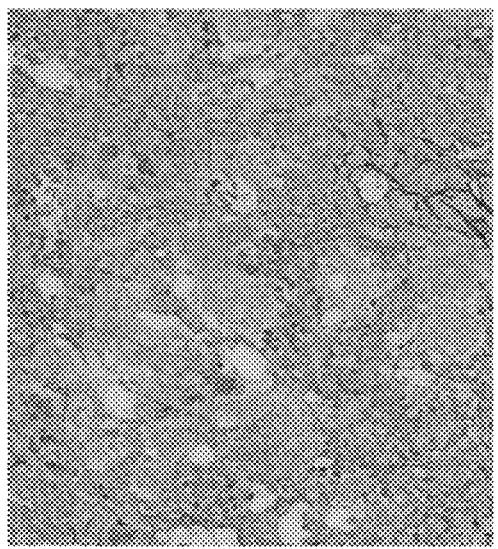
Figures 5A, 5B:
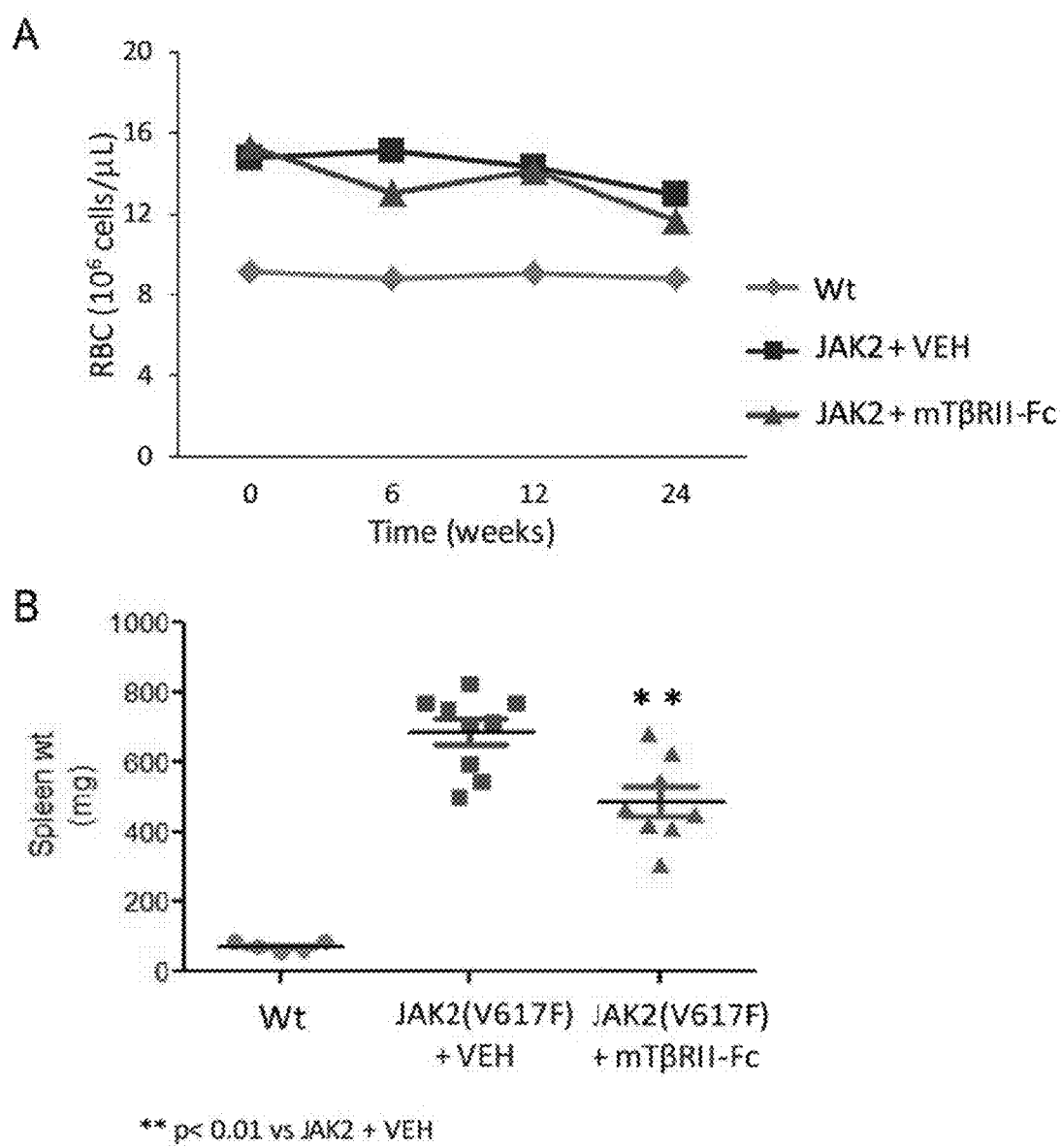
FIGS. 5A and 5B show the effect of mTβRII-Fc on red blood cell levels (FIG. 5A) and spleen weight (FIG. 5B) in JAK2V617F mice. mTβRII-Fc treatment had a modest effect on RBC levels and significantly decreased spleen weight (−29%; p<0.01) compared to vehicle treated mice.
Figure 6A:
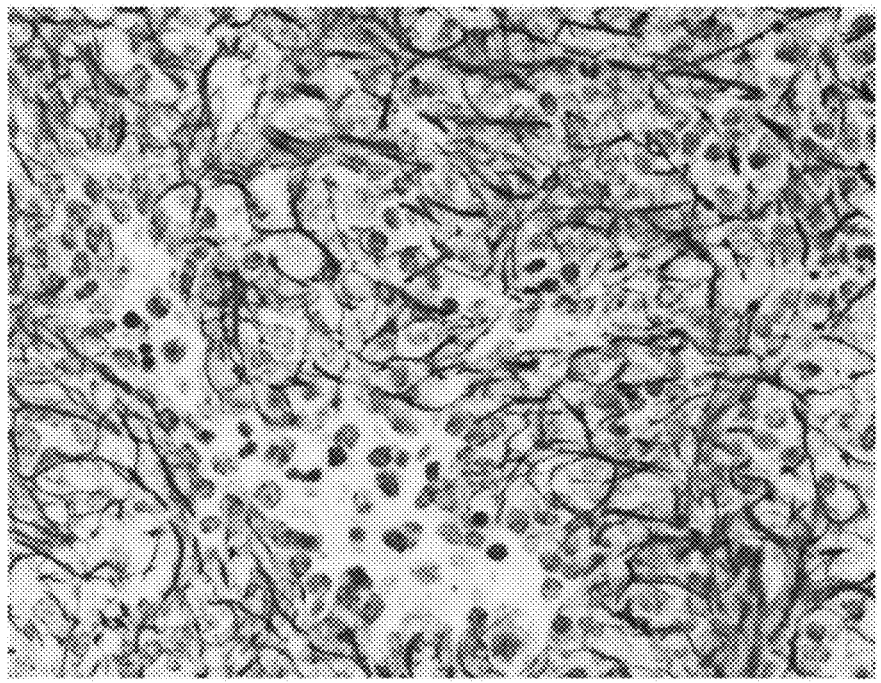
FIGS. 6A and 6B show spleen biopsy from vehicle treated JAK2V617F mice (FIG. 6A) and mTβRII-Fc treated JAK2V617F mice (FIG. 6B). Fibrosis was reduced in spleen samples from mTβRII-Fc treated JAK2V617F mice compared to control JAK2V617F mice.
Figure 6B:
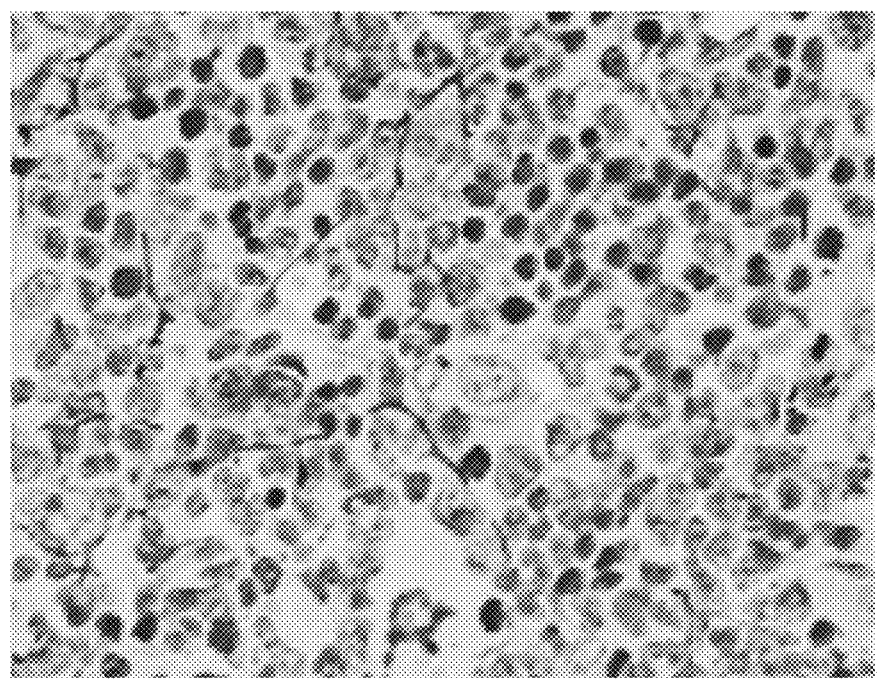

For the TβRII-Fc study, treatment was initiated at 4 months of age, which corresponds to elevated serum TGFβ1 but prior to the onset of fibrosis (at around 5 months of age). Mice were placed into one of three groups: i) treatment of JAK2V617F mice with murine (mTβRII-Fc), as described above, on a dosing schedule of 10 mg/kg twice weekly; ii) treatment of JAK2V617F mice with vehicle (TBS) twice weekly; and iii) vehicle treated wild-type mice (C57BL/6 mice). Following 6 months of treatment, vehicle treated JAK2V617F mice displayed elevated RBC levels (+37.1%, P<0.001), elevated platelets (+74.5%, P<0.001), and increased spleen weights (+9.5-fold, P<0.001) compared to wild-type mice. In addition, bone marrow sections from vehicle treated JAK2V617F mice (see FIG. 4B) revealed severe fibrosis compared to wild-type mice (see FIG. 4A). In comparison to vehicle, mTβRII-Fc JAK2V617F mice trended toward lower RBC levels (see FIG. 5A), and flow-cytometric analysis revealed reduced levels of Ter119+ erythroid precursor cells in bone marrow and spleen samples (−15%, P<0.05). Treatment also had a significant effect on splenomegaly, with mTβRII-Fc treated JAK2V617F mice having reduced spleen weights (−29%, P<0.01) compared to vehicle treatment (FIG. 5B), and fibrosis, with mTβRII-Fc treated JAK2V617F mice having reduced bone marrow fibrosis (see FIG. 4C) and spleen fibrosis compared to vehicle treatment (see FIGS. 6A and 6B). Consistent with the reduction in fibrosis, mTβRII-Fc treated JAK2V617F mice displayed reduced IL-6 levels (−48.9%, P<0.05) compared to vehicle treated mice.

Accordingly, the data show that high serum TGFβ levels are correlated with the onset fibrosis in this JAK2V617F disease model (around 5 months of age) and that treatment with a TβRII-Fc fusion protein results in reduction of fibrosis and splenomegaly as well as other morbidities associated with the disease (e.g., reduced levels of inflammatory cytokines). Together, these data demonstrate that TβRII-Fc polypeptides may be used to treat or prevent disease resultant from the JAK2V617F mutation, which indicates that such therapeutics may be used to treat myeloproliferative disorders (e.g., polycythemia vera, essential thrombocythaemia, and primary myelofibrosis, post-polycythemia vera, and post-essential thrombocythaemia) and other Janus-kinase associated disorders. In view of the positive effects on early (e.g., splenomegaly and elevated blood cell levels) and late (e.g., fibrosis and proinflammatory cytokines) stage disease pathology, TβRII-Fc polypeptides may be particular well suited for treatment of PV, ET, and MF patients. For example, TβRII-Fc treatment mitigates PV and ET pathologies as well as prevents the onset/delays or reduces the severity of fibrosis and other late stage disease complications. TβRII-Fc treatment may also be useful in preventing/delaying the transition of PV and/or ET into secondary myelofibrosis disease (post-polycythemia vera myelofibrosis and post-essential thrombocythaemia myelofibrosis).

Example 5. Effects of TβRII-Fc and Ruxolitinib in a JAK2V617F Animal Model

Figures 7A, 7B:
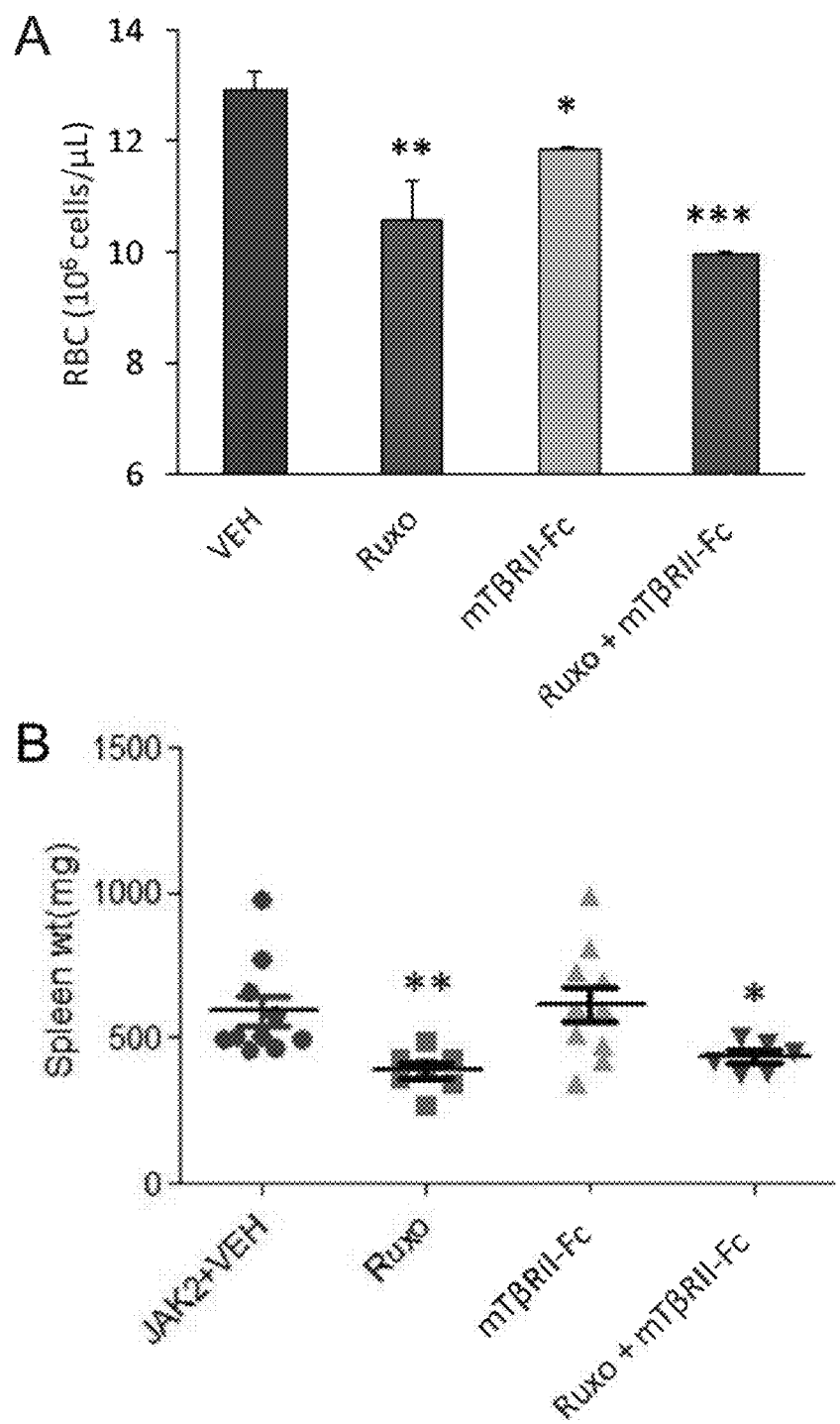
FIGS. 7A and 7B show the effect of mTβRII-Fc and ruxolitinib on red blood cell levels (FIG. 7A) and spleen weight (FIG. 7B) in JAK2V617F mice. Rux treatment alone or in combination with mTβRII-Fc significantly lowered RBC levels and reduced spleen weights compared to vehicle treated mice (* P<0.05;  P<0.01; *P<0.001 vs vehicle). mTβRII-Fc treatment alone had a more modest effect on RBC levels and spleen weights (* P<0.05 and ** P<0.01 vs vehicle).
Figures 8A, 8B, 8C, 8D:
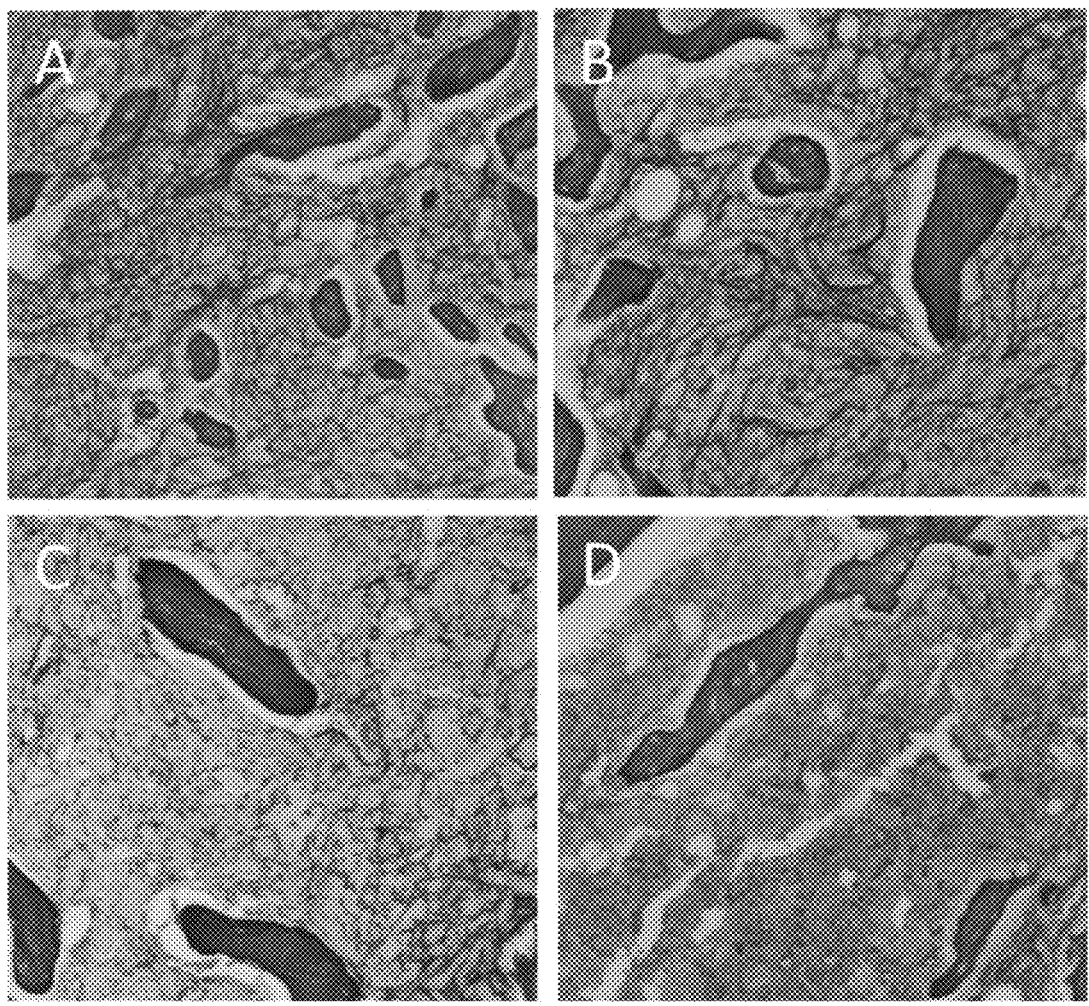
FIGS. 8A, 8B, 8C, and 8D show bone biopsy from vehicle treated JAK2V617F mice (FIG. 8A), ruxolitinib treated JAK2V617F mice (FIG. 8B), mTβRII-Fc treated JAK2V617F mice (FIG. 8C), and JAK2V617F mice treated with both mTβRII-Fc and ruxolitinib (FIG. 8D). Fibrosis was reduced in bone marrow samples from mTβRII-Fc treated JAK2V617F mice as well as JAK2V617F mice treated with both mTβRII-Fc and ruxolitinib compared to control JAK2V617F mice.

The transgenic JAK2V617F mutant mice model described above was further used to compare the effects of mTβRII-Fc and ruxolitinib (nix), separately and in combination, on myelofibrosis. In contrast to Example 4, treatment in this study was initiated at 12 months of age, which corresponds to a late stage of myelofibrosis in which mice generally have increased levels of fibrosis in various tissues (e.g., the bone marrow and spleen) and reduced red blood cell levels in comparison to younger JAK2V617 mice (e.g., 2-5 months old). Mice were placed into one of four groups: i) treatment of JAK2V617F mice with vehicle (TBS) twice weekly; ii) treatment of JAK2V617F mice with mTβRII-Fc, as described above, on a dosing schedule of 10 mg/kg twice weekly; iii) treatment of JAK2V617F mice with Tux on a dosing schedule of 60 mg/kg twice daily; and iv) treatment of JAK2V617F mice with mTβRII-Fc at 10 mg/kg twice weekly and Tux at 60 mg/kg daily. After three weeks of treatment, nix treatment alone or in combination with mTβRII-Fc significantly lowered RBC levels and reduced spleen weights compared to vehicle treated mice (see FIGS. 7A and 7B). mTβRII-Fc treatment alone had a more modest effect on RBC levels and spleen weights in the older JAK2V617F mice. Bone marrow fibrosis was also assessed after three weeks of treatment. Rux and vehicle treated mice had similar, high levels of bone marrow fibrosis, which is consistent with the observation that nix does not appear to improve bone marrow fibrosis in human patients (see FIGS. 8B and 8A, respectively). Surprisingly, mTβRII-Fc treatment alone or in combination with nix appears to reduce bone marrow fibrosis within at least as early as three weeks after starting therapy (see FIGS. 8C and 8D, respectively), suggesting that mTβRII-Fc treatment may actually reverse fibrotic scaring in patients with advanced myelofibrosis.

As demonstrated by the data, myelofibrosis is a complex disease in which patients are afflicted with many different complications including, for example, erythroid hyperplasia, splenomegaly, increased inflammatory cytokine levels, and tissue fibrosis. Rux is currently an approved therapeutic for treating myelofibrosis. While nix has been shown to reduce splenomegaly, it does not treat other complications of the disease including, for example, bone marrow fibrosis. In both the early and late stage myelofibrosis studies, Applicants have demonstrated that treatment with a TβRII-Fc fusion protein alone may be used to decrease tissue fibrosis and have other positive effects on myeloproliferative disease (e.g., reduction of splenomegaly and blood cell levels, particularly in PV and ET stages of the disease). TβRII antagonist treatment therefore has beneficial effects on treating certain complications of myelofibrosis which are not affected by nix. Accordingly, Applicants have demonstrated that a TβRII-Fc fusion protein may be used as a monotherapy, as well as a co-therapy with nix, to treat myelofibrosis as well as Janus kinase-associated disorders. Moreover, these data suggest that TβRII antagonist may have various beneficial effects in treating, preventing, or reducing the progression rate and/or severity of myeloproliferative disorders, particularly in treating, preventing, or reducing the progression rate and/or severity of one or more complications of a MF, PV, and/or ET.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A method for treating a Janus kinase-associated disorder, comprising administering to a patient in need thereof an effective amount of a soluble transforming growth factor beta type II receptor (TβRII), wherein the disorder is associated with elevated kinase activity of JAK2 as compared to healthy patients of the same age and sex, and wherein the patient is being treated with or has been treated with a Janus kinase inhibitor.

2. A method for treating a Janus kinase-associated disorder comprising administering to a patient in need thereof: i) a soluble transforming growth factor beta type II receptor (TβRII) and ii) a Janus kinase inhibitor, wherein the soluble TβRII receptor and Janus kinase inhibitor are administered in an effective amount, wherein the disorder is associated with elevated kinase activity of JAK2 as compared to healthy patients of the same age and sex.

3. The method of claim 1, wherein the soluble TβRII receptor inhibits the activity of transforming growth factor beta type I (TGFβ1) and transforming growth factor beta type 3 (TGFβ3).

4. The method of claim 1, wherein the soluble TβRII receptor is an Fc fusion protein.

5. The method of claim 4, wherein the TβRII-Fc fusion protein comprises the amino acid sequence of SEQ ID NO: 103.

6. The method of claim 1, wherein the patient has a disorder associated with a gain-of-function Janus kinase mutation.

7. The method of claim 1, wherein the patient has a disorder associated with a gain-of-function mutation in JAK2.

8. The method of claim 1, wherein the patient has a disorder associated with constitutive kinase activity of JAK2.

9. The method of claim 7, wherein the patient has a JAK2V617F-associated disorder.

10. The method of claim 1, wherein the patient has myelofibrosis.

11. The method of claim 10, wherein the patient has primary myelofibrosis.

12. The method of claim 10, wherein the patient has post-polycythemia vera myelofibrosis.

13. The method of claim 10, wherein the patient has post-essential thrombocythemia myelofibrosis.

14. The method of claim 1, wherein the patient has polycythemia vera.

15. The method of claim 1, wherein the patient has essential thrombocythemia.

16. The method of claim 1, wherein the patient is intolerant or refractory to treatment with a Janus kinase inhibitor.

17. The method of claim 1, wherein the Janus kinase inhibitor inhibits at least JAK2.

18. The method of claim 1, wherein the Janus kinase inhibitor is selected from the group consisting of: ruxolitinib, fedratinib (SAR302503), monoelotinib (CYT387), pacritinib, lestaurtinib, AZD-1480, BMS-911543, NS-018, LY2784544, SEP-701, XL019, and AT-9283.

19. The method of claim 18, wherein the Janus kinase inhibitor is ruxolitinib.

20. The method of claim 4 or 5, wherein the soluble TβRII receptor comprises one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent.

21. The method of claim 20, wherein the soluble TβRII receptor is glycosylated.

22. The method of claim 21, wherein the soluble TβRII receptor is glycosylated and has a glycosylation pattern obtainable from expression in a CHO cell.

23. The method of claim 4 or 5, wherein the soluble TβRII receptor binds to TGFβ1.

24. The method of claim 4 or 5, wherein the soluble TβRII receptor binds to TGFβ3.

25. The method of claim 4 or 5, wherein the soluble TβRII receptor binds to TGFβ1 and TGFβ3.

26. The method of claim 4 or 5, wherein the soluble TβRII receptor is isolated.

27. The method of claim 4 or 5, wherein the soluble TβRII receptor is recombinant.

28. The method of claim 4 or 5, wherein the fusion protein is a homodimer.

29. The method of claim 4, wherein the TβRII amino acid sequence consists of an amino acid sequence that is at least 95% identical to SEQ ID NO: 13; wherein the fusion polypeptide does not include a signal sequence and does not include the amino acids corresponding to amino acids 185-592 of SEQ ID NO: 6.

30. The method of claim 29, wherein the TβRII amino acid sequence consists of the amino acid sequence of SEQ ID NO: 13.

31. The method of claim 29, wherein the TβRII-Fc fusion protein comprises a heterologous amino acid sequence comprising the amino acid sequence of SEQ ID NO: 21.

32. The method of claim 31, wherein the TβRII-Fc fusion protein comprises a heterologous amino acid sequence joined to the TβRII polypeptide by a linker.

33. The method of claim 32, wherein the TβRII-Fc fusion protein binds to TGFβ1 or TGFβ3.

34. The method of claim 32, wherein the TβRII-Fc fusion protein binds to TGFβ1 and TGFβ3.

* * * * *

SEQUENCE LISTING

```
<160> NUMBER OF SEQ ID NOS: 113

<210> SEQ ID NO 1

<400> SEQUENCE: 1

000
```

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5
<211> LENGTH: 567
<212> TYPE: PRT
<213> ORGANISM: Homo sapiens

<400> SEQUENCE: 5

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
            180                 185                 190

Arg Gln Gln Lys Leu Ser Ser Thr Trp Glu Thr Gly Lys Thr Arg Lys
        195                 200                 205

Leu Met Glu Phe Ser Glu His Cys Ala Ile Ile Leu Glu Asp Asp Arg
    210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
```

```
                260                 265                 270
Thr Val Ala Val Lys Ile Phe Pro Tyr Glu Glu Tyr Ala Ser Trp Lys
            275                 280                 285

Thr Glu Lys Asp Ile Phe Ser Asp Ile Asn Leu Lys His Glu Asn Ile
290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
        355                 360                 365

Gly Arg Pro Lys Met Pro Ile Val His Arg Asp Leu Lys Ser Ser Asn
370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
            420                 425                 430

Arg Met Asn Leu Glu Asn Val Glu Ser Phe Lys Gln Thr Asp Val Tyr
        435                 440                 445

Ser Met Ala Leu Val Leu Trp Glu Met Thr Ser Arg Cys Asn Ala Val
    450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
            500                 505                 510

Val Cys Glu Thr Leu Thr Glu Cys Trp Asp His Asp Pro Glu Ala Arg
        515                 520                 525

Leu Thr Ala Gln Cys Val Ala Glu Arg Phe Ser Glu Leu Glu His Leu
    530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 6
<211> LENGTH: 592
<212> TYPE: PRT
<213> ORGANISM: Homo sapiens

<400> SEQUENCE: 6

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
            20                  25                  30

Val Glu Met Glu Ala Gln Lys Asp Glu Ile Ile Cys Pro Ser Cys Asn
        35                  40                  45

Arg Thr Ala His Pro Leu Arg His Ile Asn Asn Asp Met Ile Val Thr
    50                  55                  60
```

```
Asp Asn Asn Gly Ala Val Lys Phe Pro Gln Leu Cys Lys Phe Cys Asp
 65                  70                  75                  80

Val Arg Phe Ser Thr Cys Asp Asn Gln Lys Ser Cys Met Ser Asn Cys
                 85                  90                  95

Ser Ile Thr Ser Ile Cys Glu Lys Pro Gln Glu Val Cys Val Ala Val
            100                 105                 110

Trp Arg Lys Asn Asp Glu Asn Ile Thr Leu Glu Thr Val Cys His Asp
        115                 120                 125

Pro Lys Leu Pro Tyr His Asp Phe Ile Leu Glu Asp Ala Ala Ser Pro
    130                 135                 140

Lys Cys Ile Met Lys Glu Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
            180                 185                 190

Thr Gly Ile Ser Leu Leu Pro Pro Leu Gly Val Ala Ile Ser Val Ile
        195                 200                 205

Ile Ile Phe Tyr Cys Tyr Arg Val Asn Arg Gln Gln Lys Leu Ser Ser
    210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
            260                 265                 270

Thr Leu Val Gly Lys Gly Arg Phe Ala Glu Val Tyr Lys Ala Lys Leu
        275                 280                 285

Lys Gln Asn Thr Ser Glu Gln Phe Glu Thr Val Ala Val Lys Ile Phe
    290                 295                 300

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
            340                 345                 350

His Ala Lys Gly Asn Leu Gln Glu Tyr Leu Thr Arg His Val Ile Ser
        355                 360                 365

Trp Glu Asp Leu Arg Lys Leu Gly Ser Ser Leu Ala Arg Gly Ile Ala
    370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
                405                 410                 415

Thr Cys Cys Leu Cys Asp Phe Gly Leu Ser Leu Arg Leu Asp Pro Thr
            420                 425                 430

Leu Ser Val Asp Asp Leu Ala Asn Ser Gly Gln Val Gly Thr Ala Arg
        435                 440                 445

Tyr Met Ala Pro Glu Val Leu Glu Ser Arg Met Asn Leu Glu Asn Val
    450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
```

```
                     485                 490                 495
Pro Pro Phe Gly Ser Lys Val Arg Glu His Pro Cys Val Glu Ser Met
                500                 505                 510

Lys Asp Asn Val Leu Arg Asp Arg Gly Arg Pro Glu Ile Pro Ser Phe
                515                 520                 525

Trp Leu Asn His Gln Gly Ile Gln Met Val Cys Glu Thr Leu Thr Glu
                530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
                565                 570                 575

Cys Ser Glu Glu Lys Ile Pro Glu Asp Gly Ser Leu Asn Thr Thr Lys
                580                 585                 590

<210> SEQ ID NO 7
<211> LENGTH: 137
<212> TYPE: PRT
<213> ORGANISM: Homo sapiens

<400> SEQUENCE: 7

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
                20                  25                  30

Asp Val Arg Phe Ser Thr Cys Asp Asn Gln Lys Ser Cys Met Ser Asn
                35                  40                  45

Cys Ser Ile Thr Ser Ile Cys Glu Lys Pro Gln Glu Val Cys Val Ala
                50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
                100                 105                 110

Met Cys Ser Cys Ser Ser Asp Glu Cys Asn Asp Asn Ile Ile Phe Ser
                115                 120                 125

Glu Glu Tyr Asn Thr Ser Asn Pro Asp
    130                 135

<210> SEQ ID NO 8
<211> LENGTH: 137
<212> TYPE: PRT
<213> ORGANISM: Homo sapiens

<400> SEQUENCE: 8

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
                20                  25                  30

Asp Val Arg Phe Ser Thr Cys Asp Asn Gln Lys Ser Cys Met Ser Asn
                35                  40                  45

Cys Ser Ile Thr Ser Ile Cys Glu Lys Pro Gln Glu Val Cys Val Ala
                50                  55                  60

Val Trp Arg Lys Asn Asp Glu Asn Ile Thr Leu Glu Thr Val Cys His
65                  70                  75                  80

Asp Pro Lys Leu Pro Tyr His Lys Phe Ile Leu Glu Asp Ala Ala Ser
```

```
                     85                  90                  95

Pro Lys Cys Ile Met Lys Glu Lys Lys Pro Gly Glu Thr Phe Phe
                    100                 105                 110

Met Cys Ser Cys Ser Ser Asp Glu Cys Asn Asp Asn Ile Ile Phe Ser
                115                 120                 125

Glu Glu Tyr Asn Thr Ser Asn Pro Asp
            130                 135

<210> SEQ ID NO 9
<211> LENGTH: 131
<212> TYPE: PRT
<213> ORGANISM: Homo sapiens

<400> SEQUENCE: 9

Gln Lys Ser Val Asn Asn Asp Met Ile Val Thr Asp Asn Asn Gly Ala
1               5                   10                  15

Val Lys Phe Pro Gln Leu Cys Lys Phe Cys Asp Val Arg Phe Ser Thr
                20                  25                  30

Cys Asp Asn Gln Lys Ser Cys Met Ser Asn Cys Ser Ile Thr Ser Ile
            35                  40                  45

Cys Glu Lys Pro Gln Glu Val Cys Val Ala Val Trp Arg Lys Asn Asp
50                  55                  60

Glu Asn Ile Thr Leu Glu Thr Val Cys His Asp Pro Lys Leu Pro Tyr
65                  70                  75                  80

His Asp Phe Ile Leu Glu Asp Ala Ala Ser Pro Lys Cys Ile Met Lys
                85                  90                  95

Glu Lys Lys Lys Pro Gly Glu Thr Phe Phe Met Cys Ser Cys Ser Ser
                100                 105                 110

Asp Glu Cys Asn Asp Asn Ile Ile Phe Ser Glu Glu Tyr Asn Thr Ser
            115                 120                 125

Asn Pro Asp
    130

<210> SEQ ID NO 10
<211> LENGTH: 125
<212> TYPE: PRT
<213> ORGANISM: Homo sapiens

<400> SEQUENCE: 10

Asp Met Ile Val Thr Asp Asn Asn Gly Ala Val Lys Phe Pro Gln Leu
1               5                   10                  15

Cys Lys Phe Cys Asp Val Arg Phe Ser Thr Cys Asp Asn Gln Lys Ser
                20                  25                  30

Cys Met Ser Asn Cys Ser Ile Thr Ser Ile Cys Glu Lys Pro Gln Glu
            35                  40                  45

Val Cys Val Ala Val Trp Arg Lys Asn Asp Glu Asn Ile Thr Leu Glu
50                  55                  60

Thr Val Cys His Asp Pro Lys Leu Pro Tyr His Asp Phe Ile Leu Glu
65                  70                  75                  80

Asp Ala Ala Ser Pro Lys Cys Ile Met Lys Glu Lys Lys Lys Pro Gly
                85                  90                  95

Glu Thr Phe Phe Met Cys Ser Cys Ser Ser Asp Glu Cys Asn Asp Asn
                100                 105                 110

Ile Ile Phe Ser Glu Glu Tyr Asn Thr Ser Asn Pro Asp
            115                 120                 125
```

<210> SEQ ID NO 11
<211> LENGTH: 131
<212> TYPE: PRT
<213> ORGANISM: Homo sapiens

<400> SEQUENCE: 11

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
            115                 120                 125

Glu Glu Tyr
        130

<210> SEQ ID NO 12
<211> LENGTH: 131
<212> TYPE: PRT
<213> ORGANISM: Homo sapiens

<400> SEQUENCE: 12

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asp
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
            115                 120                 125

Glu Glu Tyr
        130

<210> SEQ ID NO 13
<211> LENGTH: 162
<212> TYPE: PRT
<213> ORGANISM: Homo sapiens

<400> SEQUENCE: 13

Thr Ile Pro Pro His Val Gln Lys Ser Asp Val Glu Met Glu Ala Gln
1               5                   10                  15

```
Lys Asp Glu Ile Ile Cys Pro Ser Cys Asn Arg Thr Ala His Pro Leu
                20                  25                  30

Arg His Ile Asn Asn Asp Met Ile Val Thr Asp Asn Asn Gly Ala Val
            35                  40                  45

Lys Phe Pro Gln Leu Cys Lys Phe Cys Asp Val Arg Phe Ser Thr Cys
 50                  55                  60

Asp Asn Gln Lys Ser Cys Met Ser Asn Cys Ser Ile Thr Ser Ile Cys
 65                  70                  75                  80

Glu Lys Pro Gln Glu Val Cys Val Ala Val Trp Arg Lys Asn Asp Glu
                 85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
            115                 120                 125

Lys Lys Lys Pro Gly Glu Thr Phe Phe Met Cys Ser Cys Ser Ser Asp
        130                 135                 140

Glu Cys Asn Asp Asn Ile Ile Phe Ser Glu Glu Tyr Asn Thr Ser Asn
145                 150                 155                 160

Pro Asp

<210> SEQ ID NO 14
<211> LENGTH: 162
<212> TYPE: PRT
<213> ORGANISM: Homo sapiens

<400> SEQUENCE: 14

Thr Ile Pro Pro His Val Gln Lys Ser Asp Val Glu Met Glu Ala Gln
 1                5                  10                  15

Lys Asp Glu Ile Ile Cys Pro Ser Cys Asn Arg Thr Ala His Pro Leu
                20                  25                  30

Arg His Ile Asn Asn Asp Met Ile Val Thr Asp Asn Asn Gly Ala Val
            35                  40                  45

Lys Phe Pro Gln Leu Cys Lys Phe Cys Asp Val Arg Phe Ser Thr Cys
 50                  55                  60

Asp Asn Gln Lys Ser Cys Met Ser Asn Cys Ser Ile Thr Ser Ile Cys
 65                  70                  75                  80

Glu Lys Pro Gln Glu Val Cys Val Ala Val Trp Arg Lys Asn Asp Glu
                 85                  90                  95

Asn Ile Thr Leu Glu Thr Val Cys His Asp Pro Lys Leu Pro Tyr His
            100                 105                 110

Lys Phe Ile Leu Glu Asp Ala Ala Ser Pro Lys Cys Ile Met Lys Glu
            115                 120                 125

Lys Lys Lys Pro Gly Glu Thr Phe Phe Met Cys Ser Cys Ser Ser Asp
        130                 135                 140

Glu Cys Asn Asp Asn Ile Ile Phe Ser Glu Glu Tyr Asn Thr Ser Asn
145                 150                 155                 160

Pro Asp

<210> SEQ ID NO 15
<211> LENGTH: 156
<212> TYPE: PRT
<213> ORGANISM: Homo sapiens

<400> SEQUENCE: 15

Gln Lys Ser Asp Val Glu Met Glu Ala Gln Lys Asp Glu Ile Ile Cys
```

```
  1               5                  10                 15
Pro Ser Cys Asn Arg Thr Ala His Pro Leu Arg His Ile Asn Asn Asp
                20                 25                 30

Met Ile Val Thr Asp Asn Asn Gly Ala Val Lys Phe Pro Gln Leu Cys
                35                 40                 45

Lys Phe Cys Asp Val Arg Phe Ser Thr Cys Asp Asn Gln Lys Ser Cys
                50                 55                 60

Met Ser Asn Cys Ser Ile Thr Ser Ile Cys Glu Lys Pro Gln Glu Val
 65                 70                 75                 80

Cys Val Ala Val Trp Arg Lys Asn Asp Glu Asn Ile Thr Leu Glu Thr
                    85                 90                 95

Val Cys His Asp Pro Lys Leu Pro Tyr His Asp Phe Ile Leu Glu Asp
                  100                105                110

Ala Ala Ser Pro Lys Cys Ile Met Lys Glu Lys Lys Pro Gly Glu
                  115                120                125

Thr Phe Phe Met Cys Ser Cys Ser Ser Asp Glu Cys Asn Asp Asn Ile
                  130                135                140

Ile Phe Ser Glu Glu Tyr Asn Thr Ser Asn Pro Asp
145                 150                155

<210> SEQ ID NO 16
<211> LENGTH: 156
<212> TYPE: PRT
<213> ORGANISM: Homo sapiens

<400> SEQUENCE: 16

Thr Ile Pro Pro His Val Gln Lys Ser Asp Val Glu Met Glu Ala Gln
 1               5                  10                 15

Lys Asp Glu Ile Ile Cys Pro Ser Cys Asn Arg Thr Ala His Pro Leu
                20                 25                 30

Arg His Ile Asn Asn Asp Met Ile Val Thr Asp Asn Asn Gly Ala Val
                35                 40                 45

Lys Phe Pro Gln Leu Cys Lys Phe Cys Asp Val Arg Phe Ser Thr Cys
                50                 55                 60

Asp Asn Gln Lys Ser Cys Met Ser Asn Cys Ser Ile Thr Ser Ile Cys
 65                 70                 75                 80

Glu Lys Pro Gln Glu Val Cys Val Ala Val Trp Arg Lys Asn Asp Glu
                    85                 90                 95

Asn Ile Thr Leu Glu Thr Val Cys His Asp Pro Lys Leu Pro Tyr His
                  100                105                110

Asp Phe Ile Leu Glu Asp Ala Ala Ser Pro Lys Cys Ile Met Lys Glu
                  115                120                125

Lys Lys Pro Gly Glu Thr Phe Phe Met Cys Ser Cys Ser Ser Asp
130                 135                140

Glu Cys Asn Asp Asn Ile Ile Phe Ser Glu Glu Tyr
145                 150                155

<210> SEQ ID NO 17
<211> LENGTH: 156
<212> TYPE: PRT
<213> ORGANISM: Homo sapiens

<400> SEQUENCE: 17

Thr Ile Pro Pro His Val Gln Lys Ser Asp Val Glu Met Glu Ala Gln
 1               5                  10                 15

Lys Asp Glu Ile Ile Cys Pro Ser Cys Asn Arg Thr Ala His Pro Leu
```

```
                20                  25                  30
Arg His Ile Asn Asn Asp Met Ile Val Thr Asp Asn Asn Gly Ala Val
            35                  40                  45
Lys Phe Pro Gln Leu Cys Lys Phe Cys Asp Val Arg Phe Ser Thr Cys
        50                  55                  60
Asp Asn Gln Lys Ser Cys Met Ser Asp Cys Ser Ile Thr Ser Ile Cys
65                  70                  75                  80
Glu Lys Pro Gln Glu Val Cys Val Ala Val Trp Arg Lys Asn Asp Glu
                85                  90                  95
Asn Ile Thr Leu Glu Thr Val Cys His Asp Pro Lys Leu Pro Tyr His
            100                 105                 110
Asp Phe Ile Leu Glu Asp Ala Ala Ser Pro Lys Cys Ile Met Lys Glu
        115                 120                 125
Lys Lys Lys Pro Gly Glu Thr Phe Phe Met Cys Ser Cys Ser Ser Asp
        130                 135                 140
Glu Cys Asn Asp Asn Ile Ile Phe Ser Glu Glu Tyr
145                 150                 155
```

<210> SEQ ID NO 18
<211> LENGTH: 36
<212> TYPE: PRT
<213> ORGANISM: Homo sapiens

<400> SEQUENCE: 18

```
Gly Arg Cys Lys Ile Arg His Ile Gly Ser Asn Asn Arg Leu Gln Arg
1               5                   10                  15
Ser Thr Cys Gln Asn Thr Gly Trp Glu Ser Ala His Val Met Lys Thr
                20                  25                  30
Pro Gly Phe Arg
            35
```

<210> SEQ ID NO 19
<211> LENGTH: 223
<212> TYPE: PRT
<213> ORGANISM: Homo sapiens

<400> SEQUENCE: 19

```
Val Glu Cys Pro Pro Cys Pro Ala Pro Pro Val Ala Gly Pro Ser Val
1               5                   10                  15
Phe Leu Phe Pro Pro Lys Pro Lys Asp Thr Leu Met Ile Ser Arg Thr
                20                  25                  30
Pro Glu Val Thr Cys Val Val Val Asp Val Ser His Glu Asp Pro Glu
            35                  40                  45
Val Gln Phe Asn Trp Tyr Val Asp Gly Val Glu Val His Asn Ala Lys
        50                  55                  60
Thr Lys Pro Arg Glu Glu Gln Phe Asn Ser Thr Phe Arg Val Val Ser
65                  70                  75                  80
Val Leu Thr Val Val His Gln Asp Trp Leu Asn Gly Lys Glu Tyr Lys
                85                  90                  95
Cys Lys Val Ser Asn Lys Gly Leu Pro Ala Pro Ile Glu Lys Thr Ile
            100                 105                 110
Ser Lys Thr Lys Gly Gln Pro Arg Glu Pro Gln Val Tyr Thr Leu Pro
        115                 120                 125
Pro Ser Arg Glu Glu Met Thr Lys Asn Gln Val Ser Leu Thr Cys Leu
        130                 135                 140
Val Lys Gly Phe Tyr Pro Ser Asp Ile Ala Val Glu Trp Glu Ser Asn
```

```
145                 150                 155                 160
Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
                180                 185                 190

Trp Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
        210                 215                 220
```

<210> SEQ ID NO 20
<211> LENGTH: 233
<212> TYPE: PRT
<213> ORGANISM: Homo sapiens

<400> SEQUENCE: 20

```
Gly Gly Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
                20                  25                  30

Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Glu Glu Met
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230
```

<210> SEQ ID NO 21
<211> LENGTH: 225
<212> TYPE: PRT
<213> ORGANISM: Homo sapiens

<400> SEQUENCE: 21

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
```

```
                  20                  25                  30
Arg Thr Pro Glu Val Thr Cys Val Val Asp Val Ser His Glu Asp
            35                  40                  45
Pro Glu Val Lys Phe Asn Trp Tyr Val Asp Gly Val Glu Val His Asn
        50                  55                  60
Ala Lys Thr Lys Pro Arg Glu Glu Gln Tyr Asn Ser Thr Tyr Arg Val
 65                  70                  75                  80
Val Ser Val Leu Thr Val Leu His Gln Asp Trp Leu Asn Gly Lys Glu
                85                  90                  95
Tyr Lys Cys Lys Val Ser Asn Lys Ala Leu Pro Ala Pro Ile Glu Lys
            100                 105                 110
Thr Ile Ser Lys Ala Lys Gly Gln Pro Arg Glu Pro Gln Val Tyr Thr
        115                 120                 125
Leu Pro Pro Ser Arg Glu Glu Met Thr Lys Asn Gln Val Ser Leu Thr
        130                 135                 140
Cys Leu Val Lys Gly Phe Tyr Pro Ser Asp Ile Ala Val Glu Trp Glu
145                 150                 155                 160
Ser Asn Gly Gln Pro Glu Asn Asn Tyr Lys Thr Thr Pro Pro Val Leu
                165                 170                 175
Asp Ser Asp Gly Ser Phe Phe Leu Tyr Ser Lys Leu Thr Val Asp Lys
            180                 185                 190
Ser Arg Trp Gln Gln Gly Asn Val Phe Ser Cys Ser Val Met His Glu
        195                 200                 205
Ala Leu His Asn His Tyr Thr Gln Lys Ser Leu Ser Leu Ser Pro Gly
        210                 215                 220
Lys
225

<210> SEQ ID NO 22
<211> LENGTH: 22
<212> TYPE: PRT
<213> ORGANISM: Homo sapiens

<400> SEQUENCE: 22

Met Gly Arg Gly Leu Leu Arg Gly Leu Trp Pro Leu His Ile Val Leu
 1               5                  10                  15
Trp Thr Arg Ile Ala Ser
            20

<210> SEQ ID NO 23
<211> LENGTH: 22
<212> TYPE: PRT
<213> ORGANISM: Homo sapiens

<400> SEQUENCE: 23

Met Asp Ala Met Lys Arg Gly Leu Cys Cys Val Leu Leu Leu Cys Gly
 1               5                  10                  15
Ala Val Phe Val Ser Pro
            20

<210> SEQ ID NO 24
<211> LENGTH: 21
<212> TYPE: PRT
<213> ORGANISM: Apis mellifera

<400> SEQUENCE: 24

Met Lys Phe Leu Val Asn Val Ala Leu Val Phe Met Val Val Tyr Ile
 1               5                  10                  15
```

Ser Tyr Ile Tyr Ala
            20

<210> SEQ ID NO 25
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Asp Ala Met Lys Arg Gly Leu Cys Cys Val Leu Leu Cys Gly
1               5                   10                  15

Ala Val Phe Val Ser Pro Gly Ala Thr Ile Pro His Val Gln Lys
                20                  25                  30

Ser Val Asn Asn Asp Met Ile Val Thr Asp Asn Asn Gly Ala Val Lys
            35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Lys
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
    130                 135                 140

Cys Asn Asp Asn Ile Ile Phe Ser Glu Glu Tyr Asn Thr Ser Asn Pro
145                 150                 155                 160

Asp Thr Gly Gly Gly Val Glu Cys Pro Pro Cys Pro Ala Pro Pro Val
                165                 170                 175

Ala Gly Pro Ser Val Phe Leu Phe Pro Pro Lys Pro Lys Asp Thr Leu
            180                 185                 190

Met Ile Ser Arg Thr Pro Glu Val Thr Cys Val Val Val Asp Val Ser
        195                 200                 205

His Glu Asp Pro Glu Val Gln Phe Asn Trp Tyr Val Asp Gly Val Glu
    210                 215                 220

Val His Asn Ala Lys Thr Lys Pro Arg Glu Glu Gln Phe Asn Ser Thr
225                 230                 235                 240

Phe Arg Val Val Ser Val Leu Thr Val Val His Gln Asp Trp Leu Asn
                245                 250                 255

Gly Lys Glu Tyr Lys Cys Lys Val Ser Asn Lys Gly Leu Pro Ala Pro
            260                 265                 270

Ile Glu Lys Thr Ile Ser Lys Thr Lys Gly Gln Pro Arg Glu Pro Gln
        275                 280                 285

Val Tyr Thr Leu Pro Pro Ser Arg Glu Glu Met Thr Lys Asn Gln Val
    290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
                325                 330                 335

Pro Met Leu Asp Ser Asp Gly Ser Phe Phe Leu Tyr Ser Lys Leu Thr

```
            340                 345                 350
Val Asp Lys Ser Arg Trp Gln Gln Gly Asn Val Phe Ser Cys Ser Val
            355                 360                 365

Met His Glu Ala Leu His Asn His Tyr Thr Gln Lys Ser Leu Ser Leu
    370                 375                 380

Ser Pro Gly Lys
385
```

```
<210> SEQ ID NO 26
<211> LENGTH: 1164
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
atggatgcaa tgaagagagg gctctgctgt gtgctgctgc tgtgtggagc agtcttcgtt      60
tcgcccggcg ccacgatccc accgcacgtt cagaagtcgg ttaataacga catgatagtc     120
actgacaaca acggtgcagt caagtttcca caactgtgta aattttgtga tgtgagattt     180
tccacctgtg acaaccagaa atcctgcatg agcaactgca gcatcacctc catctgtgag     240
aagccacagg aagtctgtgt ggctgtatgg agaaagaatg acgagaacat aacactagag     300
acagtttgcc atgaccccaa gctcccctac cataagttta ttctggaaga tgctgcttct     360
ccaaagtgca ttatgaagga aaaaaaaaag cctggtgaga ctttcttcat gtgttcctgt     420
agctctgatg agtgcaatga caacatcatc ttctcagaag aatataacac cagcaatcct     480
gacaccggtg gtggagtcga gtgcccaccg tgcccagcac acctgtggc aggaccgtca     540 gtcttcctct ccccccaaa acccaaggac accctcatga tctcccggac ccctgaggtc     600
acgtgcgtgg tggtggacgt gagccacgaa gaccccgagg tccagttcaa ctggtacgtg     660
gacggcgtgg aggtgcataa tgccaagaca aagccacggg aggagcagtt caacagcacg     720
ttccgtgtgg tcagcgtcct caccgtcgtg caccaggact ggctgaacgg caaggagtac     780
aagtgcaagg tctccaacaa aggcctccca gcccccatcg agaaaaccat ctccaaaacc     840
aaagggcagc cccgagaacc acaggtgtac accctgcccc catcccggga ggagatgacc     900
aagaaccagg tcagcctgac ctgcctggtc aaaggcttct accccagcga catcgccgtg     960
gagtgggaga gcaatgggca gccggagaac aactacaaga ccacacctcc catgctggac    1020
tccgacggct ccttcttcct ctacagcaag ctcaccgtgg acaagagcag gtggcagcag    1080
gggaacgtct tctcatgctc cgtgatgcat gaggctctgc acaaccacta cacgcagaag    1140
agcctctccc tgtctccggg taaa                                            1164
```

```
<210> SEQ ID NO 27
<211> LENGTH: 390
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30
```

```
Ser Val Asn Asn Asp Met Ile Val Thr Asp Asn Asn Gly Ala Val Lys
         35                  40                  45

Phe Pro Gln Leu Cys Lys Phe Cys Asp Val Arg Phe Ser Thr Cys Asp
 50                  55                  60

Asn Gln Lys Ser Cys Met Ser Asn Cys Ser Ile Thr Ser Ile Cys Glu
 65                  70                  75                  80

Lys Pro Gln Glu Val Cys Val Ala Val Trp Arg Lys Asn Asp Glu Asn
                 85                  90                  95

Ile Thr Leu Glu Thr Val Cys His Asp Pro Lys Leu Pro Tyr His Lys
             100                 105                 110

Phe Ile Leu Glu Asp Ala Ala Ser Pro Lys Cys Ile Met Lys Glu Lys
         115                 120                 125

Lys Lys Pro Gly Glu Thr Phe Phe Met Cys Ser Cys Ser Ser Asp Glu
130                 135                 140

Cys Asn Asp Asn Ile Ile Phe Ser Glu Glu Tyr Asn Thr Ser Asn Pro
145                 150                 155                 160

Asp Thr Gly Gly Gly Thr His Thr Cys Pro Pro Cys Pro Ala Pro Glu
                165                 170                 175

Leu Leu Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
        195                 200                 205

Val Ser His Glu Asp Pro Glu Val Lys Phe Asn Trp Tyr Val Asp Gly
    210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
            260                 265                 270

Ala Pro Ile Glu Lys Thr Ile Ser Lys Ala Lys Gly Gln Pro Arg Glu
        275                 280                 285

Pro Gln Val Tyr Thr Leu Pro Pro Ser Arg Glu Glu Met Thr Lys Asn
    290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Asp Ser Asp Gly Ser Phe Phe Leu Tyr Ser Lys
            340                 345                 350

Leu Thr Val Asp Lys Ser Arg Trp Gln Gln Gly Asn Val Phe Ser Cys
        355                 360                 365

Ser Val Met His Glu Ala Leu His Asn His Tyr Thr Gln Lys Ser Leu
370                 375                 380

Ser Leu Ser Pro Gly Lys
385                 390

<210> SEQ ID NO 28
<211> LENGTH: 1170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
```

```
atggatgcaa tgaagagagg gctctgctgt gtgctgctgc tgtgtggagc agtcttcgtt      60
tcgcccggcg ccacgatccc accgcacgtt cagaagtcgg ttaataacga catgatagtc     120
actgacaaca acggtgcagt caagtttcca caactgtgta aattttgtga tgtgagattt     180
tccacctgtg acaaccagaa atcctgcatg agcaactgca gcatcacctc catctgtgag     240
aagccacagg aagtctgtgt ggctgtatgg agaaagaatg acgagaacat aacactagag     300
acagtttgcc atgaccccaa gctcccctac cataagttta ttctggaaga tgctgcttct     360
ccaaagtgca ttatgaagga aaaaaaaaag cctggtgaga ctttcttcat gtgttcctgt     420
agctctgatg agtgcaatga caacatcatc ttctcagaag aatataacac cagcaatcct     480
gacaccggtg gtggaactca cacatgccca ccgtgcccag cacctgaact cctgggggga     540
ccgtcagtct tcctcttccc cccaaaaccc aaggacaccc tcatgatctc ccggaccccct    600
gaggtcacat gcgtggtggt ggacgtgagc cacgaagacc ctgaggtcaa gttcaactgg     660
tacgtggacg gcgtggaggt gcataatgcc aagacaaagc cgcgggagga gcagtacaac     720
agcacgtacc gtgtggtcag cgtcctcacc gtcctgcacc aggactggct gaatggcaag     780
gagtacaagt gcaaggtctc caacaaagcc ctcccagccc ccatcgagaa aaccatctcc     840
aaagccaaag ggcagccccg agaaccacag gtgtacaccc tgcccccatc ccgggaggag     900
atgaccaaga accaggtcag cctgacctgc ctggtcaaag cttctatccc agcgacatc     960
gccgtggagt gggagagcaa tgggcagccg gagaacaact acaagaccac gcctcccgtg    1020
ctggactccg acggctcctt cttcctctat agcaagctca ccgtggacaa gagcaggtgg    1080
cagcagggga acgtcttctc atgctccgtg atgcatgagg ctctgcacaa ccactacacg    1140
cagaagagcc tctccctgtc cccgggtaaa                                     1170
```

<210> SEQ ID NO 29
<211> LENGTH: 382
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Met Asp Ala Met Lys Arg Gly Leu Cys Cys Val Leu Leu Cys Gly
1               5                   10                  15

Ala Val Phe Val Ser Pro Gly Ala Gln Lys Ser Val Asn Asn Asp Met
                20                  25                  30

Ile Val Thr Asp Asn Asn Gly Ala Val Lys Phe Pro Gln Leu Cys Lys
            35                  40                  45

Phe Cys Asp Val Arg Phe Ser Thr Cys Asp Asn Gln Lys Ser Cys Met
        50                  55                  60

Ser Asn Cys Ser Ile Thr Ser Ile Cys Glu Lys Pro Gln Glu Val Cys
65                  70                  75                  80

Val Ala Val Trp Arg Lys Asn Asp Glu Asn Ile Thr Leu Glu Thr Val
                85                  90                  95

Cys His Asp Pro Lys Leu Pro Tyr His Asp Phe Ile Leu Glu Asp Ala
            100                 105                 110

Ala Ser Pro Lys Cys Ile Met Lys Glu Lys Lys Pro Gly Glu Thr
        115                 120                 125

Phe Phe Met Cys Ser Cys Ser Asp Glu Cys Asn Asp Asn Ile Ile
    130                 135                 140
```

Phe Ser Glu Glu Tyr Asn Thr Ser Asn Pro Asp Thr Gly Gly Gly Val
145                 150                 155                 160

Glu Cys Pro Pro Cys Pro Ala Pro Pro Val Ala Gly Pro Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser His Glu Asp Pro Glu Val
        195                 200                 205

Gln Phe Asn Trp Tyr Val Asp Gly Val Glu Val His Asn Ala Lys Thr
    210                 215                 220

Lys Pro Arg Glu Glu Gln Phe Asn Ser Thr Phe Arg Val Val Ser Val
225                 230                 235                 240

Leu Thr Val Val His Gln Asp Trp Leu Asn Gly Lys Glu Tyr Lys Cys
                245                 250                 255

Lys Val Ser Asn Lys Gly Leu Pro Ala Pro Ile Glu Lys Thr Ile Ser
                260                 265                 270

Lys Thr Lys Gly Gln Pro Arg Glu Pro Gln Val Tyr Thr Leu Pro Pro
            275                 280                 285

Ser Arg Glu Glu Met Thr Lys Asn Gln Val Ser Leu Thr Cys Leu Val
290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Met Leu Asp Ser Asp
                325                 330                 335

Gly Ser Phe Phe Leu Tyr Ser Lys Leu Thr Val Asp Lys Ser Arg Trp
                340                 345                 350

Gln Gln Gly Asn Val Phe Ser Cys Ser Val Met His Glu Ala Leu His
            355                 360                 365

Asn His Tyr Thr Gln Lys Ser Leu Ser Leu Ser Pro Gly Lys
            370                 375                 380

<210> SEQ ID NO 30
<211> LENGTH: 1146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
atggatgcaa tgaagagagg gctctgctgt gtgctgctgc tgtgtggagc agtcttcgtt      60
tcgcccggcg cccagaagtc ggttaataac gacatgatag tcactgacaa caacggtgca     120
gtcaagtttc acaactgtg taaattttgt gatgtgagat tttccacctg tgacaaccag     180
aaatcctgca tgagcaactg cagcatcacc tccatctgtg agaagccaca ggaagtctgt     240
gtggctgtat ggagaaagaa tgacgagaac ataacactag agacagtttg ccatgacccc     300 aagctccccct accatgactt tattctggaa gatgctgctt ctccaaagtg cattatgaag     360
gaaaaaaaaa agcctggtga cttcttc atgtgttcct gtagctctga tgagtgcaat     420
gacaacatca tcttctcaga agaatataac accagcaatc ctgacaccgg tggtggagtc     480
gagtgcccac cgtgcccagc accacctgtg gcaggaccgt cagtcttcct cttccccca     540 aaacccaagg acaccctcat gatctcccgg acccctgagg tcacgtgcgt ggtggtggac     600
gtgagccacg agaccccga ggtccagttc aactggtacg tggacggcgt ggaggtgcat     660
aatgccaaga caaagccacg ggaggagcag ttcaacagca cgttccgtgt ggtcagcgtc     720

-continued

```
ctcaccgtcg tgcaccagga ctggctgaac ggcaaggagt acaagtgcaa ggtctccaac    780
aaaggcctcc cagcccccat cgagaaaacc atctccaaaa ccaaagggca gccccgagaa    840
ccacaggtgt acaccctgcc cccatcccgg gaggagatga ccaagaacca ggtcagcctg    900
acctgcctgg tcaaaggctt ctaccccagc gacatcgccg tggagtggga gagcaatggg    960
cagccggaga caactacaa gaccacacct cccatgctgg actccgacgg ctccttcttc     1020
ctctacagca agctcaccgt ggacaagagc aggtggcagc aggggaacgt cttctcatgc    1080
tccgtgatgc atgaggctct gcacaaccac tacacgcaga gagcctctc cctgtctccg     1140 ggtaaa                                                               1146
```

<210> SEQ ID NO 31
<211> LENGTH: 384
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

```
Met Asp Ala Met Lys Arg Gly Leu Cys Cys Val Leu Leu Leu Cys Gly
1               5                   10                  15

Ala Val Phe Val Ser Pro Gly Ala Gln Lys Ser Val Asn Asn Asp Met
            20                  25                  30

Ile Val Thr Asp Asn Asn Gly Ala Val Lys Phe Pro Gln Leu Cys Lys
        35                  40                  45

Phe Cys Asp Val Arg Phe Ser Thr Cys Asp Asn Gln Lys Ser Cys Met
    50                  55                  60

Ser Asn Cys Ser Ile Thr Ser Ile Cys Glu Lys Pro Gln Glu Val Cys
65                  70                  75                  80

Val Ala Val Trp Arg Lys Asn Asp Glu Asn Ile Thr Leu Glu Thr Val
                85                  90                  95

Cys His Asp Pro Lys Leu Pro Tyr His Asp Phe Ile Leu Glu Asp Ala
            100                 105                 110

Ala Ser Pro Lys Cys Ile Met Lys Glu Lys Lys Pro Gly Glu Thr
        115                 120                 125

Phe Phe Met Cys Ser Cys Ser Ser Asp Glu Cys Asn Asp Asn Ile Ile
    130                 135                 140

Phe Ser Glu Glu Tyr Asn Thr Ser Asn Pro Asp Thr Gly Gly Gly Thr
145                 150                 155                 160

His Thr Cys Pro Pro Cys Pro Ala Pro Glu Leu Leu Gly Gly Pro Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Val Asp Val Ser His Glu Asp Pro
        195                 200                 205

Glu Val Lys Phe Asn Trp Tyr Val Asp Gly Val Glu Val His Asn Ala
    210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
            260                 265                 270
```

```
Ile Ser Lys Ala Lys Gly Gln Pro Arg Glu Pro Gln Val Tyr Thr Leu
        275                 280                 285

Pro Pro Ser Arg Glu Glu Met Thr Lys Asn Gln Val Ser Leu Thr Cys
290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
                340                 345                 350

Arg Trp Gln Gln Gly Asn Val Phe Ser Cys Ser Val Met His Glu Ala
        355                 360                 365

Leu His Asn His Tyr Thr Gln Lys Ser Leu Ser Leu Ser Pro Gly Lys
        370                 375                 380

<210> SEQ ID NO 32
<211> LENGTH: 1152
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
atggatgcaa tgaagagagg gctctgctgt gtgctgctgc tgtgtggagc agtcttcgtt        60
tcgcccggcg cccagaagtc ggttaataac gacatgatag tcactgacaa caacggtgca       120
gtcaagtttc cacaactgtg taaattttgt gatgtgagat tttccacctg tgacaaccag       180
aaatcctgca tgagcaactg cagcatcacc tccatctgtg agaagccaca ggaagtctgt       240
gtggctgtat ggagaaagaa tgacgagaac ataacactag acagtttgt ccatgacccc       300 aagctcccct accatgactt tattctggaa gatgctgctt ctccaaagtg cattatgaag       360
gaaaaaaaaa agcctggtga ctttcttc atgtgttcct gtagctctga tgagtgcaat        420
gacaacatca tcttctcaga agaatataac accagcaatc ctgacaccgg tggtggaact       480
cacacatgcc accgtgccc agcacctgaa ctcctggggg gaccgtcagt cttcctcttc        540
cccccaaaac ccaaggacac cctcatgatc tcccggaccc ctgaggtcac atgcgtggtg       600
gtggacgtga gccacgaaga ccctgaggtc aagttcaact ggtacgtgga cggcgtggag       660
gtgcataatg ccaagacaaa gccgcgggag gagcagtaca acagcacgta ccgtgtggtc       720
agcgtcctca ccgtcctgca ccaggactgg ctgaatggca aggagtacaa gtgcaaggtc       780
tccaacaaag ccctcccagc ccccatcgag aaaaccatct ccaaagccaa agggcagccc       840
cgagaaccac aggtgtacac cctgccccca tcccgggagg agatgaccaa gaaccaggtc       900
agcctgacct gcctggtcaa aggcttctat cccagcgaca tcgccgtgga gtgggagagc       960
aatgggcagc cggagaacaa ctacaagacc acgcctcccg tgctggactc cgacggctcc      1020
ttcttcctct atagcaagct caccgtggac aagagcaggt ggcagcaggg gaacgtcttc      1080
tcatgctccg tgatgcatga ggctctgcac aaccactaca cgcagaagag cctctccctg      1140
tccccgggta aa                                                          1152

<210> SEQ ID NO 33
<211> LENGTH: 376
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 33

```
Met Asp Ala Met Lys Arg Gly Leu Cys Cys Val Leu Leu Leu Cys Gly
1               5                   10                  15
Ala Val Phe Val Ser Pro Gly Ala Asp Met Ile Val Thr Asp Asn Asn
            20                  25                  30
Gly Ala Val Lys Phe Pro Gln Leu Cys Lys Phe Cys Asp Val Arg Phe
        35                  40                  45
Ser Thr Cys Asp Asn Gln Lys Ser Cys Met Ser Asn Cys Ser Ile Thr
    50                  55                  60
Ser Ile Cys Glu Lys Pro Gln Glu Val Cys Val Ala Val Trp Arg Lys
65                  70                  75                  80
Asn Asp Glu Asn Ile Thr Leu Glu Thr Val Cys His Asp Pro Lys Leu
                85                  90                  95
Pro Tyr His Asp Phe Ile Leu Glu Asp Ala Ala Ser Pro Lys Cys Ile
            100                 105                 110
Met Lys Glu Lys Lys Pro Gly Glu Thr Phe Phe Met Cys Ser Cys
        115                 120                 125
Ser Ser Asp Glu Cys Asn Asp Asn Ile Ile Phe Ser Glu Glu Tyr Asn
    130                 135                 140
Thr Ser Asn Pro Asp Thr Gly Gly Val Glu Cys Pro Pro Cys Pro
145                 150                 155                 160
Ala Pro Pro Val Ala Gly Pro Ser Val Phe Leu Phe Pro Pro Lys Pro
                165                 170                 175
Lys Asp Thr Leu Met Ile Ser Arg Thr Pro Glu Val Thr Cys Val Val
            180                 185                 190
Val Asp Val Ser His Glu Asp Pro Glu Val Gln Phe Asn Trp Tyr Val
        195                 200                 205
Asp Gly Val Glu Val His Asn Ala Lys Thr Lys Pro Arg Glu Glu Gln
    210                 215                 220
Phe Asn Ser Thr Phe Arg Val Val Ser Val Leu Thr Val Val His Gln
225                 230                 235                 240
Asp Trp Leu Asn Gly Lys Glu Tyr Lys Cys Lys Val Ser Asn Lys Gly
                245                 250                 255
Leu Pro Ala Pro Ile Glu Lys Thr Ile Ser Lys Thr Lys Gly Gln Pro
            260                 265                 270
Arg Glu Pro Gln Val Tyr Thr Leu Pro Pro Ser Arg Glu Glu Met Thr
        275                 280                 285
Lys Asn Gln Val Ser Leu Thr Cys Leu Val Lys Gly Phe Tyr Pro Ser
    290                 295                 300
Asp Ile Ala Val Glu Trp Glu Ser Asn Gly Gln Pro Glu Asn Asn Tyr
305                 310                 315                 320
Lys Thr Thr Pro Pro Met Leu Asp Ser Asp Gly Ser Phe Phe Leu Tyr
                325                 330                 335
Ser Lys Leu Thr Val Asp Lys Ser Arg Trp Gln Gln Gly Asn Val Phe
            340                 345                 350
Ser Cys Ser Val Met His Glu Ala Leu His Asn His Tyr Thr Gln Lys
        355                 360                 365
Ser Leu Ser Leu Ser Pro Gly Lys
    370                 375
```

<210> SEQ ID NO 34
<211> LENGTH: 1128

<210> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
atggatgcaa tgaagagagg gctctgctgt gtgctgctgc tgtgtggagc agtcttcgtt      60
tcgcccggcg ccgacatgat agtcactgac aacaacggtg cagtcaagtt tccacaactg     120
tgtaaatttt gtgatgtgag attttccacc tgtgacaacc agaaatcctg catgagcaac     180
tgcagcatca cctccatctg tgagaagcca caggaagtct gtgtggctgt atggagaaag     240
aatgacgaga acataacact agagacagtt tgccatgacc ccaagctccc ctaccatgac     300
tttattctgg aagatgctgc ttctccaaag tgcattatga aggaaaaaaa aaagcctggt     360
gagactttct tcatgtgttc ctgtagctct gatgagtgca atgacaacat catcttctca     420
gaagaatata acaccagcaa tcctgacacc ggtggtggag tcgagtgccc accgtgccca     480
gcaccacctg tggcaggacc gtcagtcttc ctcttccccc caaaacccaa ggacaccctc     540
atgatctccc ggacccctga ggtcacgtgc gtggtggtgg acgtgagcca cgaagacccc     600
gaggtccagt tcaactggta cgtggacggc gtggaggtgc ataatgccaa gacaaagcca     660
cgggaggagc agttcaacag cacgttccgt gtggtcagcg tcctcaccgt cgtgcaccag     720
gactggctga acggcaagga gtacaagtgc aaggtctcca acaaaggcct cccagccccc     780
atcgagaaaa ccatctccaa aaccaaaggg cagccccgag aaccacaggt gtacaccctg     840
cccccatccc gggaggagat gaccaagaac caggtcagcc tgacctgcct ggtcaaaggc     900
ttctaccccc gcgacatcgc cgtggagtgg gagagcaatg ggcagccgga gaacaactac     960
aagaccacac ctcccatgct ggactccgac ggctccttct cctctacag caagctcacc    1020
gtggacaaga gcaggtggca gcaggggaac gtcttctcat gctccgtgat gcatgaggct    1080
ctgcacaacc actacacgca gaagagcctc tccctgtctc cgggtaaa              1128
```

<210> SEQ ID NO 35
<211> LENGTH: 378
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Met Asp Ala Met Lys Arg Gly Leu Cys Cys Val Leu Leu Cys Gly
1               5                   10                  15

Ala Val Phe Val Ser Pro Gly Ala Asp Met Ile Val Thr Asp Asn Asn
            20                  25                  30

Gly Ala Val Lys Phe Pro Gln Leu Cys Lys Phe Cys Asp Val Arg Phe
        35                  40                  45

Ser Thr Cys Asp Asn Gln Lys Ser Cys Met Ser Asn Cys Ser Ile Thr
    50                  55                  60

Ser Ile Cys Glu Lys Pro Gln Glu Val Cys Val Ala Val Trp Arg Lys
65                  70                  75                  80

Asn Asp Glu Asn Ile Thr Leu Glu Thr Val Cys His Asp Pro Lys Leu
                85                  90                  95

Pro Tyr His Asp Phe Ile Leu Glu Asp Ala Ala Ser Pro Lys Cys Ile
            100                 105                 110

Met Lys Glu Lys Lys Lys Pro Gly Glu Thr Phe Phe Met Cys Ser Cys
```

|  |  |  |  |  |  |  |  |  |  |  |  |  |
|---|---|---|---|---|---|---|---|---|---|---|---|---|
|  |  | 115 |  |  |  | 120 |  |  |  | 125 |  |  |

Ser Ser Asp Glu Cys Asn Asp Asn Ile Ile Phe Ser Glu Glu Tyr Asn
    130                 135                 140

Thr Ser Asn Pro Asp Thr Gly Gly Thr His Thr Cys Pro Pro Cys
145                 150                 155                 160

Pro Ala Pro Glu Leu Leu Gly Gly Pro Ser Val Phe Leu Phe Pro Pro
                165                 170                 175

Lys Pro Lys Asp Thr Leu Met Ile Ser Arg Thr Pro Glu Val Thr Cys
            180                 185                 190

Val Val Val Asp Val Ser His Glu Asp Pro Glu Val Lys Phe Asn Trp
        195                 200                 205

Tyr Val Asp Gly Val Glu Val His Asn Ala Lys Thr Lys Pro Arg Glu
    210                 215                 220

Glu Gln Tyr Asn Ser Thr Tyr Arg Val Val Ser Val Leu Thr Val Leu
225                 230                 235                 240

His Gln Asp Trp Leu Asn Gly Lys Glu Tyr Lys Cys Lys Val Ser Asn
                245                 250                 255

Lys Ala Leu Pro Ala Pro Ile Glu Lys Thr Ile Ser Lys Ala Lys Gly
            260                 265                 270

Gln Pro Arg Glu Pro Gln Val Tyr Thr Leu Pro Pro Ser Arg Glu Glu
        275                 280                 285

Met Thr Lys Asn Gln Val Ser Leu Thr Cys Leu Val Lys Gly Phe Tyr
    290                 295                 300

Pro Ser Asp Ile Ala Val Glu Trp Glu Ser Asn Gly Gln Pro Glu Asn
305                 310                 315                 320

Asn Tyr Lys Thr Thr Pro Pro Val Leu Asp Ser Asp Gly Ser Phe Phe
                325                 330                 335

Leu Tyr Ser Lys Leu Thr Val Asp Lys Ser Arg Trp Gln Gln Gly Asn
            340                 345                 350

Val Phe Ser Cys Ser Val Met His Glu Ala Leu His Asn His Tyr Thr
        355                 360                 365

Gln Lys Ser Leu Ser Leu Ser Pro Gly Lys
    370                 375

<210> SEQ ID NO 36
<211> LENGTH: 1134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
atggatgcaa tgaagagagg gctctgctgt gtgctgctgc tgtgtggagc agtcttcgtt      60
tcgcccggcg ccgacatgat agtcactgac aacaacggtg cagtcaagtt tccacaactg     120
tgtaaatttt gtgatgtgag attttccacc tgtgacaacc agaaatcctg catgagcaac     180
tgcagcatca cctccatctg tgagaagcca caggaagtct gtgtggctgt atggagaaag     240
aatgacgaga acataacact agagacagtt tgccatgacc ccaagctccc ctaccatgac     300
tttattctgg aagatgctgc ttctccaaag tgcattatga ggaaaaaaa aaagcctggt     360 gagactttct tcatgtgttc ctgtagctct gatgagtgca atgacaacat catcttctca     420
gaagaatata acaccagcaa tcctgacacc ggtggtggaa ctcacacatg cccaccgtgc     480
ccagcacctg aactcctggg gggaccgtca gtcttcctct tccccccaaa acccaaggac     540

```
accctcatga tctcccggac ccctgaggtc acatgcgtgg tggtggacgt gagccacgaa    600
gaccctgagg tcaagttcaa ctggtacgtg gacggcgtgg aggtgcataa tgccaagaca    660
aagccgcggg aggagcagta caacagcacg taccgtgtgg tcagcgtcct caccgtcctg    720
caccaggact ggctgaatgg caaggagtac aagtgcaagg tctccaacaa agccctccca    780 gccccatcg agaaaaccat ctccaaagcc aagggcagc cccgagaacc acaggtgtac    840
accctgcccc catcccggga ggagatgacc aagaaccagg tcagcctgac ctgcctggtc    900
aaaggcttct atcccagcga catcgccgtg gagtgggaga gcaatgggca gccggagaac    960
aactacaaga ccacgcctcc cgtgctggac tccgacggct ccttcttcct ctatagcaag   1020
ctcaccgtgg acaagagcag gtggcagcag gggaacgtct tctcatgctc cgtgatgcat   1080
gaggctctgc acaaccacta cacgcagaag agcctctccc tgtccccggg taaa         1134
```

<210> SEQ ID NO 37
<211> LENGTH: 382
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Met Asp Ala Met Lys Arg Gly Leu Cys Cys Val Leu Leu Cys Gly
1               5                   10                  15

Ala Val Phe Val Ser Pro Gly Ala Thr Ile Pro Pro His Val Gln Lys
                20                  25                  30

Ser Val Asn Asn Asp Met Ile Val Thr Asp Asn Gly Ala Val Lys
            35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
    130                 135                 140

Cys Asn Asp Asn Ile Ile Phe Ser Glu Glu Tyr Thr Gly Gly Gly Val
145                 150                 155                 160

Glu Cys Pro Pro Cys Pro Ala Pro Val Ala Gly Pro Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser His Glu Asp Pro Glu Val
        195                 200                 205

Gln Phe Asn Trp Tyr Val Asp Gly Val Glu Val His Asn Ala Lys Thr
    210                 215                 220

Lys Pro Arg Glu Glu Gln Phe Asn Ser Thr Phe Arg Val Val Ser Val
225                 230                 235                 240

Leu Thr Val Val His Gln Asp Trp Leu Asn Gly Lys Glu Tyr Lys Cys
                245                 250                 255
```

| | | | | | | | | | | | |
|---|---|---|---|---|---|---|---|---|---|---|---|
|Lys|Val|Ser|Asn 260|Lys|Gly|Leu|Pro 265|Ala|Pro|Ile|Glu Lys Thr Ile Ser 270|

Lys Thr Lys Gly Gln Pro Arg Glu Pro Gln Val Tyr Thr Leu Pro Pro
            275                 280                 285

Ser Arg Glu Glu Met Thr Lys Asn Gln Val Ser Leu Thr Cys Leu Val
        290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Met Leu Asp Ser Asp
                325                 330                 335

Gly Ser Phe Phe Leu Tyr Ser Lys Leu Thr Val Asp Lys Ser Arg Trp
            340                 345                 350

Gln Gln Gly Asn Val Phe Ser Cys Ser Val Met His Glu Ala Leu His
        355                 360                 365

Asn His Tyr Thr Gln Lys Ser Leu Ser Leu Ser Pro Gly Lys
    370                 375                 380

```
<210> SEQ ID NO 38
<211> LENGTH: 1146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
atggatgcaa tgaagagagg gctctgctgt gtgctgctgc tgtgtggagc agtcttcgtt      60
tcgcccggcg ccacgatccc accgcacgtt cagaagtcgg ttaataacga catgatagtc     120
actgacaaca acggtgcagt caagtttcca caactgtgta aattttgtga tgtgagattt     180
tccacctgtg acaaccagaa atcctgcatg agcaactgca gcatcacctc catctgtgag     240
aagccacagg aagtctgtgt ggctgtatgg agaaagaatg acgagaacat aacactagag     300
acagtttgcc atgaccccaa gctcccctac catgacttta ttctggaaga tgctgcttct     360
ccaaagtgca ttatgaagga aaaaaaaaag cctggtgaga ctttcttcat gtgttcctgt     420
agctctgatg agtgcaatga caacatcatc ttctcagaag aatataccgg tggtggagtc     480
gagtgcccac cgtgcccagc accacctgtg gcaggaccgt cagtcttcct cttcccccca     540
aaacccaagg acaccctcat gatctcccgg acccctgagg tcacgtgcgt ggtggtggac     600
gtgagccacg aagaccccga ggtccagttc aactggtacg tggacggcgt ggaggtgcat     660
aatgccaaga caaagccacg ggaggagcag ttcaacagca cgttccgtgt ggtcagcgtc     720
ctcaccgtcg tgcaccagga ctggctgaac ggcaaggagt acaagtgcaa ggtctccaac     780
aaaggcctcc cagcccccat cgagaaaacc atctccaaaa ccaagggcag ccccgagaa     840 ccacaggtgt acaccctgcc cccatcccgg gaggagatga ccaagaacca ggtcagcctg     900
acctgcctgg tcaaaggctt ctaccccagc gacatcgccg tggagtggga gagcaatggg     960
cagccggaga acaactacaa gaccacacct cccatgctgg actccgacgg ctccttcttc    1020
ctctacagca agctcaccgt ggacaagagc aggtggcagc aggggaacgt cttctcatgc    1080
tccgtgatgc atgaggctct gcacaaccac tacacgcaga gagcctctc cctgtctccg    1140 ggtaaa                                                              1146

<210> SEQ ID NO 39
<211> LENGTH: 384
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 39

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Val Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
130                 135                 140

Cys Asn Asp Asn Ile Ile Phe Ser Glu Glu Tyr Thr Gly Gly Gly Thr
145                 150                 155                 160

His Thr Cys Pro Pro Cys Pro Ala Pro Glu Leu Leu Gly Gly Pro Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Val Asp Val Ser His Glu Asp Pro
        195                 200                 205

Glu Val Lys Phe Asn Trp Tyr Val Asp Gly Val Glu Val His Asn Ala
    210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
            260                 265                 270

Ile Ser Lys Ala Lys Gly Gln Pro Arg Glu Pro Gln Val Tyr Thr Leu
        275                 280                 285

Pro Pro Ser Arg Glu Glu Met Thr Lys Asn Gln Val Ser Leu Thr Cys
    290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
            340                 345                 350

Arg Trp Gln Gln Gly Asn Val Phe Ser Cys Ser Val Met His Glu Ala
        355                 360                 365

Leu His Asn His Tyr Thr Gln Lys Ser Leu Ser Leu Ser Pro Gly Lys
    370                 375                 380

-continued

<210> SEQ ID NO 40
<211> LENGTH: 1152
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
atggatgcaa tgaagagagg gctctgctgt gtgctgctgc tgtgtggagc agtcttcgtt      60
tcgcccggcg ccacgatccc accgcacgtt cagaagtcgg ttaataacga catgatagtc     120
actgacaaca acggtgcagt caagtttcca caactgtgta aattttgtga tgtgagattt     180
tccacctgtg acaaccagaa atcctgcatg agcaactgca gcatcacctc catctgtgag     240
aagccacagg aagtctgtgt ggctgtatgg agaaagaatg acgagaacat aacactagag     300
acagtttgcc atgaccccaa gctcccctac catgacttta ttctggaaga tgctgcttct     360
ccaaagtgca ttatgaagga aaaaaaaaag cctggtgaga cttttcttca tgtgttcctgt     420 agctctgatg agtgcaatga acacatcatc ttctcagaag aatataccgg tggtggaact     480
cacacatgcc accgtgccc agcacctgaa ctcctggggg gaccgtcagt cttcctcttc     540
cccccaaaac ccaaggacac cctcatgatc tcccggaccc ctgaggtcac atgcgtggtg     600
gtggacgtga gccacgaaga ccctgaggtc aagttcaact ggtacgtgga cggcgtggag     660
gtgcataatg ccaagacaaa gccgcgggag gagcagtaca acagcacgta ccgtgtggtc     720
agcgtcctca ccgtcctgca ccaggactgg ctgaatggca aggagtacaa gtgcaaggtc     780
tccaacaaag ccctcccagc ccccatcgag aaaaccatct ccaaagccaa agggcagccc     840
cgagaaccac aggtgtacac cctgccccca tcccgggagg agatgaccaa gaaccaggtc     900
agcctgacct gcctggtcaa aggcttctat cccagcgaca tcgccgtgga gtgggagagc     960
aatgggcagc cggagaacaa ctacaagacc acgcctcccg tgctggactc cgacggctcc    1020
ttcttcctct atagcaagct caccgtggac aagagcaggt ggcagcaggg gaacgtcttc    1080
tcatgctccg tgatgcatga ggctctgcac aaccactaca cgcagaagag cctctccctg    1140
tccccgggta aa                                                        1152

<210> SEQ ID NO 41
<211> LENGTH: 382
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Val Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp
    50                  55                  60

Asn Gln Lys Ser Cys Met Ser Asp Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
130                 135                 140

Cys Asn Asp Asn Ile Ile Phe Ser Glu Glu Tyr Thr Gly Gly Gly Val
145                 150                 155                 160

Glu Cys Pro Pro Cys Pro Ala Pro Val Ala Gly Pro Ser Val Phe
                165                 170                 175

Leu Phe Pro Pro Lys Pro Lys Asp Thr Leu Met Ile Ser Arg Thr Pro
        180                 185                 190

Glu Val Thr Cys Val Val Val Asp Val Ser His Glu Asp Pro Glu Val
        195                 200                 205

Gln Phe Asn Trp Tyr Val Asp Gly Val Glu Val His Asn Ala Lys Thr
    210                 215                 220

Lys Pro Arg Glu Glu Gln Phe Asn Ser Thr Phe Arg Val Val Ser Val
225                 230                 235                 240

Leu Thr Val Val His Gln Asp Trp Leu Asn Gly Lys Glu Tyr Lys Cys
                245                 250                 255

Lys Val Ser Asn Lys Gly Leu Pro Ala Pro Ile Glu Lys Thr Ile Ser
            260                 265                 270

Lys Thr Lys Gly Gln Pro Arg Glu Pro Gln Val Tyr Thr Leu Pro Pro
        275                 280                 285

Ser Arg Glu Glu Met Thr Lys Asn Gln Val Ser Leu Thr Cys Leu Val
    290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Met Leu Asp Ser Asp
                325                 330                 335

Gly Ser Phe Phe Leu Tyr Ser Lys Leu Thr Val Asp Lys Ser Arg Trp
            340                 345                 350

Gln Gln Gly Asn Val Phe Ser Cys Ser Val Met His Glu Ala Leu His
        355                 360                 365

Asn His Tyr Thr Gln Lys Ser Leu Ser Leu Ser Pro Gly Lys
    370                 375                 380

<210> SEQ ID NO 42
<211> LENGTH: 1146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
atggatgcaa tgaagagagg gctctgctgt gtgctgctgc tgtgtggagc agtcttcgtt      60
tcgcccggcg ccacgatccc accgcacgtt cagaagtcgg ttaataacga catgatagtc     120
actgacaaca acggtgcagt caagtttcca caactgtgta aattttgtga tgtgagattt     180
tccacctgtg acaaccagaa atcctgcatg agcgactgca gcatcacctc catctgtgag     240
aagccacagg aagtctgtgt ggctgtatgg agaagaatga cgagaacat aacactagag     300 acagtttgcc atgaccccaa gctcccctac atgacttta ttctggaaga tgctgcttct     360
ccaaagtgca ttatgaagga aaaaaaaaag cctggtgaga ctttcttcat gtgttcctgt     420

```
agctctgatg agtgcaatga caacatcatc ttctcagaag aatataccgg tggtggagtc    480
gagtgcccac cgtgcccagc accacctgtg caggaccgt cagtcttcct cttccccca     540 aaacccaagg acaccctcat gatctcccgg acccctgagg tcacgtgcgt ggtggtggac    600
gtgagccacg aagaccccga ggtccagttc aactggtacg tggacggcgt ggaggtgcat    660
aatgccaaga caaagccacg ggaggagcag ttcaacagca cgttccgtgt ggtcagcgtc    720
ctcaccgtcg tgcaccagga ctggctgaac ggcaaggagt acaagtgcaa ggtctccaac    780
aaaggcctcc cagcccccat cgagaaaacc atctccaaaa ccaaagggca gccccgagaa    840
ccacaggtgt acaccctgcc cccatcccgg gaggagatga ccaagaacca ggtcagcctg    900
acctgcctgg tcaaaggctt ctaccccagc gacatcgccg tggagtggga gagcaatggg    960
cagccggaga acaactacaa gaccacacct cccatgctgg actccgacgg ctccttcttc   1020
ctctacagca agctcaccgt ggacaagagc aggtggcagc aggggaacgt cttctcatgc   1080
tccgtgatgc atgaggctct gcacaaccac tacacgcaga gagcctctc cctgtctccg    1140 ggtaaa                                                             1146
```

<210> SEQ ID NO 43
<211> LENGTH: 384
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Asp Ala Met Lys Arg Gly Leu Cys Cys Val Leu Leu Cys Gly
1               5                   10                  15

Ala Val Phe Val Ser Pro Gly Ala Thr Ile Pro Pro His Val Gln Lys
            20                  25                  30

Ser Val Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp
    50                  55                  60

Asn Gln Lys Ser Cys Met Ser Asp Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
    130                 135                 140

Cys Asn Asp Asn Ile Ile Phe Ser Glu Glu Tyr Thr Gly Gly Gly Thr
145                 150                 155                 160

His Thr Cys Pro Pro Cys Pro Ala Pro Glu Leu Leu Gly Gly Pro Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Val Asp Val Ser His Glu Asp Pro
        195                 200                 205

Glu Val Lys Phe Asn Trp Tyr Val Asp Gly Val Glu Val His Asn Ala
    210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
            245                 250                 255

Lys Cys Lys Val Ser Asn Lys Ala Leu Pro Ala Pro Ile Glu Lys Thr
        260                 265                 270

Ile Ser Lys Ala Lys Gly Gln Pro Arg Glu Pro Gln Val Tyr Thr Leu
    275                 280                 285

Pro Pro Ser Arg Glu Glu Met Thr Lys Asn Gln Val Ser Leu Thr Cys
290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
            325                 330                 335

Ser Asp Gly Ser Phe Phe Leu Tyr Ser Lys Leu Thr Val Asp Lys Ser
        340                 345                 350

Arg Trp Gln Gln Gly Asn Val Phe Ser Cys Ser Val Met His Glu Ala
    355                 360                 365

Leu His Asn His Tyr Thr Gln Lys Ser Leu Ser Leu Ser Pro Gly Lys
370                 375                 380

<210> SEQ ID NO 44
<211> LENGTH: 1152
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
atggatgcaa tgaagagagg gctctgctgt gtgctgctgc tgtgtggagc agtcttcgtt    60
tcgcccggcg ccacgatccc accgcacgtt cagaagtcgg ttaataacga catgatagtc   120
actgacaaca acggtgcagt caagtttcca caactgtgta aattttgtga tgtgagattt   180
tccacctgtg acaaccagaa atcctgcatg agcgactgca gcatcacctc catctgtgag   240
aagccacagg aagtctgtgt ggctgtatgg agaaagaatg acgagaacat aacactagag   300
acagtttgcc atgaccccaa gctcccctac catgacttta ttctggaaga tgctgcttct   360
ccaaagtgca ttatgaagga aaaaaaaaag cctggtgaga ctttcttcat gtgttcctgt   420
agctctgatg agtgcaatga caacatcatc ttctcagaag aatataccgg tggtggaact   480
cacacatgcc caccgtgccc agcacctgaa ctcctggggg gaccgtcagt cttcctcttc   540
cccccaaaac ccaaggacac cctcatgatc tcccggaccc ctgaggtcac atgcgtggtg   600
gtggacgtga gccacgaaga ccctgaggtc aagttcaact ggtacgtgga cggcgtggag   660
gtgcataatg ccaagacaaa gccgcgggag gagcagtaca acagcacgta ccgtgtggtc   720
agcgtcctca ccgtcctgca ccaggactgg ctgaatggca aggagtacaa gtgcaaggtc   780
tccaacaaag ccctcccagc ccccatcgag aaaaccatct ccaaagccaa agggcagccc   840
cgagaaccac aggtgtacac cctgccccca tcccgggagg agatgaccaa gaaccaggtc   900
agcctgacct gcctggtcaa aggcttctat cccagcgaca tcgccgtgga gtgggagagc   960
aatgggcagc cggagaacaa ctacaagacc acgcctcccg tgctggactc cgacggctcc  1020
ttcttcctct atagcaagct caccgtggac aagagcaggt ggcagcaggg gaacgtcttc  1080
tcatgctccg tgatgcatga ggctctgcac aaccactaca cgcagaagag cctctccctg  1140

<210> SEQ ID NO 45

<400> SEQUENCE: 45

000

<210> SEQ ID NO 46

<400> SEQUENCE: 46

000

<210> SEQ ID NO 47
<211> LENGTH: 119
<212> TYPE: PRT
<213> ORGANISM: Homo sapiens

<400> SEQUENCE: 47

```
Asp Met Ile Val Thr Asp Asn Asn Gly Ala Val Lys Phe Pro Gln Leu
1               5                   10                  15

Cys Lys Phe Cys Asp Val Arg Phe Ser Thr Cys Asp Asn Gln Lys Ser
            20                  25                  30

Cys Met Ser Asn Cys Ser Ile Thr Ser Ile Cys Glu Lys Pro Gln Glu
        35                  40                  45

Val Cys Val Ala Val Trp Arg Lys Asn Asp Glu Asn Ile Thr Leu Glu
    50                  55                  60

Thr Val Cys His Asp Pro Lys Leu Pro Tyr His Asp Phe Ile Leu Glu
65                  70                  75                  80

Asp Ala Ala Ser Pro Lys Cys Ile Met Lys Glu Lys Lys Lys Pro Gly
                85                  90                  95

Glu Thr Phe Phe Met Cys Ser Cys Ser Ser Asp Glu Cys Asn Asp Asn
            100                 105                 110

Ile Ile Phe Ser Glu Glu Tyr
        115
```

<210> SEQ ID NO 48
<211> LENGTH: 125
<212> TYPE: PRT
<213> ORGANISM: Homo sapiens

<400> SEQUENCE: 48

```
Gln Lys Ser Val Asn Asn Asp Met Ile Val Thr Asp Asn Asn Gly Ala
1               5                   10                  15

Val Lys Phe Pro Gln Leu Cys Lys Phe Cys Asp Val Arg Phe Ser Thr
            20                  25                  30

Cys Asp Asn Gln Lys Ser Cys Met Ser Asn Cys Ser Ile Thr Ser Ile
        35                  40                  45

Cys Glu Lys Pro Gln Glu Val Cys Val Ala Val Trp Arg Lys Asn Asp
    50                  55                  60

Glu Asn Ile Thr Leu Glu Thr Val Cys His Asp Pro Lys Leu Pro Tyr
65                  70                  75                  80

His Asp Phe Ile Leu Glu Asp Ala Ala Ser Pro Lys Cys Ile Met Lys
                85                  90                  95

Glu Lys Lys Lys Pro Gly Glu Thr Phe Phe Met Cys Ser Cys Ser Ser
            100                 105                 110

Asp Glu Cys Asn Asp Asn Ile Ile Phe Ser Glu Glu Tyr
```

115                 120                 125

<210> SEQ ID NO 49
<211> LENGTH: 150
<212> TYPE: PRT
<213> ORGANISM: Homo sapiens

<400> SEQUENCE: 49

Gln Lys Ser Asp Val Glu Met Glu Ala Gln Lys Asp Glu Ile Ile Cys
1               5                   10                  15

Pro Ser Cys Asn Arg Thr Ala His Pro Leu Arg His Ile Asn Asn Asp
            20                  25                  30

Met Ile Val Thr Asp Asn Asn Gly Ala Val Lys Phe Pro Gln Leu Cys
        35                  40                  45

Lys Phe Cys Asp Val Arg Phe Ser Thr Cys Asp Asn Gln Lys Ser Cys
    50                  55                  60

Met Ser Asn Cys Ser Ile Thr Ser Ile Cys Glu Lys Pro Gln Glu Val
65                  70                  75                  80

Cys Val Ala Val Trp Arg Lys Asn Asp Glu Asn Ile Thr Leu Glu Thr
                85                  90                  95

Val Cys His Asp Pro Lys Leu Pro Tyr His Asp Phe Ile Leu Glu Asp
            100                 105                 110

Ala Ala Ser Pro Lys Cys Ile Met Lys Glu Lys Lys Pro Gly Glu
        115                 120                 125

Thr Phe Phe Met Cys Ser Cys Ser Ser Asp Glu Cys Asn Asp Asn Ile
    130                 135                 140

Ile Phe Ser Glu Glu Tyr
145                 150

<210> SEQ ID NO 50
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Thr Gly Gly Val Glu Cys
    130                 135                 140

Pro Pro Cys Pro Ala Pro Pro Val Ala Gly Pro Ser Val Phe Leu Phe

```
145                 150                 155                 160
Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Gln Phe
            180                 185                 190

Asn Trp Tyr Val Asp Gly Val Glu Val His Asn Ala Lys Thr Lys Pro
        195                 200                 205

Arg Glu Glu Gln Phe Asn Ser Thr Phe Arg Val Val Ser Val Leu Thr
    210                 215                 220

Val Val His Gln Asp Trp Leu Asn Gly Lys Glu Tyr Lys Cys Lys Val
225                 230                 235                 240

Ser Asn Lys Gly Leu Pro Ala Pro Ile Glu Lys Thr Ile Ser Lys Thr
                245                 250                 255

Lys Gly Gln Pro Arg Glu Pro Gln Val Tyr Thr Leu Pro Pro Ser Arg
            260                 265                 270

Glu Glu Met Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Met Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
        355                 360

<210> SEQ ID NO 51
<211> LENGTH: 1164
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
atggatgcaa tgaagagagg gctctgctgt gtgctgctgc tgtgtggagc agtcttcgtt      60
tcgcccggcg ccacgatccc accgcacgtt cagaagtcgg ttaataacga catgatagtc     120
actgacaaca acggtgcagt caagtttcca caactgtgta aattttgtga tgtgagattt     180
tccacctgtg acaaccagaa atcctgcatg agcaactgca gcatcacctc catctgtgag     240
aagccacagg aagtctgtgt ggctgtatgg agaaagaatg acgagaacat aacactagag     300
acagtttgcc atgaccccaa gctcccctac catgacttta ttctggaaga tgctgcttct     360
ccaaagtgca ttatgaagga aaaaaaaaag cctggtgaga ctttcttcat gtgttcctgt     420
agctctgatg agtgcaatga caacatcatc ttctcagaag aatataacac cagcaatcct     480
gacaccggtg gtggagtcga gtgcccaccg tgcccagcac acctgtggca ggaccgtca      540 gtcttcctct ccccccaaa acccaaggac accctcatga tctcccggac ccctgaggtc      600
acgtgcgtgg tggtggacgt gagccacgaa gaccccgagg tccagttcaa ctggtacgtg     660
gacggcgtgg aggtgcataa tgccaagaca aagccacggg aggagcagtt caacagcacg     720
ttccgtgtgt tcagcgtcct caccgtcgtg caccaggact ggctgaacgg caaggagtac     780
aagtgcaagg tctccaacaa aggcctccca gcccccatcg agaaaaccat ctccaaaacc     840
```

```
aaagggcagc cccgagaacc acaggtgtac accctgcccc catcccggga ggagatgacc    900
aagaaccagg tcagcctgac ctgcctggtc aaaggcttct accccagcga catcgccgtg    960
gagtgggaga gcaatgggca gccggagaac aactacaaga ccacacctcc catgctggac   1020
tccgacggct ccttcttcct ctacagcaag ctcaccgtgg acaagagcag gtggcagcag   1080
gggaacgtct tctcatgctc cgtgatgcat gaggctctgc acaaccacta cacgcagaag   1140
agcctctccc tgtctccggg taaa                                          1164
```

<210> SEQ ID NO 52
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Val Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
    130                 135                 140

Cys Asn Asp Asn Ile Ile Phe Ser Glu Glu Tyr Asn Thr Ser Asn Pro
145                 150                 155                 160

Asp Thr Gly Gly Gly Val Glu Cys Pro Pro Cys Pro Ala Pro Pro Val
                165                 170                 175

Ala Gly Pro Ser Val Phe Leu Phe Pro Pro Lys Pro Lys Asp Thr Leu
            180                 185                 190

Met Ile Ser Arg Thr Pro Glu Val Thr Cys Val Val Val Asp Val Ser
        195                 200                 205

His Glu Asp Pro Glu Val Gln Phe Asn Trp Tyr Val Asp Gly Val Glu
    210                 215                 220

Val His Asn Ala Lys Thr Lys Pro Arg Glu Glu Gln Phe Asn Ser Thr
225                 230                 235                 240

Phe Arg Val Val Ser Val Leu Thr Val Val His Gln Asp Trp Leu Asn
                245                 250                 255

Gly Lys Glu Tyr Lys Cys Lys Val Ser Asn Lys Gly Leu Pro Ala Pro
            260                 265                 270

Ile Glu Lys Thr Ile Ser Lys Thr Lys Gly Gln Pro Arg Glu Pro Gln
        275                 280                 285

Val Tyr Thr Leu Pro Pro Ser Arg Glu Glu Met Thr Lys Asn Gln Val
```

```
                290                 295                 300
Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
                325                 330                 335

Pro Met Leu Asp Ser Asp Gly Ser Phe Phe Leu Tyr Ser Lys Leu Thr
                340                 345                 350

Val Asp Lys Ser Arg Trp Gln Gln Gly Asn Val Phe Ser Cys Ser Val
                355                 360                 365

Met His Glu Ala Leu His Asn His Tyr Thr Gln Lys Ser Leu Ser Leu
                370                 375                 380

Ser Pro Gly Lys
385

<210> SEQ ID NO 53
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
                20                  25                  30

Asp Val Arg Phe Ser Thr Cys Asp Asn Gln Lys Ser Cys Met Ser Asn
                35                  40                  45

Cys Ser Ile Thr Ser Ile Cys Glu Lys Pro Gln Glu Val Cys Val Ala
50                  55                  60

Val Trp Arg Lys Asn Asp Glu Asn Ile Thr Leu Glu Thr Val Cys His
65                  70                  75                  80

Asp Pro Lys Leu Pro Tyr His Lys Phe Ile Leu Glu Asp Ala Ala Ser
                85                  90                  95

Pro Lys Cys Ile Met Lys Glu Lys Lys Pro Gly Glu Thr Phe Phe
                100                 105                 110

Met Cys Ser Cys Ser Ser Asp Glu Cys Asn Asp Asn Ile Ile Phe Ser
                115                 120                 125

Glu Glu Tyr Asn Thr Ser Asn Pro Asp Thr Gly Gly Gly Val Glu Cys
                130                 135                 140

Pro Pro Cys Pro Ala Pro Pro Val Ala Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Gln Phe
                180                 185                 190

Asn Trp Tyr Val Asp Gly Val Glu Val His Asn Ala Lys Thr Lys Pro
                195                 200                 205

Arg Glu Glu Gln Phe Asn Ser Thr Phe Arg Val Val Ser Val Leu Thr
                210                 215                 220

Val Val His Gln Asp Trp Leu Asn Gly Lys Glu Tyr Lys Cys Lys Val
225                 230                 235                 240

Ser Asn Lys Gly Leu Pro Ala Pro Ile Glu Lys Thr Ile Ser Lys Thr
                245                 250                 255
```

```
Lys Gly Gln Pro Arg Glu Pro Gln Val Tyr Thr Leu Pro Pro Ser Arg
            260                 265                 270

Glu Glu Met Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Met Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
            355                 360
```

<210> SEQ ID NO 54
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Lys Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Thr Gly Gly Gly Thr His Thr
    130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255
```

Lys Ala Lys Gly Gln Pro Arg Glu Pro Gln Val Tyr Thr Leu Pro Pro
            260                 265                 270

Ser Arg Glu Glu Met Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Val Leu Asp Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
        355                 360                 365

<210> SEQ ID NO 55
<211> LENGTH: 358
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Lys Ser Val Asn Asn Asp Met Ile Val Thr Asp Asn Asn Gly Ala
1               5                   10                  15

Val Lys Phe Pro Gln Leu Cys Lys Phe Cys Asp Val Arg Phe Ser Thr
            20                  25                  30

Cys Asp Asn Gln Lys Ser Cys Met Ser Asn Cys Ser Ile Thr Ser Ile
        35                  40                  45

Cys Glu Lys Pro Gln Glu Val Cys Val Ala Val Trp Arg Lys Asn Asp
    50                  55                  60

Glu Asn Ile Thr Leu Glu Thr Val Cys His Asp Pro Lys Leu Pro Tyr
65                  70                  75                  80

His Asp Phe Ile Leu Glu Asp Ala Ala Ser Pro Lys Cys Ile Met Lys
                85                  90                  95

Glu Lys Lys Lys Pro Gly Glu Thr Phe Phe Met Cys Ser Cys Ser Ser
            100                 105                 110

Asp Glu Cys Asn Asp Asn Ile Ile Phe Ser Glu Glu Tyr Asn Thr Ser
        115                 120                 125

Asn Pro Asp Thr Gly Gly Gly Val Glu Cys Pro Pro Cys Pro Ala Pro
    130                 135                 140

Pro Val Ala Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Gln Phe Asn Trp Tyr Val Asp Gly
            180                 185                 190

Val Glu Val His Asn Ala Lys Thr Lys Pro Arg Glu Glu Gln Phe Asn
        195                 200                 205

Ser Thr Phe Arg Val Val Ser Val Leu Thr Val His Gln Asp Trp
    210                 215                 220

Leu Asn Gly Lys Glu Tyr Lys Cys Lys Val Ser Asn Lys Gly Leu Pro
225                 230                 235                 240

Ala Pro Ile Glu Lys Thr Ile Ser Lys Thr Lys Gly Gln Pro Arg Glu

-continued

```
                245                 250                 255
Pro Gln Val Tyr Thr Leu Pro Pro Ser Arg Glu Glu Met Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Met Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
            355

<210> SEQ ID NO 56
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Lys Ser Val Asn Asn Asp Met Ile Val Thr Asp Asn Asn Gly Ala
1               5                   10                  15

Val Lys Phe Pro Gln Leu Cys Lys Phe Cys Asp Val Arg Phe Ser Thr
            20                  25                  30

Cys Asp Asn Gln Lys Ser Cys Met Ser Asn Cys Ser Ile Thr Ser Ile
        35                  40                  45

Cys Glu Lys Pro Gln Glu Val Cys Val Ala Val Trp Arg Lys Asn Asp
    50                  55                  60

Glu Asn Ile Thr Leu Glu Thr Val Cys His Asp Pro Lys Leu Pro Tyr
65                  70                  75                  80

His Asp Phe Ile Leu Glu Asp Ala Ala Ser Pro Lys Cys Ile Met Lys
                85                  90                  95

Glu Lys Lys Lys Pro Gly Glu Thr Phe Phe Met Cys Ser Cys Ser Ser
            100                 105                 110

Asp Glu Cys Asn Asp Asn Ile Ile Phe Ser Glu Glu Tyr Asn Thr Ser
        115                 120                 125

Asn Pro Asp Thr Gly Gly Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240
```

```
Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 57
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Met Ile Val Thr Asp Asn Asn Gly Ala Val Lys Phe Pro Gln Leu
1               5                   10                  15

Cys Lys Phe Cys Asp Val Arg Phe Ser Thr Cys Asp Asn Gln Lys Ser
            20                  25                  30

Cys Met Ser Asn Cys Ser Ile Thr Ser Ile Cys Glu Lys Pro Gln Glu
        35                  40                  45

Val Cys Val Ala Val Trp Arg Lys Asn Asp Glu Asn Ile Thr Leu Glu
    50                  55                  60

Thr Val Cys His Asp Pro Lys Leu Pro Tyr His Asp Phe Ile Leu Glu
65                  70                  75                  80

Asp Ala Ala Ser Pro Lys Cys Ile Met Lys Glu Lys Lys Lys Pro Gly
                85                  90                  95

Glu Thr Phe Phe Met Cys Ser Cys Ser Ser Asp Glu Cys Asn Asp Asn
            100                 105                 110

Ile Ile Phe Ser Glu Glu Tyr Asn Thr Ser Asn Pro Asp Thr Gly Gly
        115                 120                 125

Gly Val Glu Cys Pro Pro Cys Pro Ala Pro Pro Val Ala Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Phe Arg Val Val
        195                 200                 205

Ser Val Leu Thr Val Val His Gln Asp Trp Leu Asn Gly Lys Glu Tyr
    210                 215                 220

Lys Cys Lys Val Ser Asn Lys Gly Leu Pro Ala Pro Ile Glu Lys Thr
225                 230                 235                 240
```

```
Ile Ser Lys Thr Lys Gly Gln Pro Arg Glu Pro Gln Val Tyr Thr Leu
            245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
            275                 280                 285

Asn Gly Gln Pro Glu Asn Asn Tyr Lys Thr Thr Pro Pro Met Leu Asp
            290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

<210> SEQ ID NO 58
<211> LENGTH: 354
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Met Ile Val Thr Asp Asn Asn Gly Ala Val Lys Phe Pro Gln Leu
1               5                   10                  15

Cys Lys Phe Cys Asp Val Arg Phe Ser Thr Cys Asp Asn Gln Lys Ser
            20                  25                  30

Cys Met Ser Asn Cys Ser Ile Thr Ser Ile Cys Glu Lys Pro Gln Glu
            35                  40                  45

Val Cys Val Ala Val Trp Arg Lys Asn Asp Glu Asn Ile Thr Leu Glu
    50                  55                  60

Thr Val Cys His Asp Pro Lys Leu Pro Tyr His Asp Phe Ile Leu Glu
65                  70                  75                  80

Asp Ala Ala Ser Pro Lys Cys Ile Met Lys Glu Lys Lys Pro Gly
                85                  90                  95

Glu Thr Phe Phe Met Cys Ser Cys Ser Ser Asp Glu Cys Asn Asp Asn
            100                 105                 110

Ile Ile Phe Ser Glu Glu Tyr Asn Thr Ser Asn Pro Asp Thr Gly Gly
            115                 120                 125

Gly Thr His Thr Cys Pro Pro Cys Pro Ala Pro Glu Leu Leu Gly Gly
            130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
            195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
```

245                 250                 255
Thr Leu Pro Pro Ser Arg Glu Glu Met Thr Lys Asn Gln Val Ser Leu
            260                 265                 270

Thr Cys Leu Val Lys Gly Phe Tyr Pro Ser Asp Ile Ala Val Glu Trp
            275                 280                 285

Glu Ser Asn Gly Gln Pro Glu Asn Asn Tyr Lys Thr Thr Pro Pro Val
            290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
            325                 330                 335

Glu Ala Leu His Asn His Tyr Thr Gln Lys Ser Leu Ser Leu Ser Pro
            340                 345                 350

Gly Lys

<210> SEQ ID NO 59
<211> LENGTH: 358
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
            35                  40                  45

Cys Ser Ile Thr Ser Ile Cys Glu Lys Pro Gln Glu Val Cys Val Ala
        50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Thr Gly Gly Gly Val Glu Cys Pro Cys Pro Ala Pro
    130                 135                 140

Pro Val Ala Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Gln Phe Asn Trp Tyr Val Asp Gly
            180                 185                 190

Val Glu Val His Asn Ala Lys Thr Lys Pro Arg Glu Glu Gln Phe Asn
        195                 200                 205

Ser Thr Phe Arg Val Val Ser Val Leu Thr Val Val His Gln Asp Trp
    210                 215                 220

Leu Asn Gly Lys Glu Tyr Lys Cys Lys Val Ser Asn Lys Gly Leu Pro
225                 230                 235                 240

Ala Pro Ile Glu Lys Thr Ile Ser Lys Thr Lys Gly Gln Pro Arg Glu

```
                        245                 250                 255

Pro Gln Val Tyr Thr Leu Pro Pro Ser Arg Glu Glu Met Thr Lys Asn
            260                 265                 270

Gln Val Ser Leu Thr Cys Leu Val Lys Gly Phe Tyr Pro Ser Asp Ile
            275                 280                 285

Ala Val Glu Trp Glu Ser Asn Gly Gln Pro Glu Asn Asn Tyr Lys Thr
            290                 295                 300

Thr Pro Pro Met Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
                340                 345                 350

Ser Leu Ser Pro Gly Lys
                355

<210> SEQ ID NO 60
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
            35                  40                  45

Cys Ser Ile Thr Ser Ile Cys Glu Lys Pro Gln Glu Val Cys Val Ala
        50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Thr Gly Gly Thr His Thr Cys Pro Pro Cys Pro Ala
            130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
                180                 185                 190

Asp Gly Val Glu Val His Asn Ala Lys Thr Lys Pro Arg Glu Glu Gln
            195                 200                 205

Tyr Asn Ser Thr Tyr Arg Val Val Ser Val Leu Thr Val Leu His Gln
        210                 215                 220

Asp Trp Leu Asn Gly Lys Glu Tyr Lys Cys Lys Val Ser Asn Lys Ala
225                 230                 235                 240
```

```
Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 61
<211> LENGTH: 358
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asp
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Thr Gly Gly Gly Val Glu Cys Pro Pro Cys Pro Ala Pro
    130                 135                 140

Pro Val Ala Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Gln Phe Asn Trp Tyr Val Asp Gly
            180                 185                 190

Val Glu Val His Asn Ala Lys Thr Lys Pro Arg Glu Glu Gln Phe Asn
        195                 200                 205

Ser Thr Phe Arg Val Val Ser Val Leu Thr Val Val His Gln Asp Trp
    210                 215                 220

Leu Asn Gly Lys Glu Tyr Lys Cys Lys Val Ser Asn Lys Gly Leu Pro
225                 230                 235                 240
```

```
Ala Pro Ile Glu Lys Thr Ile Ser Lys Thr Lys Gly Gln Pro Arg Glu
                245                 250                 255

Pro Gln Val Tyr Thr Leu Pro Pro Ser Arg Glu Glu Met Thr Lys Asn
            260                 265                 270

Gln Val Ser Leu Thr Cys Leu Val Lys Gly Phe Tyr Pro Ser Asp Ile
            275                 280                 285

Ala Val Glu Trp Glu Ser Asn Gly Gln Pro Glu Asn Asn Tyr Lys Thr
            290                 295                 300

Thr Pro Pro Met Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
                340                 345                 350

Ser Leu Ser Pro Gly Lys
            355

<210> SEQ ID NO 62
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asp
            35                  40                  45

Cys Ser Ile Thr Ser Ile Cys Glu Lys Pro Gln Glu Val Cys Val Ala
        50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
            115                 120                 125

Glu Glu Tyr Thr Gly Gly Gly Thr His Thr Cys Pro Pro Cys Pro Ala
            130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
            195                 200                 205

Tyr Asn Ser Thr Tyr Arg Val Val Ser Val Leu Thr Val Leu His Gln
            210                 215                 220

Asp Trp Leu Asn Gly Lys Glu Tyr Lys Cys Lys Val Ser Asn Lys Ala
```

```
                225                 230                 235                 240
Leu Pro Ala Pro Ile Glu Lys Thr Ile Ser Lys Ala Lys Gly Gln Pro
                    245                 250                 255
Arg Glu Pro Gln Val Tyr Thr Leu Pro Pro Ser Arg Glu Glu Met Thr
                260                 265                 270
Lys Asn Gln Val Ser Leu Thr Cys Leu Val Lys Gly Phe Tyr Pro Ser
            275                 280                 285
Asp Ile Ala Val Glu Trp Glu Ser Asn Gly Gln Pro Glu Asn Asn Tyr
        290                 295                 300
Lys Thr Thr Pro Pro Val Leu Asp Ser Asp Gly Ser Phe Phe Leu Tyr
305                 310                 315                 320
Ser Lys Leu Thr Val Asp Lys Ser Arg Trp Gln Gln Gly Asn Val Phe
                325                 330                 335
Ser Cys Ser Val Met His Glu Ala Leu His Asn His Tyr Thr Gln Lys
                340                 345                 350
Ser Leu Ser Leu Ser Pro Gly Lys
            355                 360

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70
```

000

<210> SEQ ID NO 71
<400> SEQUENCE: 71
000

<210> SEQ ID NO 72
<400> SEQUENCE: 72
000

<210> SEQ ID NO 73
<400> SEQUENCE: 73
000

<210> SEQ ID NO 74
<400> SEQUENCE: 74
000

<210> SEQ ID NO 75
<400> SEQUENCE: 75
000

<210> SEQ ID NO 76
<400> SEQUENCE: 76
000

<210> SEQ ID NO 77
<400> SEQUENCE: 77
000

<210> SEQ ID NO 78
<400> SEQUENCE: 78
000

<210> SEQ ID NO 79
<400> SEQUENCE: 79
000

<210> SEQ ID NO 80
<400> SEQUENCE: 80
000

<210> SEQ ID NO 81
<400> SEQUENCE: 81
000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93
<400> SEQUENCE: 93
000

<210> SEQ ID NO 94
<400> SEQUENCE: 94
000

<210> SEQ ID NO 95
<400> SEQUENCE: 95
000

<210> SEQ ID NO 96
<400> SEQUENCE: 96
000

<210> SEQ ID NO 97
<400> SEQUENCE: 97
000

<210> SEQ ID NO 98
<400> SEQUENCE: 98
000

<210> SEQ ID NO 99
<400> SEQUENCE: 99
000

<210> SEQ ID NO 100
<400> SEQUENCE: 100
000

<210> SEQ ID NO 101
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
        35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe

```
                65                  70                  75                  80
Cys Asp Val Arg Phe Ser Thr Cys Asp Asn Gln Lys Ser Cys Met Ser
                    85                  90                  95

Asn Cys Ser Ile Thr Ser Ile Cys Glu Lys Pro Gln Glu Val Cys Val
                100                 105                 110

Ala Val Trp Arg Lys Asn Asp Glu Asn Ile Thr Leu Glu Thr Val Cys
                115                 120                 125

His Asp Pro Lys Leu Pro Tyr His Asp Phe Ile Leu Glu Asp Ala Ala
            130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Thr His
                180                 185                 190

Thr Cys Pro Pro Cys Pro Ala Pro Glu Leu Leu Gly Gly Pro Ser Val
                195                 200                 205

Phe Leu Phe Pro Pro Lys Pro Lys Asp Thr Leu Met Ile Ser Arg Thr
            210                 215                 220

Pro Glu Val Thr Cys Val Val Val Asp Val Ser His Glu Asp Pro Glu
225                 230                 235                 240

Val Lys Phe Asn Trp Tyr Val Asp Gly Val Glu Val His Asn Ala Lys
                245                 250                 255

Thr Lys Pro Arg Glu Glu Gln Tyr Asn Ser Thr Tyr Arg Val Val Ser
                260                 265                 270

Val Leu Thr Val Leu His Gln Asp Trp Leu Asn Gly Lys Glu Tyr Lys
            275                 280                 285

Cys Lys Val Ser Asn Lys Ala Leu Pro Ala Pro Ile Glu Lys Thr Ile
        290                 295                 300

Ser Lys Ala Lys Gly Gln Pro Arg Glu Pro Gln Val Tyr Thr Leu Pro
305                 310                 315                 320

Pro Ser Arg Glu Glu Met Thr Lys Asn Gln Val Ser Leu Thr Cys Leu
                325                 330                 335

Val Lys Gly Phe Tyr Pro Ser Asp Ile Ala Val Glu Trp Glu Ser Asn
                340                 345                 350

Gly Gln Pro Glu Asn Asn Tyr Lys Thr Thr Pro Pro Val Leu Asp Ser
            355                 360                 365

Asp Gly Ser Phe Phe Leu Tyr Ser Lys Leu Thr Val Asp Lys Ser Arg
        370                 375                 380

Trp Gln Gln Gly Asn Val Phe Ser Cys Ser Val Met His Glu Ala Leu
385                 390                 395                 400

His Asn His Tyr Thr Gln Lys Ser Leu Ser Leu Ser Pro Gly Lys
                405                 410                 415

<210> SEQ ID NO 102
<211> LENGTH: 1248
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
atggatgcaa tgaagagagg gctctgctgt gtgctgctgc tgtgtggagc agtcttcgtt     60
tcgcccggcg ccacgatccc accgcacgtt cagaagtcgg atgtggaaat ggaggcccag    120
```

```
aaagatgaaa tcatctgccc cagctgtaat aggactgccc atccactgag acatattaat    180
aacgacatga tagtcactga caacaacggt gcagtcaagt ttccacaact gtgtaaattt    240
tgtgatgtga gattttccac ctgtgacaac cagaaatcct gcatgagcaa ctgcagcatc    300
acctccatct gtgagaagcc acaggaagtc tgtgtggctg tatggagaaa gaatgacgag    360
aacataacac tagagacagt ttgccatgac cccaagctcc cctaccatga ctttattctg    420
gaagatgctg cttctccaaa gtgcattatg aaggaaaaaa aaaagcctgg tgagactttc    480
ttcatgtgtt cctgtagctc tgatgagtgc aatgacaaca tcatcttctc agaagaatat    540
aacaccagca atcctgacac cggtggtgga actcacacat gcccaccgtg cccagcacct    600
gaactcctgg ggggaccgtc agtcttcctc ttccccccaa acccaaggac caccctcatg    660
atctcccgga cccctgaggt cacatgcgtg gtggtggacg tgagccacga agaccctgag    720
gtcaagttca actggtacgt ggacggcgtg gaggtgcata atgccaagac aaagccgcgg    780
gaggagcagt acaacagcac gtaccgtgtg gtcagcgtcc tcaccgtcct gcaccaggac    840
tggctgaatg gcaaggagta caagtgcaag gtctccaaca agcccctccc agcccccatc    900
gagaaaacca tctccaaagc caaagggcag ccccgagaac cacaggtgta caccctgccc    960
ccatcccggg aggagatgac caagaaccag gtcagcctga cctgcctggt caaaggcttc   1020
tatcccagcg acatcgccgt ggagtgggag agcaatgggc agccggagaa caactacaag   1080
accacgcctc ccgtgctgga ctccgacggc tccttcttcc tctatagcaa gctcaccgtg   1140
gacaagagca ggtggcagca ggggaacgtc ttctcatgct ccgtgatgca tgaggctctg   1200
cacaaccact acacgcagaa gagcctctcc ctgtctccgg gtaaatga             1248
```

<210> SEQ ID NO 103
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

```
Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160
```

```
Pro Asp Thr Gly Gly Gly Thr His Thr Cys Pro Pro Cys Pro Ala Pro
                165                 170                 175

Glu Leu Leu Gly Gly Pro Ser Val Phe Leu Phe Pro Pro Lys Pro Lys
            180                 185                 190

Asp Thr Leu Met Ile Ser Arg Thr Pro Glu Val Thr Cys Val Val Val
        195                 200                 205

Asp Val Ser His Glu Asp Pro Glu Val Lys Phe Asn Trp Tyr Val Asp
    210                 215                 220

Gly Val Glu Val His Asn Ala Lys Thr Lys Pro Arg Glu Glu Gln Tyr
225                 230                 235                 240

Asn Ser Thr Tyr Arg Val Val Ser Val Leu Thr Val Leu His Gln Asp
                245                 250                 255

Trp Leu Asn Gly Lys Glu Tyr Lys Cys Lys Val Ser Asn Lys Ala Leu
            260                 265                 270

Pro Ala Pro Ile Glu Lys Thr Ile Ser Lys Ala Lys Gly Gln Pro Arg
        275                 280                 285

Glu Pro Gln Val Tyr Thr Leu Pro Pro Ser Arg Glu Glu Met Thr Lys
    290                 295                 300

Asn Gln Val Ser Leu Thr Cys Leu Val Lys Gly Phe Tyr Pro Ser Asp
305                 310                 315                 320

Ile Ala Val Glu Trp Glu Ser Asn Gly Gln Pro Glu Asn Asn Tyr Lys
                325                 330                 335

Thr Thr Pro Pro Val Leu Asp Ser Asp Gly Ser Phe Phe Leu Tyr Ser
            340                 345                 350

Lys Leu Thr Val Asp Lys Ser Arg Trp Gln Gln Gly Asn Val Phe Ser
        355                 360                 365

Cys Ser Val Met His Glu Ala Leu His Asn His Tyr Thr Gln Lys Ser
370                 375                 380

Leu Ser Leu Ser Pro Gly Lys
385                 390

<210> SEQ ID NO 104
<211> LENGTH: 125
<212> TYPE: PRT
<213> ORGANISM: Homo sapiens

<400> SEQUENCE: 104

Asp Met Ile Val Thr Asp Asn Asn Gly Ala Val Lys Phe Pro Gln Leu
1               5                   10                  15

Cys Lys Phe Cys Asp Val Arg Phe Ser Thr Cys Asp Asn Gln Lys Ser
            20                  25                  30

Cys Met Ser Asn Cys Ser Ile Thr Ser Ile Cys Glu Lys Pro Gln Glu
        35                  40                  45

Val Cys Val Ala Val Trp Arg Lys Asn Asp Glu Asn Ile Thr Leu Glu
    50                  55                  60

Thr Val Cys His Asp Pro Lys Leu Pro Tyr His Asp Phe Ile Leu Glu
65                  70                  75                  80

Asp Ala Ala Ser Pro Lys Cys Ile Met Lys Glu Lys Lys Lys Pro Gly
                85                  90                  95

Glu Thr Phe Phe Met Cys Ser Cys Ser Ser Asp Glu Cys Asn Asp Asn
            100                 105                 110

Ile Ile Phe Ser Glu Glu Tyr Asn Thr Ser Asn Pro Asp
        115                 120                 125
```

```
<210> SEQ ID NO 105
<211> LENGTH: 131
<212> TYPE: PRT
<213> ORGANISM: Homo sapiens

<400> SEQUENCE: 105
```

Gln Lys Ser Val Asn Asn Asp Met Ile Val Thr Asp Asn Asn Gly Ala
1               5                   10                  15

Val Lys Phe Pro Gln Leu Cys Lys Phe Cys Asp Val Arg Phe Ser Thr
            20                  25                  30

Cys Asp Asn Gln Lys Ser Cys Met Ser Asn Cys Ser Ile Thr Ser Ile
        35                  40                  45

Cys Glu Lys Pro Gln Glu Val Cys Val Ala Val Trp Arg Lys Asn Asp
    50                  55                  60

Glu Asn Ile Thr Leu Glu Thr Val Cys His Asp Pro Lys Leu Pro Tyr
65                  70                  75                  80

His Asp Phe Ile Leu Glu Asp Ala Ala Ser Pro Lys Cys Ile Met Lys
                85                  90                  95

Glu Lys Lys Lys Pro Gly Glu Thr Phe Phe Met Cys Ser Cys Ser Ser
            100                 105                 110

Asp Glu Cys Asn Asp Asn Ile Ile Phe Ser Glu Glu Tyr Asn Thr Ser
        115                 120                 125

Asn Pro Asp
    130

```
<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 106
```

His His His His His His
1               5

```
<210> SEQ ID NO 107
<211> LENGTH: 38
<212> TYPE: PRT
<213> ORGANISM: Homo sapiens

<400> SEQUENCE: 107
```

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val
        35

```
<210> SEQ ID NO 108
<211> LENGTH: 16
<212> TYPE: PRT
<213> ORGANISM: Homo sapiens

<400> SEQUENCE: 108
```

Thr Ile Pro Pro His Val Gln Lys Ser Val Asn Asn Asp Met Ile Val
1               5                   10                  15

<210> SEQ ID NO 109
<211> LENGTH: 10
<212> TYPE: PRT
<213> ORGANISM: Homo sapiens

<400> SEQUENCE: 109

Gln Lys Ser Val Asn Asn Asp Met Ile Val
1               5                   10

<210> SEQ ID NO 110
<211> LENGTH: 4
<212> TYPE: PRT
<213> ORGANISM: Homo sapiens

<400> SEQUENCE: 110

Asp Met Ile Val
1

<210> SEQ ID NO 111
<211> LENGTH: 63
<212> TYPE: PRT
<213> ORGANISM: Homo sapiens

<400> SEQUENCE: 111

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
            20                  25                  30

Val Glu Met Glu Ala Gln Lys Asp Glu Ile Ile Cys Pro Ser Cys Asn
        35                  40                  45

Arg Thr Ala His Pro Leu Arg His Ile Asn Asn Asp Met Ile Val
    50                  55                  60

<210> SEQ ID NO 112
<211> LENGTH: 41
<212> TYPE: PRT
<213> ORGANISM: Homo sapiens

<400> SEQUENCE: 112

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val
        35                  40

<210> SEQ ID NO 113
<211> LENGTH: 35
<212> TYPE: PRT
<213> ORGANISM: Homo sapiens

<400> SEQUENCE: 113

Gln Lys Ser Asp Val Glu Met Glu Ala Gln Lys Asp Glu Ile Ile Cys
1               5                   10                  15

Pro Ser Cys Asn Arg Thr Ala His Pro Leu Arg His Ile Asn Asn Asp
            20                  25                  30

Met Ile Val
        35